United States Patent
Apte et al.

(10) Patent No.: US 6,391,610 B1
(45) Date of Patent: May 21, 2002

(54) NUCLEIC ACIDS ENCODING ZINC METALLOPROTEASES

(75) Inventors: Suneel S. Apte, Shaker Heights, OH (US); Tiina L. Hurskainen, Oulu (FI); Satoshi Hirohata, Mayfield Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 09/369,364

(22) Filed: Aug. 6, 1999

(51) Int. Cl.$^7$ .................................................. C12N 9/64
(52) U.S. Cl. ............... 435/226; 219/252.33; 219/320.1; 536/23.2
(58) Field of Search ................................ 435/219, 226, 435/252.33, 320.1; 536/23.2

(56) References Cited

U.S. PATENT DOCUMENTS 6,046,031 A * 4/2000 Ni et al. .................... 435/69.1

FOREIGN PATENT DOCUMENTS

WO 99/05291 2/1999

OTHER PUBLICATIONS

"cDNA cloning and expression of bovine procollagen I N–preteinase: A new member of the superfamily of zinc–metalloproteinases with binding sites for cells and other matrix components" by Colige, et al., *Proc. Natl. Acad. Sci. USA*, vol. 94, Mar. 1997, pp. 2374–2379.

"Purification and Cloning of Aggrecanase–1: A Member of the ADAMTS Family of Proteins" of Tortorella, et al., *Science*, vol. 284, Jun. 4, 1999, pp. 664–666.

"ADAM–TS5, ADAM–TS6, and ADAM–TS7, Novel Members of a New Family of Zinc Metalloproteases" by Hurskainen, et al., *The Journal of Biological Chemistry*, vol. 274, No. 36, Sep. 3, 1999, pp. 25555–25563.

"The Exon/Intron Organization and Chromosomal Mapping of the Mouse ADAMTS–1 Gene Encoding an ADAM Family Protein with TSP Motifs" by Kuno, et al., *Gemonics*, 46, (1997), pp. 466–471.

"Molecular Cloning of a Gene Encoding a New Type of Metalloproteinase–disintegrin Family Protein with Thrombospondin Motifs as an Inflammation Associated Gene" by Kuno, et al., *the Journal of Biological Chemistry*,vol. 272, No. 1, Jan. 3, 1997, pp. 556–562.

"ADAMTS–1 Protein Anchors at the Extracellular Matrix through the Thrombospondin Type 1 Motifs and Its Spacing Region" by Kuno, et al., *The Journal of Biological Chemistry*, vol. 273, No. 22, May 29, 1998, pp. 13912–13917.

"ADAMTS: A novel family of proteases with an ADAM protease domain and thrombospondin 1 repeats" by Tang, et al, *FEBS Letters* 445 (1999) pp. 223–225.

"Generation and Characterization of Aggrecanase: A soluble, Cartilage–Derived Aggrecan–Degrading Activity" by Arner, et al., *The Journal of Biological Chemistry*, vol. 274, No. 10, Mar. 5, 1999, pp. 6594–6601.

"METH–1, a Human Ortholog of ADAMTS–1, and METH–2 Are Members of a New Family of Proteins with Angio–inhibitory Activity" by Vazquez, et al., *The Journal of Biological Chemistry*, vol. 274, No. 33, Apr. 13, 1999, pp. 23349–23357.

"Cloning and Characterization of *ADAMTS11*, an Aggrecanase from the ADAMTS Family" by Abbaszade, et al *The Journal of Biological Chemistry*, vol. 274, No. 33, Aug. 13, 1999, pp. 23443–23450.

GenBank Accession No. AB014588, Feb. 6, 1999.
GenBank Accession No. AB002364, Feb. 13, 1999.
GenBank Accession No. X96389, Mar. 1, 1997.
GenBank Acession No. D67076, Mar. 21, 1997.
GenBank Accession No. AB002364, Jun. 23, 1997.

* cited by examiner

*Primary Examiner*—Nashaat T. Nashed
*Assistant Examiner*—Christian L. Fronda
(74) *Attorney, Agent, or Firm*—Calfee, Halter & Griswold LLP

(57) ABSTRACT

Isolated mammalian proteins having disintegrin-like and metalloprotease domains with thrombospondin type I motifs, i.e., ADAMTS proteins, are provided. The proteins are ADAMTS-5, ADAMTS-6, ADAMTS-7, ADAMTS-8, ADAMTS-9 and ADAMTS-10, collectively referred to as "ADAMTS-N". The present invention also provides isolated polynucleotides which encode an ADAMTS-N protein or a variant thereof, polynucleotide sequences complementary to such polynucleotides, vectors containing such polynucleotides, and host cells transformed or transfected with such vectors. The present invention also relates to antibodies which are immunospecific for one or more of the ADAMTS-N proteins. The present invention also relates to a protein referred to hereinafter as ADAMTS-R1 (ADAM-TS Related protein-1) and the polynucleotides which encode such protein.

12 Claims, 35 Drawing Sheets

Fig. 1A

```
FEATURES         Location/Qualifiers
    source       1..3002
                 /organism="Mus musculus"
                 /db_xref="taxon:10090"
                 /chromosome="Mouse 16"
                 /map="58 cM (consensus position)"
    gene         1..3002
                 /note="a disintegrin-like and metalloprotease domain with
                 thrombospondin type I repeats)"
                 /gene="Adamts5"
    CDS          18..2810
                 /gene="Adamts5"
                 /note="putative secreted metalloprotease"
                 /codon_start=1
                 /product="ADAM-TS5 (a disintegrin-like and metalloprotease
                 domain with thrombospondin type I repeats)"
                 /translation="MRLEWASLLLLLLLLLSASCLSLAADSPAAAPAQDKTRQPQAAAA
                 AAEPDQPQGEETRERGHLQPLAGQRRSGGLVHNIDQLYSGGGKVGYLVYAGGRRFLLD
                 LERDDTVGAAGSIVTAGGGLSASSGHRGHCFYRGTVDGSPRSLAVFDLCGGLDGFFAV
                 KHARYTLKPLLRGSWAEYERIYGDGSSRILHVYNREGFSFEALPPRASCETPASPSGP
                 QESPSVHSRSRRRSALAPQLLDHSAFSPSGNAGPQTWWRRRRRSISRARQVELLLVAD
                 SSMARMYGRGLQHYLLTLASIANRLYSHASIENHIRLAVVKVVVLTDKDTSLEVSKNA
                 ATTLKNFCKWQHQHNQLGDDHEEHYDAAILFTREDLCGHHSCDTLGMADVGTICSPER
                 SCAVIEDDGLHAAFTVAHEIGHLLGLSHDDSKFCEENFGTTEDKRLMSSILTSIDASK
                 PWSKCTSATITEFLDDGHGNCLLDLPRKQILGPEELPGQTYDATQQCNLTFGPEYSVC
                 PGMDVCARLWCAVVRQGQMVCLTKKLPAVEGTPCGKGRVCLQGKCVDKTKKKYYSTSS
                 HGNWGSWGPWGQCSRSCGGVQFAYRHCNNPAPRNSGRYCTGKRAIYRSCSVTPCPPN
```

Fig. 1B

GKSFRHEQCEAKNGYQSDAKGVKTFVEWVPKYAGVLPADVCKLTCRAKGTGYYVVFSP
KVTDGTECRPYSNSVCVRGRCVRTGCDGIIGSKLQYDKCGVCGGDNSSCTKIIGTFNK
KSKGYTDVVRIPEGATHIKVRQFKAKDQTRFPAYLALKKKTGEYLINGKYMISTSETI
IDINGTVMNYSGWSHRDDFLHGMGYSATKEILIVQILATDPTKALGVRYSFFVPKKTT
QKVNSVISHGSNKVGPHSTQLQWVTGPWLACSRTCDTGWHTRTVQCQDGNRKLAKGCL
LSQRPSAFKQCLLKKC*

```
BASE COUNT      726 a       788 c      845 g      643 t
ORIGIN
        1 ccggcgggca gcgcactatg cggctcgagt gggcgtcctt gttgctgcta ctgctgctgc
       61 tgagcgcgtc ctgcctgtcc ctggccgctg acagccccgc cgcggcacct gcccaggata
      121 aaaccaggca gcctcaggct gcagcagcgg ccgccgagcc ggaccagccg caggggagg
      181 aaacacggga gcgaggccat ttacaaccct tggccgggca gcgcaggagc ggcgggctgg
      241 tccataatat agaccaactc tactctggcg gtggcaaagt gggctacctt gtctacgcgg
      301 gcggccggag gttcctgctg gacctggaga gagatgacac agtgggtgc gctggtagca
      361 tcgttactgc aggaggaggg ctgagcgcat cctctggcca ccggggtcac tgtttctaca
      421 gaggcaccgt ggacggcagc cctcgatccc tagctgtctt tgacctctgc ggggtctcg
      481 atggcttctt tgcagtcaag catgcgcgct acactctaaa gccactcctg cgtgggtcct
      541 gggcagagta tgaacgaatt tatggggat gatcttcccg catcctgcat gtctacaacc
      601 gcgagggctt tagcttcgag gccctgccgc cacgcgccag ttgcgagact cctgcatccc
      661 catctgggcc ccaagagagc ccctcggtgc acagtagatc taggagacgc tcagcgctgg
      721 ccccgcagct gctggaccac tcagctttct cgccatctgg gaacgcggga cctcagactt
      781 ggtggaggcg taggcgccgt tccatctcca gggcccgcca ggtggagctc ctcttggtgg
      841 ctgactcgtc catggccagg atgtatgggc ggggcctgca gcattacctg ctgaccctgg
      901 cctccatcgc caacaggctg tacagtcatg caagcattga gaaccacatc cgcctggcgg
      961 tggtgaaggt ggtggtgctg acggacaagg acacgagtct ggaggtgagc aagaatgcgg
     1021 ccacgaccct caagaacttt tgcaaatggc agcaccaaca taaccagcta ggggatgatc
     1081 acgaagagca ctacgatgca gccatcctgt tcacccgaga ggatttatgt gggcatcatt
     1141 catgtgacac cctgggaatg gcagacgttg ggaccatatg ttctccggag cgcagctgtg
     1201 cagtgattga agatgatggc ctccatgcag ccttcactgt ggctcatgaa attgggcatc
     1261 tacttggcct ttctcatgac gattccaaat tctgtgaaga gaacttcggt actacagaag
     1321 acaagcgttt aatgtcttca atccttacca gcatcgatgc atccaagccc tggtccaaat
     1381 gcacgtcagc caccatcaca gaattcctgg atgatggtca tggtaattgt ttgctagacc
     1441 taccacggaa gcagattttg ggtcccgagg aactcccagg acagacctac gatgccaccc
     1501 agcagtgcaa cttgacattt gggcctgagt actcggtgtg ccctggcatg gatgtctgtg
     1561 cgcggctgtg gtgtgctgtg gtgcgccaag gccaaatggt gtgtctgacc aagaagctgc
     1621 cggctgtgga gggcactccc tgtgggaagg gaagagtctg ccttcaaggc aaatgtgtgg
     1681 acaaaactaa gaaaaaatat tactcgacat caagccatgg aaattggggg tcctggggcc
     1741 cctggggtca gtgttctcgc tcatgcgggg gaggagtgca gtttgcctac cgccattgta
     1801 ataaccctgc acctcgaaac agtggccgct actgcacagg gaagagggcc atataccgtt
     1861 cctgcagtgt tacaccctgc ccacccaatg gtaaatcttt tgccatgag cagtgtgaag
     1921 ccaaaaatgg ctatcagtct gatgcaaaag gagtcaaaac atttgtagaa tgggttccca
     1981 aatatgcagg tgtcctgccg gcagatgtgt gcaagcttac ctgcagagct aagggcacag
     2041 gctactatgt ggtcttttct ccaaaggtta cggatgggac tgaatgcagg ccgtacagca
     2101 actctgtgtg tgtccgagga cggtgtgtga gaactggatg tgacggcatt attggctcaa
     2161 agctacaata tgacaagtgt gggagtgtgcg gaggggataa ctccagttgt acaaagatta
     2221 tcggaacctt caataaaaaa agcaagggtt atactgacgt tgtgaggatc cctgaaggag
     2281 caacccacat aaaagtccga cagttcaaag ccaaagacca gactagattc cctgcctact
     2341 tagccctgaa gaagaaact ggcgagtacc ttatcaatgg caagtacatg atttccactt
     2401 cagagaccat catcgacatc aatggtaccg tcatgaacta cagtggatgg agccacagag
     2461 atgattttt acatgggatg ggctattcag ccacaaaaga aatcctgatc gtgcagatcc
     2521 ttgccacaga cccaactaaa gcgctaggcg tccgttacag cttttttgtt cccaagaaga
     2581 ccactcaaaa agtaaactct gtcatcagcc atggcagcaa caaggtggga ccacactcta
     2641 cacagctgca gtgggtgaca ggtccatggc tggcctgctc caggacctgt gacacaggct
     2701 ggcacactag gaccgtgcag tgccaggatg gaaacaggaa attagctaaa ggatgccttc
     2761 tctctcagag gccttctgca tttaagcaat gtctgctgaa gaaatgttag cctgtggttt
     2821 actctaatgc acaaaaaaac aacaggagga tcatcgcaga tacagctgtg gtgaagacaa
     2881 ggcctaccca agcacagaa agtcatgcct tcatgtcatt gtcaccacga gtcgaattat
     2941 gggcagaatc tgctctctgc gaccaaaagg tttactctac ttggtgaatg atggtaccgt
     3001 ga
```

Fig. 2A

```
FEATURES            Location/Qualifiers
     source         1..1520
                    /organism="Homo sapiens"
                    /db_xref="taxon:9606"
                    /chromosome="21"
BASE COUNT      416 a    372 c    376 g    352 t      4 others
ORIGIN
        1 ggacatttac ttggcctctc ccatgacgat tccaaattct gtgaagagac ctttggttcc
       61 acagaagata agcgcttaat gtcttccatc cttaccagca ttgatgcatc taagccctgg
      121 tccaaatgca cttcagccac catcacagaa ttcctggatg atggccatgg taactgtttg
      181 ctggacctac cacgaaagca gatcctgggc cccgaagaac tcccaggaca gacctacgat
      241 gccacccagc agtgcaacct gacattcggg cctgagtact ccgtgtgtcc cggcanggat
      301 gtctgtgctc gcctgtggtg tgctgtggta cgccagggcc agatggtctg tctgaccaag
      361 gagtgcagtt tgcctatcgt cactgtaata accctgctcc cagaaacaac ggacgctact
      421 gcacagggaa gagggccatc taccactcct gcagtctcat gccctgccca cccaatggta
      481 aatcatttcg tcatgaacag tgtgaggcca aaaatggcta tcagtctgat gcaaaaggag
      541 tcaaaacttt tgtggaatgg gttcccaaat atgcaggtgt cctgccagcg gatgtgtgca
      601 agctgacctg cagagccaag ggcactggct actatgtggt attttctcca aaggtgaccg
      661 atggcactga atgtaggccg tacagtaatt ccgtctgcgt ccgggggaag tgtgtgagaa
      721 ctggctgtga cggcatcatt ggctcaaagc tgcagtatga caagtgcgga gtatgtggag
      781 gagacaactc cagctgtaca aagattgttg gaacctttaa taagaaaagt aagggttaca
      841 ctgacgtggt gaggattcct gaaggggcaa cccacataaa agttcgacag ttcaaagcca
      901 aagaccagac tagattcact gcctatttag ccctgaaaaa gaaaaacggt gagtaccta
      961 tcaatggaaa gtacatgatc tccacttcag agactatcat tgacatcaat ggaacagtca
     1021 tgaactatag cggttggagc cacagggatg acttcctgca tggcatgggc tactctgcca
     1081 cgaaggaaat tctaatagtg cagattcttg caacagaccc cactaaacca ttagatgtcc
     1141 gttatagctt ttttgttccc aagaagtcca ctccaaaagt aaactctgtc actagtcatg
     1201 gcagcaataa agtgggatca cacacttcgc agccgcagtg ggtcacgggc ccatggctcg
     1261 cctgctctag gacctgtgac acaggttggc acaccagaac ggtgcagtgc caggatggaa
     1321 accggaagtt agcaaaagga tgtcctctct cccaaaggcc ttctgcgttt aagcaatgct
     1381 tgttgaagaa atgttagcct gtgggttatg atcttattgc acaaaagata ctggaggatt
     1441 cancacccgt gcaatcnngg tgaacaggaa ggctacctta acgcacagaa agtcatgctt
     1501 taatgacatt gtcaaccagg
```

Fig. 2B

```
          10         20         30         40
    |||||||||| |||||||||| |||||||||| ||||||||||
    GHLLGLSHDD SKFCEETFGS TEDKRLMSSI LTSIDASKPW  40
    SKCTSATITE FLDDGHGNCL LDLPRKQILG PEELPGQTYD  80
    ATQQCNLTFG PEYSVCPGXD VCARLWCAVV RQGQMVCLTK 120
    KLPAVEGTPC GKGRICLQGK CVDKTKKKYY STSSHGNWGS 160
    WGSWGQCSRS CGGGVQFAYR HCNNPAPRNN GRYCTGKRAI 200
         210        220        230        240
    |||||||||| |||||||||| |||||||||| ||||||||||
    YHSCSLMPCP PNGKSFRHEQ CEAKNGYQSD AKGVKTFVEW 240
    VPKYAGVLPA DVCKLTCRAK GTGYYVVFSP KVTDGTECRP 280
    YSNSVCVRGK CVRTGCDGII GSKLQYDKCG VCGGDNSSCT 320
    KTVGTFNKKS KGYTDVVRIP EGATHIKVRQ FKAKDQTRFT 360
    AYLALKKKNG EYLINGKYMI STSETIIDIN GIVMNYSGWS 400
         410        420        430        440
    |||||||||| |||||||||| |||||||||| ||||||||||
    HRDDFLHGMG YSATKEILIV QILATDPTKP LDVRYSFFVP 440
    KKSTPKVNSV TSHGSNKVGS HTSQPQWVTG PWLACSRTCD 480
    TGAHIRTVQC QDGNRKLAKG CPLSQRPSAF KQCLLKKC   518
```

Fig. 3A

| FEATURES | Location/Qualifiers |
|---|---|
| source | 1..2848 |
| | /organism="Homo sapiens" |
| | /db_xref="taxon:9606" |
| | /chromosome="5" |
| gene | 1..2848 |
| | /note=" A Disintegrin-like And Metalloprotease domain with ThromboSpondin type I motifs 6" |
| | /gene="ADAMTS6" |
| CDS | 22..2602 |
| | /gene="ADAMTS6" |
| | /note="zinc metalloprotease" |
| | /codon_start=1 |
| | /product=" A Disintegrin-like And Metalloprotease domain with ThromboSpondin type I motifs-6 (ADAM-TS6)" |
| | /translation="MEILWKTLTWILSLIMASSEFHSDHRLSYSSQEEFLTYLEHYQL TIPIRVDQNGAFLSFTVKNDKHSRRRRSMDPIDFQQAVSKLFFKLSAYGKHFHLNLTL NTDFVSKHFTVEYWGKDGPQWKHDFLDNCHYTGYLQDQRSTTKVALSNCVGLHGVIAT EDEEYFIEPLKNTTEDSKHFSYENGHPHVIYKKSALQQRHLYDHSHCGVSDFTRSGKP WWLNDTSTVSYSLPINNTHIHHRQKRSVSIERFVETLVVADKMMVGYHGRRDIEHYIL SVMNIVAKLYRDSSLGNVVNIIVARLIVLTEDQPNLEINHHADKSLDSFCKWQKSILS HQSDGNTIPENGIAHHDNAVLITRYDICTYKNKPCGTLGLASVAGMCEPERSCSINED IGLGSAFTIAHEIVHNFGMNHDGIGNSCGRKVMKQQNYGSSHYCEYQSFFLVCLQSRX HHQLFREVCRELWCLSKSNRCVTNSIPAAEGTLCQTGNIEKGWCYQGDCVPFGTWPQS IDGGWGPWSLWGECSRTCGGGVSSSLRHCDSPAPSGGGKYCLGERKRYRSCNTDPCPL GSRDFREKQCADFDNMPFRGKYYNWKPYTGGGVKPCALNCLAEGYNFYTERAPAVIDG TQCNADSLDICINGECKHVGCDNILGSDAREDRCRVCGGGGSTCDAIEGFFNDSLPRG |

Fig. 3B

```
GYMEVVQIPRGSVHIEVREVAMSKNYIALKSEGDDYYINGAWTIDWPRKFDVAGTAFH
YKRPTDEPESLEALGPTSENLIVMVLLQEQNLGIRYKFNVPITRTGSGDNEVGFIWNH
QPWSECSATCAGGKMPTRQPTQRARWRTKHILSYALCLLKKLIGNISCRFASSCNLAK
ETLL*
```

BASE COUNT    837 a    551 c    664 g    794 t    2 others
ORIGIN

```
   1 aatcatccag ttttctaaat tatggaaatt ttgtggaaga cgttgacctg gattttgagc
  61 ctcatcatgg cttcatcgga atttcatagt gaccacaggc tttcatacag ttctcaagag
 121 gaattcctga cttatcttga acactaccag ctaactattc caataagggt tgatcaaaat
 181 ggagcatttc tcagctttac tgtgaaaaat gataaacact caaggagaag acggagtatg
 241 gaccctattg atccacagca ggcagtatct aagttatttt ttaaactttc agcctatggc
 301 aagcactttc atctaaactt gactctcaac acagattttg tgtccaaaca ttttacagta
 361 gaatattggg ggaaagatgg accccagtgg aaacatgatt ttttagacaa ctgtcattac
 421 acaggatatt tgcaagatca acgtagtaca actaaagtgg ctttaagcaa ctgtgttggg
 481 ttgcatggtg ttattgctac agaagatgaa gagtatttta tcgaacccttt aaagaatacc
 541 acagaggatt ccaagcattt tagttatgaa atggccacc ctcatgttat ttacaaaaag
 601 tctgcccttc aacaacgaca tctgtatgat cactctcatt gtggggtttc ggatttcaca
 661 agaagtggca aaccttggtg gctgaatgac acatccactg tttcttattc actaccaatt
 721 aacaacacac atatccacca cagacagaag agatcagtga gcattgaacg gtttgtggag
 781 acattggtag tggcagacaa aatgatggtg ggctaccatg gccgcaaaga cattgaacat
 841 tacattttga gtgtgatgaa tattgttgcc aaactttacc gtgattccag cctaggaaac
 901 gttgtgaata ttatagtggc ccgcttaatt gttctcacag aagatcagcc aaacttggag
 961 ataaaccacc atgcagacaa gtccctcgat agcttctgta atggcagaa atccattctc
1021 tcccaccaaa gtgatggaaa caccattcca gaaatggga ttgcccacca cgataatgca
1081 gttcttatta ctagatatga tatctgcact tataaaaata gccctgtgg aacactgggc
1141 ttggcctctg tggctggaat gtgtgagcct gaaaggagct gcagcattaa tgaagacatt
1201 ggcctgggtt cagcttttac cattgcacat gagattgttc acaatttggg tatgaaccat
1261 gatggaattg gaaattcttg tggacgaaag gtcatgaagc agcaaaatta tggcagctca
1321 cattactgcg aataccaatc ctttttcctg gtctgcttgc agtcgagant acatcaccag
1381 cttttagag aagtgtgtag agagctctgg tgtctcagca aaagcaaccg ctgtgtcacc
1441 aacagtattc cagcagctga ggggacactg tgtcaaactg gaatattga aaaagggtgg
1501 tgttatcagg gagattgtgt tccttttggc acttggcccc agagcataga tgggggctgg
1561 ggtccctggt cactatgggg agagtgcagc aggacctgcg ggggaggcgt ntcctcatcc
1621 ctaagacact gtgacagtcc agcaccttca ggaggtggaa aatattgcct tggggaaagg
1681 aaacggtatc gctcctgtaa cacagatcca tgcccttggg gttcccgaga ttttcgagag
1741 aaacagtgtg cagactttga caatatgcct ttccgaggaa agtattataa ctggaaaccc
1801 tatactggag gtggggtaaa accttgtgca ttaaactgct tggctgaagg ttataatttc
1861 tacactgaac gtgctcctgc ggtgatcgat gggacccagt gcaatgcgga ttcactggat
1921 atctgcatca atggagaatg caagcacgta ggctgtgata atatttgg atctgatgct
1981 agggaagata gatgtcgagt ctgtggaggg ggcggaagca catgtgatgc cattgaaggg
2041 ttcttcaatg attcactgcc caggggaggc tacatggaag tggtgcagat accaagaggc
2101 tctgttcaca ttgaagttag agaagttgcc atgtcaaaga actatattgc tttaaaatct
2161 gaaggagatg attactatat taatggtgcc tggactattg actggcctag gaaatttgat
2221 gttgctggga cagcttttca ttacaagaga ccaactgatg aaccagaatc cttggaagct
2281 ctaggtccta cctcagaaaa tctcatcgtc atggttctgc ttcaagaaca gaatttggga
2341 attaggtata agttcaatgt tcccatcact cgaactggca gtggagataa tgaagttggc
2401 tttacatgga atcatcagcc ttggtcagaa tgctcagcta cttgtgctgg aggtaagatg
2461 cccactaggc agcccaccca gagggcaaga tggagaacaa aacacattct gagctatgct
2521 ttgtgtttgt taaaaagct aattggaaac atttcttgca ggtttgcttc aagctgtaat
2581 ttagcaaaag aaactttgct ttaattatat tatattccat ttgttttcaa cctcatgtaa
2641 tttgtgcaga tttgttggta aaatacatct tggcacaatg agtgtctctg ctggtgcttc
2701 tcccaagact atcttgaagg tgggctgttt gcctttcgtg aacacattct tggtaaagaa
2761 catcaaaagt tttaaaaaag aaaatgagca agaatcagac atcacagatg caacttcttg
2821 taatgggaga tgagaatgta cggctgtg
```

Fig. 4A

```
FEATURES          Location/Qualifiers
     source       1..3218
                  /organism="Homo sapiens"
                  /db_xref="taxon:9606"
                  /chromosome="15"
     gene         1..3218
                  /gene="ADAMTS7"
     CDS          13..3003
                  /gene="ADAMTS7"
                  /note="ZINC METALLOPROTEASE"
                  /codon_start=1
                  /product=" A Disintegrin-like And Metalloprotease domain
                  with ThromboSpondin type I motifs-7 (ADAM-TS7)"
                  /translation="MPGGPSPRSPAPLLRPLLLLLCALAPGAPGPAPGRATEGRAALD
                  IVHPVRVDAGGSFLSYELWPRALRKRDVSVRRDAPAFYELQYRGRELRFNLTANQHLL
                  APGFVSETRRRGGLGRAHIRAHTPACHLLGEVQDPELEGGLAAISACDGLKGVFQLSN
                  EDYFIEPLDSAPARPGHAQPHVVYKRQAPERLAQRGDSSAPSTCGVQVYPELESRRER
                  WEQRQQWRRPRLRRLHQRSVSKEKWVETLVVADAKMVEYHGQPQVESYVLTIMNMVAG
                  LFHDPSIGNPIHITIVRLVLLEDEEEDLKITHHADNTLKSFCKWQKSINMKGDAHPLH
                  HDTAILLTRKDLCAAMNRPCETLGLSHVAGMCQPHRSCSINEDTGLPLAFTVAHELGH
                  SFGIQHDGSGNDCEPVGKRPFIMSPQLLYDAAPLTWSRCSRQYITRFLDRGWGLCLDD
                  PPAKDIIDFPSVPPGVLYDVSHQCRLQYGAYSAFCEDMDNVCHTLWCSVGTTCHSKLD
                  AAVDGTRCGENKWCLSGECVPVGFRPEAVDGGWSGWSAWSICSRSCGMGVQSAERQCT
                  QPTPKYKGRYCVGERKRFRLCNLQACPAGRPSFRHVQCSHFDAMLYKGQLHTWVPVVN
                  DVNPCELHCRPANEYFAKKLRDAVVDGTPCYQVRASRDLCINGICKNVGCDFEIDSGA
                  MEDRCGVCHGNGSTCHTVSGTFEEAEGLGYVDVGLIPAGAREIRIQEVAEAANFLALR
                  SEDPEKYFLNGGWTIQWNGDYQVAGTTFTYARRGNWENLTSPGPTKEPVWIQVPASRG
```

Fig. 4B

```
PGGGSRGGVPRPSTLHGRSRPGGVSFGSVTEPGSEPGPPAAASTSVSPSLKWPNLVAA
VHRGGWGQAPLGLGGWRRHLVLMGPRLPTQLLFQESNPGVHYEYTIHREAGGHDEVPP
PVFSWHYGPWTKCTVTCGRGEKWGRHSPTCRGLVSGQGHWLQLPAHCWATTGLEVCFS
EPQFSICEMRLAIALCPRPAGRVHG"
```

BASE COUNT      584 a    1041 c    1003 g    590 t
ORIGIN
```
   1 ccggttcctg ccatgcccgg cggccccagt ccccgcagcc ccgcgccttt gctgcgcccc
  61 ctcctcctgc tcctctgcgc tctggctccc ggcgcccccg gacccgcacc aggacgtgca
 121 accgagggcc gggcggcact ggacatcgtg cacccggttc gagtcgacgc gggggggctcc
 181 ttcctgtcct acgagctgtg gccccgcgca ctgcgcaagc gggatgtatc tgtgcgccga
 241 gacgcgcccg ccttctacga gctacaatac cgcgggcgcg agctgcgctt caacctgacc
 301 gccaatcagc acctgctggc gcccggcttt gtgagcgaga cgcggcggcg cggcggcctg
 361 ggccgcgcgc acatccgggc ccacaccccg gcctgccacc tgcttggcga ggtgcaggac
 421 cctgagctcg agggtggcct ggcggccatc agcgcctgcg acggcctgaa aggtgtgttc
 481 cagctctcca acgaggacta cttcattgag ccctggaca gtgccccggc ccggcctggc
 541 cacgcccagc ccatgtggt gtacaagcgt caggccccgg agaggctggc acagcgggt
 601 gattccagtg ctccaagcac ctgtggagtg caagtgtacc cagagctgga gtctcgacgg
 661 gagcgttggg agcagcggca gcagtggcgg cggccatggc tgaggcgtct acaccagcgg
 721 tcggtcagca aagagaagtg ggtggagacc ctggtagtag ctgatgccaa aatggtggag
 781 taccacggac agccgcaggt tgagagctat gtgctgacca tcatgaacat ggtggctggc
 841 ctgtttcatg accccagcat tgggaacccc atccacatca ccattgtgcg cctggtcctg
 901 ctggaagatg aggaggagga cctaaagatc acgcaccatg cagacaacac cctgaagagc
 961 ttctgcaagt ggcagaaaag catcaacatg aagggggatg cccatcccct gcaccatgac
1021 actgccatcc tgctcaccag aaaggacctg tgtgcagcca tgaaccggcc ctgtgagacc
1081 ctgggactgt cccatgtggc gggcatgtgc cagccgcacc gcagctgcag catcaacgag
1141 gacacgggcc tgccgctggc cttcactgta gcccacgagc tcgggcacag ttttggcatt
1201 cagcatgacg gaagcggcaa tgactgtgag cccgttggga aacgaccttt catcatgtct
1261 ccacagctcc tgtacgacgc cgctcccctc acctggtccc gctgcagccg ccagtatatc
1321 accaggttcc ttgaccgtgg gtggggcctg tgcctggacg accctcctgc caaggacatt
1381 atcgacttcc cctcggtgcc acctggcgtc ctctatgatg taagccacca gtgccgcctc
1441 cagtacgggg cctactctgc cttctgcgag gacatggata atgtctgcca cacactctgg
1501 tgctctgtgg ggaccacctg tcactccaag ctggatgcag ctgtggacgg caccccggtgt
1561 ggggagaata agtggtgtct cagtggggag tgcgtacccg tgggcttccg gcccgaggcc
1621 gtggatggtg gctggtctgg ctggagcgcc tggtccatct gctcacggag ctgtggcatg
1681 ggcgtacaga gcgccgagcg gcagtgcacg cagcctacgc caaatacaa aggcagatac
1741 tgtgtgggtg agcgcaagcg cttccgcctc tgcaacctgc aggcctgcc tgctggccgc
1801 ccctccttcc gccacgtcca gtgcagccac tttgacgcta tgctctacaa gggccagctg
1861 cacacatggg tgcccgtggt caatgacgtg aacccctgcg agctgcactg ccggcccgcg
1921 aatgagtact tgccaagaa gctgcgggac gccgtggtcg atggcacccc ctgctaccag
1981 gtccgagcca gccgggacct ctgcatcaac ggcatctgta agaacgtggg ctgtgacttc
2041 gagattgact ccggtgctat ggaggaccgc tgtggtgtgt gccacggcaa cggctccacc
2101 tgccacaccg tgagcgggac cttcgaggag gccgagggtc tgggtatgt ggatgtgggg
2161 ctgatcccag cgggcgcacg cgagatccgc atccaagagg ttgccgaggc tgccaacttc
2221 ctggcactgc ggagcgagga cccggagaag tacttcctca atggtggctg gaccatccag
2281 tggaacgggg actaccaggt ggcagggacc accttcacat acgcacgcag gggcaactgg
2341 gagaacctca cgtccccggg tcccaccaag gagcctgtct ggatccaggt gcctgcctcc
2401 cgtggcccag gcggggggag cagaggcgga gtccccaggc ccagcaccct ccatggcagg
2461 tctcgtcctg gaggagtgag ccctggttca gtcacagagc ctggctctga gccaggccct
2521 cctgctgcgg cctctacctc agtttcccca tctttaaaat ggcccaatct tgtagctgca
2581 gttcacagag gtggctgggg tcaagctcct ttaggactgg gtggatggag aagacccttt
2641 gtgctcatgg gccccgcct gcccacccag ctgctgttcc aggagagcaa ccctggggtg
2701 cactacgagt acaccatcca cagggaggca ggtggccacg acgaggtccc gccgccgtg
2761 ttctcctggc attatgggcc ctggaccaag tgcacagtca cctgcggcag aggtgagaag
2821 tggggcaggc acagccccac ctgcaggggc ttagtgtctg acagggaca ctggcttcag
2881 ctcccagctc actgctgggc caccacgggt ttggaagttt gcttctctga gcctcagttc
2941 tccatctgtg agatgaggct agcgattgcc ctgtgtccca ggcccgctgg gagggtacat
3001 ggatgaggca ggtgggtgct ggctcgcggc gcatgttcag tgtgctccag ctcttggcgt
3061 tctccctcca ggggacacag ctcccctcg atagaccagt ccagtggccc ctcaccacac
3121 tgacttatttt ccctaaacta tttataaaaa gtagggcaat ttcattaact ctgactctta
3181 cctgcccggg cggccgctcg agccgagtaa tcactagt
```

Fig. 5A$_1$

```
          10        20        30        40        50        60        70
     ....|....|....|....|....|....|....|....|....|....|....|....|....|....|
     tagggcgactgcacgggacgccgcggaggacgcgcgctcgcggcccggggcgccacgtgctcgagttctg   70
     ctaggttggctggcgcaggaggagcgggctgcgcgatccagaggggccgccagggaccgccgcgccacgt  140
     gccgctagccgagtcggcctccccatccgattgatcattttcctggacagagcgacccggccgcctcgg  210
     gccaccagcacctgccgcgcgcggcgatcttcttccctctcccgcgctccgcagcactctgccccATG    280
     CTCCGCGACCCCACCACCACCGGGTGGCCGCCCCTCCTGCTGCTGCTATTGCAGCTGCCGCCGCCGCCAC  350
          360       370       380       390       400       410       420
     ....|....|....|....|....|....|....|....|....|....|....|....|....|....|
     TCGTCTGCGGAGCCCCGGCGGGGCCGGGAACCGGGGCGCAGGCCTCGGAGCTAGTGGTGCCCACGCGGTT  420
     GCCCGGCAGCGCGAGCGAGCTCGCCTTCCACCTGTCCGCCTTCGGCCAGGGCTTCGTGCTGCGCCTGGCG  490
     CCTGACGCCAGCTTCCTGGCGCCCGGAATTCAAGATCGAGCGCCTCGGGGCTCGAGCGCGGCGGCCGGGG  560
     GCGAGCCGGGACTGCGTGGCTGCTTCTTCTCTGGCACAGTGAATGGAGAACGGGAGTCGCTGGCGGCGAT  630
     GAGCTGTGTCGCGGGCTGGAGCGGCTCGTTCTTGCTGGCAGGCGAGGAGTTCACCATCCAGCCACAGGGC  700
          710       720       730       740       750       760       770
     ....|....|....|....|....|....|....|....|....|....|....|....|....|....|
     GCTGGGGACTCCCTGGACCAGCCTCATCGCCTGCAGCGCTGGGGGCCGGGACAGCGCCGCGAAGACCCCG  770
     GGCTCGCTGCCGCCGAAGTTTTCCCCCTCCCTCAAGGACTGGAGTGGGAGGTGGAGATGGGTAATGGGCA  840
     GGGACAGGAGAGAAGTGACAACGAAGAGGACAGGAAGCAGGACAAGGAGGGGTTGCTCAAAGAGACAGAA  910
     GACTCCCGCAAAGTGCCACCACCCTTCGGATCCAAAACTAGAAGCAAGAGGTTTGTGTCCGAGGCTCGCT  980
     TCGTGGAAACACTTCTGGTTGGCTGATGCGTCCATGGCTGCCTTCTATGGGACCGACCTGCAGAACCACAT 1050
          1060      1070      1080      1090      1100      1110      1120
     ....|....|....|....|....|....|....|....|....|....|....|....|....|....|
     CCTCACGGTGATGTCAATGGCAGCCCGAATCTACAAGCACCCGAGCATCAGGAACTCCGTCAACCTTGTG 1120
     GTGGTGAAAGTGCTAATAGTGGAAAAAGAAAGATGGGGCCCGGAAGTGTCCGACAACGGGGGCTCACAC  1190
     TGCGCAACTTCTGCAGCTGGCAACGGCGTTTCAACAAGCCCAGTGACCGCCACCCGGAGCACTATGACAC 1260
     TGCCATCTTGTTCACCAGACAGAACTTCTGTGGGAAGGGAGAGCAGTGTGACACCCTGGGATGGCAGAC  1330
     GTTGGCACCATCTGTGACCCCGACAAGAGCTGCTCAGTGATCAAGGATGAGGGACTGCAGGCAGCCTACA 1400
          1410      1420      1430      1440      1450      1460      1470
     ....|....|....|....|....|....|....|....|....|....|....|....|....|....|
     CCCTGGCCCATGAGCTAGGGCACGTTCTCAGCATGCCCCATGATGATTCTAAGCCCTGTGTGAGATTGTT 1470
     TGGGCCCATGGCAAGTACCACATGATGGCGCCATTCTTCATCCACGTGAACAAGACGCTGCCCTGGTCT  1540
     CCCTGCAGTGCTGTCTACCTCACAGAGCTCCTGGATGATGGTCACGGAGATTGTCTTCTGGATGCCCCA  1610
     CCTCGGTTCTGCCCCTCCCCACAGGCCTCCGGGCCACAGCACCCTCTACGAGCTGGACCAGCAGTGCAA  1680
     GCAGATCTTTGGGCCTGATTTCCGACACTGCCCCAACACCTCTGTGGAGGACATCTGTGTCCAGCTCTGT 1750
```

Fig. 5A$_2$

```
         1760      1770      1780      1790      1800      1810      1820
     ....|....|....|....|....|....|....|....|....|....|....|....|....|....|
GCCCGTCATCGGGATAGTGATGAGCCCATTTGCCACACAAAGAATGGTAGCCTGCTCTGGGCTGATGGTA 1820
CACCCTGTGGCCCTGGGCACCTGTGCCTGGATGGTAGCTGTGTACTCAAGGAGGATGTGGAGAATCCCAA 1890
GGCTGTGGTAGATGGAGACTGGGGTCCCTGGAGACCCTGGGGACAATGTTCTCGCACCTGTGGTGGAGGG 1960
ATACAATTCTCGAACCGTGAATGTGATAATCCAATGCCTCAGAATGGAGGAAGATTTTGCCTGGGTGAAA 2030
GAGTCAAGTACCAATCATGCAACACAGAGGAATGTCCACCAAACGGAAAAAGCTTCCGGGAGCAGCAGTG 2100
         2110      2120      2130      2140      2150      2160      2170
     ....|....|....|....|....|....|....|....|....|....|....|....|....|....|
TGAGAAATATAATGCCTACAACCACACTGACCTGGATGGGAATTTCCTGCAGTGGGTCCCCAAGTATTCA 2170
GGAGTGTCCCCCCGAGACCGATGCAAGCTGTTTTGCAGAGCCCGTGGGAGGAGTGAGTTCAAAGTGTTTG 2240
AAGCTAAGGTGATCGATGGCACTCTGTGTGGACCGGATACTCTGTCCATCTGCGTCCGGGGCAATGTGT 2310
TAAGGCTGGCTGTGACCATGTGGTGAACTCACCTAAGAAGCTGGACAAATGTGGGGTGTGTGGGGCAAA 2380
GGCACTGCCTGTAGGAAGATCTCCGGTTCTTTCACCCCCTTCAGTTATGGCTACAATGACATTGTCACCA 2450
         2460      2470      2480      2490      2500      2510      2520
     ....|....|....|....|....|....|....|....|....|....|....|....|....|....|
TCCCAGCTGGTGCCACAAACATTGATGTGAAACAGCGGAGTCACCCAGGGGTCAGGAACGACGGCAGCTA 2520
CCTGGCGCTGAAGACAGCCAATGGGCAGTACCTGCTCAATGGTAACCTGGCCATCTCTGCCATAGAGCAA 2590
GACATCTTGGTGAAGGGGACCATCCTGAAGTACAGTGGCTCCATGGCTACCCTGGAGCGGCTGCAGAGCT 2660
TCCAGGCCCTGCCTGAGCCTCTTACAGTACAGCTCCTGACTGTGTCTGGTGAGGTCTTCCCTCCAAAAGT 2730
CAGATATACCTTCTTTGTCCCCAATGACATGGACTTCAGCGTGCAGAATAGCAAGGAAAGAGCAACCACC 2800
         2810      2820      2830      2840      2850      2860      2870
     ....|....|....|....|....|....|....|....|....|....|....|....|....|....|
AACATCATTCAGTCACTGCCCTCTGCGGAGTGGGTTCTGGGAGACTGGTCTGAATGTCCGAGCACGTGCA 2870
GAGGTAGCTGGCAGCGGCGGACTGTGGAATGCAGGGACCCCTCAGGTCAGGCCTCTGACACCTGTGATGA 2940
GGCTCTGAAACCTGAGGATGCCAAGCCCTGTGGAAGCCAGCCGTGTCCCCTCtgatccccttggtggaaa 3010
tctcttaggcttatggatttgggctactggtgtaacagacaaaggtcccctccaaggtgatactacatat 3080
caagatggcacggcccttcaggccttctattactacaacccttgggtactacctaattcataaggaag 3150
         3160      3170      3180      3190      3200      3210      3220
     ....|....|....|....|....|....|....|....|....|....|....|....|....|....|
agagaagagggtataagggtaacagattgtaaagttgactgtctggtggactggaccttgcttatgacca 3220
agaagtcgggataggttaaaaggtagaagtgcacttattgatccaaatgggagatttcagagccagtctc 3290
tttgcaaaggactagcaaagctaaatgaaaagaagaattttttttttctatttggtttccccaataatc 3360
aatctacctcacagcggggaaaaatcagtatacaagaggtataaggccaggtgttggcagtgaacgccaa 3430
agcaagctccataggtatctccaagctatcttcagaaatgtccgtggctgttttcagtattaaaatctgt 3500
         3510      3520      3530      3540      3550      3560      3570
     ....|....|....|....|....|....|....|....|....|....|....|....|....|....|
tgtctaaaagggcagcagtgtccatcacagggttatagaaagccacttttctcaggctgccacctgctgg 3570
ggcggacccatttcaagtatttatgcaaatatgtctccgaactaaagtgtgtcttacaccaaaagngc 3638
```

Fig. 5B

*MOUSE ADAM TS8*

```
         10        20        30        40
   |....|....|....|....|....|....|....|....|
MLRDPTTTGWPPLLLLLLQLPPPPLVCGAPAGPGTGAQAS    40
ELVVPTRLPGSASELAFHLSAFGQGFVLRLAPDASFLAPE   80
FKIERLGGSSAAAGGEPGLRGCFFSGTVNGERESLAAMSC  120
VAGWSGSFLLAGEEFTIQPQGAGDSLDQPHRLQRWGPGQR  160
REDPGLAAAEVFPLPQGLEWEVEMGNGQGQERSLNEEDRK  200

210       220       230       240
   |....|....|....|....|....|....|....|....|
QDKEGLLKEIEDSRKVPPPFGSKTRSKR FVSEARFVEILL  240
VADASMAAFYGIDLQNHILITVMSMAARIYKHPSIRNSVNL  280
VVVKVLIVEKERWGPEVSDNGGLITLRNFCSWQRRFNKPSD  320
RHPEHYDTAILFTRQNFCGKGEQCDILGMADVGTICDPDK  360
SCSVIKDEGLQAAYTLAHELGHVLSMPHDDSKPCVRLFGP  400

410       420       430       440
   |....|....|....|....|....|....|....|....|
MGKYHMMAPFFIHVNKSLPWSPCSAVYLTELLDDGHGDCL  440
LDAPTSVLPLPTGLPGHSTLYELDQQCKQIFGPDFRHCPN  480
TSVEDICVQLCARHRDSDEPICHTKNSSLLWADGTPCGPG  520
HLCLDGSCVLKEDVENPKAVVDGDWGPWRPWGQCSRTCGG  560
GIQFSNRECDNPMPQNGGRFCLGERVKYQSCNTEECPPNG  600

610       620       630       640
   |....|....|....|....|....|....|....|....|
KSFREQQCEKYNAYNHHDLDGNFLQWVPKYSGVSPRDRCK  640
LFCRARGRSEFKVFEAKVIDGTLCGPDTLSICVRGQCVKA  680
GCDHVVNSPKKLDKCGVCGGKGTACRKLSGSFTPFSYGYN  720
DIVTIPAGATNIDVKQRSHPGVRNDGSYLALKTANGQYLL  760
NGNLATSATEQDILVKGTTLKYSGSMATLERLQSFQALPE  800

810       820       830       840
   |....|....|....|....|....|....|....|....|
PLTVQLLITVSGEVFPPKVRYTFFVPNDMDFSVQNSKERAT  840
TNTIQSLPSAEWVLGDWSECPSTCRGSWQRRTVECRDPSG  880
QASDTCDEALKPEDAKPCGSQPCPL  905
```

Annotations:
- N-terminus of mature protease: FVSEAR.....
- 5 *Cys*
- 3 *Cys*
- 8 *Cys*
- 10 *Cys*
- Spacer ~146 aa

Fig. 6A

CATALYTIC DOMAIN, ADAM TS-8 (HUMAN)

```
         10        20        30        40
         |         |         |         |
CGAGGGCAGAAGGCGCTAGCGAGCCGCCACCGCCCCTGGG  40
GGCCACGAGTAGGACCAAGCGGTTTGTGTCTGAGGCGCGC  80
TTCGTGGAGACGCTGCTGGTGGCCGATGCGTCCATGGCTG 120
CCTTCTACGGGGCCGACCTGCAGAACCACATCCTGACGTT 160
AATGTCTGTGGCAGCCCGAATCTACAAGCACCCCAGCATC 200
        210       220       230       240
         |         |         |         |
AAGAATTCCATCAACCTGATGGTGGTAAAAGTGCTGATCG 240
TAGAAGATGAAAAATGGGGCCCAGAGGTGTCCGACAATGG 280
GGGGCTTACACTGCGTAACTTCTGCAACTGGCAGCGGCGT 320
TTCAACCAGCCCAGCGACCGCCACCCAGAGCACTACGACA 360
CGGCCATCCTGCTCACCAGACAGAACTTCTGTGGGCAGGA 400
        410       420       430       440
         |         |         |         |
GGGGCTGTGTGACACCCTGGGTGTGGCAGACATCGGGACC 440
ATTTGTGACCCCAACAAAAGCTGCTCCGTGATCGAGGATG 480
AGGGGCTCCAGGCGGCCCACACCCTGGCCCATGAACTAGG 520
GCACGTCCTCAGCATGCCCCACGACGACTCCAAGCCCTGC 560
ACACGGCTCTTCGGGCCCATGGGCAAGCACCACGTGATGG 600
        610       620       630       640
         |         |         |         |
CACCGCTGTTCGTCCACCTGAACCAGACGCTGCCCTGGTC 640
CCCCTGCAGCGCCATGTTCTCAGGCTGCCACCTGCAGGGG 680
TGGATCCATTTCAAGTATTTATGCAAATGTGTCTCTGAAC 720
TAAAGTGTGATCTTATGCC 739
```

Fig. 6B

CATALYTIC DOMAIN
13/54

```
         10        20↗ Mature protease  FVSEAR.---
                      30        40
    ┬┬┬┬┬┬┬┬┬┬┬┬┬┬┬┬┬┬|┬┬┬┬┬┬┬┬┬┬┬┬┬┬┬┬┬
·RAEGASEPPPPLGATSRIKRFVSEARFVEILLVADASMAA  40
FYGADLQNHILILMSVAARIYKHPSIKNSINLMVVKVLIV   80
EDEKWGPEVSINGGLTLRNFCNWQRRFNQPSDRHPEHYDT  120
AILLITRQNFCGQEGLCDILGVADIGTICDPNKSCSVIEDE 160
GLQAAHTLAHELGHVLSMPHDDSKPCTRLFGPMGKHHVMA  200

210       220       230       240
    ┬┬┬┬┬┬┬┬┬┬┬┬┬┬┬┬┬┬┬┬┬┬┬┬┬┬┬┬┬┬┬┬┬┬┬┬┬
PLFVHLNQTLPWSPCSAMFSGCHLQGWIHFKYLCKCVSEL  240
KCDLM 245
```

Fig. 7A₁ human ADAM-TS9

```
          10        20        30        40        50        60        70
GAAGCACCATGCAGTTTGTATCCTGGGCCACACTGCTAACGCTCCTGGTGCGGGACCTGGCCGAGATGGG  70
GAGCCCAGACGCCGCGGCGGCCGTGCGCAAGGACAGGCTGCACCCGAGGCAAGTGAAATTATTAGAGACC 140
CTGAGCGAATACGAAATCGTGTCTCCCATCCGAGTGAACGCTCTCGGAGAACCCTTTCCCACGAACGTCC 210
ACTTCAAAAGAACGCGACGGAGCATTAACTCTGCCACTGACCCCTGGCCTGCCTTCGCCTCCTCCTCTTC 280
CTCCTCTACCTCCTCCCAGGCGCATTACCGCCTCTCTGCCTTCGGCCAGCAGTTTCTATTTAATCTCACC 350
          360       370       380       390       400       410       420
GCCAATGCCGGATTTATCGCTCCACTGTTCACTGTCACCCTCCTTGGGACGCCCGGGGTGAATCAGACCA 420
AGTTTTATTCCGAAGAGGAAGCGGAACTAAAGCACTGTTTCTACAAAAGGCTATGTCAATACCAACTCCG 490
AGCACACGGCCGTCATCAGCCTCTGCTCAGGAATGAACACAAAAATAGGCACAGTAAAGACAAGAAGAAA 560
ACCAGAGCAAGAAAATGGGGAGAAAGGATTAACCTGGCTGGTGACGTAGCAGCATTAAACAGCGGCTTAG 630
CAACAGAGGCATTTTCTGCTTATGGTAATAAGACGGACAACACAAGAGAAAAGAGGACCCACAGAAGGAC 700
          710       720       730       740       750       760       770
AAAACGTTTTTTATCCTATCCACGGTTTGTAGAAGTCTTGGTGGTGGCAGACAACAGAATGGTTTCATAC 770
CATGGAGAAAACCTTCAACACTATATTTTAACTTTAATGTCAATTGTAGCCTCTATCTATAAAGACCCAA 840
GTATTGGAAATTTAATTAATATTGTTATTGTGAACTTAATTGTGATTCATAATGAACAGGATGGCCTTC 910
CATATCTTTTAATGCTCAGACAACATTAAAAAACTTTTGCCAGTGGCAGCATTCGAACAGTCCAGGTGGA 980
ATCCATCATGATACTGCTGTTCTCTTAACAAGACAGGATATCTGCAGAGCTCACGACAAATGTGATACCT 1050
          1060      1070      1080      1090      1100      1110      1120
TAGGCCTGGCTGAACTGGGAACCATTTGTGATCCCTATAGAAGCTGTTCTATTAGTGAAGATAGTGGATT 1120
GAGTACAGCTTTTACGATCGCCCATGAGCTGGGCCATGTGTTTAACATGCCTCATGATGACAACAACAAA 1190
TGTAAAGAAGAAGGAGTTAAGAGTCCCCAGCATGTCATGGCTCCAACACTGAACTTCTACACCAACCCCT 1260
GGATGTGGTCAAAGTGTAGTCGAAAATATATCACTGAGTTTTTAGACACTGGTTATGGCGAGTGTTTGCT 1330
TAACGAACCTGAATCCAGACCCTACCCTTTGCCTGTCCAACTGCCAGGCATCCTTTACAACGTGAATAAA 1400
          1410      1420      1430      1440      1450      1460      1470
CAATGNGAATTGATTTTTGGACCAGGTTCTCAGGTGTGCCCATATATGATGCAGTGCAGACGGCTCTGGT 1470
GCAATAACGTCAATGGAGTACACAAAGGCTGCCCGACTCAGCACACACCCTGGGCCGATGGACGGAGTG 1540
CGAGCCTGGAAAGCACTGCAAGNATGGATTTTGTGTTCCCAAAGAAATGGATGTCCCCGTGACAGATGGA 1610
TCCTGCGGAAGTTGGAGTCCCTTTGGAACCTGCTCCAGAACATGTGGAGGGGCATCAAAACAGCCATTC 1680
GAGAGTGCAACAGACCAGAACCAAAAAATGGTGGAAAATACTGTGTAGGACGTAGAATGAAATTTAAGTC 1750
```

Fig. 7A$_2$

```
          1760      1770      1780      1790      1800      1810      1820
         |    |    |    |    |    |    |    |    |    |    |    |    |    |
CTGCAACACGGAGCCATGTCTCAAGCAGAAGCGAGACTTCCGAGATGAACAGTGTGCTCACTTTGACGGG  1820
AAGCATTTTAACATCAACGGTCTGCTTCCCAATGTGCGCTGGGTCCCTAAATACAGTGGAATTCTGATGA  1890
AGGACCGGTGCAAGTTGTTCTGCAGAGTGGCAGGGAACACAGCCTACTATCAGCTTCGAGACAGAGTGAT  1960
AGATGGAACTCCTTGTGGCCAGGACACAAATGATATCTGTGTCCAGGGCCTTTGCCGGCAAGCTGGATGC  2030
GATCATGTTTTAAACTCAAAAGCCCGGAGAGATAAATGCGGGGTTTGTGGTGGCGATAATTCTTCATGCA  2100
          2110      2120      2130      2140      2150      2160      2170
         |    |    |    |    |    |    |    |    |    |    |    |    |    |
AAACAGTGGCAGGAACATTTAATACAGTACATTATGGTTACAATACTGTGGTCCGAATTCCAGCTGGTGC  2170
TACCAATATTGATGTGCGGCAGCACAGTTTCTCAGGGGAAACAGACGATGACAACTACTTAGCTTTATCA  2240
AGCAGTAAAGGTGAATTCTTGCTAAATGGAAACTTTGTTGTCACAATGGCCAAAAGGGAAATTCGCATTG  2310
GGAATGCTGTGGTAGAGTACAGTGGGTCCGAGACTGCCGTAGAAAGAATTAACTCAACAGATCGCATTGA  2380
GCAAGAACTTTTGCTTCAGGTTTTGTCGGTGGGAAAGTTGTACAACCCCGATGTACGCTATTCTTTCAAT  2450
          2460      2470      2480      2490      2500      2510      2520
         |    |    |    |    |    |    |    |    |    |    |    |    |    |
ATTCCAATTGAAGATAAACCTCAGCAGTTTTACTGGAACAGTCATGGGCCATGGCAAGCATGCAGTAAAC  2520
CCTGCCAAGGGGAACGGAAACGAAAACTTGTTTGCACCAGGGAATCTGATCAGCTTACTGTTTCTGATCA  2590
AAGATGCGATCGGCTGCCCCAGCCTGGACACATTACTGAACCCTGTGGTACAGGCTGTGACCTGAGGTGG  2660
CATGTTGCCAGCAGGAGTGAATGTAGTGCCCAGTGTGGCTTGGGTTACCGCACATTGGACATCTACTGTG  2730
CCAAATATAGCAGGCTGGATGGAAGACTGAGAAGGTTGATGATGGTTTTTGCAGCAGCCATCCCAAACC  2800
          2810      2820      2830      2840      2850      2860      2870
         |    |    |    |    |    |    |    |    |    |    |    |    |    |
AAGCAACCGTGAAAAATGCTCAGGGGAATGTAACACGGGTGGCTGGCGCTATTCTGCCTGGACTGAATGT  2870
TCAAAAAGCTGTGACGGTGGGACCCAGAGGAGAAGGGCTATTTGTGTCAATACCCGAAATGATGTACTGG  2940
ATGACAGCAAATGCACACATCAAGAGAAAGTTACCATTCAGAGGTGCAGTGAGTTCCCTTGTCCACAGTG  3010
GAAATCTGGAGACTGGTCAGAGTGCTTGGTCACCTGTGGAAAAGGGCATAAGCACCGCCAGGTCTGGTGT  3080
CAGTTTGGTGAAGATCGATTAAATGATAGAATGTGTGACCCTGAGACCAAGCCAACATCTATGCAGACTT  3150
          3160      3170      3180      3190      3200      3210      3220
         |    |    |    |    |    |    |    |    |    |    |    |    |    |
GTCAGCAGCCGGAATGTGCATCCTGGCAGGCGGGTCCCTGGGTACAGTGCAGTGTCACTTGTGGACAGGG  3220
ATACCAGCTAAGAGCAGTGAAATGCATCATTGGGACTTATATGTCAGTGGTAGATGACAATGACTGTAAT  3290
GCAGCAACTAGACCAACTGATACCCAGGACTGTGAATTACCATCATGTCATCCTCCCCAGCTGCCCCGG  3360
AAACGAGGAGAAGCACATACAGTGCACCAAGAACCCAGTGGCGATTTGGGTCTTGGACCCCATGCTCAGC  3430
CACTTGTGGGAAAGGTACCCGGATGAGATACGTCAGCTGCCGAGATGAGAATGGCTCTGTGGCTGACGAG  3500
```

Fig. 7A₃

```
         3510      3520      3530      3540      3550      3560      3570
AGTGCCTGTGCTACCCTGCCTAGACCAGTGGCAAAGGAAGAATGTTCTGTGACACCCTGTGGGCAATGGA 3570
AGGCCTTGCACTGGAGCTCTTGCTCTGTGACCTGTGGGCAAGGTAGGGCAACCCGGCAAGTGATGTGTGT 3640
CAACTACAGTGACCACGTGATCGATCGGAGTGAGTGTGACCAGGATTATATCCCAGAAACTGACCAGGAC 3710
TGTTCCATGTCACCATGCCCTCAAAGGACCCCAGACAGTGGCTTAGCTCAGCACCCCTTCCAAAATGAGG 3780
ACTATCGTCCCCGGAGCGCCAGCCCCAGCCGCACCCATGTGCTCGGTGGAAACCAGTGGAGAACTGGCCC 3850
         3860      3870      3880      3890      3900      3910      3920
CTGGGGAGCATGTTCCAGTACCTGTGCTGGCGGATCCCAGCGGCGTGTTGTTGTATGTCAGGATGAAAAT 3920
GGATACACCGCAAACGACTGTGTGGAGAGAATAAAACCTGATGAGCAAAGAGCCTGTGAATCCGGCCCTT 3990
GTCCTCAGTGGGCTTATGGCAACTGGGAGAGTGCACTAAGCTGTGTGGTGGAGGCATAAGAACAAGACT 4060
GGTGGTCTGTCAGCGGTCCAACGGTGAACGGTTTCCAGATTTGAGCTGTGAAATTCTTGATAAACCTCCC 4130
GATCGTGAGCAGTGTAACACACATGCTTGTCCACACGACGCTGCATGGAGTACTGGCCCTTGGAGCTCGT 4200
         4210      4220      4230      4240      4250      4260      4270
GTTCTGTCTCTTGTGGTCGAGGGCATAAACAACGAAATGTTTACTGCATGGCAAAAGATGGAAGCCATTT 4270
AGAAAGTGATTACTGTAAGCACCTGGCTAAGCCACATGGGCACAGAAAGTGCCGAGGAGGAAGATGCCCC 4340
AAATGGAAAGCTGGCGCTTGGAGTCAGTGCTCTGTGTCCTGTGGCCGAGGCGTACAGCAGAGGCATGTGG 4410
GCTGTCAGATCGGAACACACAAAATAGCCAGAGAGACCGAGTGCAACCCATACACCAGACCGGAGTCGGA 4480
ATGCGAATGCCAAGGCCCACGGTGTCCCCTTTACACTTGGAGGGCAGAGGAATGGCAAGAATGCACCAAG 4550
         4560      4570      4580      4590      4600      4610      4620
ACCTGCGGCGAAGGCTCCAGGTACCGCAAGGTGGTGTGTGTGGATGACAACAAAAACGAGGTGCATGGGG 4620
CACGCTGTGACGTGAGCAAGCGGCCGGTGGACCGTGAAAGCTGTAGTTTGCAACCCTGCGAGTATGTCTG 4690
GATCACAGGAGAATGGTCAGAGTGCTCAGTGACCTGTGGAAAAGGCTACAAACAAAGGCTTGTCTCGTGC 4760
AGCGAGATTTACACCGGGAAAGAGAATTATGAATACAGCTACCAAACCACCATCAACTGCCCAGGCACGC 4830
AGCCCCCAGTGTTCACCCCTGTTACCTGAGGGAGTGCCCTGTCTCGGCACCTGGAGAGTTGGCAACTG 4900
         4910      4920      4930      4940      4950      4960      4970
GGGAGCTGCTCAGTGTCTTGTGGTGTTGGAGTGATGCAGAGATCTGTGCAATGtttaaccaatgaggac 4970
caacccagccacttatgccacactgatctgaagccagaagaacgaaaaacctgccgtaatgtctataact 5040
gtgagttaccccagaattgcaaggaggtaaaaagacttaaaggtgccagtgaagatggtgaatatttcct 5110
gatgattagaggaaagcttctgaagatattctgtgcggggatgcactctgaccaccccaaagagtacgtg 5180
acactggtgcatggagactctgagaatttctccgaggtttatgggcacaggttacacaACCCAACAGAAT 5250
         5260      5270      5280      5290      5300      5310      5320
GTCCCTATAACGGGAGCCGGCGCGATGACTGCCAATGTCGGAAGGATTACACGGCCGCTGGGTTTTCCAG 5320
TTTTCAGAAAATCAGAATAGACCTGACCAGCATGCAGATAATCACCACTGACTTACAGTTTGCAAGGACA 5390
AGCGAAGGACATCCCGTCCCTTTTGCCACAGCCGGGGATTGCTACAGCGCTGCCAAGTGCCCACAGGGTC 5460
GTTTTAGCATCAACCTTTATGGAACCGGCTTGTCTTTAACTGAATCTGCCAGATGGATATCACAAGGGAA 5530
TTATGCTGTCTCTGACATCAACGAAGTCGCCGGATGGTACCCGAGTCGTAGGGAAATGCGGTGGTTACTGT 5600
         5610      5620      5630      5640      5650      5660      5670
GGAAAATGCACTCCATCCTCTGGTACTGGCCTGGAGGTGCGAGTTTTATAGCTAAGGTGCTTTGAAGAGG 5670
AAGCCATTATGGATGGATGAAGGATAGTAATGCAATACCTCCACCTTAATTTGGGTGCATGTGTATGTGT 5740
GTGTGTGTTTGTGTGTGACTTGTATGCTTGTGTGTGTAAATGTGTGTACATATACATATATACA 5804
```

Fig. 7B

*Handwritten annotations: "Possible start cor" (at position ~10), "human ADAM TS-9" (at top), "Mature protease FLSYPR" (pointing to position ~380-410)*

```
         10        20        30        40        50        60        70
         |         |         |         |         |         |         |
STMQFVSWATLITLVRDLAEMGSPDAAAAVRKDRLHPRQVKLLETLSEYEIVSPIRVNALGEPFPTNVH  70
FKRTRRSINSATDPWPAFASSSSSSTSSQAHYRLSAFGQQFLFNLTANAGFIAPLFTVTLLGTPGVNQIK 140
FYSEEEAFLKHCFYKRLCQYQLRAHGRHQPLLRNEHKNRHSKDKKKTRARKWGERINLAGDVAALNSGLA 210
TEAFSAYGNKIIDNTREKRTHRRTKRFLSYPRFVEVLVVADNRMVSYHGENLQHYILTLMSIVASIYKDPS 280
IGNLINIVIVNLIVIHNEQDGPSISFNAQTTLKNFCQWQHSNSPGGIHHDTAVLLTRQDICRAHDKCDIL 350

360       370       380       390       400       410       420
         |         |         |         |         |         |         |
GLAELGTICDPYRSCSISEDSGLSTAFTIAHELGHVFNMPHDDNNKCKEEGVKSPQHVMAPTLNFYINPW 420
MWSKCSRKYITEFLDTGYGECLINEPESRPYPLPVQLPGILYNVNKQXELIFGPGSQVCPYMMQCRRLWC 490
NNVNGVHKGCRTQHTPWADGTECEPGKHCKXGFCVPKEMDVFVTDGSWGSWSPFGTCSRTCGGGIKTAIR 560
ECNRPEPKNGGKYCVGRRMKFKSCNTEPCLKQKRDFRDEQCAHFDGKHFNINGLLPNVRWVPKYSGILMK 630
DRCKLFCRVAGNTAYYQLRDRVIDGTPCGQDINDICVQGLCRQAGCDHVLNSKARRDKCGVCGGDNSSCK 700

710       720       730       740       750       760       770
         |         |         |         |         |         |         |
TVAGIFNIVHYGYNIVVRIPAGATNIDVRQHSFSGETDDINYLALSSSKGEFLLNGNFVVTMAKREIRIG 770
NAVVEYSGGETAVERINSTDRIEQELLLQVLSVGKLYNPDVRYSFNIPIEDKPQQFYWNSHGPWQACSKP 840
CQGERKRKLVCTRESDQLTVSDQRCDRLPQPGHTTEPCGTGCDLRWHVASRSECSAQCGLGYRTLDIYCA 910
KYSRLDGKTEKVDDGFCSSHPKPSNREKCSGECNTGGWRYSAWTECSKSCDGGTQRRRAICVNTRNDVLD 980
DSKCIHQEKVTIQRCSEFPCPQWKSGDWSECLVTCGKGHKHRQVWCQFGEDRLNDRMCDPETKPTSMQTC 1050

1060      1070      1080      1090      1100      1110      1120
         |         |         |         |         |         |         |
QQPECASWQAGFWVQCSVTCGQGYQLRAVKCIIGTYMSVVDDNDCNAATRPTDTQDCELPSCHPPPAAPE 1120
TRRSTYSAPRTQWRFGSWTPCSATCGKGTRMRYVSCRDENGSVADESACATTLPRFVAKEECSVTPCGQWK 1190
ALDWSSCSVTCGQGRATRQVMCVNYSDHVIDRSECDQDYIPEITDQDCSMSPCPQRTPDSGLAQHPFQNED 1260
YRPRSASPSRTHVLGGNQWRTGPWGACSSTCAGGSQRRVVVCQDENGYTANDCVERIKPDEQRACESGPC 1330
PQWAYGNWGECTKLCGGGIRTRLVVCQRSNGERFPDLSCEILDKPPDREQCNIHACPHDAAWSTGPWSSC 1400

1410      1420      1430      1440      1450      1460      1470
         |         |         |         |         |         |         |
SVSCGRGHKQRNVYCMAKDGSHLESDYCKHLAKPHGHRKCRGGRCPKWKAGAWSQCSVSCGRGVQQRHVG 1470
CQIGTHKIARETECNPYTRPESECECQGFRCPLYTWRAEEWQECTKTCGEGSRYRKVVCVDDNKNEVHGA 1540
RCDVSKRPVDRESCSLQPCEYVWITGEWSECSVTCGKGYKQRLVSCSEIYTGKENYEYSYQTTINCPGTQ 1610
PPSVHPCYLRECPVSATWRVGNWGSCSVSCGVGVMQRSVQCLTINEDQPSHLCHTDLKPEERKTCRNVYNC 1680
ELPQNCKEVKRLKGASEDGEYFLMIRGKLLKIFCAGMHSDHPKEYVTLVHGDSENFSEVYGHRLHNPTEC 1750

1760      1770      1780      1790      1800      1810      1820
         |         |         |         |         |         |         |
PYNGSRRDDCQCRKDYTAAGFSSFQKIRIDLTSMQIITTDLQFARTSEGHPVPFATAGDCYSAAKCPQGR 1820
FSINLYGTGLSLTESARWISQGNYAVSDIKKSPDGTRVVGKCGGYCGKCTPSSGTGLEVRVL.LRCFEEE 1890
AIMDG.RIVMQYLHLNLGACVCVCVFVCDLYACVCKCVYIYIYT 1934
```

Fig. 8A

```
ORF=2                                       protein
    HTAVISLCSGMMGTFRSHDGDYFIEPLQSVDEQEDEEEQN  40
    KPHTIYRHSTPQREPSTGKHACATSELKNSHSKDKRKIRM  80
    RKRRKRNSLADDVALLKSGLATKVLSGYSNQINNTRDRWN 120
    HKRTKRFLSYPRFVEVMVVADHRMVLYHGANLQHYILTLM 160
    SIVASTYKDSSIGNLINIVIVNLVVIHNEQEGPYINFNAQ 200
    TTLKNFCQWQHSKNYLGGIQHDTAVLVTREDICRAQDKCD 240
    TLGLAELGTICDPYRSCSISEDSGLSTAFTIAHELGHVFN 280
    MPHDDSNKCKEEGVKSPQHVMAPTLNFYINFWMWSKCSRK 320
    YITEFLDTGYGECLLNEPASRTYPLPSQLPGLLYNVNKQC 360
    ELIFGPGSQVCPYMMQCRRLWCNNVDGAHKGCRTQHTPWA 400
    DGTECEPGKHCKFGFCVPKEMEGPAIDGSWGGWSHFGICS 440
    RTCGGGIKTAIRECNRPEPKNGGKYCVGRRMKFKSCNTEP 480
    CMKQKRDFREEQCAHFDGKHFNINGLLPSVRWFPKYSGIL 520
    MKDRCKLFCRVAGNTAYYQLRDRVIDGTPCGQDTNDICVQ 560
    GLCRQAGCDHILNSKVRKDKCGICGGINSSCKTVAGIFNT 600
    VHYGYNIVVRIPAGATSIDVRQHSFSGKSEDDNYLALSNS 640
    KGEFLLNGDFVVSMSKREVRVGSAVIEYSGSINVVERLNC 680
    TDRIEEELLLQVLSVGKLYNPDVRYSFNIPIEDKPQQFYW 720
    NSHGFWQACSKPCQGERRRKLVCTRESDQLTVSDQRCDRL 760
    PQPGPVTEACGTDCDLRWHVASKSECSAQCGLGYRTLDIH 800
    CAKYSRMDGKTEKVDDSFCSSQPRPSNQEKCSGECSTGGW 840
    RYSAWTECSRSCDGGTQRRRAICVNTRNDVLDDS       874
```

→ mature ADAM TS9
FLSYPRF...

Mouse ADAM-TS9
partial sequence
(see figure)

Created: Saturday, April 10, 1999 11:40 AM

DNA

```
         10        20        30        40        50        60        70
         |         |         |         |         |         |         |
    GCACACTGCGGTCATCAGCCTGTGCTCCGGAATGATGGGCACGTTCCGCTCTCACGATGGAGATTATTTC  70
    ATTGAACCACTGCAGTCTGTGGATGAGCAAGAGGATGAAGAGGAACAAAACAAACCCCACATTATTTATA 140
    GGCACAGCACCCCTCAGAGGGAACCCTCCACAGGAAAGCATGCCTGTGCCACCTCAGAACTCAAAAATAG 210
    TCACAGTAAAGACAAGCGGAAAATCAGAATGCGAAAACGGAGAAAGAGGAATAGCCTGGCTGACGACGTG 280
    GCACTGCTAAAGAGCGGTTTGGCAACAAAGGTGCTCTCTGGCTATAGCAACCAGACAAACAACACAAGGG 350
```

Fig. 8B

```
          360       370       380       390       400       410       420
  ACAGATGGAACCACAAAAGAACCAAACGCTTTCTGTCCTACCCACGGTTTGTAGAGGTGATGGTGGTGGC 420
  TGACCACAGGATGGTTTTATACCACGGAGCAAACCTTCAACATTATATCTTAACCTTAATGTCCATTGTA 490
  GCTTCTATCTATAAAGACTCAAGTATTGGAAATTTAATTAATATTGTTATTGTGAACTTAGTTGTGATTC 560
  ATAATGAACAGGAAGGACCTTACATAAATTTCAATGCCCAGACAACATTAAAGAACTTTTGCCAGTGGCA 630
  GCACTCAAAGAACTACTTGGGTGGGATTCAGCACGACACAGCCGTTCTGGTCACAAGGGAAGATATCTGC 700
          710       720       730       740       750       760       770
  AGAGCTCAGGACAAATGTGACACCTTAGGTCTTGCTGAACTGGGAACCATTTGCGACCCCTACCGAAGCT 770
  GTTCCATTAGTGAAGACAGTGGGCTGAGCACAGCTTTCACAATAGCTCACGAGCTGGGCCATGTGTTTAA 840
  TATGCCTCACGATGACAGCAATAAATGCAAAGAAGAAGGAGTTAAGAGTCCCCAGCATGTCATGGCACCA 910
  ACACTGAACTTCTACACCAACCCCTGGATGTGGTCAAAGTGCAGTCGGAAATACATCACTGAGTTCCTAG 980
  ACACTGGGTACGGAGAGTGCTTGCTGAATGAACCTGCATCCAGGACCTATCCTTTGCCTTCCCAACTGCC 1050
          1060      1070      1080      1090      1100      1110      1120
  CGGCCTTCTCTACAACGTGAATAAACAATGTGAACTGATTTTTGGGCCAGGCTCTCAAGTGTGCCCCTAT 1120
  ATGATGCAGTGCAGACGGCTCTGGTGCAATAATGTGGATGGAGCACACAAAGGCTGCAGGACTCAGCACA 1190
  CGCCCTGGGCAGATGGAACCGAGTGTGAGCCTGGAAAGCACTGCAAGTTTGGATTTTGTGTTCCCAAAGA 1260
  AATGGAGGGCCCTGCAATTGATGGATCCTGGGGAGGTTGGAGCCACTTTGGGACCTGCTCAAGAACGTGT 1330
  GGAGGAGGCATCAAAACAGCCATCAGAGAGTGCAACAGACCAGAGCCAAAAAATGGTGGAAGTACTGTG 1400
          1410      1420      1430      1440      1450      1460      1470
  TAGGAAGGAGAATGAAGTTCAAATCCTGCAACACGGAGCCCTGCATGAAGCAGAAGCGAGACTTCCGAGA 1470
  GGAGCAGTGTGCTCACTTTGATGGCAAACACTTCAACATCAATGGTCTGCTGCCCAGCGTACGCTGGTTT 1540
  CCTAAGTACAGCGGAATTTTGATGAAGGACCGGTGCAAGTTGTTCTGCAGAGTGGCAGGAAACACAGCCT 1610
  ACTACCAGCTCCGAGACAGAGTGATTGACGGAACCCCTTGTGGCCAGGACACAAATGACATCTGTGTCCA 1680
  AGGCCTTTGCCCGGCAAGCTGGATGTGATCATATTTTAAACTCAAAGGTCCGGAAAGATAAATGTGGATT 1750
          1760      1770      1780      1790      1800      1810      1820
  TGTGGTGGAGATAATTCTTCATGCAAAACAGTGGCAGGAACATTTAACACTGTCCATTATGGTTACAATA 1820
  CTGTTGTCCGAATTCCGGCTGGTGCTACCAGCATTGACGTGCGTCAGCACAGCTTCTCAGGGAAGTCTGA 1890
  GGATGACAACTACCTAGCTTTATCAAACAGTAAAGGTGAATTCCTGCTAAATGGAGACTTTGTTGTCTCC 1960
  ATGTCCAAAAGGGAGGTCCGCGTGGGGAGCGCCGTCATTGAGTACAGCGGATCGGACAATGTGGTGAAA 2030
  GACTGAACTGTACGGACCGTATCGAGGAAGAACTTCTCCTTCAGGTGTTGTCCGTGGGAAAGCTGTATAA 2100
          2110      2120      2130      2140      2150      2160      2170
  CCCAGATGTGCGGTACTCATTCAATATTCCCATTGAGGACAAACCTCAGCAATTTTACTGGAACAGTCAC 2170
  GGGCCGTGGCAAGCATGCAGCAAGCCCTGCCAAGGGGAGCGGAGACGAAAACTTGTTTGCACCAGGGAGT 2240
  CTGATCAGCTAACCGTTTCTGATCAAAGATGTGACCGGCTGCCCCAGCCAGGACCTGTCACTGAAGCGTG 2310
  CGGCACAGACTGTGACTTGAGGTGGCACGTTGCCAGCAAGAGCGAATGCAGTGCCCAGTGTGGTTTGGGC 2380
  TACCGTACTTTAGACATCCACTGTGCCAAATACAGCAGGATGGACGGGAAGACGGAGAAGGTGGATGACA 2450
          2460      2470      2480      2490      2500      2510      2520
  GTTTCTGTAGCAGTCAACCCAGACCGAGTAACCAGGAGAAATGCTCAGGAGAGTGCAGCACAGGTGGATG 2520
  GCGCTATTCAGCCTGGACCGAATGTTCTAGAAGCTGTGATGGTGGTACCCAGAGAAGAAGAGCAATTTGT 2590
  GTCAACACCCGCAATGATGTCCTGGATGACAGCAA 2625
```

Fig. 9A₁

```
         10        20        30        40        50        60        70
    ....|....|....|....|....|....|....|....|....|....|....|....|....|....|
TCACGCACGCCTTCCGGTCTCAAGATGAGTTCCTGTCCAGTCTGGAGAGCTATGAGATCGCCTTCCCCAC  70
CCGCGTGGACCACAACGGGGCACTGCTGGCCTTCTCGCCACCTCCTCCCCGGAGCAGCGCCGCGGCACGG 140
GGGCCACAGCCGAGTCCCGCCTCTTCTACAAAGTGGCCTCGCCAGCACCCACTTCCTGCTGAACCTGACC 210
CGCAGCTCCCGTCTACTGGCAGGGCGCGTCTCCGTGGAGTACTGGACACGGGAGGGCCTGGCCTGGCAGA 280
GGGCGGCCCGGCCCCACTGCCTCTACGCTGGTCACCTGCAGGGCCAGGCCAGCAGCTCCCATGTGGCCAT 350
         360       370       380       390       400       410       420
    ....|....|....|....|....|....|....|....|....|....|....|....|....|....|
CAGCACCTGTGGAGGCCTGCACGGCCTGATCGTGGCAGACGAGGAAGAGTACCTGATTGAGCCCCTGCAC 420
GGTGGGCCCAAGGGTTCTCGGAGCCCGGAGGAAAGTGGACCACATGTGGTGTACAAGCGTTCCTCTCTGC 490
GTCACCCCCACCTGGACACAGCCTGTGGAGTGAGAGATGAGAAACCGTGGAAAGGCGGCCATGGTGGCT  560
GCCGACCTTGAAGCCACCGCCTGCCAGACCCCTGGGGAATGAAACAGAGCGTGGCCAGCCAGGCCTGAAG 630
CGATCGGTCAGCCGAGAGCGCTACGTGGAGACCCTGGTGGTGGCTGACAAGATGATGGTGGCCTATCACG 700
         710       720       730       740       750       760       770
    ....|....|....|....|....|....|....|....|....|....|....|....|....|....|
GGCGCCGGGATGTGGAGCAGTATGTCCTGGCCATCATGAACATTGTTGCCAAACTTTTCCAGGACTCGAG 770
TCTGGGAAGCACCGTTAACATCCTCGTAACTCGCCTCATCCTGCTCACGGAGGACCAGCCCACTCTGGAG 840
ATCACCCACCATGCCGGGAAGTCCCTAGACAGCTTCTGTAAGTGGCAGAAATCCATCGTGAACCACAGCG 910
GCCATGGCAATGCCATTCCAGAGAACGGTGTGGCTAACCATGACACAGCAGTGCTCATCACACGCTATGA 980
CATCTGCATCTACAAGAACAAACCCTGCGGCACACTAGGCCTGGCCCGGTGGCGGAATGTGTGAGCGCG 1050
         1060      1070      1080      1090      1100      1110      1120
    ....|....|....|....|....|....|....|....|....|....|....|....|....|....|
AGAGAAGCTGCAGCGTCAATGAGGACATTGGCTGCCACAAGCGTTCACCATTGCCACGAGATCGGGCACA 1120
CATTCGGCATGAACCATGACGGCGTGGGAAACAGCTGTGGGGCCCGTGGTCAGGACCCAGCCAAGCTCAT 1190
GGCTGCCCACATTACCATGAAGACCAACCCATTCGTGTGGTCATCCTGCAACCGTGACTACATCACCAGC 1260
TTTCTAGACTCGGGCCTGGGCTCTGCCTGAACAACCGGCCCCCAGACAGGACTTTGTGTACCCGACAG   1330
TGGCACCGCGCCAAGCCTACGATGCAGATGAGCAATGCCGCTTTCAGCATGGAGTCAAATCGCGTCAGTG 1400
         1410      1420      1430      1440      1450      1460      1470
    ....|....|....|....|....|....|....|....|....|....|....|....|....|....|
TAAATACGGGAGGTCTGCAGCGAGCTGTGGTGTCTGAGCAAGAGCAACCGGTGCATCACCAACAGCATC  1470
CCGGCCGCCGAGGGCACGCTGTGCCAGACGCACACCATCGACAAGGGGTGGTGCTACAAACGGTCTGTG  1540
TCCCCTTTGGGTCGCGCCCAGAGGGTGTGGACGGAGCCTGGGGCCGTGGACTCCATGGGGCGACTGCAG  1610
CCGGACCTGTGGCGGCGGCGTGTCCTCTTCTAGTCGTCACTGCGACAGCCCCAGGCCAACCATCGGGGC  1680
AAGTACTGTCTGGGTGAGAGAAGGCGGCACCGCTCCTGCAACACGGATGACTGTCCCCCTGGCTCCCAGG 1750
```

Fig. 9A₂

```
         1760      1770      1780      1790      1800      1810      1820
ACTTCAGAGAAGTGCAGTGTTCTGAATTTGACAGCATCCCTTTCCGTGGGAAATTCTACAAGTGGAAAAC 1820
GTACCGGCGAGGGGCGTGAAGGCCTGCTCGCTCACGAGCCTAGCGGAAGGCTTCAACTTCTACACGGAG 1890
AGGGCGGCAGCCGTGGTGGACGGGACACCCTGCCGTCCAGACACGGTGGACATTTGCGTCAGTGCCAAT 1960
GCAAGCACGTGGGCTGCGACCGAGTCCTGGGCTCCGACCTGCGGGAGGACAAGTGCCGAGTGTGTGGCGG 2030
TGACGGCAGTGCCTGCGAGACCATCGAGGGCGTCTTCAGCCCAGCCTCACCTGGGGCCGGGTACGAGGAT 2100

2110      2120      2130      2140      2150      2160      2170
GTCGTCTGGATTCCCAAAGGCTCCGTCCACATCTTCATCCAGGATCTGAACCTCTCTCTCAGTCACTTGG 2170
CCCTGAAGGGAGACCAGGAGTCCCTGCTGCTGGAGGGGCTGCCTGGGACCCCCAGCCCCACCGTCTGCC 2240
TCTAGCTGGGACCACCTTTCAACTGCGACAGGGGCCAGACCAGGTCCAGAGCCTCGAAGCCCTGGGACCG 2310
ATTAATGCATCTCTCATCGTCATGGTGCTGGCCCGGACCGAGCTGCCTGCCCTCCGCTACCGCTTCAATG 2380
CCCCCATCGCCCGTGACTCGCTGCCCCCTACTCCTGGCACTATGCGCCCTGGACCAAGTGCTCGGCCCA 2450

2460      2470      2480      2490      2500      2510      2520
GTGTGCAGGCGGTAGCCAGGTGCAGGCGGTGGAGTGCCGCAACCAGCTGGACAGCTCCGCGGTCGCCCCC 2520
CACTACTGCAGTGCCCACAGCAAGCTGCCCAAAAGGCAGCGCGCCTGCAACACGGAGCCTTGCCCTCCAG 2590
ACTGGGTTGTAGGGAACTGGTCGCTCTGCAGCCGCAGCTGCGATGCAGGCGTGCGCAGTCGCTCGGTCGT 2660
GTGCCAGCGCCGCGTCTCTGCCGCGGAGGAGAAGGCGCTGGACGACAGCGCATGCCCGCAGCCGCGCCCA 2730
CCTGTACTGGAGGCCTGCCACGGCCCCACTTGCCCTCCGGAGTGGGCAACCCTCGACTGGTCTGAGTGTA 2800

2810      2820      2830      2840      2850      2860      2870
CCCCAAGCTGTGGGCCTGGTCTCCGCCACCGAGTGGTCCTTTGTAAGAGTGCAGATCAACGATCTACTCT 2870
GCCCCCTGGGCACTGCCTTCCTGCAGCCAAGCCACCATCTACTATGCGATGTAACTTGCGCCGCTGCCCT 2940
CCTGCCCGCTGGGTGACCAGTGAGTGGGGTGAGTGTTCCACACAGTGTGGCCTCGGCCAGCAGCAGCGCA 3010
CAGTGCGCTGCACCAGCCACACCGGCCAGCCATCTCGAGAGTGCACTGAAGCCTTGCGGCCATCCACCAT 3080
GCAGCAGTGTGAGGCCAAGTGTGACAGTGTGGTGCCGCCTGGAGATGGCCCAGAAGAATGCAAGGATGTG 3150

3160      3170      3180      3190      3200      3210      3220
AACAAGGTGGCTTACTGCCCCCTGGTGCTCAAATTTCAGTTCTGTAGCCGAGCCTACTTCCGCCAGATGT 3220
GCTGCAAAACCTGCCAAGGCCGCtagggtacctggaaccaacctggagcacaggctgaggcaggggacat 3290
cccactggagagggcatgagggaaagggggggcttgaattgaagggtgagatgcagttgaaagttatttat 3360
tgggtaaccctacagggctcctgactaagggtggagaagagctggctacccagggaccctctgctgtat 3430
cttgccagttgatagtgaagagagaggactccttgttgcacacatatttaagtccctagcacccctccc 3500

3510      3520      3530      3540      3550      3560      3570
acccttgatcggaatatgtactgtgaagagtggggtgggagggtgtgctggtgccctgccccctgc 3570
actgttctatccctacactctgagctgggggattatatctgctatggggggagtaggcttgataccac 3640
ctccctgtagccctcccccagactgacgaaggggaagatccaccccaacctctgccctgcctgccccagg 3710
ggggagttcaacatccaggccgttccccatcatggtgctacaagccctgccctggggcccacacactcct 3780
caccaagaagccttacattaaaaaagttgtgttatcctacaaaaaaaaaaaaaaactcgagggggggccc 3850

3860      3870      3880      3890      3900      3910      3920
ggtacccaattcgcgctatagtaaatngggtnttta 3885
```

Fig. 9B

*human ADAM TS-10* (handwritten)

```
         10        20        30        40
    ..|....|....|....|....|....|....|....|
SRTPSGLKMSSCPVWRAMRSPSPPAWTTTGHCWPSRHLLP  40
GAAPRHGGHSRVPPLLQSGLASTHFLLNLTRSSRLLAGRV  80
SVEYWTREGLAWQRAARPHCLYAGHLQGQASSSHVAISTC  120
GGLHGLIVADEEEYLIEPLHGGPKGSRSPEESGPHVVYKR  160
SSLRHPHLDTACGVRDEKPWKGRPWWLRTLKPPPARPLGN  200
         210       220       230       240
    ..|....|....|....|....|....|....|....|
ETERGQPGLKR|SVSRERYVETLVVADKMMVAYHGRRDVEQ  240
YVLAIMNIVAKLFQDSSLGSTVNILVTRLILLTEDQPTLE  280
ITHHAGKSLDSFCKWQKSIVNHSGHGNAIPENGVANHDTA  320
VLITRYDICIYKNKPCGTLGLARWAECVSAREAAASMRTL  360
AATSVHHCHEIGHTFGMNHDGVGNSCGARGQDPAKLMAAH  400
         410       420       430       440
    ..|....|....|....|....|....|....|....|
ITMKTNPFVWSSCNRDYTTSFLDSGLGLCLNNRPPRQDFV  440
YPTVAPGQAYDADEQCRFQHGVKSRQCKYGEVCSELWCLS  480
KSNRCITNSIPAAEGTLCQTHTIDKGWCYKRVCVPFGSRP  520
EGVDGAWGHWTPWGDCSRTCGGGVSSSSRHCDSPRPTIGG  560
KYCLGERRRHRSCNTDDCPPGSQDFREVQCSEFDSIPFRG  600
         610       620       630       640
    ..|....|....|....|....|....|....|....|
KFYKWKTYRGGGVKACSLTSLAEGFNFYTERAAAVVDGTP  640
CRPDIVDICVSGECKHVGCDRVLGSDLREDKCRVCGGDGS  680
ACETIEGVFSPASPGAGYEDVVWIPKGSVHIFIQDLNLSL  720
SHLALKGDQESLLLEGLPGTPQPHRLPLAGTTFQLRQGPD  760
QVQSLEALGPINASLIVMVLARTELPALRYRFNAPIARDS  800
         810       820       830       840
    ..|....|....|....|....|....|....|....|
LPPYSWHYAPWTKCSAQCAGGSQVQAVECRNQLDSSAVAP  840
HYCSAHSKLPKRQRACNTEPCPPDWVVGNWSLCSRSCDAG  880
VRSRSVVCQRRVSAAEEKALDDSACPQPRPPVLEACHGPT  920
CPPEWATLDWSECTPSCGPGLRHRVVLCKSADQRSTLPFG  960
HCLPAAKPPSTMRCNLRRCPPARWVTSEWGECSTQCGLGQ  1000
         1010      1020      1030      1040
    ..|....|....|....|....|....|....|....|
QQRTVRCTSHIGQPSRECTEALRPSTMQQCEAKCDSVVPP  1040
GDGPEECKDVNKVAYCPLVLKFQFCSRAYFRQMCCKTCQG  1080
R  1081
```

→ Mature protease (handwritten)

SVSRERY......... (handwritten)

Fig. 10A₁

*partial sequence of mouse ADAM TS-10*
*(see figure)*

```
         10        20        30        40
    |....|....|....|....|....|....|....|....|
AGCAGCAGCTGTGGTGGATGGAACACCCTGCCGCCCTGAC    40
ACGGTGGACATTTGTGTCAGCGGCGAGTGCAAGCATGTAG    80
GCTGTGACAGGGTCCTGGGTTCTGATCTCCGAGAGGACAA   120
ATGCCGTGTGTGTGGGGTGATGGCAGTGCCTGTGAGACC    160
ATTGAAGGTGTCTTTAGCCCAGCTTTGCCAGGAACTGGGT   200
        210       220       230       240
    |....|....|....|....|....|....|....|....|
ATGAGGACGTCGTCTGGATCCCCAAAGGCTCGGTCCACAT   240
TTTCATCCAAGATCTGAACCTGTCCCTGAGTCACCTGGCC   280
CTAAAGGGGACCAAGAGTCTCTGCTACTGGAGGGGCTAC   320
CTGGACCCCCAACCTNACCGCCTTCCCCTGGNTGGGAC    360
CACATTTCATCTACGGCAGGGGCCGGACCAGGCACAGAGC   400
        410       420       430       440
    |....|....|....|....|....|....|....|....|
CTGGAAGCCCTGGGACCCATTAATGCATCTCTCATCATCA   440
TGGTGCTGGCCCAGGCAGAGTTGCCTGCTCTCCACTACCG   480
CTTCAATGCACCCATTGCCCGGGATGCACTGCCTCCCTAC   520
TCCTGGCACTATGCCCCCTGGACCAAATGCTCAGCCCAGT   560
GTGCAGGCGGCAGCCAGGTCCAAGTAGTGGAGTGCCGAAA   600
        610       620       630       640
    |....|....|....|....|....|....|....|....|
TCAGCTGGACAGCTCAGCAGTGGCCCCACACTACTGTAGT   640
GGCCACAGTAAATTGCCCAAGAGGCAGCGTGCCTGCAACA   680
CAGAACCATGTCCACCAGATTGGGTTGTAGGAAACTGGTC   720
ACGCTGCAGCCGTAGCTGTGACGCTGGTGTGCGTAGCCGC   760
TCAGTGGTGTGCCAACGCCGGGTGTCTGCTGCAGAGGAAA   800
        810       820       830       840
    |....|....|....|....|....|....|....|....|
AAGCCTTAGACGACAGTGCCTGTCCACAGCCACGCCCACC   840
TGTGCTGGAGGCCTGCCAAGGCCCAATGTGCCCTCCTGAG   880
TGGGCAACCCTCGACTGGTCTGAGTGTACCCCAAGCTGTG   920
GGCCTGGTCTCCGCCACCGAGTGGTCCTTTGTAAGAGTGC   960
AGATCAACGATCTACTCTGCCCCCTGGGCACTGCCTTCCT 1000
```

Fig. 10A$_2$

```
          1010      1020      1030      1040
       |    |    |    |    |    |    |    |
GCAGCCAAGCCACCATCTACTATGCGATGTAACTTGCGCC 1040
GCTGCCCTCCTGCCCGCTGGGTGACCAGTGAGTGGGGTGA 1080
GTGTTCCACACAGTGTGGCCTCGGCCAGCAGCAGCGCACA 1120
GTGCGCTGCACCAGCCACACCGGCCAGCCATCTCGAGAGT 1160
GCACTGAAGCCTTGCGGCCATCCACCATGCAGCAGTGTGA 1200
          1210      1220      1230      1240
       |    |    |    |    |    |    |    |
GGCCAAGTGTGACAGTGTGGTGCCGCCTGGAGATGGCCCA 1240
GAAGAATGCAAGGATGTGAACAAGGTGGCTTACTGCCCCC 1280
TGGTGCTCAAATTTCAGTTCTGTAGCCGAGCCTACTTCCG 1320
CCAGATGTGCTGCAAAACCTGCCAAGGCCGCTAGGGTACC 1360
TGGAACCAACCTGGAGCACAGGCTGAGGCAGGGACATCC 1400
          1410      1420      1430      1440
       |    |    |    |    |    |    |    |
CACTGGAGAGGGCATGAGGGAAAGGGGGGCTTGAATTGAA 1440
GGGTGAGATGCAAGTTGAAAGTATTTATTTGGGTAACCCC 1480
TACAGGGCTTCTGACTTAAGGGGTGGAGAANAGCTGGCTA 1520
CCCCAGGGACCCTTTTGTTGGATCTTGGCCCANTTGATAG 1560
TGAAGAGAGAGGACTTCTTGGTGNACACATTTTTAAGTCC 1600
          1610      1620      1630      1640
       |    |    |    |    |    |    |    |
TTAGACCCTTCCACCNTTGATCGGATATGTCTGGGAAGAG 1640
GN 1642
```

Fig. 10B

Mouse ADAM TS10

```
         10        20        30        40
AAAVVDGTPCRPDIVDICVSGECKHVGCDRVLGSDLREDK   40
CRVCGGDGSACETIEGVFSPALPGTGYEDVVWIPKGSVHI   80
FIQDLNLSLSHLALKGDQESLLLEGLPGTPQPXRLPLXGT  120
TFHLRQGPDQAQSLEALGPINASLIIMVLAQAELPALHYR  160
FNAPIARDALPPYSWHYAPWTKCSAQCAGGSQVQVVECRN  200
        210       220       230       240
QLDSSAVAPHYCSGHSKLPKRQRACNTEPCPPDWVVGNWS  240
RCSRSCDAGVRSRSVVCQRRVSAAEEKALDDSACPQPRPP  280
VLEACQGPMCPPEWATLDWSECTPSCGPGLRHRVVLCKSA  320
DQRSTLPPCHCLPAAKPPSTMRCNLRRCPPARWVTSEWGE  360
CSTQCGLGQQQRTVRCTSHTGQPSRECTEALRPSTMQQCE  400
        410       420       430       440
AKCDSVVPFGDGPEECKDVNKVAYCPLVLKFQFCSRAYFR  440
QMCCKTCQGR  450
```

Fig. 11A₁

Ligated 459225+482392 with Sac I(168)&Eco RI(or Not I)
Cloning site:5';Eco RI 3';Not I    Vector; PT7T3 pac.

You can put this construct to pcDNA3.1(+) for transfection
5'-UTR is 50bp &3'-UTR is 175bp 210-215; in 482392 it's TCCTAC(SY).

```
         10        20        30        40
     ....|....|....|....|....|....|....|....|
gaattcggcacgaggcagtgtccgattctgattccggcaa  40
ggatccaagcATGGAATGCTGCCGTCGGGCAACTCCTGGC  80
ACACTGCTCCTCTTTCTGGCTTTCCTGCTCCTGAGTTCCA  120
GGACCGCACgctCCGAGGAGGACCGGGACGGCCTATGGA   160
TGCCTGGGGCCCATGGAGTGAATGCTCACGCACCTGCGGG 200
         210       220       230       240
     ....|....|....|....|....|....|....|....|
GGTGGGGCCGCCAACTCTCTGAGGCGCTGCCTGAGCAGCA  240
AGAGCTGTGAAGGAAGAAATATCCGATACAGAACATGCAG  280
TAATGTGGACTGCCCACCAGAAGCAGGTGATTTCCGAGCT  320
CAGCAATGCTCAGCTCATAATGATGTCAAGCACCATGGCC  360
AGTTTTATGAATGGCTTCCTGTGTCTAATGACCCTGACAA  400
         410       420       430       440
     ....|....|....|....|....|....|....|....|
CCCATGTTCACTCAAGTGCCAAGCCAAAGGAACAACCCTG  440
GTTGTTGAACTAGCACCTAAGGTCTTAGATGGTACGCGTT  480
GCTATACAGAATCTTTGGATATGTGCATCAGTGGTTTATG  520
CCAAATTGTTGGCTGCGATCACCAGCTGGGAAGCACCGTC  560
AAGGAAGATAACTGTGGGGTCTGCAACGGAGATGGGTCCA  600
         610       620       630       640
     ....|....|....|....|....|....|....|....|
CCTGCCGGCTGGTCCGAGGGCAGTATAAATCCCAGCTCTC  640
CGCAACCAAATCGGATGATACTGTGGTTGCAATTCCCTAT  680
GGAAGTAGACATATTCGCCTTGTCTTAAAAGGTCCTGATC  720
ACTTATATCTGGAAACCAAAACCCTCCAGGGGACTAAAGG  760
TGAAAACAGTCTCAGCTCCACAGGAACTTTCCTTGTGGAC  800
```

Fig. 11A$_2$

```
            810       820       830       840
        ....|....|....|....|....|....|....|....|
        AATTCTAGTGTGGACTTCCAGAAATTTCCAGACAAAGACA  840
        TACTGAGAATGGCTGGACCACTCACAGCAGATTTCATTGT   880
        CAAGATTCGTAACTCGGGCTCCGCTGACAGTACAGTCCAG   920
        TTCATCTTCTATCAACCCATCATCCACCGATGGAGGGAGA   960
        CGGATTTCTTTCCTTGCTCAGCAACCTGTGGAGGAGGTTA  1000
           1010      1020      1030      1040
        ....|....|....|....|....|....|....|....|
        TCAGCTGACATCGGCTGAGTGCTACGATCTGAGGAGCAAC  1040
        CGTGTGGTTGCTGACCAATACTGTCACTATTACCCAGAGA  1080
        ACATCAAACCCAAACCCAAGCTTCAGGAGTGCAACTTGGA  1120
        TCCTTGTCCAGCCAGTGACGGATACAAGCAGATCATGCCT  1160
        TATGACCTCTACCATCCCCTTCCTCGGTGGGAGGCCACCC  1200
           1210      1220      1230      1240
        ....|....|....|....|....|....|....|....|
        CATGGACCGCGTGCTCCTCCTCGTGTGGGGGGGGCATCCA  1240
        GAGCCGGGCAGTTTCCTGTGTGGAGGAGGACATCCAGGGG  1280
        CATGTCACTTCAGTGGAAGAGTGGAAATGCATGTACACCC  1320
        CTAAGATGCCCATCGCGCAGCCCTGCAACATTTTTGACTG  1360
        CCCTAAATGGCTGGCACAGGAGTGGTCTCCGTGCACAGTG  1400
           1410      1420      1430      1440
        ....|....|....|....|....|....|....|....|
        ACGTGTGGCCAGGGCCTCAGATACCGTGTGGTCCTCTGCA  1440
        TCGACCATCGAGGAATGCACACAGGAGGCTGTAGCCCAAA  1480
        AACAAAGCCCCACATAAAAGAGGAATGCATCGTACCCACT  1520
        CCCTGCTATAAACCCAAAGAGAAACTTCCAGTCGAGGCCA  1560
        AGTTGCCATGGTTCAAACAAGCTCAAGAGCTAGAAGAAGG  1600
           1610      1620      1630      1640
        ....|....|....|....|....|....|....|....|
        AGCTGCTGTGTCAGAGGAGCCCTCGTAAgttgtaaaagca  1640
        cagactgttctatatttgaaacttttgtttaaagaaagca  1680
        gtgtctcactggttgtagctttcatgggttctgaactaag  1720
        tgtaatcatctcaccaaagcttttggctctcaaattaaa   1760
        gattgattagtttcaaaaaaaaaaaaaaaaaagatgcggc  1800
           1810      1820      1830      1840
        ....|....|....|....|....|....|....|....|
        cgc 1803
```

Fig. 11B

| | | | | | | | | | | | |
|---|---|---|---|---|---|---|---|---|---|---|---|
| ---- | Asp(D) | 30 | # | cua | Leu(L) | 3 | # | uca | Ser(S) | 6 | # guu Val(V) 6 |
| ugc | Cys(C) | 26 | # | cuc | Leu(L) | 11 | # | ucc | Ser(S) | 10 | # ---- Val(V) 29 |
| ugu | Cys(C) | 10 | # | cug | Leu(L) | 14 | # | ucg | Ser(S) | 5 | # nnn ???(X) 0 |
| ---- | Cys(C) | 36 | # | cuu | Leu(L) | 6 | # | ucu | Ser(S) | 5 | # TOTAL 526 |
| caa | Gln(Q) | 7 | # | uua | Leu(L) | 4 | # | ---- | Ser(S) | 43 | # |

Created: Wednesday, May 5, 1999 10:19 AM

Ligated 459225+482392 with Sac I(168)&Eco RI(or Not I)
Cloning site:5';Eco RI 3';Not I   Vector; PT7T3 pac.

*human ADAM-TSR1*
*Adam-TS related protein - 1.*

```
          10        20        30        40
   ....|....|....|....|....|....|....|....|
 1 MECCRRATPGTLLLFLAFLLLSSRTARSEEDRDGLWDAWG 40      — Signal peptide
   PWSECSRTCGGGAANSLRRCLSSKSCEGRNIRYRTCSNVD 80
   CPPEAGDFRAQQCSAHNDVKHHGQFYEWLPVSNDPDNPCS 120
   LKCQAKGTTLVVELAPKVLDGTRCYTESLDMCISGLCQIV 160
   GCDHQLGSTVKEDNCGVCNGDGSTCRLVRGQYKSQLSATK 200
         210       220       230       240
   ....|....|....|....|....|....|....|....|
   SDDIVVAIPYGSRHIRLVLKGPDHLYLEIKTLQGIKGENS 240
   LSSTGIFLVDNSSVDFQKFPLKEILRMAGPLTADFIVKIR 280
   NSGSADS1VQFIFYQPIIHRWRETDFFPCSATCGGGYQLT 320
   SAECYDLRSNRVVADQYCHYYPENIKPKPKLQECNLDPCP 360   (C) YYPENIKPKPKLQE
   ASDGYKQIMPYDLYHPLPRWEATPWTACSSSCGGGIQSRA 400
         410       420       430       440
   ....|....|....|....|....|....|....|....|
   VSCVEEDIQGHVTSVEEWKCMYTPKMPIAQPCNIFDCPKW 440
   LAQEWSPCTVTCGQGLRYRVVLCIDHRGMHIGGCSPKTKP 480   (C)QELEEGAAV
   HIKEECIVPTPCYKPKEKLPVEAKLPWFKQAQELEEGAAV 520   C-terminal epitope for Ab-
   SEEPS. 526
```

Similar to ADAM-TS family but lacks the prometalloprotease and disintegrin domain. Our hypothesis is that this may be a inhibitor of the family

Fig. 13A a

```
MRLEWASLLLLLLLLLSASCLSLAADSPAAAPAQDKTRQPQAAAAAAEPDQPQGEETREFGHLQPLAGQRRSGGLVHNIDQ   80

LYSGGGKVGYLVYAGGRRFLLDLERDDTVGAAGSIVTAGGGLSASSGHRGHCFYRGTVDCSPRSLAVFDLCGGLDGFFAV  160
                                        *                          *
KHARYTLKPLLRGSWAEYERIYGDGSSRILHVYNREGFSFEALPPRASCETPASPSGPQESPSVHSRSRRRSALAPQLLD  240
                                              ●                   ↓
HSAFSPSGNAGPQTWWRRRRKSISRARQVELLLVADSSMARMYGRGLQHYLLTLASIANRLYSHASIENHIRLAVVKVVV  320
               ↓↓
LTDKDTSLEVSKNAATTLKNFCKWQHQHNQLGDDHEEHYDAAILFTREDLCGHHSCDTLGMADVGTICSPERSCAVIEDD  400
              *                       *     *                      *          *
GLHAAFIVA HEIGHLLGLSHD DSKFCEENFGTTEDKRI MSSILTSIDASKPWSKCTSATTTEFLDDGHGNCLLDLPRKQI  480
--------- ---GHLLGLSHD DSKFCEEIFGSTEDKRI MSSILTSIDASKPWSKCTSATTTEFLDDGHGNCLLDLPRKQI
|→Dis              *
LGPEELPGQTYDATQQCNLTFGPEYSVCPGMDVCARLWCAVVRQGQMVCLTKKLPAVEGTPCGKGRVCLQGKCVDKTKKK  560
LGPEELPGQTYDATQQCNLTFGPEYSVCPGXDVCARLWCAVVRQGQMVCLTKKLPAVEGTPCGKGRICLQGKCVDKTKKK
        *   *              *          *                   *     *         *
YYSTSSHGNWGSWGPWGQCSRSCGGGVQFAYRHCNNPAPRNSGRYCTGKRAIYRSCSVTPCPPNGKSFRHEQCEAKNGYQ  640
YYSTSSHGNWGSWGSWGQCSRSCGGGVQFAYRHCNNPAPRNNGRYCTGKRAIYHSCSLMPCPPNGKSFRHEQCEAKNGYQ
    * *                   *               * *        *    *     *
SDAKGVKTFVEWVPKYAGVLPADVCKLTCRAKGTGYYVVFSPKVTDGTECRPYSNSVCVRGRCVRTGCDGIIGSKLQYDK  720
SDAKGVKTFVEWVPKYAGVLPADVCKLTCRAKGTGYYVVFSPKVTDGTECRPYSNSVCVRGKCVRTGCDGIIGSKLQYDK
  *  *       →|→ Spacer domain
CGVCGGDNSSCTKIIGTFNKKSKGYTDVVRIPEGATHIKVRQFKAKDQTRFPAYLALKKKTGEYLINGKYMISTSETTID  800
CGVCGGDNSSCTKIVGTFNKKSKGYTDVVRIPEGATHIKVRQFKAKDQTRFTAYLALKKKNGEYLINGKYMISTSETTID INGIVMNYSGWSHRDDFLHGMGYSATKEILIVQILATDPTKALGVRYSFFVPKKTTQKVNSVISHGSNKVGPHSTQLQWV  880
INGIVMNYSGWSHRDDFLHGMGYSATKEILIVQILATDPTKPLDVRYSFFVPKKSTPKVNSVTSHGSNKVGSHTSQPQWV
    *  *           *         *          * *
TGPWLACSRTCDIGWHTRTVQCQDGNRKLAKGCLLSQRPSAFKQCLLKKC                                930
TGPWLACSRTCDIGWHTRTVQCQDGNRKLAKGCPLSQRPSAFKQCLLKKC
```

Fig. 13B b

MEILWKILTWILSLIMASS...SDHRLSYSSQEEFLTYLEHYQLTIPIRVDQNGA...FTVKNDKHSRRRRSMDPIDPQQ 80
AVSKLFFKLSAYGKHFHLNLTLNIDFVSKHFTVEYWGKDGPQWKHDFLDNCHYTGYLQDQRSTTKVALSNCVGLHGVIAT 160
EDEEYFIEPLKNITEDSKHFSYENGHPHVIYKKSALQQRHLYDHSHCGVSDFTRSGKFWWLNDTSTVSYSLPINNIHIHH 240
RQKRSVSIERFVETLVVADKMMVGYHGRKDIEHYILSVMNIVAKLYRDSSLGNVVNIIVARLIVLTEDQFNLEINHHADK 320
SLDSFCKWQKSILSHQSDGNTIPENGIAHHDNAVLITRYDICTYKNKPCGTLGLASVAGMCEPERSCSINEDIGLGSAFT 400
LAHEIVHIIFGMNHDGIGNSCGRKVMKQQNYGSSHYCEYQSFFLVCLQSRLHHQLFREVCRELWCLSKSNRCVINSIPAAE 480
|→Dis
GTLCQTGIIEKGWCYQGDCVPFGIWPQSIDGGWGFWSLWGECSRTCGGGVSSSLRHCDSPAPSGGGKYCLGERKRYRSCN 560
TDPCPLGSRDFREKQCADFLNMPFRGKYYNWKPYTGGGVKPCALNCLAEGYNFYTERAPAVIDGTQCNADSLDICINGEC 640
KHVGCDNILGSDAREDRCRVCGGGGSTCDAIEGFFNDSLPRGGYMEVVQIPRGSVHIEVREVAMSKNYIALKSEGDDYYI 720
|→Spacer domain
NGAWTIDWPRKFDVAGTAFHYKRPTDEPESLEALGPTSENLIVMVLLQEQNLGIRYKFNVPITRTGSGDNEVGFIWNHQP 800
WSECSATTAGGKMPTRQPTQRARWRTKHILSYALCLLKKLIGNISCRFASSCNLAKETLL 860 c

MPGGPSPRSPAPLLRPLLLLLCALAPGAPGPAPGRATEGRAALDIVHPVRVDAGGSFLSYELWPRALRKRDVSVRRDAPA 80
FYELQYRGRELRFNLTANQHLLAPGFVSETRRRGGLGRAHIRAHTPACHLLGEVQDPELEGGLAAISACDGLKGVFQLSN 160
EDYFIEPLDSAPARPGHAQPHVVYKRQAPERLAQRGDSSAPSTCGVQVYPELESRRERWEQRQQWRRPRLRRLHQRSVSK 240
EKWVETLVVADAKMVEYHGQPQVESYVLTIMNMVAGLFHDPSIGNPIHTTIVRLVLLEDEEEDLKITHHADNTLKSFCKW 320
QKSINMKGDAHPLHHDTAILLTRKDLCAAMNRPCEITLGLSHVAGMCQPHRSCSINEDTGLPLAFIVAHELGHSFGIQHIG 400
|→Dis
SGNDCEPVGKRPFIMSPQLLYDAAPLIWSRCSRQYTTRFLDRGWGLCLDDPPAKDIIDFPSVPPGVLYDVSHQCRLQYGA 480
YSAFCELMDNVCHTLWCSVGTTCHSKLDAAVDGTRCGENKWCLSGECVPVGFRPEAVDGGWSGWSAWSICSRSCGMGVQS 560
AERQCTQPTPKYKGRYCVGERKRFRLCNLQACPAGRPSFRHVQCSHFDAMLYKGQLHTWVPVVNDVNPCELHCRPANEYF 640
|→Spacer domain
AKKLRDAVVDGTPCYQVRASRDLCINGICKNVGCDFEIDSGAMEDRCGVCHGNGSTCHTVSGTFEEABGLGYVDVGLIPA 720
GAREIRIQEVAEAANFLALRSEDPEKYFLNGGWTIQWNGDYQVAGTTFTYARRGNWENLTSPGPTKEPVWIQVPASRGPG 800
GGSRGGVPRPSTLHGRSRPGGVSPGSVTEPGSEPGPPAAASTSVSPSLKWFNLVAAVHRGGWGQAPLGLGGWRRHLVLMG 880
PRLPTQLLFQESNPGVHYEYTIHREAGGHDEVPPPVFSWHYGPWIKCIVTCGRGEKWGRHSPTCRGLVSGQGHWLQLPAH 960
CWATTGIEVCFSEPQFSICEMRLATALCPRPAGRVHG 997

Fig. 13C a

|  | |
|---|---|
| adamalysin II | H E L G H N L G M E HD |
| atrolysin A | H E L G H N L G M V HD |
| hADAM-9 | H E L G H N L G M N HD |
| hADAM-10 | H E V G H N F G S P HD |
| hADAM-15 | H E L G H S L G L D HD |
| hADAM-17 | H E L G H N F G A E HD |
| mADAM-19 | H E I G H N F G M S HD |
| mADAM-TS1 | H E L G H V F N M P HD |
| hADAM-TS2 | H E T G H V L G M E HD |
| hADAM-TS3 | H E T G H V L G M E HD |
| hADAM-TS4 | H E L G H V F N M L HD |
| mADAM-TS5 | H E I G H L L G L S HD |
| hADAM-TS6 | H E I V H N F G M N HD |
| hADAM-TS7 | H E L G H S F G I Q HD | b

```
mADAM-TS1   W G P W G P W G D C S R T C G G G V Q Y   20
hADAM-TS2   W G A W S P F G S C S R T C G T G V K F   20
hADAM-TS3   W G S W S P F G S C S R T C G T G V K F   20
hADAM-TS4   W G P W G P W G D C S R T C G T G V K F   20
hADAM-TS5   W G S W G S W G D C S R T C G G G V Q F   20
hADAM-TS6   W G P W S L W G E C S R T C G G G V Q F   20
hADAM-TS7   W S G W S A W S I C S R S C G M G V L S   20 mADAM-TS1   T M R E C D N P V P K N G G K Y C E G K   40
hADAM-TS2   R T R Q C D N P H P A N G G R T C S G L   40
hADAM-TS3   R T R Q C D N P H P A N G G R T C S G L   40
hADAM-TS4   S S R D C T R P V P A N G G K Y C S G L   40
hADAM-TS5   A Y R H C N N P A P R N G G R Y C T G K   40
hADAM-TS6   S L R H C D S P A P S G G G K Y C T G E   40
hADAM-TS7   A E R Q C T Q P T P K Y K G R Y C V G E   40 mADAM-TS1   R V R Y R S C N I E D C              52
hADAM-TS2   A Y D F Q L C N S Q D C              52
hADAM-TS3   A Y D F Q L C S R Q D C              52
hADAM-TS4   R T R F R S C N T E D C              52
hADAM-TS5   R A I Y H S C S L M P C              52
hADAM-TS6   R K R Y R S C N T D P C              52
hADAM-TS7   R K R F R L C N L Q A C              52
```

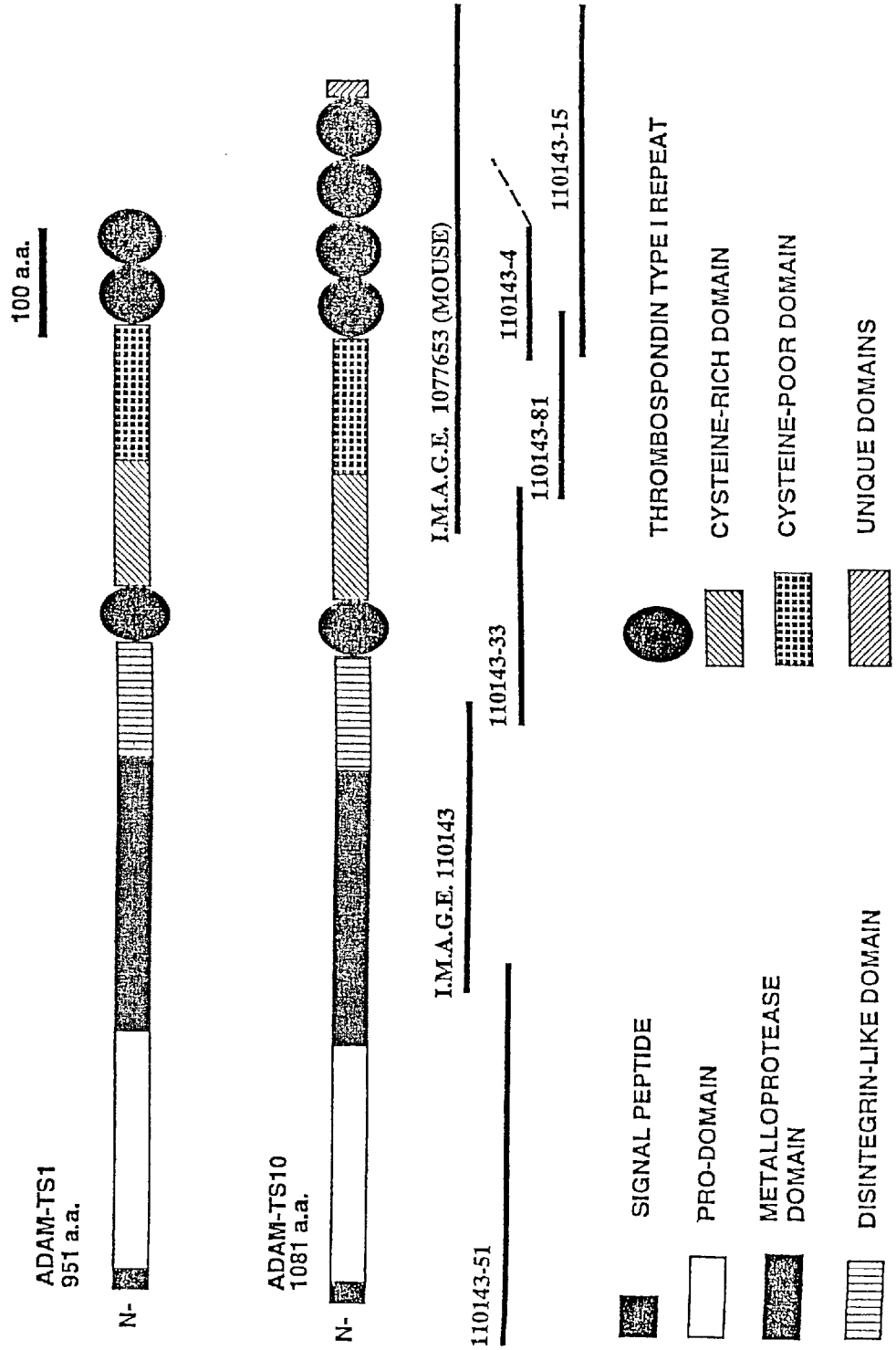

NUCLEIC ACIDS ENCODING ZINC METALLOPROTEASES

BACKGROUND OF THE INVENTION

This invention relates to isolated nucleic acid molecules which encode proteins belonging to a zinc metalloprotease family. The zinc metalloproteases have been implicated in a variety of diseases and development disorders that involve enhanced or depressed proteolysis of components of the extracellular matrix, receptors, or other extracellular molecules.

More particularly, the invention relates to isolated nucleic acid molecules encoding proteins belonging to a subfamily of zinc metalloproteases referred to as "ADAMTS", an abbreviation for ADisintegrin-like And Metalloprotease domain with ThromboSpondin type I motifs. Proteins in the ADAMTS subfamily all possess a Zn protease catalytic site consensus sequence (HEXXH+H), which suggests an intact catalytic activity for each of these proteins. The ADAMTS proteins also have putative N-terminal signal peptides and lack transmembrane domains, which suggests that the proteins in this subfamily are secreted. The proteins in the ADAMTS subfamily also possess at least one thrombospondin type (TSP 1) motif, which suggests a binding of these proteins to components of the extracellular matrix (ECM) or to cell surface components.

Members of the ADAMTS subfamily of proteins are ADAMTS-1, ADAMTS-2, ADAMTS-3, and ADAMTS-4. ADAMTS-1 protein is selectively expressed in colon 26 adenocarcinoma cachexigenic sublines. ADAMTS-1 mRNA is induced by the inflammatory cytokine interleukin-1 in vitro and by intravenous administration of lipopolysaccharide in vivo. Thus, the ADAMTS-1 protein is believed to play a role in tumor cachexia and inflammation.

The ADAMTS-2 protein is also known as procollagen I/II amino-propetide processing enzyme or PCINP. The ADAMTS-2 protein catalyzes cleavage of native triple-helical procollagen I and procollagen II. The ADAMTS-2 protein also has an affinity for collagen XIV. Lack of the ADAMTS-2 protein is known to cause dermatosparaxis in cattle, or Ehlers-Danlos syndrome type VIIC (EDS-VIIC) in humans. EDS-VIIC is characterized clinically by severe skin fragility, and biochemically by the presence in skin of procollagen which is incompletely processed at the amino terminus. Thus, it is believed that the ADAMTS-2 protein plays a role in processing of procollagen to mature collagen, an essential step for correct assembly of collagen into collagen fibrils. The ADAMTS-3 protein is similar in sequence to ADAMTS-2 and may have similar function.

The ADAMTS-4 protein catalyzes cleavage of the core protein of the extracellular matrix proteoglycan, aggrecan. Aggrecan degradation is an important factor in the erosion of articular cartilage in arthritic disease. Aggrecan fragments have been identified in cultures undergoing cartilage matrix degradation and in arthritic synovial fluids. Therefore, over-expression or activation of ADAMTS-4 protein may be related to both inflammatory and non-inflammatory arthritis.

On the basis of the structure, location, and the demonstrated proteolytic activity of ADAMTS proteins 1–4, it is expected that other members of the ADAMTS subfamily play a role in the cleavage of proteoglycan core proteins that are found in the extracellular matrix, such as, for example, versican, brevican, neuracan, NG-2, aggrecan, as well as molecules such as collagen. It is also expected that other members of the ADAMTS subfamily play a role in embryogenesis, implantation of a fertilized egg, angiogenesis, arthritic degradation of cartilage, inflammation, nerve regeneration, tumor growth, and metastases.

Thus, it is desirable to have other members of the ADAMTS subfamily of proteins, the nucleic acids that encode such proteins, and antibodies that are specific for such proteins. Such molecules are useful research tools for studying development of the extracellular matrix during embryogenesis and fetal development, and for studying disorders or diseases that are characterized by improper development of the extracellular matrix or enhanced or reduced destruction of the extracellular matrix. Such molecules, particularly the nucleic acids and the antibodies, are also useful tools for diagnosing such diseases or for monitoring the efficacy of therapeutic agents that have been developed to treat such diseases.

SUMMARY OF THE INVENTION

The present invention provides novel, isolated, and substantially purified proteins having the characteristics of an ADAMTS protein. The novel proteins are referred to hereinafter individually as "ADAMTS-5", "ADAMTS-6", "ADAMTS-7", "ADAMTS-8", "ADAMTS-9" and "ADAMTS-10", and collectively as "ADAMTS-N". In one embodiment, the ADAMTS-5 protein is a mature mouse protein which comprises amino acid 231 through amino acid 930 of the sequence set forth in SEQ ID NO: 2. In another embodiment, ADAMTS-5 is a human ADAMTS-5 protein which comprises amino acid 1 through amino acid 518 of the sequence set forth in SEQ ID NO: 4. In one embodiment, mature human ADAMTS-6 protein comprises amino acid 245 through amino acid 860 of SEQ ID NO:6. In one embodiment, mature human ADAMTS-7 protein comprises amino acid 233 through amino acid 997 of the sequence set forth in SEQ ID NO: 8. In one embodiment, mature ADAMTS-8 protein is a mouse protein which comprises amino acid 229 through amino acid 905 of the sequence set forth in SEQ ID NO: 10. In another embodiment, ADAMTS-8 protein is a human protein which comprises amino acid 1 through amino acid 245 of the sequence set forth in SEQ ID NO: 12. In one embodiment, mature ADAMTS-9 protein is a human protein which comprises amino acid 236 through amino acid 1882 of the sequence set forth in SEQ ID NO: 14. In another embodiment, ADAMTS-9 protein is a mouse protein which comprises amino acid 1 through amino acid 874 of the sequence set forth in SEQ ID NO: 16. In one embodiment, mature ADAMTS-10 protein is a human protein which comprises amino acid 212 through amino acid 1081 of the sequence set forth in SEQ ID NO: 18. In another embodiment, ADAMTS-10 protein is a mouse protein which comprises amino acid 1 through amino acid 547 of the sequence set forth in SEQ ID NO: 20.

The present invention also provides isolated polynucleotides which encode an ADAMTS-N protein or a variant thereof, polynucleotide sequences complementary to such polynucleotides, vectors containing such polynucleotides, and host cells transformed or transfected with such vectors. The present invention also relates to antibodies which are immunospecific for one or more of the ADAMTS-N proteins. The present invention also relates to a protein referred to hereinafter as ADAMTS-R1 (ADAM-TS Related protein -1) and the polynucleotides which encode such protein. In one embodiment, the ADAMTS-R1 protein comprises amino acid 1 through amino acid 525 of the sequence set forth in SEQ. ID NO: 22.

BRIEF DESCRIPTION OF THE DRAWINGS

FIG. 1 shows an amino acid sequence (SEQ ID NO:2) of a full-length mouse ADAMTS-5 protein and a nucleic acid sequence (SEQ ID NO: 1) which encodes such protein.

FIG. 2 shows an amino acid sequence of a partial human ADAMTS-5 protein and a nucleic acid sequence (SEQ ID NO:3) which encodes such protein.

FIG. 3 shows an amino acid sequence (SEQ ID NO:5) of a full-length human ADAMTS-6 protein and a nucleic acid sequence (SEQ ID NO:4) which encodes such protein.

FIG. 4 shows an amino acid sequence (SEQ ID NO:7) of a full-length human ADAMTS-7 protein and a nucleic acid sequence (SEQ ID NO:6) which encodes such protein.

FIG. 5 shows an amino acid sequence (SEQ ID NO:9) of a full-length mouse ADAMTS-8 protein and a nucleic acid sequence (SEQ ID NO:8) which encodes such protein.

FIG. 6 shows an amino acid sequence (SEQ ID NO:11) of a partial human ADAMTS-8 protein and a nucleic acid sequence (SEQ ID NO:10) which encodes such amino acid sequence.

FIG. 7 shows an amino acid sequence (SEQ ID NO:13), of a full-length human ADAMTS-9 protein and a nucleic acid sequence (SEQ ID NO:12) which encodes such protein.

FIG. 8 shows an amino acid sequence (SEQ ID NO:15) of a partial mouse ADAMTS-9 protein and a nucleic acid sequence (SEQ ID NO:14) which encodes such amino acid sequence.

FIG. 9 shows an amino acid sequence (SEQ ID NO:17) of a full-length human ADAMTS-10 protein and a nucleic acid sequence (SEQ ID NO:16) which encodes such protein.

FIG. 10 shows an amino acid sequence (SEQ ID NO:19) of a partial mouse ADAMTS-10 protein and a nucleic acid sequence (SEQ ID NO:18) which encodes such amino acid sequence.

FIG. 11 shows an amino acid sequence (SEQ ID NO:21) of a full length ADAMTS-R1 protein and a nucleic acid sequence (SEQ ID NO:20) which encodes such protein.

FIG. 12 depicts the cloning strategy used for isolation of a. mouse and human ADAMTScDNAs b. human ADAMTS-6 cDNA and c. human ADAMTS-7 cDNA. The domain organization of each protein relative to the cDNA clones (thin line) is shown as is the extent of overlap between clones. The original I.M.A.G.E. clones used are underlined. Intronic regions of incompletely spliced transcripts are shown by the angled dotted lines. DNA scale marker (in bp) and amino acid scale marker are at upper right. Location of the probe used for in situ hybridization (ISH) is shown in a.

FIG. 13 shows the predicted amino acid sequences of a. the mouse and human ADAMTS-5 proteins(alignment shows mouse sequence above, partial human sequence below) b. ADAMTS-6, and c. ADAMTS-7. The active-site sequences and proposed Met-turn are enclosed in boxes. Potential furin cleavage site(s) are indicated by arrows. Thrombospondin type- 1 modules are underlined. Potential sites for N-inked glycosylation are overlined. Cysteine residues within the context of an MMP-like "cysteine switch" are indicated by the solid circles. Other cysteine residues are indicated by asterisks. The prodomain extends until the furin cleavage site, and the catalytic domain extends from the furin cleavage site to the approximate start of the disintegrin-like sequence (Dis). The start of the spacer domain is indicated; the region between the N-terminal TS domain and the spacer domain is the cysteine-rich domain. The single letter amino acid code is used.

DETAILED DESCRIPTION OF THE INVENTION

ADAMTS-N Proteins

Figure 12:
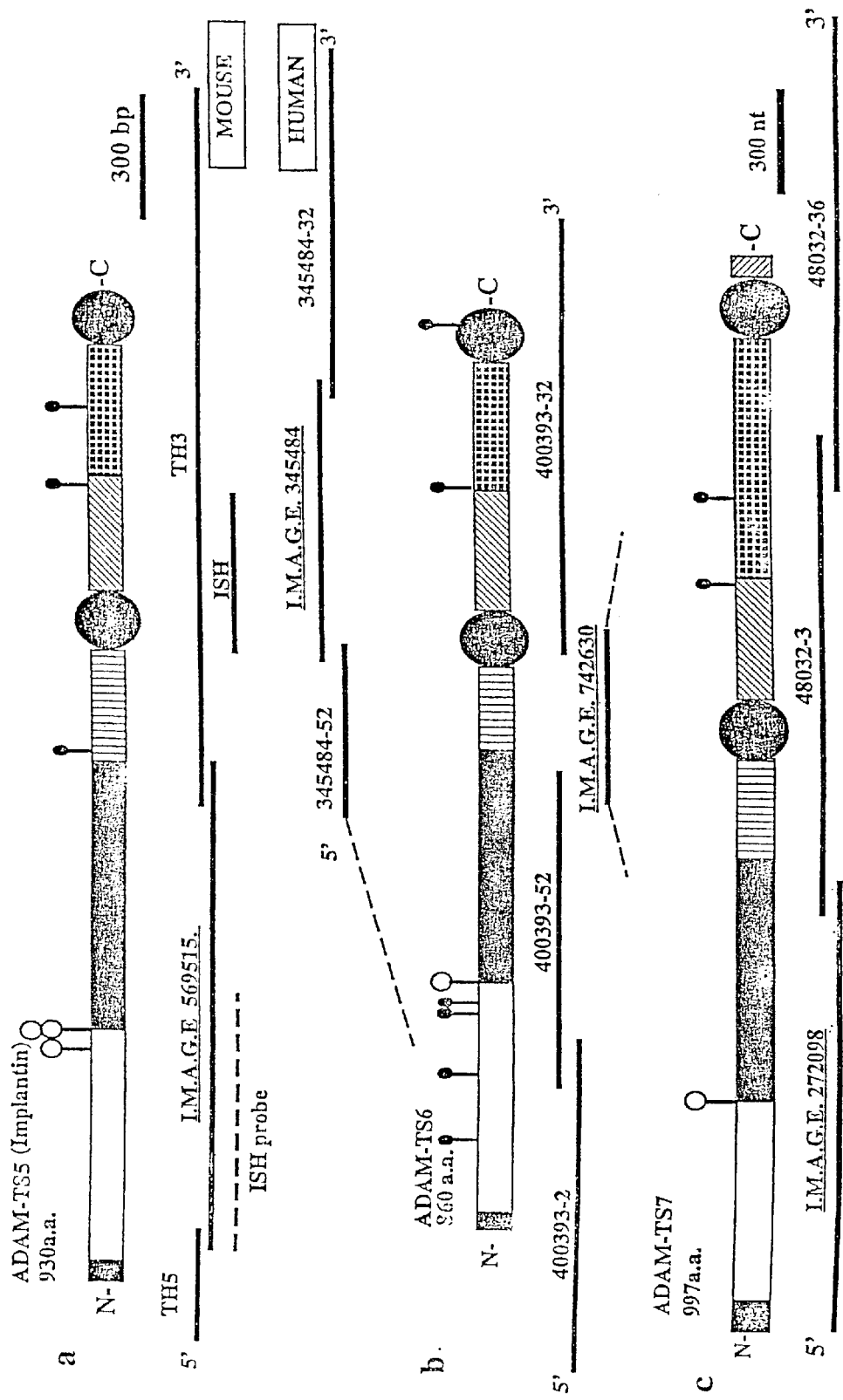

The present invention relates to novel, isolated, substantially purified, mammalian proteins belonging to the ADAMTS subfamily of metalloproteases. As used herein, the term "substantially purified" refers to a protein that is removed from its natural environment, isolated or separated, and at least 60% free, preferably 75% free, and most preferably 90% free from other components with which it is naturally associated.

The novel mammalian proteins are ADAMTS-5, ADAMTS-6, ADAMTS-7, ADAMTS-8, ADAMTS-9 and ADAMTS-10, collectively ADAMTS-N. In one embodiment, the ADAMTS-5 protein is a mature mouse protein which comprises amino acid 231 through amino acid 930 of the sequence set forth in SEQ ID NO: 2. In one embodiment, ADAMTS-6 protein is a mature human protein which comprises amino acid 245 through amino acid 860 of SEQ ID NO:5. In one embodiment, the ADAMTS-7 protein is a mature human protein which comprises amino acid 233 through amino acid 997 of the sequence set forth in SEQ ID NO: 7. In one embodiment, the ADAMTS-8 protein is a mature mouse protein which comprises amino acid 229 through amino acid 905 of the sequence set forth in SEQ ID NO:9. In another embodiment, the ADAMTS-8 protein is a human protein which comprises amino acid I through amino acid 245 of the sequence set forth in SEQ ID NO: 11. In one embodiment, the ADAMTS-9 is a mature human protein which comprises amino acid 236 through amino acid 1882 of the sequence set forth in SEQ ID NO: 13. In another embodiment, the ADAMTS-9 protein is a mouse protein which comprises amino acid 1 through amino acid 874 of the sequence set forth in SEQ ID NO: 15. In one embodiment, the ADAMTS-10 protein is a mature human protein which comprises amino acid 212 through amino acid 1081 of the sequence set forth in SEQ ID NO: 18. In another embodiment the ADAMTS-10 protein is a mouse protein which comprises amino acid 1 through amino acid 525 of the sequence set forth in SEQ ID NO:19.

All of the novel ADAMTS-N proteins starting at the amino terminus comprise a signal sequence followed by a putative pro region which contains a consensus sequence for furin cleavage (except for ADAMTS-10), a catalytic domain, a domain of 60–90 residues with 35 to 45% similarity to snake venom disintegrins, a TS module, a cysteine rich domain containing multiple conserved cysteine residues, a spacer domain, and one or multiple C terminal TS modules. (See FIG. 12.) As determined using the BLAST software from the National Center for Biotechnology Information, the predicted mature forms of the ADAMTS-N proteins show an overall 20–30% similarity to each other and to ADAMTS-1–4, although this may be considerably higher or lower for individual domains as described below.

The ADAMTS-N proteins also encompass variants of the ADAMTS-N proteins shown in FIGS. 1–10. A "variant" as used herein, refers to a protein whose amino acid sequence is similar to one of the amino acid sequences shown in FIGS. 1–10, hereinafter referred to as the reference amino acid sequence, but does not have 100% identity with the reference sequence. The variant protein has an altered sequence in which one or more of the amino acids in the reference sequence is deleted or substituted, or one or more amino acids are inserted into the sequence of the reference amino acid sequence. As a result of the alterations, the variant protein has an amino acid sequence which is at least 95% identical to the reference sequence, preferably, at least 97% identical, more preferably at least 98% identical, most preferably at least 99% identical to the reference sequence. Variant sequences which are at least 95% identical have no more than 5 alterations, i.e. any combination of deletions, insertions or substitutions, per 100 amino acids of the reference sequence. Percent identity is determined by comparing the amino acid sequence of the variant with the reference sequence using MEGALIGN project in the DNA STAR program. Sequences are aligned for identity calculations using the method of the software basic local alignment search tool in the BLAST network service (the National Center for Biotechnology Information, Bethesda, Md) which employs the method of Altschul, S. F., Gish, W., Miller, W., Myers, E. W. & Lipman, D. J. (1990) *J Mol. Biol.* 215, 403–410. Identities are calculated by the Align program (DNAstar, Inc.) In all cases, internal gaps and amino acid insertions in the candidate sequence as aligned are not ignored when making the identity calculation.

While it is possible to have nonconservative amino acid substitutions, it is preferred that the substitutions be conservative amino acid substitutions, in which the substituted amino acid has similar structural or chemical properties with the corresponding amino acid in the reference sequence. By way of example, conservative amino acid substitutions involve substitution of one aliphatic or hydrophobic amino acids, e.g. alanine, valine, leucine and isoleucine, with another; substitution of one hydroxyl-containing amino acid, e.g. serine and threonine, with another; substitution of one acidic residue, e.g. glutamic acid or aspartic acid, with another; replacement of one amide-containing residue, e.g. asparagine and glutamine, with another; replacement of one aromatic residue, e.g. phenylalanine and tyrosine, with another; replacement of one basic residue, e.g. lysine, arginine and histidine, with another; and replacement of one small amino acid, e.g., alanine, serine, threonine, methionine, and glycine, with another.

The alterations are designed not to abolish the immunoreactivity of the variant protein with antibodies that bind to the reference protein. Guidance in determining which amino acid residues may be substituted, inserted or deleted without abolishing immunoreactivity of the variant protein with an antibody specific for the respective reference protein are found using computer programs well known in the art, for example, DNASTAR software.

The ADAMTS-N proteins also encompass fusion proteins comprising an ADAMTS-N protein and a tag, i.e., a second protein or one or more amino acids, preferably from about 2 to 65 amino acids, more preferably from about 34 to about 62 amino acids, which are added to the amino terminus of, the carboxy terminus of, or any point within the amino acid sequence of an ADAMTS-N protein, or a variant of such protein. Typically, such additions are made to stabilize the resulting fusion protein or to simplify purification of an expressed recombinant form of the corresponding ADAMTS-N protein or variant of such protein. Such tags are known in the art. Representative examples of such tags include sequences which encode a series of histidine residues, the epitope tag FLAG, the Herpes simplex glycoprotein D, beta-galactosidase, maltose binding protein, or glutathione S-transferase.

The ADAMTS-N proteins also encompass ADAMTS-N proteins in which one or more amino acids, preferably no more than 10 amino acids, in the respective ADAMTS-N protein are altered by posttranslation processes or synthetic methods. Examples of such modifications include, but are not limited to, acetylation, amidation, ADP-ribosylation, covalent attachment of flavin, covalent attachment of a heme moiety, covalent attachment of a nucleotide or a lipid, cross-linking gamma-carboxylation, glycosylation, hydroxylation, iodination, methylation, myristoylation, oxidation, pegylation, proteolytic processing, phosphorylation, prenylation, racemization, sulfation, and transfer-RNA mediated additions of amino acids to proteins such as arginylation and ubiquitination.

The ADAMTS-N proteins are immunogenic and, thus, are useful for preparing antibodies. Such antibodies are useful for identifying and diagnosing disorders which are associated with decreased expression or activity or increased expression of an ADAMTS-N protein. The ADAMTS-N protein may also be useful for treating such disorder.

Diseases involving enhanced or depressed proteolyisis of the core proteins of the extracellular may involve enhanced expression or activity or decreased expression or activity of one or more ADAMTS-N proteins. Thus, ADAMST-N proteins may be used to identify drugs, polypeptides, autoantibodies, or other natural compounds which bind to an ADAMTS-N protein with sufficient affinity to block or facilitate its activity. The activity of the ADAMTS-N protein is assayed in the presence and the absence of the putative inhibitor or facilitator using any of a variety of protease assays known in the art. In general, the activity of the ADAMTS-N protein is assayed through the use of a peptide or protein substrate having a known or putative cleavage site for the ADAMTS-N protein. To detect cleavage or to monitor the extent of cleavage, the substrate is tagged in a manner which provides a detectable signal upon cleavage. For example, the substrate may be tagged with a fluorescent group on one side of the cleavage site and with a fluorescence-quenching group on the opposite side of the cleavage site. Upon cleavage by the substrate, quenching is eliminated and a detectable signal is produced. Alternatively, the substrate is tagged with a calorimetric leaving group that more strongly absorbs upon cleavage. Agents which block ADAMTS-N-catalyzed cleavage of a protein substrate may be administered to a subject to block proteolysis of the corresponding protein substrate.

ADAMTS-R1 Protein

The present invention also relates to a protein, referred to hereinafter as "ADAMTS-R1". From its amino to its carboxyl terminus, ADAMTS-R1 comprises a signal peptide sequence, a TS1 module, a cysteine-rich domain, a spacer domain, and three TS 1 modules. Thus, ADAMTS-R1 has a structure which is related to or similar to an ADAMTS-N protein, but which lacks a catalytic domain and a disintegrin-like domain. In one embodiment, ADAMTS-R1 protein comprises amino acid 1 through amino acid 525 of the amino acid sequence, SEQ ID NO:21, shown in FIG. 11. Such protein has a 30–40% overall sequence identity with similar regions of the ADAMTS-N proteins. The ADAMTS-R1 proteins also encompass variants of the amino acid sequence shown in FIG. 11 and fusion proteins which contain the amino acid sequence shown in FIG. 11 or a variant thereof. On the basis of its domain organization, it is expected that ADAMTS-R1 can bind to extracellular matrix or cell surface molecules, including ADAMTS-N substrates. Thus, it is expected that ADAMTS-R1 can be used as an cell-matrix or cell-cell adhesion molecule or an ADAMTS-N competitive inhibitor. The ADAMTS-R1 proteins are also useful for preparing antibodies. Such antibodies are useful for identifying tissues where ADAMTS-R1 is expressed and for diagnosing disorders which are associated with decreased expression or increased expression of an ADAMTS-R1 protein.

Polynucleotides

The present invention also provides isolated polynucleotides which encode the mammalian ADAMTS-N proteins and the mammalian ADAMTS-R1 protein. FIG. 1 shows one embodiment of a polynucleotide, SEQ ID NO: 1, which encodes the full-length mouse ADAMTS-5 protein. FIG. 2 shows one embodiment of a polynucleotide; SEQ ID NO: 3, which encodes a partial human ADAMTS-5 protein. FIG. 3 shows one embodiment of a polynucleotide; SEQ ID NO: 5, which encodes a full-length human ADAMTS-6 protein. FIG. 4 shows one embodiment of a polynucleotide; SEQ ID NO: 7, which encodes a full-length human ADAMTS-7 protein. FIG. 5 shows one embodiment of a polynucleotide; SEQ ID NO: 9, which encodes a full-length mouse ADAMTS-8 protein. FIG. 6 shows one embodiment of a polynucleotide; SEQ ID NO: 11, which encodes a partial human ADAMTS-8 protein. FIG. 7 shows one embodiment of a polynucleotide; SEQ ID NO: 13, which encodes a full-length human ADAMTS-9 protein. FIG. 8 shows one embodiment of a polynucleotide; SEQ ID NO: 15, which encodes a partial ADAMTS-9 protein. FIG. 9 shows one embodiment of a polynucleotide; SEQ ID NO: 17, which encodes a full-length human ADAMTS-10 protein. FIG. 10 shows one embodiment of a polynucleotide; SEQ ID NO: 19, which encodes a partial mouse ADAMTS-10 protein. FIG. 11 shows one embodiment of a polynucleotide; SEQ ID NO: 21, which encodes a full-length ADAMTS-R1 protein.

Due to the known degeneracy of the genetic code wherein more than one codon can encode the same amino acid, a DNA sequence may vary from that shown in SEQ ID NO: 1 and still encode an ADAMTS-5 protein having the amino acid sequence of SEQ ID NO: 2. Similarly, a DNA sequence may vary from that shown in SEQ ID NO:5, and still encode an ADAMTS-6 protein having the amino acid sequence set forth in SEQ ID NO:6. Similarly a DNA sequence may vary from that shown in SEQ ID NOS: 7, 9, 11, and 13, and still encode the amino acid sequences shown in SEQ ID NOS: 8, 10, 12, and 14, respectively. Such variant DNA sequence may result from silent mutations, such as for example those that occur during PCR amplification or from deliberate mutagenesis of a native sequence.

The present polynucleotides also encompass polynucleotides having sequences that are capable of hybridizing to the nucleotide sequences of FIGS 1–11 under stringent conditions, preferably highly stringent conditions. Hybridization conditions are based on the melting temperature™ of the nucleic acid binding complex or probe, as described in Berger and Kimmel (1987) Guide to Molecular Cloning Techniques, Methods in Enzymology, vol 152, Academic Press. The term "stringent conditions, as used herein, is the "stringency" which occurs within a range from about Tm-5 (5° below the melting temperature of the probe) to about 20° C. below Tm. As used herein "highly stringent" conditions employ at least 0.2 ×SSC buffer and at least 65° C. As recognized in the art, stringency conditions can be attained by varying a number of factors such as the length and nature, i.e, DNA or RNA, of the probe; the length and nature of the target sequence, the concentration of the salts and other components, such as formamide, dextran sulfate, and polyethylene glycol, of the hybridization solution. All of these factors may be varied to generate conditions of stringency which are equivalent to the conditions listed above.

The present polynucleotides also encompasses alleles of the ADAMTS-N and ADAMTS-R1 encoding sequences. As used herein, an allele or allelic sequence is an alternative form of an ADAMTS-N or ADAMTS-R1 encoding sequence which is present at the same gene locus. The allele may result from one or more mutations in the ADAMTS-N or ADAMTS-R1 encoding sequence. Such mutations typically arise from natural addition, deletion of substitution of nucleotides in the open reading frame sequences. Any gene which encodes an ADAMTS-N protein or ADAMTS-R1 protein may have none, one, or several allelic forms. Such alleles are identified using conventional techniques, such as for example screening libraries with probes having sequences identical to or complementary with one or more ADAMTS-N polynucleotides.

The present polynucleotides also encompass altered polynucleotides which encode ADAMTS-N proteins, ADAMTS-R1 proteins, and variants thereof. Such alterations include deletions, additions, or substitutions. Such alterations may produce a silent change and result in an ADAMTS-N protein having the same amino acid sequence as the ADAMTS-N protein encoded by the unaltered polynucleotide. Such alterations may produce a nucleotide sequence possessing non-naturally occurring codons. For example, codons preferred by a particular prokaryotic or eucaryotic host may be incorporated into the nucleotide sequences shown in FIGS. 1–11 to increase the rate of expression of the proteins encoded by such sequences. Such alterations may also introduce new restriction sites into the sequence or result in the production of an ADAMTS-N or ADAMTS-R1 variant. Typically, such alterations are accomplished using site-directed mutagenesis.

The polynucleotides are useful for producing ADAMTS-N or ADAMTS-R1 proteins. For example, an RNA molecule encoding an ADAMTS-N protein is used in a cell-free translation systems to prepare such protein. Alternatively, a DNA molecule encoding an ADAMTS-N protein is introduced into an expression vector and used to transform cells. Suitable expression vectors include for example chromosomal, nonchromosomal and synthetic DNA sequences, e.g., derivatives of SV40, bacterial plasmids, phage DNAs; yeast plasmids, vectors derived from combinations of plasmids and phage DNAs, viral DNA such as vaccinia, adenovirus, fowl pox virus, pseudorabies, baculovirus, and retrovirus. The DNA sequence is introduced into the expression vector by conventional procedures.

Accordingly, the present invention also relates to recombinant constructs comprising one or more of the present polynucleotide sequences. Suitable constructs include, for example, vectors, such as a plasmid, phagemid, or viral vector, into which a sequence that encodes an ADAMTS-N protein or an ADAMTS-Ri protein has been inserted. In the expression vector, the DNA sequence which encodes the ADAMTS-N protein is operatively linked to an expression control sequence, i.e., a promoter, which directs mRNA synthesis. Representative examples of such promoters, include the LTR or SV40 promoter, the E. coli lac or trp, the phage lambda PL promoter and other promoters known to control expression of genes in prokaryotic or eukaryotic cells or in viruses. The promoter may also be the natural promoter of the ADAMTS-N encoding sequence. The expression vector, preferably, also contains a ribosome binding site for translation initiation and a transcription terminator. Preferably, the recombinant expression vectors also include an origin of replication and a selectable marker, such as for example, the ampicillin resistance gene of E. coli to permit selection of transformed cells, i.e. cells that are expressing the heterologous DNA sequences. The polynucleotide sequence encoding the ADAMTS-N protein is incorporated into the vector in frame with translation initiation and termination sequences.

The polynucleotides encoding an ADAMTS-N or ADAMTS-R1 protein are used to express recombinant protein using techniques well known in the art. Such techniques are described in Sambrook, J. et al (1989) Molecular Cloning A Laboratory Manual, Cold Spring Harbor Press, Plainview, N.Y. and Ausubel, F. M. et al. (1989) Cuurent Protocols in Molecular Biology, John Wile & Sons, New York, NY.

Polynucleotides encoding an ADAMTS-N or ADAMTS-R1 protein may also be used for diagnostic purposes. The polynucleotides may be used to detect and quantify ADAMTS-N or ADAMTS-R1 gene transcripts in biopsied tissues in which enhanced expression or reduced expression of the corresponding ADAMTS-N or ADAMTS-R1 gene is correlated with a disease. The diagnostic assay may be used to determine whether expression is absent, present, or altered and to determine whether certain therapeutic agents modulate expression of the corresponding ADAMTS-N or ADAMTS-R1 gene.

Also encompassed by the present invention, are single stranded polynucleotides, hereinafter referred to as antisense polynucleotides, having sequences which are complementary to the DNA and RNA sequences which encode the ADAMTS-N or ADAMTS-R1 proteins. The term complementary as used herein refers to the natural binding of the polynucleotides under permissive salt and temperature conditions by base pairing.

The present invention also encompasses oligonucleotides that are used as primers in polymerase chain reaction (PCR) technologies to amplify transcripts of the genes which encode the ADAMTS-N and ADAMTSR-1 proteins or portions of such transcripts. Preferably, the primers comprise 18–30 nucleotides, more preferably 19–25 nucleotides. Preferably, the primers have a G+C content of 40% or greater. Such oligonucleotides are at least 98% complementary with a portion of the DNA strand, i.e., the sense strand, which encodes the respective ADAM-TS family protein or a portion of its corresponding antisense strand. Preferably, the primer has at least 99% complementarity, more preferably 100% complementarity, with such sense strand or its corresponding antisense strand. Primers which are which have 100% complementarity with the antisense strand of a double-stranded DNA molecule which encodes an ADAMTS-N protein have a sequence which is identical to a sequence contained within the sense strand. The identity of primers which are 15 nucleotides in length and have full complementarity with a portion of the antisense strand of a double-stranded DNA molecule which encodes the ADAMTS-N protein is determined using the nucleotide sequences, shown in FIGS. 1–11 and described by the general formula a–b; where a is any integer between 1 and the position number of the nucleotide which is located 15 residues upstream of the 3'end of the sense or antisense strand of the cDNA sequences shown in FIGS. 1–11; where b is equal to a+14; and where both a and b correspond to the positions of nucleotide residues of the cDNA sequences shown in FIGS. 1–11.

The present invention also encompasses oligonucleotides that are useful as hybridization probes for for isolating and identifying cDNA clones and genomic clones encoding the ADAMTS-N or ADAMTS-R1 protein or allelic forms thereof. Such hybridization probes are also useful for detecting transcripts of the genes which encode the ADAMTS-N family proteins or for mapping of the genes which encode the ADAMTS-N proteins Preferably, such oligonucleotides comprise at least 210 nucleotides, more preferably at least 230, most preferably from about 210 to 280 nucleotides. Such hybridization probes have a sequence which is at least 90% complementary with a sequence contained within the sense strand of a DNA molecule which encodes an ADAMTS-N protein or ADAMTS-R1 protein or with a sequence contained within its corresponding antisense strand. Such hybridization probes bind to the sense strand under stringent conditions. The term "stringent conditions" as used herein is the binding which occurs within a range from about Tm 5° C. (5° C. below the melting temperature Tm of the probe) to about 20° C. to 25° C. below Tm. The probes are used in Northern assays to detect transcripts of ADAMTS-N homologous genes and in Southern assays to detect ADAMTS-N homologous genes. The identity of probes which are 200 nucleotides in length and have full complementarity with a portion of the antisense strand of a double-stranded DNA molecule which encodes the ADAMTS-N protein is determined using the nucleotide sequences shown in FIGS. 1–10 and described by the general formula a–b; where a is any integer between 1 and the position number of the nucleotide which is located 200 residues upstream of the 3' end of the sense or antisense strand of the cDNA sequences shown in FIGS. 1–10; b is equal to a +200; and where both a and b correspond to the positions of nucleotide residues of the cDNA sequences shown in FIGS. 1–10.

Such probes or primers are also useful for identifying tissues or cells in which the corresponding ADAMTS-N or ADAMTS-R1 gene is preferentially expressed either constitutively or at particular state of tissue differentiation or development or in disease states. Expression of the is ADAMTS-N or ADAMTS-R1 gene in a particular tissue or group of cells is determined using conventional procedures including, but not limited to, Northern analysis, in situ hybridization to RNA or RT- PCR amplification. Isolated polynucleotides encoding an ADAMTS-N or ADAMTS-R1 protein are also useful as chromosome markers to map linked gene positions, to identify chromosomal aberrations such as translocations, inversions and trisomies, to compare with endogenous DNA sequences in patients to identify potential genetic disorders, and as probes to hybridize and thus discover novel, related DNA sequences. For use in such studies and assays, the probes may be labeled with radioisotopes, fluorescent labels, or enzymatic labels. The assays include, but are not limited to, Southern blot, in situ hybridization to DNA in cells and chromosomes, PCR, and allele specific hybridization.

Antibodies

In another aspect, the present invention relates to antibodies which are specific for and bind to the ADAMTS-5 protein, the ADAMTS-6 protein, the ADAMTS-7 protein, the ADAMTS-8 protein, the ADAMTS-9 protein, the ADAMTS-10 protein, or the ADAMTS-R1 protein. Such antibodies are useful research tools for identifying tissues that contain elevated levels of the respective protein and for purifying the respective protein from cell or tissue extracts, medium of cultured cells, or partially purified preparations of intracellular and extracellular proteins by affinity chromatography. Such antibodies are also useful for identifying and diagnosing diseases associated with elevated or reduced levels of an ADAMTS-N protein or ADAMTS-R1 protein. Such antibodies are also useful for monitoring the effect of therapeutic agents on the synthesis and secretion of ADAMTS-N proteins by cells in vitro and in vivo. Such antibodies may also be employed in procedures, such as co-immunoprecipitation and co-affinity chromatography, for identifying other proteins, activators and inhibitors which bind to an ADAMTS-N or ADAMTS-R1 protein.

The present invention also provides a method for detecting an ADAMTS-N or ADAMTS-R1 protein in a bodily sample from a patient using antibodies immunospecific for an ADAMTS-N or ADAMTS-R1 protein. The method comprises contacting the antibody with a sample taken from the patient; and assaying for the formation of a complex between the antibody and the corresponding ADAMTS-N or ADAMTS-R1 protein present in the sample. The sample may be a tissue or a biological fluid, including but not limited to whole blood, serum, synovial fluid, stool, urine, cerebrospinal fluid, semen, diagnostic washes from trachea, stomach and other bowel segments, tissue biopsies or excised tissue, cells obtained from swabs and smears. To monitor changes in expression of the ADAMTS-N protein during fetal development and pregnancy, it is preferred that the sample be amniotic fluid. To monitor changes in expression of the ADAMTS-N protein during joint disorders, the preferred sample is synovial fluid. To monitor changes in expression of ADAMTS-N proteins during cancer, the preferred samples include, but are not limited to, serum, body fluids, or biopsy tissue. To monitor changes in expression of ADAMTS-N proteins during inflammation the preferred samples include, but are not limited to, serum, body fluids, or biopsy tissue.

The sample may be untreated, or subjected to precipitation, fractionation, separation, or purification before combining with the anti-ADAMTS-N protein antibody. For ease of detection, it is preferred that isolated proteins from the sample be attached to a substrate such as a column, plastic dish, matrix, or membrane, preferably nitrocellulose. Preferably, the detection method employs an enzyme-linked immunosorbent assay (ELISA) or a Western immunoblot procedure.

Interactions between an ADAMTS-N protein in the sample and the corresponding anti-ADAMTS-N antibody are detected by radiometric, calorimetric, or fluorometric means, size-separation, or precipitation. Preferably, detection of the antibody-ADAMTS-N protein complex is by addition of a secondary antibody that is coupled to a detectable tag, such as for example, an enzyme, fluorophore, or chromophore. Formation of the complex is indicative of the presence of the ADAMTS-N protein in the test sample. Thus, the method is used to determine whether there is a decrease or increase in the levels of the ADAMTS-N protein in a test sample as compared to levels of the ADAMTS-N protein in a control sample and to quantify the amount of the ADAMTS-N protein in the test sample. Deviation between control and test values establishes the parameters for diagnosing the disease.

Preparing the ADAMTS-N Proteins and the ADAMTS-R1 Protein

The ADAMTS-N proteins and the ADAMT-SR1 protein may be produced by conventional peptide synthesizers. The ADAMTS-N proteins and the ADAMTS-R1 protein may also be produced using cell-free translation systems and RNA molecules derived from DNA constructs that encode an ADAMTS-N protein or an ADAMTS-R1 protein. Alternatively, ADAMTS-N proteins are made by transfecting host cells with expression vectors that comprise a DNA sequence that encodes the respective ADAMTS-N protein and then inducing expression of the protein in the host cells. For recombinant production, recombinant constructs comprising one or more of the sequences which encode the ADAMTS-N protein or a variant thereof are introduced into host cells by conventional methods such as calcium phosphate transfection, DEAE-dextran mediated transfection, transvection, microinjection, cationic lipid-mediated transfection, electroporation, transduction, scrape lading, ballistic introduction or infection.

The ADAMTS-N protein and the ADAMTS-R1 protein may be expressed in suitable host cells, such as for example, mammalian cells, yeast, bacteria, insect cells or other cells under the control of appropriate promoters using conventional techniques. Suitable hosts include, but are not limited to, E. coli, P. pastoris, Cos cells and 293 HEK cells. Following transformation of the suitable host strain and growth of the host strain to an appropriate cell density, the cells are harvested by centrifugation, disrupted by physical or chemical means, and the resulting crude extract retained for further purification of the ADAMTS-N protein or the ADAMTS-R1 protein.

Conventional procedures for isolating recombinant proteins from transformed host cells, such as isolation by initial extraction from cell pellets or from cell culture medium, followed by salting-out, and one or more chromatography steps, including aqueous ion exchange chromatography, size exclusion chromatography steps, and high performance liquid chromatography (HPLC), and affinity chromatography may be used to isolate the recombinant ADAMTS-N protein or ADAMTS-R1 protein Preparation of Antibodies The ADAMTS-N proteins, and variants thereof are used as immunogens to produce antibodies immunospecific for one or more ADAMTS-N protein. The term "immunospecific" means the antibodies have substantially greater affinity for one or more ADAMTS-N protein than for other proteins. Such antibodies may include, but are not limited to, polyclonal, monoclonal, chimeric, single chain, and Fab fragments.

Antibodies are also prepared using an oligopeptide having a sequence which is identical to a portion of the amino acid sequence of an ADAMTS-N protein. Preferably the oligopeptide has an amino acid sequence of at least five amino acids, and more preferably, at least 10 amino acids that are identical to a portion of the amino acid sequence of an ADAMTS-N protein. Such peptides are conventionally fused with those of another protein such as keyhole limpet hemocyanin and antibody produced against the chimeric molecule. One preferred oligopeptide for preparing an antibody to mouse ADAMTS-5 has the sequence (C)HIKVRQFKAKDQTRF, SEQ ID NO: 30. Another preferred oligopeptide for preparing an antibody to ADAMTS-5 is CEAKNGYQSDAKGVKTFVEWVPKYAG, SEQ ID NO: 31. One preferred oligopeptide for preparing an antibody to ADAMTS-6 has the sequence SVSIERFVETLVVADK(C), SEQ ID NO:23. One preferred oligopeptide for preparing an antibody to ADAMTS-7 has the sequence (C)EVAEAANFLALRSEDPEKY, SEQ ID NO:24. One preferred oligopeptide for preparing an antibody to ADAMTS-8 has the sequence CVKEDVENPKAVVDGDWGP, SEQ ID NO:25. One preferred oligopeptide for preparing an antibody to ADAMTS-9 has the sequence QHPFQNEDYRPRSASPSRTH, SEQ ID NO:26. Another preferred oligopeptide for preparing an antibody to ADAMTS-9 has the sequence PQNCKEVKRLKGASEDGEYF, SEQ ID NO:27. One preferred oligopeptide for preparing an antibody for ADAMTS-R1 has the sequence QELEEGAAVSEEPS, SEQ ID NO:28. Another preferred oligopeptide for preparing an antibody for ADAMTS-R1 has the sequence YYPENIKPKPKLQE; SEQ ID NO:29.

Polyclonal antibodies are generated using conventional techniques by administering the ADAMTS-N protein or a chimeric molecule to a host animal. Depending on the host species, various adjuvants may be used to increase immunological response. Among adjuvants used in humans, Bacilli Calmette-Guerin (BCG), and Corynebacterium parvum are especially preferable. Conventional protocols are also used to collect blood from the immunized animals and to isolate the serum and or the IgG fraction from the blood.

For preparation of monoclonal antibodies, conventional hybridoma techniques are used. Such antibodies are produced by continuous cell lines in culture. Suitable techniques for preparing monoclonal antibodies include, but are not limited to, the hybridoma technique, the human B-cell hybridoma technique, and the EBV hybridoma technique.

Various immunoassays may be used for screening to identify antibodies having the desired specificity. These include protocols which involve competitive binding or immunoradiometric assays and typically involve the measurement of complex formation between the respective ADAMTS-N protein and the antibody.

Polynucleotides that Encode ADAMTS-N Proteins

Polynucleotides comprising sequences encoding an ADAMTS-N protein or an ADAMTS-R1 protein may be synthesized in whole or in part using chemical methods. Polynucleotides which encode an ADAMTS-N protein, particularly alleles of the genes which encode the ADAMTS-N protein, may be obtained by screening a genomic library or cDNA library with a probe comprising sequences identical or complementary to the sequences shown in FIGS. 1–10 or with antibodies immunospecific for a ADAMTS-N protein to identify clones containing such polynucleotide.

EXAMPLE 1

ADAMTS-5 Protein

A cDNA encoding mouse ADAMTS-5 protein was obtained using IMAGE Clone 569515, purchased from Research Genetics, Huntsville, Alabama and 7 day old mouse embryo cDNA library from Clontech, Palo Alto, Calif. A cDNA encoding human ADAMTS-5 protein was obtained using IMAGE Clone 345484 purchased from Research Genetics, Huntsville, Alabama and a human fetal brain cDNA from Clontech. The clone inserts were sequenced in their entirety. Using oligonucleotide primers based on the sequences at the ends of the clone inserts as template, successive rounds of RACE (Rapid Amplification of cDNA Ends) by PCR was performed at 5' and 3 ends. RACE primers were generated 50–200 bp from the ends of the sequences so that the contiguity of RACE clones with the I.M.A.G.E. clone could be clearly established. A single round of 5' and 3' RACE sufficed for cloning of the entire coding sequence of the mouse ADAMTS-5 protein and part of the catalytic zinc binding site through to the stop codon of the human ADAMTS-5 protein. Primers were designed with calculated $T_m$>72° C. and RACE was performed with nested primers for each amplification. PCR used the Advantage PCR reagents (Clontech, Palo Alto, Calif.); the polymerase mix contained both Taq polymerase as well as proofreading polymerase to minimize PCR errors and employed "hot-start" PCR for optimal efficiency. RACE used the following "touch-down" cycle conditions; 95° C. for 1 minute followed by 5 cycles of 95° C. for 0.5 minutes, 72° C. for 5 minutes, then 5 cycles of 95° C. for 0.5 minutes, 70° C. for 5 minutes and 20 cycles of 95° C. for 0.5 minutes, 68° C. for 5 minutes. The PCR products were analyzed by Southern blotting, initially using [$\alpha^{32}$P]-dCTP labeled.

Hybridizing bands were ligated into pGEM-T Easy (Promega, Madison, Wis.) and individual clones were selected by another round of Southern analysis. Automated nucleotide sequencing of both strands of each clone were done at the Molecular Biotechnology Core of the Lerner Research Institute, Cleveland Clinic Foundation and nucleotide sequence data were analyzed using the DNAStar software. By integration of the overlapping sequences thus obtained, a contiguous nucleotide sequence was determined. The nucleotide sequence of the mouse ADAMTS-5 cDNA and the predicted amino acid sequence of the protein encoded by this cDNA are shown in FIG. 1. The nucleotide sequence of the human ADAMTS-5 cDNA and the predicted partial amino acid sequence of the protein encoded by this cDNA are shown in FIG. 2

The predicted molecular mass (Mr) of the mature ADAMTS-5 protein is 73717.50 daltons. It is expected that the actual Mr of the active ADAMTS-5 protein is different due to post-translational modification, which could potentially increase the Mr. The predicted domain organization of ADAMTS-5 protein relative to the cloned cDNA is shown in FIG. 12. The pro-domain of the full-length mouse ADAMTS-5 protein has 3 consensus cleavage signals for furin. The most carboxyl-terminal furin cleavage site in ADAMTS-5 predicts the processing site for generation of the mature protein The catalytic domain of the ADAMTS-5 protein contains eight cysteine residues and a reprolysin -zinc binding signature sequence, i.e., HEIGHLLGLSHD. Five cysteine residues are upstream of the zinc binding sequence, while three residues are downstream, an arrangement that is shared with other ADAMTS members. The zinc binding signature is followed by a "Met-turn". The catalytic domain is followed by a domain with 35% similarity to snake venom disintegrins The disintegrin domain contains eight cysteine residues. The first TS repeat contains 52 residues and is followed by a conserved cysteine-rich sequence termed the cysteine-rich domain, designated "CRD", to distinguish it from the cysteine-free spacer domain. The CRD contains ten conserved cysteines and demonstrates high sequence homology with the CRD of other ADAMTS-N proteins. The spacer domain of mouse ADAMTS-5 is 158 amino acids in length and is followed by a second TS module. ADAMTS-5 contains three potential glycosylation sites in the mature protease one of which is just upstream of the start of the spacer domain and the second lies within the spacer domain and the third is near the start of the disintegrin domain. The human ADAMTS-5 protein and the mouse ADAMTS-protein have 96% sequence identity. ADAMTS-5 bears 46% sequence identity to ADAMTS-4 (KIAA0688), which is characterized as being involved in catabolism of aggrecan core protein in arthritis and 60% identity to ADAMTS-1 which is involved in inflammation.

EXAMPLE 2

ADAMTS-6

The nucleotide sequence of a human cDNA encoding the full-length ADAMTS-6 protein was obtained using IMAGE clone 742630, which encodes EST AA400393, and a human fetal brain cDNA from Clontech. RACE was performed as described above in Example 1. The I.M.A.G.E. clone 742630 contained an ORF flanked by consensus splice sequences, indicating the presence of introns. Two successive rounds of RACE at the 5' end and a single round of RACE at the 3' end provided the complete coding sequence of ADAMTS-6. The putative ATG codon is within a Kozak consensus sequence and encodes the first methionine within the ORF.

The nucleotide sequence of the ADAMTS-6 DNA is shown in FIG. 3 The predicted amino acid sequence, SEQ ID NO:6, of the ADAMTS-6 protein is also shown in FIG. 3. The predicted Mr of the full-length, unprocessed ADAMTS-6 protein is 97,115 daltons, and the predicted Mr of the mature ADAMTS-6 protein is 68412.10 daltons. The domain organization of the ADAMTS-6 protein is shown in FIG. 12. The pro-domain of the full-length ADAMTS-6 protein has one consensus cleavage signal for furin. The catalytic domain of the ADAMTS-6 contains six cysteine residues and the reprolysin -zinc binding signature sequence, HEIVHNFGMNHD, which is followed by a "Met-turn". The catalytic domain is followed by a domain with 35% similarity to snake venom disintegrins The disintegrin domain contains eight cysteine residues. The first TS repeat contains 52 residues and is followed by a conserve CRD sequence which contains ten conserved cysteines and demonstrates high sequence homology with the CRD of other ADAMTS proteins. The spacer domain of ADAMTS-6 is 127 amino acids in length and is followed by a second TS module. ADAMTS-6 contains four potential glycosylation sites within the pro-domain and two in the mature protease one of which is in the cysteine rich domain and the other of which is in the spacer domain. ADAMTS-6 bears 46% sequence identity to ADAMTS- 1, which is involved in inflammation.

EXAMPLE 3

ADAMTS-7.

The nucleotide sequence of a cDNA encoding an ADAMTS-7 protein was obtained using IMAGE clone 272098, which encodes EST N48032, and a human fetal brain cDNA from Clontech. RACE was performed as described above in Example 1. The I.M.A.G.E. clone 272098 encoded a putative pre-pro region and was extended in the 3' -direction by two successive rounds of RACE. A typical signal peptide sequence lies downstream of the first methionine in the translated ORF. This methionine codon lies within a satisfactory Kozak consensus for translation initiation.

The nucleotide sequence of the ADAMTS-7 cDNA is shown in FIG. 4. The predicted amino acid sequence, SEQ ID NO: 8, of the ADAMTS-7 protein is also shown in FIG. 4. The predicted Mr of the full-length, unprocessed ADAMTS-7 protein is 116,607 daltons, and the predicted Mr of the mature ADAMTS-7 protein is 84005 daltons. The domain organization of the ADAMTS-7 protein is shown in FIG. 12. The pro-domain of the full-length ADAMTS-7 protein has one consensus cleavage signal for furin. The catalytic domain of the ADAMTS-7 protein contains eight cysteine residues and the reprolysin -zinc binding signature sequence, HELGHSFGIQHD, which is followed by a "Met-turn". The catalytic domain is followed by a domain with 30% similarity to snake venom disintegrins The disintegrin domain contains eight cysteine residues. The first TS repeat contains 52 residues and is followed by a conserved CRD sequence which contains ten conserved cysteines. The spacer domain of ADAMTS-7 is 221 amino acids in length and is followed by a second TS module and a short sequence containing two cysteine residues. ADAMTS-7 contains three potential glycosylation sites within the mature protease; one of which is just upstream of the spacer domain and one of which is within the spacer domain. ADAMTS-7 bears 35% sequence identity to ADAMTS-1, which is characterized as being involved in inflammation and 32% identity to ADAMTS-2 which is a procollagen processing enzyme.

EXAMPLE 4

ADAMTS-8

The nucleotide sequence of a cDNA encoding a full-length, mouse ADAMTS-8 protein was obtained using IMAGE clone 1260693, which encodes EST AA855532, and a mouse embryo cDNA from Clonetech. The nucleotide sequence of a cDNA encoding a partial ADAMTS-8 human protein was obtained using IMAGE clone 2119838, which encodes EST AI400905, and a human fetal brain cDNA library from Clontech. RACE was performed as described above in Example 1. The nucleotide sequence of the cDNA encoding the full-length ADAMTS-8 mouse protein and the amino acid sequence of such protein is shown in FIG. 5. The nucleotide sequence of the cDNA encoding the partial ADAMTS-8 human protein and the amino acid sequence of such protein is shown in FIG. 6.

The predicted Mr of the full-length, unprocessed ADAMTS-8 mouse protein is 1260693 daltons, and the predicted Mr of the mature ADAMTS-8 protein is 68412.10 daltons. The pro-domain of the full-length ADAMTS-8 protein has one consensus cleavage signal for furin. The catalytic domain contains eight cysteine residues and the reprolysin -zinc binding signature sequence, HELGHVLSMPHD, which is followed by a "Met-turn". The catalytic domain is followed by a domain with 20–30% similarity to snake venom disintegrins The disintegrin-like domain contains eight cysteine residues. The first TS repeat is followed by a conserved CRD sequence which contains 10 conserved cysteines. The spacer domain of ADAMTS-8 is 146 amino acids in length and is followed by a second TS module. The ADAMTS-8 protein contains 4 potential glycosylation sites within the mature protease: one is in the cyteine-rich domain; one is in the catalytic domain; and two are in the disintegrin-like domain. ADAMTS-8 bears 46% sequence identity to ADAMTS-1 and 42% identity to ADAMTS-4.

EXAMPLE 5

ADAMTS-9

The nucleotide sequence of a cDNA encoding a full-length, human ADAMTS-9 protein was obtained using IMAGE clone 646675, which encodes EST AA205581, and a human fetal brain cDNA from Clonetech. The nucleotide sequence of a cDNA encoding a partial ADAMTS-9 mouse protein was obtained using IMAGE clone 535663, which encodes EST AA106215, and a mouse cDNA library obtained from Clonetech. RACE was performed as described above in Example 1. The nucleotide sequence of the cDNA encoding the full-length ADAMTS-9 human protein and the amino acid sequence of such protein is shown in FIG. 6. The nucleotide sequence of the cDNA encoding the partial ADAMTS-9 mouse protein and the amino acid sequence of such protein is shown in FIG. 7.

The predicted Mr of the mature human ADAMTS-9 protein is 189777.20 daltons. The pro-domain of the predicted ADAMTS-9 protein has 3 consensus cleavage signal for furin. The catalytic domain of the ADAMTS-9 contains eight cysteine residues and the reprolysin-zinc binding signature sequence, HELGHVFNMPHD, which is followed by a "Met-turn". The catalytic domain is followed by a domain with 25–30% similarity to snake venom disintegrins The disintegrin domain contains eight cysteine residues. The first TS repeat contains is followed by a conserved CRD sequence which contains 10 conserved cysteines. The spacer domain of ADAMTS-9 is 124 amino acids in length and is followed by 14 additional TS modules and a C-terminal domain. The ADAMTS-9 protein contains 6 potential glycosylation sites within the mature protease: one in the spacer domain, one in TSP1–7, one in TSP1–8, and 3 in the C-terminal domain. The ADAMTS-9 bears 44% sequence identity to ADAMTS-4.

EXAMPLE 6

ADAMTS-10

The nucleotide sequence of a cDNA encoding a full-length ADAMTS-10 protein was obtained using IMAGE clone 110403, which encodes EST AA588434, and a human fetal brain cDNA from Clonetech. The nucleotide sequence of a cDNA encoding a partial, mouse ADAMTS- 10 protein was obtained using IMAGE clone 1077653, which encodes EST AA822090, and a mouse embryo cDNA library from Clonetech. RACE was performed as described above in Example 1. The nucleotide sequence of the human ADAMTS-10 cDNA and the predicted amino acid sequence, SEQ ID 18, of the human ADAMTS-10 protein encoded by such DNA is shown in FIG. 9. The nucleotide sequence of the cDNA encoding the partial mouse ADAMTS-10 protein and the amino acid sequence of such protein is shown in FIG. 10.

The predicted Mr of the mature ADAMTS-10 protein is 95238 daltons. The pro-domain of the full-length ADAMTS-10 protein has no consensus cleavage signal for furin. The catalytic domain of the ADAMTS-10 contains eight cysteine residues and the reprolysin -zinc binding signature sequence, HEIGHTFGMNHD, which is followed by a "Met-turn". The catalytic domain is followed by a domain with 30% similarity to snake venom disintegrins. The disintegrin-like domain contains eight cysteine residues. The first TS repeat is followed by a conserved CRD sequence which contains 8 conserved cysteines. The spacer domain of ADAMTS-10 is followed by 4 additional TS modules and a Kunitz domain. The ADAMTS-10 protein contains 2 potential glycosylation sites within the mature protease: one in the catalytic domain, and one in the TS1–3 domain. ADAMTS-10 bears approximately 40% sequence identity to ADAM-TS 1, which is characterized as being involved in inflammation.

Comparison of the ADAMTS-N Proteins

As shown in FIG. 11, the ADAMTS-5, ADAMTS-6, and ADAMTS-7 proteins share a common domain organization. From amino to carboxyl termini, they are as follows:

1. A pre-pro region. A typical signal sequence of variable length is followed by a putative pro-region of variable length but demonstrating short stretches of sequence identity. Three cysteine residues are predicted within each novel pro-domain, of which the most C-terminal is an "asymmetric" cysteine lying within a sequence context similar to the cysteine "switch" of the MMPs. All three novel cDNAs predict consensus cleavage signals for furin, three in the case of ADAMTS-5, and one each in the case of ADAMTS-6 and ADAMTS-7. The most carboxyl-terminal furin cleavage site in ADAMTS-5 predicts the processing site for generation of the mature protease. The amino terminus of the mature proteins is predicted to start at the residue immediately following the cleavage sites.
2. A catalytic domain. The catalytic domains are very similar to each other and contain eight cysteine residues and a typical reprolysin-type zinc binding signature followed by a "Met-turn". Five cysteine residues are upstream of the zinc binding sequence, while three residues are downstream, an arrangement that is shared with other ADAMTS members. The methionine of the met-turn is not at a constant distance from the zinc-binding signature, but in all three novel proteases, a constant cysteine residue is present in that interval.
3. A disintegrin-like domain. The catalytic domain is followed by a domain of 60–90 residues with 35–45% similarity to snake venom disintegrins, but without the canonical cysteine arrangement seen in the latter. This disintegrin-like domain is of comparable length in ADAMTS-5 and ADAMTS-7, it is considerably shorter in ADAMTS-6.
4. A TS module. The first TS repeat is very similar in all three novel proteases and very similar to the first TS repeat of other ADAMTSs. It contains the same number of residues (fifty-two) in all three novel proteins.
5. The cysteine-rich domain. This TS domain is followed by a conserved cysteine-rich sequence termed the cysteine-rich domain (CRD).
6. The spacer domain. This domain is of variable length, in all ADAMTSs and lacks the sequence landmarks so characteristic of all the other domains. It shows the least homology of all the domains
7. A C-terminal TS module. The sequence of the second TS module is more variant between the members of the ADAMTS family than the first TS module, despite the conservation of the number and spacing of cysteine residues.

Overall, the predicted mature forms of these proteases show 20–30% similarity to each other and to ADAMTS 1 –4 although this may be considerably higher or lower for individual domains as described above.

ADAM-TS9 and ADAM-TS 10 contain all the domains present in ADAMTS-5 through ADAMTS-8. In addition, ADAMTS-9 and ADAMTS-10 contain the following domains:

A. ADAMTS-9: After the c-terminal TS1 domain which is present in ADAMTS5–8, ADAMTS-9 contains 13 additional and homologous TS 1 domains, thus, ADAMTS-9 contains a total of 15 TS 1 domains, of which 14 are adjacent to each other in the c-terminal half of the molecule. The 15th TS 1 domain from the N-terminus is followed by a unique c-terminal domain which does not possess recognizable domain structure and contains 196 residues including 9 cysteine residues.

B. ADAMTS-10: After the c-terminal TS1 domain which is present in ADAMTS8, ADAMTS-10 contains 3 additional and homologous TS1 domains, thus, that ADAMTS-10 contains a total of 5 TS 1 domains, of which 4 are adjacent to each other in the c-terminal half of the molecule. The 5th TS 1 domain from the N-terminus is followed by an additional 47 amino acid residues including six (6) cysteine residues. These 47 residues have sequence similarity of 30%–40% to the c-terminus of pro-hormone convertase 5 and 6, and to the Kunitz family of inhibitors.

Northern Analysis

Mouse embryo northern blots and multiple tissue northern blots from human and mouse tissues (Clontech, Palo Alto, Calif.) were hybridized to the [$\alpha^{32}$P]-dCTP labeled inserts of I.M.A.G.E. clones as per the manufacturer's recommendations followed by autoradiographic exposure for 3–7 days.

In situ hybridization used cryosections of mouse embryos of gestational age 8.5 days and 10.5 days. Embryos were collected with the inclusion of the surrounding uterus and fixed overnight in 4% paraformaldehyde. Sense and anti-sense probes continuously labeled with digoxigenin-UTP (Boehringer-Mannheim, Indianapolis, IN) were transcribed with T7 and T3 RNA polymerases, respectively, using as template a 630 bp EcoRI-Sac1 fragment from the Adamts-5 clone 569515 (FIG. 14) cloned into pBluescript SK+ (Stratagene, La Jolla, Calif.). In situ hybridization was done essentially as previously described in Apte, et al. (1997) J. Biol. Chem. 272:2551–25517, which is specifically incorporated herein by reference, except that sections were pre-digested with proteinase K (Boehringer-Mannheim, Indianapolis, Ind.) at a lower concentration (1–5 $\mu$g/ml) than reported in Apte, et al. Bound, digoxigenin-labeled probe was detected using an alkaline phosphatase tagged anti-digoxigenin antibody (Boehringer-Mannheim, Indianapolis, Ind.) and nuclei were counterstained with methyl green.

Figure 14:
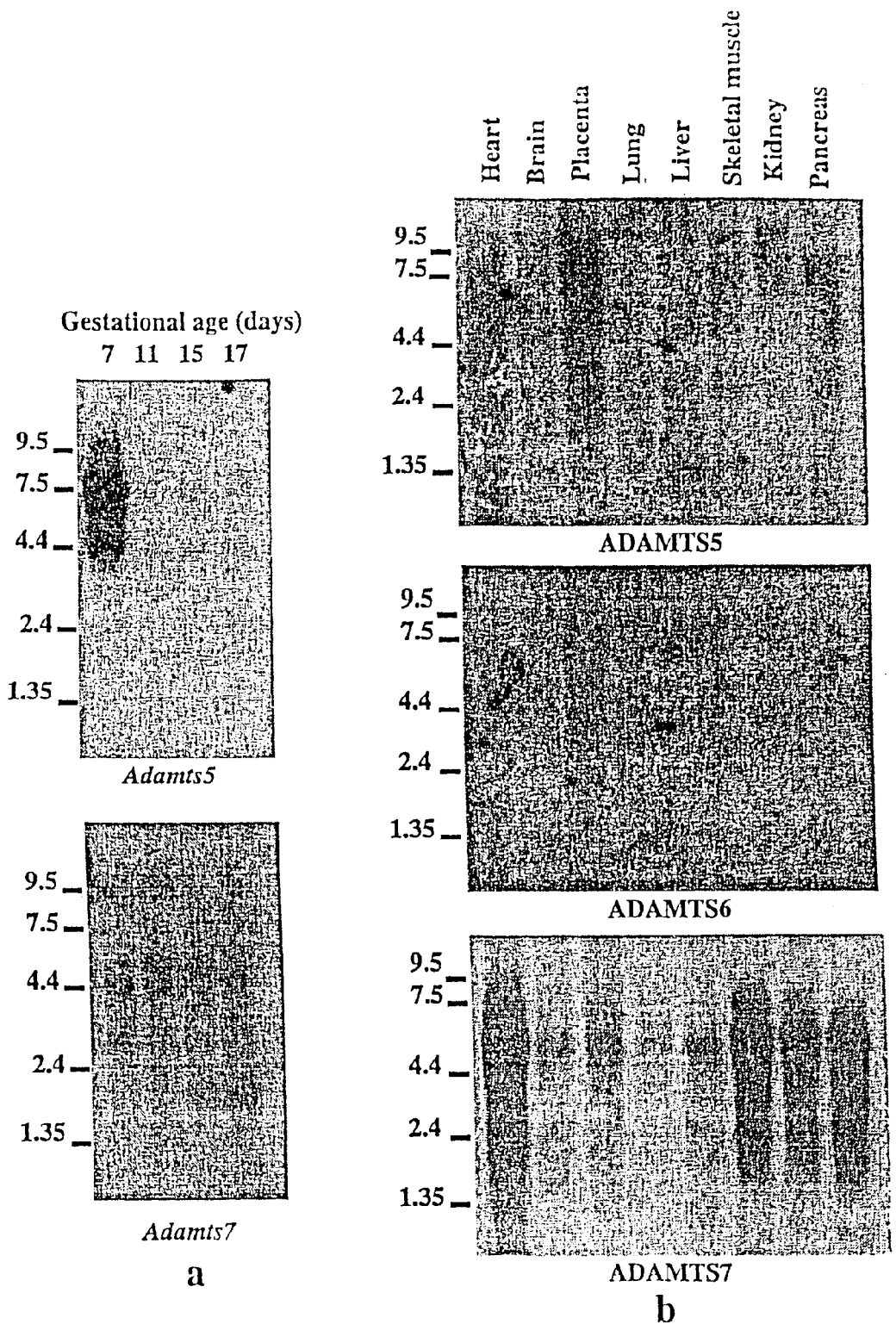
FIG. 14 shows Northern analysis of expression of ADAMTS-5, 6 and 7. RNA kilobase markers are shown at left of each autoradiogram, and tissue origin is indicated above each lane. a. Mouse embryo northern blots. b. Human multiple adult tissue northern blots.

Specific hybridization of the antisense Adamts-5 probe to sections of 8.5 day-old mouse embryos was obtained, whereas only low background staining was noted with the control sense probe Staining was uniform throughout the 8.5 day old embryos. In addition, there was labeling of mRNA in trophoblastic cells lining the uterine cavity as well as in the developing placenta (FIG. 14). The decidual reaction within the uterus also showed upregulation of Adamts-5 mRNA relative to the negative controls. In sections from 10.5 day old embryos, labeling was widespread but less intense compared to the 8.5 day-old embryo. Labeled cells were seen in mesenchyme and somites as well as in the neural tube and developing hindgut. Northern analysis also indicated that mRNA encoding ADAMTS-5 was present in human placenta but was barely detectable in adult lung, heart, brain, liver, skeletal muscle, kidney and pancreas.

Northern analysis showed undetectable expression of Adamts-6 during mouse embryo development. Northern analysis indicated that mRNA encoding ADAMTS-6 was present in human placenta but was barely detectable in adult lung, heart, brain, liver, skeletal muscle, kidney and pancreas. Adamts-7 was expressed at low levels throughout mouse development. In adult human tissues examined with human cDNA probes, ADAMTS-7 mRNA was found in all tissues examined, i.e. in lung, heart, brain, liver, skeletal muscle, kidney, pancreas and placenta. The sizes of the mRNA species recognized by the probes varied. ADAMTS-5 mRNA was approximately 10 kbp in size in human tissue. The most prominent Adamts-5 species was estimated at 7.5 kbp together with additional bands at 10 kbp and 4.5 kbp. The lone mRNA species detected by ADAMTS-6 probe was approximately 8.5 kbp, whereas the most common mRNA species detected by ADAMTS-7 probe was 5 kbp in size with an additional species seen at 7 kbp in skeletal muscle.

In mouse, ADAMTS-8 is expressed during fetal development (days 7, 11, 15, 17) and in adult mouse lung and heart with an mRNA size of approximately 3.8 kbp. In adult human tissue, ADAMTS-8 is expressed in lung and brain but not in heart, muscle, kidney, colon or thymus. The mRNA size is 3.8 kbp.

ADAMTS-9 is expressed in lung, ovary placenta, heart, brain, muscle, kidney and pancreas with a mRNA size of 8 kb. In addition, kidney and ovary contain additional transcripts of size 3 kb and 4.4 kb respectively. These additional transcripts may represent alternatively spliced or short forms of ADAMTS9.

ADAMTS-10 is expressed in thymus, prostate, testis, ovary, small intestine, colon, peripheral blood leukocytes, heart, brain, placenta, lung, liver, muscle, kidney and pancreas, as well as in many cell lines such as A549, HeLa and K562. There are two transcripts of 5 kb and 8kb present in all tissues.

EXAMPLE 7

ADAMTS-R1

The nucleotide sequence of a cDNA encoding a full-length ADAMTS-R1 protein was obtained using IMAGE clone 752797 which encodes EST AA, and a human fetal brain cDNA from Clontech. RACE was performed as described above in Example 1. The nucleotide sequence, SEQ ID NO:21, of the ADAMTS-R1 cDNA and the predicted amino acid sequence, SEQ ID NO:22, of the ADAMTS-R1 protein encoded by such DNA is shown in FIG. 11.

Figure 15A:
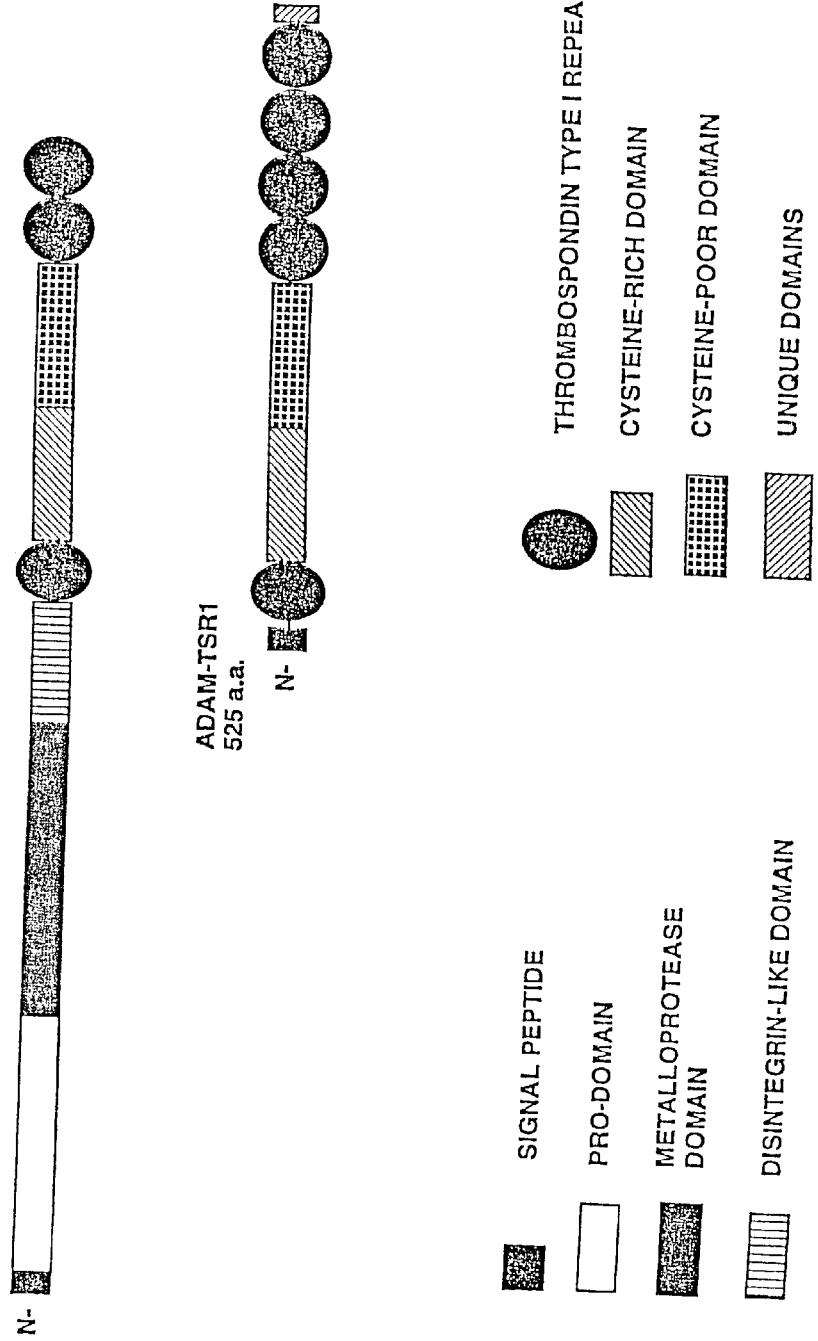
FIG. 15 is a schematic representation of the domain structure of ADAMTS-R1 protein as compared to ADAMTS-1 protein.

The predicted Mr of the full-length, unprocessed ADAMTS-R1 protein is 58358.20 daltons. The domain organization of the ADAMTS-10 protein is shown in FIG. 15. In contrast to the ADAMTS-N proteins of examples 1–6, ADAMTS-R1 protein does not have a pro-metalloprotease or disintegrin-like domain or a consensus cleavage signal for furin. ADAMTS-R1 has a signal(pre) peptide which is followed by a first TS module and a conserved CRD sequence which contains 10 conserved cysteines. The spacer domain of ADAMTS-R1 is 115 amino acids in length and is followed by 3 additional TS modules and a short sequence of 33 amino acids. The ADAMTS-R1 protein contains one potential glycosylation sites which is in the spacer domain. ADAMTS-R1 bears 30–40% sequence identity to ADAMTS1 and ADAMTS4 in the related domains. ADAMTS-R1 mRNA is present in human heart, brain, kidney, muscle, lung, placenta, testis, ovary, colon, intestine, and prostate. There are three transcripts of 2.5 kb, 4.7 kb and 6.5 kbp present in all such tissues. In mouse, expression is seen in skeletal muscle, and the transcript size is 6.5 kb.

Although certain embodiments of this invention have been shown and described, various adaptations and modifications can be made without departing from the scope of the invention as defined in the appended claims.

What is claimed is:

1. An isolated polynucleotide comprising a nucleic acid sequence encoding a metalloprotease comprising an amino acid sequence which is at least 95% identical to amino acid residues 245–860 of SEQ ID NO:5.

2. The isolated polynucleotide of claim 1, wherein said metalloprotease comprises amino acid residues 245–860 of SEQ ID NO:5.

3. The isolated polynucleotide of claim 1 wherein said nucleic acid sequence encodes a metalloprotease having a signal peptide at the amino terminus thereof.

4. The isolated polynucleotide of claim 1, wherein said polynucleotide comprises nucleotide 754 through nucleotide 2602 of SEQ ID NO:4.

5. An isolated polynucleotide which hybridizes under stringent conditions to a nucleic acid molecule comprising nucleotides 754–2602 of SEQ ID NO:4 or to a sequence which is complementary to nucleotides 754–2602 of SEQ ID NO:4, wherein said stringent conditions comprise hybridization and washing in 0.02×SSC buffer at 65° C.

6. An isolated polynucleotide comprising a sequence which is complementary to the protein encoding sequence of the polynucleotide of claim 1.

7. An expression vector comprising a polynucleotide of claim 1.

8. A host cell transformed or transfected with an expression vector of claim 7.

9. A method for producing an ADAMTS-N protein, said method comprising the steps of (a) culturing a host cell of claim 8 under conditions suitable for expression of an ADAMTS-N protein; and (b) recovering said ADAMTS-N protein from the host cell culture.

10. The isolated polynucleotide of claim 1 wherein said metalloprotease comprises an amino acid sequence which is at least 97% identical to amino acid residues 245–860 of SEQ ID NO: 5.

11. The isolated polynucleotide of claim 1 wherein said metalloprotease comprises an amino acid sequence which is at least 98% identical to amino acid residues 245–860 of SEQ ID NO: 5.

12. The isolated polynucleotide of claim 1 wherein said metalloprotease comprises an amino acid sequence which is at least 99% identical to amino acid residues 245–860 of SEQ ID NO: 5.

* * * * *

UNITED STATES PATENT AND TRADEMARK OFFICE
CERTIFICATE OF CORRECTION

PATENT NO. : 6,391,610 B1
DATED : May 21, 2002
INVENTOR(S) : Suneel S. Apte, Tiina L. Hurskainen and Satoshi Hirohata It is certified that error appears in the above-identified patent and that said Letters Patent is hereby corrected as shown below:

Column 135,
Line 15, after "polynucleotide" please delete "which" and insert -- encoding a metalloprotease, wherein said polynucleotide --.
Line 20, please delete "0.02" and insert -- 0.2 --.
Line 24, please delete "An expression" and insert -- A --.
Line 24, after "comprising" please delete "a" and insert -- the --.
Line 25, after "1" please insert -- or claim 5. --.

Column 136,
Line 1, after "with" please delete "an expression" and insert -- the --.
Line 3, after "producing" please delete "an ADAMTS-N protein" and insert -- a metalloprotease --.
Line 6, after "culturing" please delete "a" and insert -- the --.
Line 7, after "of" please delete "an ADAMTS-N protein" and insert -- a metalloprotease --.
Line 8, after "said" please delete "ADAMTS-N protein" and insert -- metalloprotease --.

Signed and Sealed this

Twentieth Day of May, 2003

JAMES E. ROGAN
*Director of the United States Patent and Trademark Office*

SEQUENCE LISTING

<160> NUMBER OF SEQ ID NOS: 31

<210> SEQ ID NO 1
<211> LENGTH: 3002
<212> TYPE: DNA
<213> ORGANISM: mus musculus ADAMTS-5
<220> FEATURE:
<221> NAME/KEY: CDS
<222> LOCATION: (18)..(2810)

<400> SEQUENCE: 1

```
ccggcgggca gcgcact atg cgg ctc gag tgg gcg tcc ttg ttg ctg cta        50
                Met Arg Leu Glu Trp Ala Ser Leu Leu Leu Leu
                 1               5                  10 ctg ctg ctg ctg agc gcg tcc tgc ctg tcc ctg gcc gct gac agc ccc        98
Leu Leu Leu Leu Ser Ala Ser Cys Leu Ser Leu Ala Ala Asp Ser Pro
         15                  20                  25
```

-continued

```
gcc gcg gca cct gcc cag gat aaa acc agg cag cct cag gct gca gca      146
Ala Ala Ala Pro Ala Gln Asp Lys Thr Arg Gln Pro Gln Ala Ala Ala
            30                  35                  40 gcg gcc gcc gag ccg gac cag ccg cag ggg gag gaa aca cgg gag cga      194
Ala Ala Ala Glu Pro Asp Gln Pro Gln Gly Glu Glu Thr Arg Glu Arg
        45                  50                  55 ggc cat tta caa ccc ttg gcc ggg cag cgc agg agc ggc ggg ctg gtc      242
Gly His Leu Gln Pro Leu Ala Gly Gln Arg Arg Ser Gly Gly Leu Val
60                  65                  70                  75 cat aat ata gac caa ctc tac tct ggc ggt ggc aaa gtg ggc tac ctt      290
His Asn Ile Asp Gln Leu Tyr Ser Gly Gly Gly Lys Val Gly Tyr Leu
                80                  85                  90 gtc tac gcg ggc ggc cgg agg ttc ctg ctg gac ctg gag aga gat gac      338
Val Tyr Ala Gly Gly Arg Arg Phe Leu Leu Asp Leu Glu Arg Asp Asp
            95                 100                 105 aca gtg ggt gct gct ggt agc atc gtt act gca gga gga ggg ctg agc      386
Thr Val Gly Ala Ala Gly Ser Ile Val Thr Ala Gly Gly Gly Leu Ser
        110                 115                 120 gca tcc tct ggc cac cgg ggt cac tgt ttc tac aga ggc acc gtg gac      434
Ala Ser Ser Gly His Arg Gly His Cys Phe Tyr Arg Gly Thr Val Asp
125                 130                 135 ggc agc cct cga tcc cta gct gtc ttt gac ctc tgc ggg ggt ctc gat      482
Gly Ser Pro Arg Ser Leu Ala Val Phe Asp Leu Cys Gly Gly Leu Asp
140                 145                 150                 155 ggc ttc ttt gca gtc aag cat gcg cgc tac act cta aag cca ctc ctg      530
Gly Phe Phe Ala Val Lys His Ala Arg Tyr Thr Leu Lys Pro Leu Leu
                160                 165                 170 cgt ggg tcc tgg gca gag tat gaa cga att tat ggg gat gga tct tcc      578
Arg Gly Ser Trp Ala Glu Tyr Glu Arg Ile Tyr Gly Asp Gly Ser Ser
            175                 180                 185 cgc atc ctg cat gtc tac aac cgc gag ggc ttt agc ttc gag gcc ctg      626
Arg Ile Leu His Val Tyr Asn Arg Glu Gly Phe Ser Phe Glu Ala Leu
        190                 195                 200 ccg cca cgc gcc agt tgc gag act cct gca tcc cca tct ggg ccc caa      674
Pro Pro Arg Ala Ser Cys Glu Thr Pro Ala Ser Pro Ser Gly Pro Gln
205                 210                 215 gag agc ccc tcg gtg cac agt aga tct agg aga cgc tca gcg ctg gcc      722
Glu Ser Pro Ser Val His Ser Arg Ser Arg Arg Ser Ala Leu Ala
220                 225                 230                 235 ccg cag ctg ctg gac cac tca gct ttc tcg cca tct ggg aac gcg gga      770
Pro Gln Leu Leu Asp His Ser Ala Phe Ser Pro Ser Gly Asn Ala Gly
                240                 245                 250 cct cag act tgg tgg agg cgt agg cgc cgt tcc atc tcc agg gcc cgc      818
Pro Gln Thr Trp Trp Arg Arg Arg Arg Ser Ile Ser Arg Ala Arg
            255                 260                 265 cag gtg gag ctc ctc ttg gtg gct gac tcg tcc atg gcc agg atg tat      866
Gln Val Glu Leu Leu Leu Val Ala Asp Ser Ser Met Ala Arg Met Tyr
        270                 275                 280 ggg cgg ggc ctg cag cat tac ctg ctg acc atg gcc tcc atc gcc aac      914
Gly Arg Gly Leu Gln His Tyr Leu Leu Thr Met Ala Ser Ile Ala Asn
285                 290                 295 agg ctg tac agt cat gca agc att gag aac cac atc cgc ctg gcg gtg      962
Arg Leu Tyr Ser His Ala Ser Ile Glu Asn His Ile Arg Leu Ala Val
300                 305                 310                 315 gtg aag gtg gtg gtg ctg acg gac aag gac acg agt ctg gag gtg agc     1010
Val Lys Val Val Val Leu Thr Asp Lys Asp Thr Ser Leu Glu Val Ser
                320                 325                 330 aag aat gcg gcc acg acc ctc aag aac ttt tgc aaa tgg cag cac caa     1058
Lys Asn Ala Ala Thr Thr Leu Lys Asn Phe Cys Lys Trp Gln His Gln
```

-continued

|  | 335 |  |  |  |  | 340 |  |  |  |  | 345 |  |  |  |  |
|---|---|---|---|---|---|---|---|---|---|---|---|---|---|---|---|
| cat | aac | cag | cta | ggg | gat | gat | cac | gaa | gag | cac | tac | gat | gca | gcc | atc | 1106 |
| His | Asn | Gln | Leu | Gly | Asp | Asp | His | Glu | Glu | His | Tyr | Asp | Ala | Ala | Ile |
|  |  | 350 |  |  |  |  | 355 |  |  |  |  | 360 |  |  |  |

| ctg | ttc | acc | cga | gag | gat | tta | tgt | ggg | cat | cat | tca | tgt | gac | acc | ctg | 1154 |
| Leu | Phe | Thr | Arg | Glu | Asp | Leu | Cys | Gly | His | His | Ser | Cys | Asp | Thr | Leu |
| 365 |  |  |  |  | 370 |  |  |  |  | 375 |  |  |  |  |  |

| gga | atg | gca | gac | gtt | ggg | acc | ata | tgt | tct | ccg | gag | cgc | agc | tgt | gca | 1202 |
| Gly | Met | Ala | Asp | Val | Gly | Thr | Ile | Cys | Ser | Pro | Glu | Arg | Ser | Cys | Ala |
| 380 |  |  |  |  | 385 |  |  |  |  | 390 |  |  |  |  | 395 |

| gtg | att | gaa | gat | gat | ggc | ctc | cat | gca | gcc | ttc | act | gtg | gct | cat | gaa | 1250 |
| Val | Ile | Glu | Asp | Asp | Gly | Leu | His | Ala | Ala | Phe | Thr | Val | Ala | His | Glu |
|  |  |  |  | 400 |  |  |  |  | 405 |  |  |  |  | 410 |  |

| att | ggg | cat | cta | ctt | ggc | ctt | tct | cat | gac | gat | tcc | aaa | ttc | tgt | gaa | 1298 |
| Ile | Gly | His | Leu | Leu | Gly | Leu | Ser | His | Asp | Asp | Ser | Lys | Phe | Cys | Glu |
|  |  |  |  | 415 |  |  |  |  | 420 |  |  |  |  | 425 |  |

| gag | aac | ttc | ggt | act | aca | gaa | gac | aag | cgt | tta | atg | tct | tca | atc | ctt | 1346 |
| Glu | Asn | Phe | Gly | Thr | Thr | Glu | Asp | Lys | Arg | Leu | Met | Ser | Ser | Ile | Leu |
|  |  | 430 |  |  |  |  | 435 |  |  |  |  | 440 |  |  |  |

| acc | agc | atc | gat | gca | tcc | aag | ccc | tgg | tcc | aaa | tgc | acg | tca | gcc | acc | 1394 |
| Thr | Ser | Ile | Asp | Ala | Ser | Lys | Pro | Trp | Ser | Lys | Cys | Thr | Ser | Ala | Thr |
| 445 |  |  |  |  | 450 |  |  |  |  | 455 |  |  |  |  |  |

| atc | aca | gaa | ttc | ctg | gat | gat | ggt | cat | ggt | aat | tgt | ttg | cta | gac | cta | 1442 |
| Ile | Thr | Glu | Phe | Leu | Asp | Asp | Gly | His | Gly | Asn | Cys | Leu | Leu | Asp | Leu |
| 460 |  |  |  |  | 465 |  |  |  |  | 470 |  |  |  |  | 475 |

| cca | cgg | aag | cag | att | ttg | ggt | ccc | gag | gaa | ctc | cca | gga | cag | acc | tac | 1490 |
| Pro | Arg | Lys | Gln | Ile | Leu | Gly | Pro | Glu | Glu | Leu | Pro | Gly | Gln | Thr | Tyr |
|  |  |  |  | 480 |  |  |  |  | 485 |  |  |  |  | 490 |  |

| gat | gcc | acc | cag | cag | tgc | aac | ttg | aca | ttt | ggg | cct | gag | tac | tcg | gtg | 1538 |
| Asp | Ala | Thr | Gln | Gln | Cys | Asn | Leu | Thr | Phe | Gly | Pro | Glu | Tyr | Ser | Val |
|  |  |  |  | 495 |  |  |  |  | 500 |  |  |  |  | 505 |  |

| tgc | cct | ggc | atg | gat | gtc | tgt | gcg | cgg | ctg | tgg | tgt | gct | gtg | gtg | cgc | 1586 |
| Cys | Pro | Gly | Met | Asp | Val | Cys | Ala | Arg | Leu | Trp | Cys | Ala | Val | Val | Arg |
|  |  |  |  | 510 |  |  |  |  | 515 |  |  |  |  | 520 |  |

| caa | ggc | caa | atg | gtg | tgt | ctg | acc | aag | aag | ctg | ccg | gct | gtg | gag | ggc | 1634 |
| Gln | Gly | Gln | Met | Val | Cys | Leu | Thr | Lys | Lys | Leu | Pro | Ala | Val | Glu | Gly |
|  |  | 525 |  |  |  |  | 530 |  |  |  |  | 535 |  |  |  |

| act | ccc | tgt | ggg | aag | gga | aga | gtc | tgc | ctt | caa | ggc | aaa | tgt | gtg | gac | 1682 |
| Thr | Pro | Cys | Gly | Lys | Gly | Arg | Val | Cys | Leu | Gln | Gly | Lys | Cys | Val | Asp |
| 540 |  |  |  |  | 545 |  |  |  |  | 550 |  |  |  |  | 555 |

| aaa | act | aag | aaa | aaa | tat | tac | tcg | aca | tca | agc | cat | gga | aat | tgg | ggg | 1730 |
| Lys | Thr | Lys | Lys | Lys | Tyr | Tyr | Ser | Thr | Ser | Ser | His | Gly | Asn | Trp | Gly |
|  |  |  |  | 560 |  |  |  |  | 565 |  |  |  |  | 570 |  |

| tcc | tgg | ggc | ccc | tgg | ggt | cag | tgt | tct | cgc | tca | tgc | ggg | gga | gga | gtg | 1778 |
| Ser | Trp | Gly | Pro | Trp | Gly | Gln | Cys | Ser | Arg | Ser | Cys | Gly | Gly | Gly | Val |
|  |  |  |  | 575 |  |  |  |  | 580 |  |  |  |  | 585 |  |

| cag | ttt | gcc | tac | cgc | cat | tgt | aat | aac | cct | gca | cct | cga | aac | agt | ggc | 1826 |
| Gln | Phe | Ala | Tyr | Arg | His | Cys | Asn | Asn | Pro | Ala | Pro | Arg | Asn | Ser | Gly |
|  |  | 590 |  |  |  |  | 595 |  |  |  |  | 600 |  |  |  |

| cgc | tac | tgc | aca | ggg | aag | agg | gcc | ata | tac | cgt | tcc | tgc | agt | gtt | aca | 1874 |
| Arg | Tyr | Cys | Thr | Gly | Lys | Arg | Ala | Ile | Tyr | Arg | Ser | Cys | Ser | Val | Thr |
|  |  | 605 |  |  |  |  | 610 |  |  |  |  | 615 |  |  |  |

| ccc | tgc | cca | ccc | aat | ggt | aaa | tct | ttt | cgc | cat | gag | cag | tgt | gaa | gcc | 1922 |
| Pro | Cys | Pro | Pro | Asn | Gly | Lys | Ser | Phe | Arg | His | Glu | Gln | Cys | Glu | Ala |
| 620 |  |  |  |  | 625 |  |  |  |  | 630 |  |  |  |  | 635 |

| aaa | aat | ggc | tat | cag | tct | gat | gca | aaa | gga | gtc | aaa | aca | ttt | gta | gaa | 1970 |
| Lys | Asn | Gly | Tyr | Gln | Ser | Asp | Ala | Lys | Gly | Val | Lys | Thr | Phe | Val | Glu |
|  |  |  |  | 640 |  |  |  |  | 645 |  |  |  |  | 650 |  |

| tgg | gtt | ccc | aaa | tat | gca | ggt | gtc | ctg | ccg | gca | gat | gtg | tgc | aag | ctt | 2018 |

```
Trp Val Pro Lys Tyr Ala Gly Val Leu Pro Ala Asp Val Cys Lys Leu
            655                 660                 665 acc tgc aga gct aag ggc aca ggc tac tat gtg gtc ttt tct cca aag      2066
Thr Cys Arg Ala Lys Gly Thr Gly Tyr Tyr Val Val Phe Ser Pro Lys
            670                 675                 680 gtt acg gat ggg act gaa tgc agg ccg tac agc aac tct gtg tgt gtc      2114
Val Thr Asp Gly Thr Glu Cys Arg Pro Tyr Ser Asn Ser Val Cys Val
        685                 690                 695 cga gga cgg tgt gtg aga act gga tgt gac ggc att att ggc tca aag      2162
Arg Gly Arg Cys Val Arg Thr Gly Cys Asp Gly Ile Ile Gly Ser Lys
700                 705                 710                 715 cta caa tat gac aag tgt gga gtg tgc gga ggg gat aac tcc agt tgt      2210
Leu Gln Tyr Asp Lys Cys Gly Val Cys Gly Gly Asp Asn Ser Ser Cys
                720                 725                 730 aca aag att atc gga acc ttc aat aaa aaa agc aag ggt tat act gac      2258
Thr Lys Ile Ile Gly Thr Phe Asn Lys Lys Ser Lys Gly Tyr Thr Asp
            735                 740                 745 gtt gtg agg atc cct gaa gga gca acc cac ata aaa gtc cga cag ttc      2306
Val Val Arg Ile Pro Glu Gly Ala Thr His Ile Lys Val Arg Gln Phe
        750                 755                 760 aaa gcc aaa gac cag act aga ttc cct gcc tac tta gcc ctg aag aag      2354
Lys Ala Lys Asp Gln Thr Arg Phe Pro Ala Tyr Leu Ala Leu Lys Lys
765                 770                 775 aaa act ggc gag tac ctt atc aat ggc aag tac atg att tcc act tca      2402
Lys Thr Gly Glu Tyr Leu Ile Asn Gly Lys Tyr Met Ile Ser Thr Ser
780                 785                 790                 795 gag acc atc atc gac atc aat ggt acc gtc atg aac tac agt gga tgg      2450
Glu Thr Ile Ile Asp Ile Asn Gly Thr Val Met Asn Tyr Ser Gly Trp
                800                 805                 810 agc cac aga gat gat ttt tta cat ggg atg ggc tat tca gcc aca aaa      2498
Ser His Arg Asp Asp Phe Leu His Gly Met Gly Tyr Ser Ala Thr Lys
            815                 820                 825 gaa atc ctg atc gtg cag atc ctt gcc aca gac cca act aaa gcg cta      2546
Glu Ile Leu Ile Val Gln Ile Leu Ala Thr Asp Pro Thr Lys Ala Leu
        830                 835                 840 ggc gtc cgt tac agc ttt ttt gtt ccc aag aag acc act caa aaa gta      2594
Gly Val Arg Tyr Ser Phe Phe Val Pro Lys Lys Thr Thr Gln Lys Val
        845                 850                 855 aac tct gtc atc agc cat ggc agc aac aag gtg gga cca cac tct aca      2642
Asn Ser Val Ile Ser His Gly Ser Asn Lys Val Gly Pro His Ser Thr
860                 865                 870                 875 cag ctg cag tgg gtg aca ggt cca tgg ctg gcc tgc tcc agg acc tgt      2690
Gln Leu Gln Trp Val Thr Gly Pro Trp Leu Ala Cys Ser Arg Thr Cys
                880                 885                 890 gac aca ggc tgg cac act agg acc gtg cag tgc cag gat gga aac agg      2738
Asp Thr Gly Trp His Thr Arg Thr Val Gln Cys Gln Asp Gly Asn Arg
            895                 900                 905 aaa tta gct aaa gga tgc ctt ctc tct cag agg cct tct gca ttt aag      2786
Lys Leu Ala Lys Gly Cys Leu Leu Ser Gln Arg Pro Ser Ala Phe Lys
        910                 915                 920 caa tgt ctg ctg aag aaa tgt tag cctgtggttt actctaatgc acaaaaaac     2840
Gln Cys Leu Leu Lys Lys Cys
        925                 930 aacaggagga tcatcgcaga tacagctgtg gtgaagacaa ggcctaccca aagcacagaa   2900
agtcatgcct tcatgtcatt gtcaccacga gtcgaattat gggcagaatc tgctctctgc   2960
gaccaaaagg tttactctac ttggtgaatg atggtaccgt ga                      3002

<210> SEQ ID NO 2
```

<211> LENGTH: 930
<212> TYPE: PRT
<213> ORGANISM: mus musculus ADAMTS-5

<400> SEQUENCE: 2

```
Met Arg Leu Glu Trp Ala Ser Leu Leu Leu Leu Leu Leu Leu Leu Ser
 1               5                  10                  15

Ala Ser Cys Leu Ser Leu Ala Ala Asp Ser Pro Ala Ala Pro Ala
            20                  25                  30

Gln Asp Lys Thr Arg Gln Pro Gln Ala Ala Ala Ala Ala Glu Pro
        35                  40                  45

Asp Gln Pro Gln Gly Glu Glu Thr Arg Glu Arg Gly His Leu Gln Pro
 50                  55                  60

Leu Ala Gly Gln Arg Arg Ser Gly Gly Leu Val His Asn Ile Asp Gln
 65                  70                  75                  80

Leu Tyr Ser Gly Gly Gly Lys Val Gly Tyr Leu Val Tyr Ala Gly Gly
                85                  90                  95

Arg Arg Phe Leu Leu Asp Leu Glu Arg Asp Asp Thr Val Gly Ala Ala
            100                 105                 110

Gly Ser Ile Val Thr Ala Gly Gly Leu Ser Ala Ser Ser Gly His
        115                 120                 125

Arg Gly His Cys Phe Tyr Arg Gly Thr Val Asp Gly Ser Pro Arg Ser
130                 135                 140

Leu Ala Val Phe Asp Leu Cys Gly Gly Leu Asp Gly Phe Phe Ala Val
145                 150                 155                 160

Lys His Ala Arg Tyr Thr Leu Lys Pro Leu Leu Arg Gly Ser Trp Ala
                165                 170                 175

Glu Tyr Glu Arg Ile Tyr Gly Asp Gly Ser Ser Arg Ile Leu His Val
            180                 185                 190

Tyr Asn Arg Glu Gly Phe Ser Phe Glu Ala Leu Pro Pro Arg Ala Ser
        195                 200                 205

Cys Glu Thr Pro Ala Ser Pro Ser Gly Pro Gln Glu Ser Pro Ser Val
    210                 215                 220

His Ser Arg Ser Arg Arg Ser Ala Leu Ala Pro Gln Leu Leu Asp
225                 230                 235                 240

His Ser Ala Phe Ser Pro Ser Gly Asn Ala Gly Pro Gln Thr Trp Trp
                245                 250                 255

Arg Arg Arg Arg Arg Ser Ile Ser Arg Ala Arg Gln Val Glu Leu Leu
            260                 265                 270

Leu Val Ala Asp Ser Ser Met Ala Arg Met Tyr Gly Arg Gly Leu Gln
        275                 280                 285

His Tyr Leu Leu Thr Met Ala Ser Ile Ala Asn Arg Leu Tyr Ser His
    290                 295                 300

Ala Ser Ile Glu Asn His Ile Arg Leu Ala Val Val Lys Val Val Val
305                 310                 315                 320

Leu Thr Asp Lys Asp Thr Ser Leu Glu Val Ser Lys Asn Ala Ala Thr
                325                 330                 335

Thr Leu Lys Asn Phe Cys Lys Trp Gln His Gln His Asn Gln Leu Gly
            340                 345                 350

Asp Asp His Glu Glu His Tyr Asp Ala Ala Ile Leu Phe Thr Arg Glu
        355                 360                 365

Asp Leu Cys Gly His His Ser Cys Asp Thr Leu Gly Met Ala Asp Val
    370                 375                 380

Gly Thr Ile Cys Ser Pro Glu Arg Ser Cys Ala Val Ile Glu Asp Asp
```

-continued

```
385                 390                 395                 400

Gly Leu His Ala Ala Phe Thr Val Ala His Glu Ile Gly His Leu Leu
                405                 410                 415

Gly Leu Ser His Asp Asp Ser Lys Phe Cys Glu Glu Asn Phe Gly Thr
                420                 425                 430

Thr Glu Asp Lys Arg Leu Met Ser Ser Ile Leu Thr Ser Ile Asp Ala
                435                 440                 445

Ser Lys Pro Trp Ser Lys Cys Thr Ser Ala Thr Ile Thr Glu Phe Leu
    450                 455                 460

Asp Asp Gly His Gly Asn Cys Leu Leu Asp Leu Pro Arg Lys Gln Ile
465                 470                 475                 480

Leu Gly Pro Glu Glu Leu Pro Gly Gln Thr Tyr Asp Ala Thr Gln Gln
                485                 490                 495

Cys Asn Leu Thr Phe Gly Pro Glu Tyr Ser Val Cys Pro Gly Met Asp
                500                 505                 510

Val Cys Ala Arg Leu Trp Cys Ala Val Val Arg Gln Gly Gln Met Val
                515                 520                 525

Cys Leu Thr Lys Lys Leu Pro Ala Val Glu Gly Thr Pro Cys Gly Lys
                530                 535                 540

Gly Arg Val Cys Leu Gln Gly Lys Cys Val Asp Lys Thr Lys Lys Lys
545                 550                 555                 560

Tyr Tyr Ser Thr Ser Ser His Gly Asn Trp Gly Ser Trp Gly Pro Trp
                565                 570                 575

Gly Gln Cys Ser Arg Ser Cys Gly Gly Val Gln Phe Ala Tyr Arg
                580                 585                 590

His Cys Asn Asn Pro Ala Pro Arg Asn Ser Gly Arg Tyr Cys Thr Gly
                595                 600                 605

Lys Arg Ala Ile Tyr Arg Ser Cys Ser Val Thr Pro Cys Pro Pro Asn
610                 615                 620

Gly Lys Ser Phe Arg His Glu Gln Cys Glu Ala Lys Asn Gly Tyr Gln
625                 630                 635                 640

Ser Asp Ala Lys Gly Val Lys Thr Phe Val Glu Trp Val Pro Lys Tyr
                645                 650                 655

Ala Gly Val Leu Pro Ala Asp Val Cys Lys Leu Thr Cys Arg Ala Lys
                660                 665                 670

Gly Thr Gly Tyr Tyr Val Val Phe Ser Pro Lys Val Thr Asp Gly Thr
                675                 680                 685

Glu Cys Arg Pro Tyr Ser Asn Ser Val Cys Val Arg Gly Arg Cys Val
                690                 695                 700

Arg Thr Gly Cys Asp Gly Ile Ile Gly Ser Lys Leu Gln Tyr Asp Lys
705                 710                 715                 720

Cys Gly Val Cys Gly Gly Asp Asn Ser Ser Cys Thr Lys Ile Ile Gly
                725                 730                 735

Thr Phe Asn Lys Lys Ser Lys Gly Tyr Thr Asp Val Val Arg Ile Pro
                740                 745                 750

Glu Gly Ala Thr His Ile Lys Val Arg Gln Phe Lys Ala Lys Asp Gln
                755                 760                 765

Thr Arg Phe Pro Ala Tyr Leu Ala Leu Lys Lys Lys Thr Gly Glu Tyr
                770                 775                 780

Leu Ile Asn Gly Lys Tyr Met Ile Ser Thr Ser Glu Thr Ile Ile Asp
785                 790                 795                 800

Ile Asn Gly Thr Val Met Asn Tyr Ser Gly Trp Ser His Arg Asp Asp
                805                 810                 815
```

Phe Leu His Gly Met Gly Tyr Ser Ala Thr Lys Glu Ile Leu Ile Val
            820                 825                 830

Gln Ile Leu Ala Thr Asp Pro Thr Lys Ala Leu Gly Val Arg Tyr Ser
            835                 840                 845

Phe Phe Val Pro Lys Lys Thr Thr Gln Lys Val Asn Ser Val Ile Ser
            850                 855                 860

His Gly Ser Asn Lys Val Gly Pro His Ser Thr Gln Leu Gln Trp Val
865                 870                 875                 880

Thr Gly Pro Trp Leu Ala Cys Ser Arg Thr Cys Asp Thr Gly Trp His
                885                 890                 895

Thr Arg Thr Val Gln Cys Gln Asp Gly Asn Arg Lys Leu Ala Lys Gly
            900                 905                 910

Cys Leu Leu Ser Gln Arg Pro Ser Ala Phe Lys Gln Cys Leu Leu Lys
            915                 920                 925

Lys Cys
    930

<210> SEQ ID NO 3
<211> LENGTH: 1520
<212> TYPE: DNA
<213> ORGANISM: homo sapiens ADAMTS-5
<220> FEATURE:
<221> NAME/KEY: misc_feature
<222> LOCATION: (296)
<223> OTHER INFORMATION: n=T
<221> NAME/KEY: misc_feature
<222> LOCATION: (1443)
<223> OTHER INFORMATION: n=A
<221> NAME/KEY: misc_feature
<222> LOCATION: (1457)
<223> OTHER INFORMATION: n=G
<221> NAME/KEY: misc_feature
<222> LOCATION: (1458)
<223> OTHER INFORMATION: n =T

<400> SEQUENCE: 3

```
ggacatttac ttggcctctc ccatgacgat tccaaattct gtgaagagac ctttggttcc      60
acagaagata agcgcttaat gtcttccatc cttaccagca ttgatgcatc taagccctgg     120
tccaaatgca cttcagccac catcacagaa ttcctggatg atggccatgg taactgtttg     180
ctggacctac cacgaaagca gatcctgggc cccgaagaac tcccaggaca gacctacgat     240
gccacccagc agtgcaacct gacattcggg cctgagtact ccgtgtgtcc ggcanggat     300 gtctgtgctc gcctgtggtg tgctgtggta cgccagggcc agatggtctg tctgaccaag     360
gagtgcagtt tgcctatcgt cactgtaata accctgctcc cagaaacaac ggacgctact     420
gcacagggaa gagggccatc taccactcct gcagtctcat gccctgccca cccaatggta     480
aatcatttcg tcatgaacag tgtgaggcca aaaatggcta tcagtctgat gcaaaaggag     540
tcaaaacttt tgtggaatgg gttcccaaat atgcaggtgt cctgccagcg atgtgtgca     600 agctgacctg cagagccaag ggcactggct actatgtggt attttctcca aaggtgaccg     660
atggcactga atgtaggccg tacagtaatt ccgtctgcgt ccgggggaag tgtgtgagaa     720
ctggctgtga cggcatcatt ggctcaaagc tgcagtatga caagtgcgga gtatgtggag     780
gagacaactc cagctgtaca aagattgttg gaacctttaa taagaaaagt aagggttaca     840
ctgacgtggt gaggattcct gaaggggcaa cccacataaa agttcgacag ttcaaagcca     900
aagaccagac tagattcact gcctatttag ccctgaaaaa gaaaacggt gagtacctta     960 tcaatggaaa gtacatgatc tccacttcag agactatcat tgacatcaat ggaacagtca    1020
```

```
tgaactatag cggttggagc cacagggatg acttcctgca tggcatgggc tactctgcca    1080
cgaaggaaat tctaatagtg cagattcttg caacagaccc cactaaacca ttagatgtcc    1140
gttatagctt ttttgttccc aagaagtcca ctccaaaagt aaactctgtc actagtcatg    1200
gcagcaataa agtgggatca cacacttcgc agccgcagtg ggtcacgggc ccatggctcg    1260
cctgctctag gacctgtgac acaggttggc acaccagaac ggtgcagtgc caggatggaa    1320
accggaagtt agcaaaagga tgtcctctct cccaaaggcc ttctgcgttt aagcaatgct    1380
tgttgaagaa atgttagcct gtgggttatg atcttattgc acaaaagata ctggaggatt    1440
cancacccgt gcaatcnngg tgaacaggaa ggctaccttga acgcacagaa agtcatgctt    1500
taatgacatt gtcaaccagg                                                1520
```

<210> SEQ ID NO 4
<211> LENGTH: 2848
<212> TYPE: DNA
<213> ORGANISM: Homo sapiens ADAMTS-6
<220> FEATURE:
<221> NAME/KEY: CDS
<222> LOCATION: (22)..(2601)
<221> NAME/KEY: misc_feature
<222> LOCATION: (1369)
<223> OTHER INFORMATION: n = C
<221> NAME/KEY: misc_feature
<222> LOCATION: (1620)
<223> OTHER INFORMATION: n=C

<400> SEQUENCE: 4

```
aatcatccag ttttctaaat t atg gaa att ttg tgg aag acg ttg acc tgg          51
                        Met Glu Ile Leu Trp Lys Thr Leu Thr Trp
                         1               5                  10 att ttg agc ctc atc atg gct tca tcg gaa ttt cat agt gac cac agg         99
Ile Leu Ser Leu Ile Met Ala Ser Ser Glu Phe His Ser Asp His Arg
             15                  20                  25 ctt tca tac agt tct caa gag gaa ttc ctg act tat ctt gaa cac tac        147
Leu Ser Tyr Ser Ser Gln Glu Glu Phe Leu Thr Tyr Leu Glu His Tyr
         30                  35                  40 cag cta act att cca ata agg gtt gat caa aat gga gca ttt ctc agc        195
Gln Leu Thr Ile Pro Ile Arg Val Asp Gln Asn Gly Ala Phe Leu Ser
     45                  50                  55 ttt act gtg aaa aat gat aaa cac tca agg aga aga cgg agt atg gac        243
Phe Thr Val Lys Asn Asp Lys His Ser Arg Arg Arg Arg Ser Met Asp
 60                  65                  70 cct att gat cca cag cag gca gta tct aag tta ttt ttt aaa ctt tca        291
Pro Ile Asp Pro Gln Gln Ala Val Ser Lys Leu Phe Phe Lys Leu Ser
 75                  80                  85                  90 gcc tat ggc aag cac ttt cat cta aac ttg act ctc aac aca gat ttt        339
Ala Tyr Gly Lys His Phe His Leu Asn Leu Thr Leu Asn Thr Asp Phe
             95                 100                 105 gtg tcc aaa cat ttt aca gta gaa tat tgg ggg aaa gat gga ccc cag        387
Val Ser Lys His Phe Thr Val Glu Tyr Trp Gly Lys Asp Gly Pro Gln
         110                 115                 120 tgg aaa cat gat ttt tta gac aac tgt cat tac aca gga tat ttg caa        435
Trp Lys His Asp Phe Leu Asp Asn Cys His Tyr Thr Gly Tyr Leu Gln
     125                 130                 135 gat caa cgt agt aca act aaa gtg gct tta agc aac tgt gtt ggg ttg        483
Asp Gln Arg Ser Thr Thr Lys Val Ala Leu Ser Asn Cys Val Gly Leu
 140                 145                 150 cat ggt gtt att gct aca gaa gat gaa gag tat ttt atc gaa cct tta        531
His Gly Val Ile Ala Thr Glu Asp Glu Glu Tyr Phe Ile Glu Pro Leu
155                 160                 165                 170
```

```
aag aat acc aca gag gat tcc aag cat ttt agt tat gaa aat ggc cac      579
Lys Asn Thr Thr Glu Asp Ser Lys His Phe Ser Tyr Glu Asn Gly His
                175                 180                 185 cct cat gtt att tac aaa aag tct gcc ctt caa caa cga cat ctg tat      627
Pro His Val Ile Tyr Lys Lys Ser Ala Leu Gln Gln Arg His Leu Tyr
            190                 195                 200 gat cac tct cat tgt ggg gtt tcg gat ttc aca aga agt ggc aaa cct      675
Asp His Ser His Cys Gly Val Ser Asp Phe Thr Arg Ser Gly Lys Pro
            205                 210                 215 tgg tgg ctg aat gac act cca ctg ttt ctt att cac tac caa att aac      723
Trp Trp Leu Asn Asp Thr Pro Leu Phe Leu Ile His Tyr Gln Ile Asn
    220                 225                 230 aac aca cat atc cac cac aga cag aag aga tca gtg agc att gaa cgg      771
Asn Thr His Ile His His Arg Gln Lys Arg Ser Val Ser Ile Glu Arg
235                 240                 245                 250 ttt gtg gag aca ttg gta gtg gca gac aaa atg atg gtg ggc tac cat      819
Phe Val Glu Thr Leu Val Val Ala Asp Lys Met Met Val Gly Tyr His
                255                 260                 265 ggc cgc aaa gac att gaa cat tac att ttg agt gtg atg aat att gtt      867
Gly Arg Lys Asp Ile Glu His Tyr Ile Leu Ser Val Met Asn Ile Val
                270                 275                 280 gcc aaa ctt tac cgt gat tcc agc cta gga aac gtt gtg aat att ata      915
Ala Lys Leu Tyr Arg Asp Ser Ser Leu Gly Asn Val Val Asn Ile Ile
            285                 290                 295 gtg gcc cgc tta att gtt ctc aca gaa gat cag cca aac ttg gag ata      963
Val Ala Arg Leu Ile Val Leu Thr Glu Asp Gln Pro Asn Leu Glu Ile
            300                 305                 310 aac cac cat gca gac aag tcc ctc gat agc ttc tgt aaa tgg cag aaa     1011
Asn His His Ala Asp Lys Ser Leu Asp Ser Phe Cys Lys Trp Gln Lys
315                 320                 325                 330 tcc att ctc tcc cac caa agt gat gga aac acc att cca gaa aat ggg     1059
Ser Ile Leu Ser His Gln Ser Asp Gly Asn Thr Ile Pro Glu Asn Gly
                335                 340                 345 att gcc cac cac gat aat gca gtt ctt att act aga tat gat atc tgc     1107
Ile Ala His His Asp Asn Ala Val Leu Ile Thr Arg Tyr Asp Ile Cys
            350                 355                 360 act tat aaa aat aag ccc tgt gga aca ctg ggc ttg gcc tct gtg gct     1155
Thr Tyr Lys Asn Lys Pro Cys Gly Thr Leu Gly Leu Ala Ser Val Ala
            365                 370                 375 gga atg tgt gag cct gaa agg agc tgc agc att aat gaa gac att ggc     1203
Gly Met Cys Glu Pro Glu Arg Ser Cys Ser Ile Asn Glu Asp Ile Gly
        380                 385                 390 ctg ggt tca gct ttt acc att gca cat gag att gtt cac aat ttt ggt     1251
Leu Gly Ser Ala Phe Thr Ile Ala His Glu Ile Val His Asn Phe Gly
395                 400                 405                 410 atg aac cat gat gga att gga aat tct tgt gga cga aag gtc atg aag     1299
Met Asn His Asp Gly Ile Gly Asn Ser Cys Gly Arg Lys Val Met Lys
                415                 420                 425 cag caa aat tat ggc agc tca cat tac tgc gaa tac caa tcc ttt ttc     1347
Gln Gln Asn Tyr Gly Ser Ser His Tyr Cys Glu Tyr Gln Ser Phe Phe
                430                 435                 440 ctg gtc tgc ttg cag tcg aga nta cat cac cag ctt ttt aga gaa gtg     1395
Leu Val Cys Leu Gln Ser Arg Xaa His His Gln Leu Phe Arg Glu Val
            445                 450                 455 tgt aga gag ctc tgg tgt ctc agc aaa agc aac cgc tgt gtc acc aac     1443
Cys Arg Glu Leu Trp Cys Leu Ser Lys Ser Asn Arg Cys Val Thr Asn
460                 465                 470 agt att cca gca gct gag ggg aca ctg tgt caa act ggg aat att gaa     1491
Ser Ile Pro Ala Ala Glu Gly Thr Leu Cys Gln Thr Gly Asn Ile Glu
```

-continued

```
      475             480             485             490
aaa ggg tgg tgt tat cag gga gat tgt gtt cct ttt ggc act tgg ccc      1539
Lys Gly Trp Cys Tyr Gln Gly Asp Cys Val Pro Phe Gly Thr Trp Pro
                        495             500             505 cag agc ata gat ggg ggc tgg ggt ccc tgg tca cta tgg gga gag tgc      1587
Gln Ser Ile Asp Gly Gly Trp Gly Pro Trp Ser Leu Trp Gly Glu Cys
                510             515             520 agc agg acc tgc ggg gga ggc gtn tcc tca tcc cta aga cac tgt gac      1635
Ser Arg Thr Cys Gly Gly Gly Val Ser Ser Ser Leu Arg His Cys Asp
            525             530             535 agt cca gca cct tcg gag gtg gaa aaa tat tgc ctt ggg gaa agg aaa      1683
Ser Pro Ala Pro Ser Glu Val Glu Lys Tyr Cys Leu Gly Glu Arg Lys
        540             545             550 cgg tat cgc tcc tgt aac aca gat cca tgc cct ttg ggt tcc cga gat      1731
Arg Tyr Arg Ser Cys Asn Thr Asp Pro Cys Pro Leu Gly Ser Arg Asp
555             560             565             570 ttt cga gag aaa cag tgt gca gac ttt gac aat atg cct ttc cga gga      1779
Phe Arg Glu Lys Gln Cys Ala Asp Phe Asp Asn Met Pro Phe Arg Gly
                575             580             585 aag tat tat aac tgg aaa ccc tat act gga ggt ggg gta aaa cct tgt      1827
Lys Tyr Tyr Asn Trp Lys Pro Tyr Thr Gly Gly Gly Val Lys Pro Cys
            590             595             600 gca tta aac tgc ttg gct gaa ggt tat aat ttc tac act gaa cgt gct      1875
Ala Leu Asn Cys Leu Ala Glu Gly Tyr Asn Phe Tyr Thr Glu Arg Ala
        605             610             615 cct gcg gtg atc gat ggg acc cag tgc aat gcg gat tca ctg gat atc      1923
Pro Ala Val Ile Asp Gly Thr Gln Cys Asn Ala Asp Ser Leu Asp Ile
620             625             630 tgc atc aat gga gaa tgc aag cac gta ggc tgt gat aat att ttg gga      1971
Cys Ile Asn Gly Glu Cys Lys His Val Gly Cys Asp Asn Ile Leu Gly
635             640             645             650 tct gat gct agg gaa gat aga tgt cga gtc tgt gga ggg ggc gga agc      2019
Ser Asp Ala Arg Glu Asp Arg Cys Arg Val Cys Gly Gly Gly Gly Ser
                655             660             665 aca tgt gat gcc att gaa ggg ttc ttc aat gat tca ctg ccc agg gga      2067
Thr Cys Asp Ala Ile Glu Gly Phe Phe Asn Asp Ser Leu Pro Arg Gly
            670             675             680 ggc tac atg gaa gtg gtg cag ata cca aga ggc tct gtt cac att gaa      2115
Gly Tyr Met Glu Val Val Gln Ile Pro Arg Gly Ser Val His Ile Glu
        685             690             695 gtt aga gaa gtt gcc atg tca aag aac tat att gct tta aaa tct gaa      2163
Val Arg Glu Val Ala Met Ser Lys Asn Tyr Ile Ala Leu Lys Ser Glu
700             705             710 gga gat gat tac tat att aat ggt gcc tgg act att gac tgg cct agg      2211
Gly Asp Asp Tyr Tyr Ile Asn Gly Ala Trp Thr Ile Asp Trp Pro Arg
715             720             725             730 aaa ttt gat gtt gct ggg aca gct ttt cat tac aag aga cca act gat      2259
Lys Phe Asp Val Ala Gly Thr Ala Phe His Tyr Lys Arg Pro Thr Asp
                735             740             745 gaa cca gaa tcc ttg gaa gct cta ggt cct acc tca gaa aat ctc atc      2307
Glu Pro Glu Ser Leu Glu Ala Leu Gly Pro Thr Ser Glu Asn Leu Ile
            750             755             760 gtc atg gtt ctg ctt caa gaa cag aat ttg gga att agg tat aag ttc      2355
Val Met Val Leu Leu Gln Glu Gln Asn Leu Gly Ile Arg Tyr Lys Phe
        765             770             775 aat gtt ccc atc act cga act ggc agt gga gat aat gaa gtt ggc ttt      2403
Asn Val Pro Ile Thr Arg Thr Gly Ser Gly Asp Asn Glu Val Gly Phe
780             785             790 aca tgg aat cat cag cct tgg tca gaa tgc tca gct act tgt gct gga      2451
```

```
Thr Trp Asn His Gln Pro Trp Ser Glu Cys Ser Ala Thr Cys Ala Gly
795                 800                 805                 810 ggt aag atg ccc act agg cag ccc acc cag agg gca aga tgg aga aca    2499
Gly Lys Met Pro Thr Arg Gln Pro Thr Gln Arg Ala Arg Trp Arg Thr
                815                 820                 825 aaa cac att ctg agc tat gct ttg tgt ttg tta aaa aag cta att gga    2547
Lys His Ile Leu Ser Tyr Ala Leu Cys Leu Leu Lys Lys Leu Ile Gly
                830                 835                 840 aac att tct agg ttt gct tca agc tgt aat tta gca aaa gaa act ttg    2595
Asn Ile Ser Arg Phe Ala Ser Ser Cys Asn Leu Ala Lys Glu Thr Leu
                845                 850                 855 ctt taa ttatattata ttccatttgt tttcaacctc atgtaatttg tgcagatttg     2651
Leu
    860 ttggtaaaat acatcttggc acaatgagtg tctctgctgg tgcttctccc aagactatct  2711 tgaaggtggg ctgtttgcct ttcgtgaaca cattcttggt aaagaacatc aaagttttta  2771 aaaaagaaaa tgagcaagaa tcagacatca cagatgcaac ttcttgtaat gggagatgag  2831 gagaatgtac ggctgtg                                                 2848

<210> SEQ ID NO 5
<211> LENGTH: 859
<212> TYPE: PRT
<213> ORGANISM: Homo sapiens ADAMTS-6
<220> FEATURE:
<221> NAME/KEY: MOD_RES
<222> LOCATION: (450)
<223> OTHER INFORMATION: Xaa = L

<400> SEQUENCE: 5

Met Glu Ile Leu Trp Lys Thr Leu Thr Trp Ile Leu Ser Leu Ile Met
1               5                   10                  15

Ala Ser Ser Glu Phe His Ser Asp His Arg Leu Ser Tyr Ser Ser Gln
            20                  25                  30

Glu Glu Phe Leu Thr Tyr Leu Glu His Tyr Gln Leu Thr Ile Pro Ile
        35                  40                  45

Arg Val Asp Gln Asn Gly Ala Phe Leu Ser Phe Thr Val Lys Asn Asp
    50                  55                  60

Lys His Ser Arg Arg Arg Ser Met Asp Pro Ile Asp Pro Gln Gln
65                  70                  75                  80

Ala Val Ser Lys Leu Phe Phe Lys Leu Ser Ala Tyr Gly Lys His Phe
                85                  90                  95

His Leu Asn Leu Thr Leu Asn Thr Asp Phe Val Ser Lys His Phe Thr
            100                 105                 110

Val Glu Tyr Trp Gly Lys Asp Gly Pro Gln Trp Lys His Asp Phe Leu
        115                 120                 125

Asp Asn Cys His Tyr Thr Gly Tyr Leu Gln Asp Gln Arg Ser Thr Thr
    130                 135                 140

Lys Val Ala Leu Ser Asn Cys Val Gly Leu His Gly Val Ile Ala Thr
145                 150                 155                 160

Glu Asp Glu Glu Tyr Phe Ile Glu Pro Leu Lys Asn Thr Thr Glu Asp
                165                 170                 175

Ser Lys His Phe Ser Tyr Glu Asn Gly His Pro His Val Ile Tyr Lys
            180                 185                 190

Lys Ser Ala Leu Gln Gln Arg His Leu Tyr Asp His Ser His Cys Gly
        195                 200                 205

Val Ser Asp Phe Thr Arg Ser Gly Lys Pro Trp Trp Leu Asn Asp Thr
```

```
            210                 215                 220
Pro Leu Phe Leu Ile His Tyr Gln Ile Asn Asn Thr His Ile His His
225                 230                 235                 240
Arg Gln Lys Arg Ser Val Ser Ile Glu Arg Phe Val Glu Thr Leu Val
                245                 250                 255
Val Ala Asp Lys Met Met Val Gly Tyr His Gly Arg Lys Asp Ile Glu
                260                 265                 270
His Tyr Ile Leu Ser Val Met Asn Ile Val Ala Lys Leu Tyr Arg Asp
                275                 280                 285
Ser Ser Leu Gly Asn Val Val Asn Ile Ile Val Ala Arg Leu Ile Val
290                 295                 300
Leu Thr Glu Asp Gln Pro Asn Leu Glu Ile Asn His His Ala Asp Lys
305                 310                 315                 320
Ser Leu Asp Ser Phe Cys Lys Trp Gln Lys Ser Ile Leu Ser His Gln
                325                 330                 335
Ser Asp Gly Asn Thr Ile Pro Glu Asn Gly Ile Ala His His Asp Asn
                340                 345                 350
Ala Val Leu Ile Thr Arg Tyr Asp Ile Cys Thr Tyr Lys Asn Lys Pro
                355                 360                 365
Cys Gly Thr Leu Gly Leu Ala Ser Val Ala Gly Met Cys Glu Pro Glu
                370                 375                 380
Arg Ser Cys Ser Ile Asn Glu Asp Ile Gly Leu Gly Ser Ala Phe Thr
385                 390                 395                 400
Ile Ala His Glu Ile Val His Asn Phe Gly Met Asn His Asp Gly Ile
                405                 410                 415
Gly Asn Ser Cys Gly Arg Lys Val Met Lys Gln Gln Asn Tyr Gly Ser
                420                 425                 430
Ser His Tyr Cys Glu Tyr Gln Ser Phe Phe Leu Val Cys Leu Gln Ser
                435                 440                 445
Arg Xaa His His Gln Leu Phe Arg Glu Val Cys Arg Glu Leu Trp Cys
                450                 455                 460
Leu Ser Lys Ser Asn Arg Cys Val Thr Asn Ser Ile Pro Ala Ala Glu
465                 470                 475                 480
Gly Thr Leu Cys Gln Thr Gly Asn Ile Glu Lys Gly Trp Cys Tyr Gln
                485                 490                 495
Gly Asp Cys Val Pro Phe Gly Thr Trp Pro Gln Ser Ile Asp Gly Gly
                500                 505                 510
Trp Gly Pro Trp Ser Leu Trp Gly Glu Cys Ser Arg Thr Cys Gly Gly
                515                 520                 525
Gly Val Ser Ser Leu Arg His Cys Asp Ser Pro Ala Pro Ser Glu
                530                 535                 540
Val Glu Lys Tyr Cys Leu Gly Glu Arg Lys Arg Tyr Arg Ser Cys Asn
545                 550                 555                 560
Thr Asp Pro Cys Pro Leu Gly Ser Arg Asp Phe Arg Glu Lys Gln Cys
                565                 570                 575
Ala Asp Phe Asp Asn Met Pro Phe Arg Gly Lys Tyr Tyr Asn Trp Lys
                580                 585                 590
Pro Tyr Thr Gly Gly Gly Val Lys Pro Cys Ala Leu Asn Cys Leu Ala
                595                 600                 605
Glu Gly Tyr Asn Phe Tyr Thr Glu Arg Ala Pro Ala Val Ile Asp Gly
                610                 615                 620
Thr Gln Cys Asn Ala Asp Ser Leu Asp Ile Cys Ile Asn Gly Glu Cys
625                 630                 635                 640
```

```
Lys His Val Gly Cys Asp Asn Ile Leu Gly Ser Asp Ala Arg Glu Asp
            645                 650                 655
Arg Cys Arg Val Cys Gly Gly Gly Ser Thr Cys Asp Ala Ile Glu
        660                 665                 670
Gly Phe Phe Asn Asp Ser Leu Pro Arg Gly Gly Tyr Met Glu Val Val
            675                 680                 685
Gln Ile Pro Arg Gly Ser Val His Ile Glu Val Arg Glu Val Ala Met
    690                 695                 700
Ser Lys Asn Tyr Ile Ala Leu Lys Ser Glu Gly Asp Asp Tyr Tyr Ile
705                 710                 715                 720
Asn Gly Ala Trp Thr Ile Asp Trp Pro Arg Lys Phe Asp Val Ala Gly
                725                 730                 735
Thr Ala Phe His Tyr Lys Arg Pro Thr Asp Glu Pro Glu Ser Leu Glu
            740                 745                 750
Ala Leu Gly Pro Thr Ser Glu Asn Leu Ile Val Met Val Leu Leu Gln
            755                 760                 765
Glu Gln Asn Leu Gly Ile Arg Tyr Lys Phe Asn Val Pro Ile Thr Arg
    770                 775                 780
Thr Gly Ser Gly Asp Asn Glu Val Gly Phe Thr Trp Asn His Gln Pro
785                 790                 795                 800
Trp Ser Glu Cys Ser Ala Thr Cys Ala Gly Gly Lys Met Pro Thr Arg
                805                 810                 815
Gln Pro Thr Gln Arg Ala Arg Trp Arg Thr Lys His Ile Leu Ser Tyr
            820                 825                 830
Ala Leu Cys Leu Leu Lys Lys Leu Ile Gly Asn Ile Ser Arg Phe Ala
            835                 840                 845
Ser Ser Cys Asn Leu Ala Lys Glu Thr Leu Leu
    850                 855

<210> SEQ ID NO 6
<211> LENGTH: 3218
<212> TYPE: DNA
<213> ORGANISM: Homo sapiens ADAMTS-7
<220> FEATURE:
<221> NAME/KEY: CDS
<222> LOCATION: (13)..(3003)

<400> SEQUENCE: 6
ccggttcctg cc atg ccc ggc ggc ccc agt ccc cgc agc ccc gcg cct ttg      51
          Met Pro Gly Gly Pro Ser Pro Arg Ser Pro Ala Pro Leu
            1               5                  10 ctg cgc ccc ctc ctc ctg ctc ctc tgc gct ctg gct ccc ggc gcc ccc        99
Leu Arg Pro Leu Leu Leu Leu Leu Cys Ala Leu Ala Pro Gly Ala Pro
 15                  20                  25 gga ccc gca cca gga cgt gca acc gag ggc cgg gcg gca ctg gac atc       147
Gly Pro Ala Pro Gly Arg Ala Thr Glu Gly Arg Ala Ala Leu Asp Ile
 30                  35                  40                  45 gtg cac ccg gtt cga gtc gac gcg ggg ggc tcc ttc ctg tcc tac gag       195
Val His Pro Val Arg Val Asp Ala Gly Gly Ser Phe Leu Ser Tyr Glu
                50                  55                  60 ctg tgg ccc cgc gca ctg cgc aag cgg gat gta tct gtg cgc cga gac       243
Leu Trp Pro Arg Ala Leu Arg Lys Arg Asp Val Ser Val Arg Arg Asp
            65                  70                  75 gcg ccc gcc ttc tac gag cta caa tac cgc ggg cgc gag ctg cgc ttc       291
Ala Pro Ala Phe Tyr Glu Leu Gln Tyr Arg Gly Arg Glu Leu Arg Phe
        80                  85                  90 aac ctg acc gcc aat cag cac ctg ctg gcg ccc ggc ttt gtg agc gag       339
```

```
Asn Leu Thr Ala Asn Gln His Leu Leu Ala Pro Gly Phe Val Ser Glu
     95                 100                 105 acg cgg cgg cgc ggc ggc ctg ggc cgc gcg cac atc cgg gcc cac acc      387
Thr Arg Arg Arg Gly Gly Leu Gly Arg Ala His Ile Arg Ala His Thr
110             115                 120                 125 ccg gcc tgc cac ctg ctt ggc gag gtg cag gac cct gag ctc gag ggt      435
Pro Ala Cys His Leu Leu Gly Glu Val Gln Asp Pro Glu Leu Glu Gly
                130                 135                 140 ggc ctg gcg gcc atc agc gcc tgc gac ggc ctg aaa ggt gtg ttc cag      483
Gly Leu Ala Ala Ile Ser Ala Cys Asp Gly Leu Lys Gly Val Phe Gln
                145                 150                 155 ctc tcc aac gag gac tac ttc att gag ccc ctg gac agt gcc ccg gcc      531
Leu Ser Asn Glu Asp Tyr Phe Ile Glu Pro Leu Asp Ser Ala Pro Ala
            160                 165                 170 cgg cct ggc cac gcc cag ccc cat gtg gtg tac aag cgt cag gcc ccg      579
Arg Pro Gly His Ala Gln Pro His Val Val Tyr Lys Arg Gln Ala Pro
        175                 180                 185 gag agg ctg gca cag cgg ggt gat tcc agt gct cca agc acc tgt gga      627
Glu Arg Leu Ala Gln Arg Gly Asp Ser Ser Ala Pro Ser Thr Cys Gly
190                 195                 200                 205 gtg caa gtg tac cca gag ctg gag tct cga cgg gag cgt tgg gag cag      675
Val Gln Val Tyr Pro Glu Leu Glu Ser Arg Arg Glu Arg Trp Glu Gln
                210                 215                 220 cgg cag cag tgg cgg cgg cca cgg ctg agg cgt cta cac cag cgg tcg      723
Arg Gln Gln Trp Arg Arg Pro Arg Leu Arg Arg Leu His Gln Arg Ser
                225                 230                 235 gtc agc aaa gag aag tgg tgt gag acc ctg gta gta gct gat gcc aaa      771
Val Ser Lys Glu Lys Trp Cys Glu Thr Leu Val Val Ala Asp Ala Lys
            240                 245                 250 atg gtg gag tac cac gga cag ccg cag gtt gag agc tat gtg ctg acc      819
Met Val Glu Tyr His Gly Gln Pro Gln Val Glu Ser Tyr Val Leu Thr
255                 260                 265 atc atg aac atg gtg gct ggc ctg ttt cat gac ccc agc att ggg aac      867
Ile Met Asn Met Val Ala Gly Leu Phe His Asp Pro Ser Ile Gly Asn
270                 275                 280                 285 ccc atc cac atc acc att gtg cgc ctg gtc ctg ctg gaa gat gag gag      915
Pro Ile His Ile Thr Ile Val Arg Leu Val Leu Leu Glu Asp Glu Glu
                290                 295                 300 gag gac cta aag atc acg cac cat gca gac aac acc ctg aag agc ttc      963
Glu Asp Leu Lys Ile Thr His His Ala Asp Asn Thr Leu Lys Ser Phe
                305                 310                 315 tgc aag tgg cag aaa agc atc aac atg aag ggg gat gcc cat ccc ctg      1011
Cys Lys Trp Gln Lys Ser Ile Asn Met Lys Gly Asp Ala His Pro Leu
            320                 325                 330 cac cat gac act gcc atc ctg ctc acc aga aag gac ctg tgt gca gcc      1059
His His Asp Thr Ala Ile Leu Leu Thr Arg Lys Asp Leu Cys Ala Ala
335                 340                 345 atg aac cgg ccc tgt gag acc ctg gga ctg tcc cat gtg gcg ggc atg      1107
Met Asn Arg Pro Cys Glu Thr Leu Gly Leu Ser His Val Ala Gly Met
350                 355                 360                 365 tgc cag ccg cac cgc agc tgc agc atc aac gag gac acg ggc ctg ccg      1155
Cys Gln Pro His Arg Ser Cys Ser Ile Asn Glu Asp Thr Gly Leu Pro
                370                 375                 380 ctg gcc ttc act gta gcc cac gag ctc ggg cac agt ttt ggc att cag      1203
Leu Ala Phe Thr Val Ala His Glu Leu Gly His Ser Phe Gly Ile Gln
                385                 390                 395 cat gac gga agc ggc aat gac tgt gag ccc gtt ggg aaa cga cct ttc      1251
His Asp Gly Ser Gly Asn Asp Cys Glu Pro Val Gly Lys Arg Pro Phe
                400                 405                 410
```

-continued

| | | |
|---|---|---|
| atc atg tct cca cag ctc ctg tac gac gcc gct ccc ctc acc tgg tcc<br>Ile Met Ser Pro Gln Leu Leu Tyr Asp Ala Ala Pro Leu Thr Trp Ser<br>415                              420                      425 | 1299 |
| cgc tgc agc cgc cag tat atc acc agg ttc ctt gac cgt ggg tgg ggc<br>Arg Cys Ser Arg Gln Tyr Ile Thr Arg Phe Leu Asp Arg Gly Trp Gly<br>430                         435                  440                  445 | 1347 |
| ctg tgc ctg gac gac cct cct gcc aag gac att atc gac ttc ccc tcg<br>Leu Cys Leu Asp Asp Pro Pro Ala Lys Asp Ile Ile Asp Phe Pro Ser<br>                      450                         455                      460 | 1395 |
| gtg cca cct ggc gtc ctc tat gat gta agc cac cag tgc cgc ctc cag<br>Val Pro Pro Gly Val Leu Tyr Asp Val Ser His Gln Cys Arg Leu Gln<br>                      465                         470                      475 | 1443 |
| tac ggg gcc tac tct gcc ttc tgc gag gac atg gat aat gtc tgc cac<br>Tyr Gly Ala Tyr Ser Ala Phe Cys Glu Asp Met Asp Asn Val Cys His<br>480                              485                      490 | 1491 |
| aca ctc tgg tgc tct gtg ggg acc acc tgt cac tcc aag ctg gat gca<br>Thr Leu Trp Cys Ser Val Gly Thr Thr Cys His Ser Lys Leu Asp Ala<br>495                              500                      505 | 1539 |
| gct gtg gac ggc acc cgg tgt ggg gag aat aag tgg tgt ctc agt ggg<br>Ala Val Asp Gly Thr Arg Cys Gly Glu Asn Lys Trp Cys Leu Ser Gly<br>510                            515                  520                  525 | 1587 |
| gag tgc gta ccc gtg ggc ttc cgg ccc gag gcc gtg gat ggt ggc tgg<br>Glu Cys Val Pro Val Gly Phe Arg Pro Glu Ala Val Asp Gly Gly Trp<br>                      530                         535                      540 | 1635 |
| tct ggc tgg agc gcc tgg tcc atc tgc tca cgg agc tgt ggc atg ggc<br>Ser Gly Trp Ser Ala Trp Ser Ile Cys Ser Arg Ser Cys Gly Met Gly<br>                      545                         550                      555 | 1683 |
| gta cag agc gcc gag cgg cag tgc acg cag cct acg ccc aaa tac aaa<br>Val Gln Ser Ala Glu Arg Gln Cys Thr Gln Pro Thr Pro Lys Tyr Lys<br>                      560                         565                      570 | 1731 |
| ggc aga tac tgt gtg ggt gag cgc aag cgc ttc cgc ctc tgc aac ctg<br>Gly Arg Tyr Cys Val Gly Glu Arg Lys Arg Phe Arg Leu Cys Asn Leu<br>575                              580                      585 | 1779 |
| cag gcc tgc cct gct ggc cgc ccc tcc ttc cgc cac gtc cag tgc agc<br>Gln Ala Cys Pro Ala Gly Arg Pro Ser Phe Arg His Val Gln Cys Ser<br>590                              595                      600                  605 | 1827 |
| cac ttt gac gct atg ctc tac aag ggc cag ctg cac aca tgg gtg ccc<br>His Phe Asp Ala Met Leu Tyr Lys Gly Gln Leu His Thr Trp Val Pro<br>                      610                         615                      620 | 1875 |
| gtg gtc aat gac gtg aac ccc tgc gag ctg cac tgc cgg ccc gcg aat<br>Val Val Asn Asp Val Asn Pro Cys Glu Leu His Cys Arg Pro Ala Asn<br>                      625                         630                      635 | 1923 |
| gag tac ttt gcc aag aag ctg cgg gac gcc tgt gtc gat ggc acc ccc<br>Glu Tyr Phe Ala Lys Lys Leu Arg Asp Ala Cys Val Asp Gly Thr Pro<br>                      640                         645                      650 | 1971 |
| tgc tac cag gtc cga gcc agc cgg gac ctc tgc atc aac ggc atc tgt<br>Cys Tyr Gln Val Arg Ala Ser Arg Asp Leu Cys Ile Asn Gly Ile Cys<br>655                              660                      665 | 2019 |
| aag aac gtg ggc tgt gac ttc gag att gac tcc ggt gct atg gag gac<br>Lys Asn Val Gly Cys Asp Phe Glu Ile Asp Ser Gly Ala Met Glu Asp<br>670                              675                  680                  685 | 2067 |
| cgc tgt ggt gtg tgc cac ggc aac ggc tcc acc tgc cac acc gtg agc<br>Arg Cys Gly Val Cys His Gly Asn Gly Ser Thr Cys His Thr Val Ser<br>                      690                         695                      700 | 2115 |
| ggg acc ttc gag gag gcc gag ggt ctg ggg tat gtg gat gtg ggg ctg<br>Gly Thr Phe Glu Glu Ala Glu Gly Leu Gly Tyr Val Asp Val Gly Leu<br>                      705                         710                      715 | 2163 |
| atc cca gcg ggc gca cgc gag atc cgc atc caa gag gtt gcc gag gct<br>Ile Pro Ala Gly Ala Arg Glu Ile Arg Ile Gln Glu Val Ala Glu Ala<br>                      720                         725                      730 | 2211 |

```
gcc aac ttc ctg gca ctg cgg agc gag gac ccg gag aag tac ttc ctc    2259
Ala Asn Phe Leu Ala Leu Arg Ser Glu Asp Pro Glu Lys Tyr Phe Leu
    735                 740                 745 aat ggt ggc tgg acc atc cag tgg aac ggg gac tac cag gtg gca ggg    2307
Asn Gly Gly Trp Thr Ile Gln Trp Asn Gly Asp Tyr Gln Val Ala Gly
750                 755                 760                 765 acc acc ttc aca tac gca cgc agg ggc aac tgg gag aac ctc acg tcc    2355
Thr Thr Phe Thr Tyr Ala Arg Arg Gly Asn Trp Glu Asn Leu Thr Ser
                770                 775                 780 ccg ggt ccc acc aag gag cct gtc tgg atc cag gtg cct gcc tcc cgt    2403
Pro Gly Pro Thr Lys Glu Pro Val Trp Ile Gln Val Pro Ala Ser Arg
            785                 790                 795 ggc cca ggc ggg ggg agc aga ggc gga gtc ccc agg ccc agc acc ctc    2451
Gly Pro Gly Gly Gly Ser Arg Gly Gly Val Pro Arg Pro Ser Thr Leu
        800                 805                 810 cat ggc agg tct cgt cct gga gga gtg agc cct ggt tca gtc aca gag    2499
His Gly Arg Ser Arg Pro Gly Gly Val Ser Pro Gly Ser Val Thr Glu
    815                 820                 825 cct ggc tct gag cca ggc cct cct gct gcg gcc tct acc tca gtt tcc    2547
Pro Gly Ser Glu Pro Gly Pro Pro Ala Ala Ala Ser Thr Ser Val Ser
830                 835                 840                 845 cca tct tta aaa tgg ccc aat ctt gta gct gca gtt cac aga ggt ggc    2595
Pro Ser Leu Lys Trp Pro Asn Leu Val Ala Ala Val His Arg Gly Gly
                850                 855                 860 tgg ggt caa gct cct tta gga ctg ggt gga tgg aga aga cac ctt gtg    2643
Trp Gly Gln Ala Pro Leu Gly Leu Gly Gly Trp Arg Arg His Leu Val
            865                 870                 875 ctc atg ggc ccc cgc ctg ccc acc cag ctg ctg ttc cag gag agc aac    2691
Leu Met Gly Pro Arg Leu Pro Thr Gln Leu Leu Phe Gln Glu Ser Asn
        880                 885                 890 cct ggg gtg cac tac gag tac acc atc cac agg gag gca ggt ggc cac    2739
Pro Gly Val His Tyr Glu Tyr Thr Ile His Arg Glu Ala Gly Gly His
    895                 900                 905 gac gag gtc ccg ccg ccc gtg ttc tcc tgg cat tat ggg ccc tgg acc    2787
Asp Glu Val Pro Pro Pro Val Phe Ser Trp His Tyr Gly Pro Trp Thr
910                 915                 920                 925 aag tgc aca gtc acc tgc ggc aga ggt gag aag tgg ggc agg cac agc    2835
Lys Cys Thr Val Thr Cys Gly Arg Gly Glu Lys Trp Gly Arg His Ser
                930                 935                 940 ccc acc tgc agg ggc tta gtg tct gga cag gga cac tgg ctt cag ctc    2883
Pro Thr Cys Arg Gly Leu Val Ser Gly Gln Gly His Trp Leu Gln Leu
            945                 950                 955 cca gct cac tgc tgg gcc acc acg ggt ttg gaa gtt tgc ttc tct gag    2931
Pro Ala His Cys Trp Ala Thr Thr Gly Leu Glu Val Cys Phe Ser Glu
        960                 965                 970 cct cag ttc tcc atc tgt gag atg agg cta gcg att gcc ctg tgt ccc    2979
Pro Gln Phe Ser Ile Cys Glu Met Arg Leu Ala Ile Ala Leu Cys Pro
    975                 980                 985 agg ccc gct ggg agg gta cat gga tgaggcaggt gggtgctggc tcgcggcgca    3033
Arg Pro Ala Gly Arg Val His Gly
990                 995 tgttcagtgt gctccagctc ttggcgttct ccctccaggg gacacagctc ccctcgata    3093 gaccagtcca gtggcccctc accacactga cttatttccc taaactattt ataaaagta    3153 gggcaatttc attaactctg actcttacct gcccgggcgg ccgctcgagc cgagtaatca    3213
ctagt                                                                3218

<210> SEQ ID NO 7
```

-continued

```
<211> LENGTH: 997
<212> TYPE: PRT
<213> ORGANISM: Homo sapiens ADAMTS-7

<400> SEQUENCE: 7

Met Pro Gly Gly Pro Ser Pro Arg Ser Pro Ala Pro Leu Leu Arg Pro
1               5                   10                  15

Leu Leu Leu Leu Cys Ala Leu Ala Pro Gly Ala Pro Gly Pro Ala
            20                  25                  30

Pro Gly Arg Ala Thr Glu Gly Arg Ala Ala Leu Asp Ile Val His Pro
        35                  40                  45

Val Arg Val Asp Ala Gly Gly Ser Phe Leu Ser Tyr Glu Leu Trp Pro
    50                  55                  60

Arg Ala Leu Arg Lys Arg Asp Val Ser Val Arg Arg Asp Ala Pro Ala
65                  70                  75                  80

Phe Tyr Glu Leu Gln Tyr Arg Gly Arg Glu Leu Arg Phe Asn Leu Thr
                85                  90                  95

Ala Asn Gln His Leu Leu Ala Pro Gly Phe Val Ser Glu Thr Arg Arg
            100                 105                 110

Arg Gly Gly Leu Gly Arg Ala His Ile Arg Ala His Thr Pro Ala Cys
        115                 120                 125

His Leu Leu Gly Glu Val Gln Asp Pro Glu Leu Glu Gly Gly Leu Ala
    130                 135                 140

Ala Ile Ser Ala Cys Asp Gly Leu Lys Gly Val Phe Gln Leu Ser Asn
145                 150                 155                 160

Glu Asp Tyr Phe Ile Glu Pro Leu Asp Ser Ala Pro Ala Arg Pro Gly
                165                 170                 175

His Ala Gln Pro His Val Val Tyr Lys Arg Gln Ala Pro Glu Arg Leu
            180                 185                 190

Ala Gln Arg Gly Asp Ser Ser Ala Pro Ser Thr Cys Gly Val Gln Val
        195                 200                 205

Tyr Pro Glu Leu Glu Ser Arg Arg Glu Arg Trp Glu Gln Arg Gln Gln
    210                 215                 220

Trp Arg Arg Pro Arg Leu Arg Arg Leu His Gln Arg Ser Val Ser Lys
225                 230                 235                 240

Glu Lys Trp Cys Glu Thr Leu Val Val Ala Asp Ala Lys Met Val Glu
                245                 250                 255

Tyr His Gly Gln Pro Gln Val Glu Ser Tyr Val Leu Thr Ile Met Asn
            260                 265                 270

Met Val Ala Gly Leu Phe His Asp Pro Ser Ile Gly Asn Pro Ile His
        275                 280                 285

Ile Thr Ile Val Arg Leu Val Leu Leu Glu Asp Glu Glu Asp Leu
    290                 295                 300

Lys Ile Thr His His Ala Asp Asn Thr Leu Lys Ser Phe Cys Lys Trp
305                 310                 315                 320

Gln Lys Ser Ile Asn Met Lys Gly Asp Ala His Pro Leu His His Asp
                325                 330                 335

Thr Ala Ile Leu Leu Thr Arg Lys Asp Leu Cys Ala Ala Met Asn Arg
            340                 345                 350

Pro Cys Glu Thr Leu Gly Leu Ser His Val Ala Gly Met Cys Gln Pro
        355                 360                 365

His Arg Ser Cys Ser Ile Asn Glu Asp Thr Gly Leu Pro Leu Ala Phe
    370                 375                 380

Thr Val Ala His Glu Leu Gly His Ser Phe Gly Ile Gln His Asp Gly
```

```
                                -continued
385                 390                 395                 400

Ser Gly Asn Asp Cys Glu Pro Val Gly Lys Arg Pro Phe Ile Met Ser
            405                 410                 415

Pro Gln Leu Leu Tyr Asp Ala Ala Pro Leu Thr Trp Ser Arg Cys Ser
            420                 425                 430

Arg Gln Tyr Ile Thr Arg Phe Leu Asp Arg Gly Trp Gly Leu Cys Leu
            435                 440                 445

Asp Asp Pro Pro Ala Lys Asp Ile Ile Asp Phe Pro Ser Val Pro Pro
450                 455                 460

Gly Val Leu Tyr Asp Val Ser His Gln Cys Arg Leu Gln Tyr Gly Ala
465                 470                 475                 480

Tyr Ser Ala Phe Cys Glu Asp Met Asp Asn Val Cys His Thr Leu Trp
            485                 490                 495

Cys Ser Val Gly Thr Thr Cys His Ser Lys Leu Asp Ala Ala Val Asp
            500                 505                 510

Gly Thr Arg Cys Gly Glu Asn Lys Trp Cys Leu Ser Gly Glu Cys Val
            515                 520                 525

Pro Val Gly Phe Arg Pro Glu Ala Val Asp Gly Gly Trp Ser Gly Trp
            530                 535                 540

Ser Ala Trp Ser Ile Cys Ser Arg Ser Cys Gly Met Gly Val Gln Ser
545                 550                 555                 560

Ala Glu Arg Gln Cys Thr Gln Pro Thr Pro Lys Tyr Lys Gly Arg Tyr
            565                 570                 575

Cys Val Gly Glu Arg Lys Arg Phe Arg Leu Cys Asn Leu Gln Ala Cys
            580                 585                 590

Pro Ala Gly Arg Pro Ser Phe Arg His Val Gln Cys Ser His Phe Asp
            595                 600                 605

Ala Met Leu Tyr Lys Gly Gln Leu His Thr Trp Val Pro Val Val Asn
610                 615                 620

Asp Val Asn Pro Cys Glu Leu His Cys Arg Pro Ala Asn Glu Tyr Phe
625                 630                 635                 640

Ala Lys Lys Leu Arg Asp Ala Cys Val Asp Gly Thr Pro Cys Tyr Gln
            645                 650                 655

Val Arg Ala Ser Arg Asp Leu Cys Ile Asn Gly Ile Cys Lys Asn Val
            660                 665                 670

Gly Cys Asp Phe Glu Ile Asp Ser Gly Ala Met Glu Asp Arg Cys Gly
            675                 680                 685

Val Cys His Gly Asn Gly Ser Thr Cys His Thr Val Ser Gly Thr Phe
            690                 695                 700

Glu Glu Ala Glu Gly Leu Gly Tyr Val Asp Val Gly Leu Ile Pro Ala
705                 710                 715                 720

Gly Ala Arg Glu Ile Arg Ile Gln Glu Val Ala Glu Ala Ala Asn Phe
            725                 730                 735

Leu Ala Leu Arg Ser Glu Asp Pro Glu Lys Tyr Phe Leu Asn Gly Gly
            740                 745                 750

Trp Thr Ile Gln Trp Asn Gly Asp Tyr Gln Val Ala Gly Thr Thr Phe
            755                 760                 765

Thr Tyr Ala Arg Arg Gly Asn Trp Glu Asn Leu Thr Ser Pro Gly Pro
            770                 775                 780

Thr Lys Glu Pro Val Trp Ile Gln Val Pro Ala Ser Arg Gly Pro Gly
785                 790                 795                 800

Gly Gly Ser Arg Gly Gly Val Pro Arg Pro Ser Thr Leu His Gly Arg
            805                 810                 815
```

```
Ser Arg Pro Gly Gly Val Ser Pro Gly Ser Val Thr Glu Pro Gly Ser
            820                 825                 830

Glu Pro Gly Pro Pro Ala Ala Ala Ser Thr Ser Val Ser Pro Ser Leu
        835                 840                 845

Lys Trp Pro Asn Leu Val Ala Ala Val His Arg Gly Gly Trp Gly Gln
    850                 855                 860

Ala Pro Leu Gly Leu Gly Gly Trp Arg Arg His Leu Val Leu Met Gly
865                 870                 875                 880

Pro Arg Leu Pro Thr Gln Leu Leu Phe Gln Glu Ser Asn Pro Gly Val
                885                 890                 895

His Tyr Glu Tyr Thr Ile His Arg Glu Ala Gly Gly His Asp Glu Val
            900                 905                 910

Pro Pro Pro Val Phe Ser Trp His Tyr Gly Pro Trp Thr Lys Cys Thr
        915                 920                 925

Val Thr Cys Gly Arg Gly Glu Lys Trp Gly Arg His Ser Pro Thr Cys
    930                 935                 940

Arg Gly Leu Val Ser Gly Gln Gly His Trp Leu Gln Leu Pro Ala His
945                 950                 955                 960

Cys Trp Ala Thr Thr Gly Leu Glu Val Cys Phe Ser Glu Pro Gln Phe
                965                 970                 975

Ser Ile Cys Glu Met Arg Leu Ala Ile Ala Leu Cys Pro Arg Pro Ala
            980                 985                 990

Gly Arg Val His Gly
        995

<210> SEQ ID NO 8
<211> LENGTH: 3638
<212> TYPE: DNA
<213> ORGANISM: Mus musculus ADAMTS-8
<220> FEATURE:
<221> NAME/KEY: CDS
<222> LOCATION: (278)..(2992)
<221> NAME/KEY: misc_feature
<222> LOCATION: (3636)
<223> OTHER INFORMATION: n = T

<400> SEQUENCE: 8
tagggcgact gcacgggacg ccgcggagga cgcgcgctcg cggcccgggg cgccacgtgc      60
tcgagttctg ctaggttggc tggcgcagga ggagcgggct gcgcgatcca gaggggccgc     120
cagggaccgc cgcgccacgt gccgctagcc gagtcggcct ccccatccga ttgatcattt     180
ttcctggaca gagcgacccg gccgcctcgg gccaccagca cctgcccgcg cgcggcgatc     240
ttcttccctc tcccgcgctc cgcagcactc tgccccc atg ctc cgc gac ccc acc     295
                                        Met Leu Arg Asp Pro Thr
                                          1               5 acc acc ggg tgg ccg ccc ctc ctg ctg ctg cta ttg cag ctg ccg ccg     343
Thr Thr Gly Trp Pro Pro Leu Leu Leu Leu Leu Leu Gln Leu Pro Pro
            10                  15                  20 ccg cca ctc gtc tgc gga gcc ccg gcg ggg ccg gga acc ggg gcg cag     391
Pro Pro Leu Val Cys Gly Ala Pro Ala Gly Pro Gly Thr Gly Ala Gln
        25                  30                  35 gcc tcg gag cta gtg gtg ccc acg cgg ttg ccc ggc agc gcg agc gag     439
Ala Ser Glu Leu Val Val Pro Thr Arg Leu Pro Gly Ser Ala Ser Glu
    40                  45                  50 ctc gcc ttc cac ctg tcc gcc ttc ggc cag ggc ttc gtg ctg cgc ctg     487
Leu Ala Phe His Leu Ser Ala Phe Gly Gln Gly Phe Val Leu Arg Leu
55                  60                  65                  70
```

-continued

| | | |
|---|---|---|
| gcg cct gac gcc agc ttc ctg gcg ccg gaa ttc aag atc gag cgc ctc<br>Ala Pro Asp Ala Ser Phe Leu Ala Pro Glu Phe Lys Ile Glu Arg Leu<br>                 75                       80                     85 | 535 |
| ggc ggc tcg agc gcg gcg gcc ggg ggc gag ccg gga ctg cgt ggc tgc<br>Gly Gly Ser Ser Ala Ala Ala Gly Gly Glu Pro Gly Leu Arg Gly Cys<br>                 90                       95                   100 | 583 |
| ttc ttc tct ggc aca gtg aat gga gaa cgg gag tcg ctg gcg gcg atg<br>Phe Phe Ser Gly Thr Val Asn Gly Glu Arg Glu Ser Leu Ala Ala Met<br>                105                   110                 115 | 631 |
| agc tgt gtc gcg ggc tgg agc ggc tcg ttc ttg ctg gca ggc gag gag<br>Ser Cys Val Ala Gly Trp Ser Gly Ser Phe Leu Leu Ala Gly Glu Glu<br>           120                   125                 130 | 679 |
| ttc acc atc cag cca cag ggc gct ggg gac tcc ctg gac cag cct cat<br>Phe Thr Ile Gln Pro Gln Gly Ala Gly Asp Ser Leu Asp Gln Pro His<br>135                   140                   145                 150 | 727 |
| cgc ctg cag cgc tgg ggg ccg gga cag cgc cgc gaa gac ccc ggg ctc<br>Arg Leu Gln Arg Trp Gly Pro Gly Gln Arg Arg Glu Asp Pro Gly Leu<br>                  155                   160                 165 | 775 |
| gct gcc gcc gaa gtt ttc ccc ctc cct caa gga ctg gag tgg gag gtg<br>Ala Ala Ala Glu Val Phe Pro Leu Pro Gln Gly Leu Glu Trp Glu Val<br>           170                   175                 180 | 823 |
| gag atg ggt aat ggg cag gga cag gag aga agt gac aac gaa gag gac<br>Glu Met Gly Asn Gly Gln Gly Gln Glu Arg Ser Asp Asn Glu Glu Asp<br>                185                   190                 195 | 871 |
| aag aag cag gac aag gag ggg ttg ctc aaa gag aca gaa gac tcc cgc<br>Lys Lys Gln Asp Lys Glu Gly Leu Leu Lys Glu Thr Glu Asp Ser Arg<br>           200                   205                 210 | 919 |
| aaa gtg cca cca ccc ttc gga tcc aaa act aga agc aag agg ttt gtg<br>Lys Val Pro Pro Pro Phe Gly Ser Lys Thr Arg Ser Lys Arg Phe Val<br>215                   220                   225                 230 | 967 |
| tcc gag gct cgc ttc gtg gaa aca ctt ctg gtg gct gat gcg tcc atg<br>Ser Glu Ala Arg Phe Val Glu Thr Leu Leu Val Ala Asp Ala Ser Met<br>                  235                   240                 245 | 1015 |
| gct gcc ttc tat ggg acc gac ctg cag aac cac atc ctc acg gtg atg<br>Ala Ala Phe Tyr Gly Thr Asp Leu Gln Asn His Ile Leu Thr Val Met<br>           250                   255                 260 | 1063 |
| tca atg gca gcc cga atc tac aag cac ccg agc atc agg aac tcc gtc<br>Ser Met Ala Ala Arg Ile Tyr Lys His Pro Ser Ile Arg Asn Ser Val<br>                265                   270                 275 | 1111 |
| aac ctt gtg gtg gtg aaa gtg cta ata gtg gaa aaa gaa aga tgg ggc<br>Asn Leu Val Val Val Lys Val Leu Ile Val Glu Lys Glu Arg Trp Gly<br>280                   285                   290 | 1159 |
| ccg gaa gtg tcc gac aac ggg ggg ctc aca ctg cgc aac ttc tgc agc<br>Pro Glu Val Ser Asp Asn Gly Gly Leu Thr Leu Arg Asn Phe Cys Ser<br>295                   300                   305                 310 | 1207 |
| tgg caa cgg cgt ttc aac aag ccc agt gac cgc cac ccg gag cac tat<br>Trp Gln Arg Arg Phe Asn Lys Pro Ser Asp Arg His Pro Glu His Tyr<br>                315                   320                 325 | 1255 |
| gac act gcc atc ttg ttc acc aga cag aac ttc tgt ggg aag gga gag<br>Asp Thr Ala Ile Leu Phe Thr Arg Gln Asn Phe Cys Gly Lys Gly Glu<br>           330                   335                 340 | 1303 |
| cag tgt gac acc ctg ggg atg gca gac gtt ggc acc atc tgt gac ccc<br>Gln Cys Asp Thr Leu Gly Met Ala Asp Val Gly Thr Ile Cys Asp Pro<br>                345                   350                 355 | 1351 |
| gac aag agc tgc tca gtg atc aag gat gag gga ctg cag gca gcc tac<br>Asp Lys Ser Cys Ser Val Ile Lys Asp Glu Gly Leu Gln Ala Ala Tyr<br>           360                   365                 370 | 1399 |
| acc ctg gcc cat gag cta ggg cac gtt ctc agc atg ccc cat gat gat<br>Thr Leu Ala His Glu Leu Gly His Val Leu Ser Met Pro His Asp Asp<br>375                   380                   385                 390 | 1447 |

-continued

| | |
|---|---|
| tct aag ccc tgt gtg aga ttg ttt ggg ccc atg ggc aag tac cac atg<br>Ser Lys Pro Cys Val Arg Leu Phe Gly Pro Met Gly Lys Tyr His Met<br>395                                        400                              405 | 1495 |
| atg gcg cca ttc ttc atc cac gtg aac aag acg ctg ccc tgg tct ccc<br>Met Ala Pro Phe Phe Ile His Val Asn Lys Thr Leu Pro Trp Ser Pro<br>                  410                              415                          420 | 1543 |
| tgc agt gct gtc tac ctc aca gag ctc ctg gat gat ggt cac gga gat<br>Cys Ser Ala Val Tyr Leu Thr Glu Leu Leu Asp Asp Gly His Gly Asp<br>        425                                430                              435 | 1591 |
| tgt ctt ctg gat gcc ccc acc tcg gtt ctg ccc ctc ccc aca ggc ctc<br>Cys Leu Leu Asp Ala Pro Thr Ser Val Leu Pro Leu Pro Thr Gly Leu<br>440                                        445                              450 | 1639 |
| ccg ggc cac agc acc ctc tac gag ctg gac cag cag tgc aag cag atc<br>Pro Gly His Ser Thr Leu Tyr Glu Leu Asp Gln Gln Cys Lys Gln Ile<br>455                                  460                              465                        470 | 1687 |
| ttt ggg cct gat ttc cga cac tgc ccc aac acc tct gtg gag gac atc<br>Phe Gly Pro Asp Phe Arg His Cys Pro Asn Thr Ser Val Glu Asp Ile<br>                  475                              480                          485 | 1735 |
| tgt gtc cag ctc tgt gcc cgt cat cgg gat agt gat gag ccc att tgc<br>Cys Val Gln Leu Cys Ala Arg His Arg Asp Ser Asp Glu Pro Ile Cys<br>        490                                495                              500 | 1783 |
| cac aca aag aat ggt agc ctg ctc tgg gct gat ggt aca ccc tgt ggc<br>His Thr Lys Asn Gly Ser Leu Leu Trp Ala Asp Gly Thr Pro Cys Gly<br>505                                  510                              515 | 1831 |
| cct ggg cac ctg tgc ctg gat ggt agc tgt gta ctc aag gag gat gtg<br>Pro Gly His Leu Cys Leu Asp Gly Ser Cys Val Leu Lys Glu Asp Val<br>        520                              525                              530 | 1879 |
| gag aat ccc aag gct gtg gta gat gga gac tgg ggt ccc tgg aga ccc<br>Glu Asn Pro Lys Ala Val Val Asp Gly Asp Trp Gly Pro Trp Arg Pro<br>535                                  540                              545                        550 | 1927 |
| tgg gga caa tgt tct cgc acc tgt ggt gga ggg ata caa ttc tcg aac<br>Trp Gly Gln Cys Ser Arg Thr Cys Gly Gly Gly Ile Gln Phe Ser Asn<br>                  555                              560                          565 | 1975 |
| cgt gaa tgt gat aat cca atg cct cag aat gga gga aga ttt tgc ctg<br>Arg Glu Cys Asp Asn Pro Met Pro Gln Asn Gly Gly Arg Phe Cys Leu<br>        570                              575                              580 | 2023 |
| ggt gaa aga gtc aag tac caa tca tgc aac aca gag gaa tgt cca cca<br>Gly Glu Arg Val Lys Tyr Gln Ser Cys Asn Thr Glu Glu Cys Pro Pro<br>585                                  590                              595 | 2071 |
| aac gga aaa agc ttc cgg gag cag cag tgt gag aaa tat aat gcc tac<br>Asn Gly Lys Ser Phe Arg Glu Gln Gln Cys Glu Lys Tyr Asn Ala Tyr<br>        600                              605                            610 | 2119 |
| aac cac act gac ctg gat ggg aat ttc ctg cag tgg gtc ccc aag tat<br>Asn His Thr Asp Leu Asp Gly Asn Phe Leu Gln Trp Val Pro Lys Tyr<br>615                                  620                              625                        630 | 2167 |
| tca gga gtg tcc ccc cga gac cga tgc aag ctg ttt tgc aga gcc cgt<br>Ser Gly Val Ser Pro Arg Asp Arg Cys Lys Leu Phe Cys Arg Ala Arg<br>                  635                              640                          645 | 2215 |
| ggg agg agt gag ttc aaa gtg ttt gaa gct aag gtg atc gat ggc act<br>Gly Arg Ser Glu Phe Lys Val Phe Glu Ala Lys Val Ile Asp Gly Thr<br>        650                              655                            660 | 2263 |
| ctg tgt gga ccg gat act ctg tcc atc tgc gtc cgg ggg caa tgt gtt<br>Leu Cys Gly Pro Asp Thr Leu Ser Ile Cys Val Arg Gly Gln Cys Val<br>                  665                              670                          675 | 2311 |
| aag gct ggc tgt gac cat gtg gtg aac tca cct aag aag ctg gac aaa<br>Lys Ala Gly Cys Asp His Val Val Asn Ser Pro Lys Lys Leu Asp Lys<br>680                                  685                              690 | 2359 |
| tgt ggg gtg tgt ggg ggc aaa ggc act gcc tgt agg aag atc tcc ggt<br>Cys Gly Val Cys Gly Gly Lys Gly Thr Ala Cys Arg Lys Ile Ser Gly | 2407 |

```
                                                                        -continued 695                 700                 705                 710 tct ttc acc ccc ttc agt tat ggc tac aat gac att gtc acc atc cca          2455
Ser Phe Thr Pro Phe Ser Tyr Gly Tyr Asn Asp Ile Val Thr Ile Pro
                    715                 720                 725 gct ggt gcc aca aac att gat gtg aaa cag cgg agt cac cca ggg gtc          2503
Ala Gly Ala Thr Asn Ile Asp Val Lys Gln Arg Ser His Pro Gly Val
            730                 735                 740 agg aac gac ggc agc tac ctg gcg ctg aag aca gcc aat ggg cag tac          2551
Arg Asn Asp Gly Ser Tyr Leu Ala Leu Lys Thr Ala Asn Gly Gln Tyr
        745                 750                 755 ctg ctc aat ggt aac ctg gcc atc tct gcc ata gag caa gac atc ttg          2599
Leu Leu Asn Gly Asn Leu Ala Ile Ser Ala Ile Glu Gln Asp Ile Leu
    760                 765                 770 gtg aag ggg acc atc ctg aag tac agt ggc tcc atg gct acc ctg gag          2647
Val Lys Gly Thr Ile Leu Lys Tyr Ser Gly Ser Met Ala Thr Leu Glu
775                 780                 785                 790 cgg ctg cag agc ttc cag gcc ctg cct gag cct ctt aca gta cag ctc          2695
Arg Leu Gln Ser Phe Gln Ala Leu Pro Glu Pro Leu Thr Val Gln Leu
                795                 800                 805 ctg act gtg tct ggt gag gtc ttc cct cca aaa gtc aga tat acc ttc          2743
Leu Thr Val Ser Gly Glu Val Phe Pro Pro Lys Val Arg Tyr Thr Phe
            810                 815                 820 ttt gtc ccc aat gac atg gac ttc agc gtg cag aat agc aag gaa aga          2791
Phe Val Pro Asn Asp Met Asp Phe Ser Val Gln Asn Ser Lys Glu Arg
        825                 830                 835 gca acc acc aac atc att cag tca ctg ccc tct gcg gag tgg gtt ctg          2839
Ala Thr Thr Asn Ile Ile Gln Ser Leu Pro Ser Ala Glu Trp Val Leu
    840                 845                 850 gga gac tgg tct gaa tgt ccg agc acg tgc aga ggt agc tgg cag cgg          2887
Gly Asp Trp Ser Glu Cys Pro Ser Thr Cys Arg Gly Ser Trp Gln Arg
855                 860                 865                 870 cgg act gtg gaa tgc agg gac ccc tca ggt cag gcc tct gac acc tgt          2935
Arg Thr Val Glu Cys Arg Asp Pro Ser Gly Gln Ala Ser Asp Thr Cys
                875                 880                 885 gat gag gct ctg aaa cct gag gat gcc aag ccc tgt gga agc cag ccg          2983
Asp Glu Ala Leu Lys Pro Glu Asp Ala Lys Pro Cys Gly Ser Gln Pro
            890                 895                 900 tgt ccc ctc tgatcccctt ggtggaaatc tcttaggctt atggatttgg                  3032
Cys Pro Leu
        905 gctactggtg taacagacaa aggtcccctc caaggtgata ctacatatca agatggcacg        3092 gcccttttcag gccttctatt actacaaccc cttgggtact acctaattca taaggaagag       3152 agaagagggt ataagggtaa cagattgtaa agttgactgt ctggtggact ggaccttgct        3212 tatgaccaag aagtcgggat aggttaaaag gtagaagtgc acttattgat ccaaatggga        3272 gatttcagag ccagtctctt tgcaaaggac tagcaaagct aaatgaaaaa gaagaatttt        3332 tttttttctat ttggtttccc caataatcaa tctacctcac agcgggaaa aatcagtata       3392 caagaggtat aaggccaggt gttggcagtg aacgccaaag caagctccat aggtatctcc       3452 aagctatctt cagaaatgtc cgtggctgtt ttcagtatta aaatctgttg tctaaaaggg       3512 cagcagtgtc catcacaggg ttatagaaag ccacttttct caggctgcca cctgctgggg      3572 cggacccatt tcaagtattt atgcaaatat gtctccgaac taaagtgtgt cttacaccaa      3632 aagngc                                                                 3638

<210> SEQ ID NO 9
<211> LENGTH: 905
```

```
<212> TYPE: PRT
<213> ORGANISM: Mus musculus ADAMTS-8

<400> SEQUENCE: 9
```

| | | | | | | | | | | | | | | |
|---|---|---|---|---|---|---|---|---|---|---|---|---|---|---|
| Met | Leu | Arg | Asp | Pro | Thr | Thr | Gly | Trp | Pro | Pro | Leu | Leu | Leu | Leu |
| 1 | | | | 5 | | | | | 10 | | | | | 15 |

| | | | | | | | | | | | | | | |
|---|---|---|---|---|---|---|---|---|---|---|---|---|---|---|
| Leu | Leu | Gln | Leu | Pro | Pro | Pro | Leu | Val | Cys | Gly | Ala | Pro | Ala | Gly |
| | | | 20 | | | | | 25 | | | | | 30 | |

| | | | | | | | | | | | | | | |
|---|---|---|---|---|---|---|---|---|---|---|---|---|---|---|
| Pro | Gly | Thr | Gly | Ala | Gln | Ala | Ser | Glu | Leu | Val | Val | Pro | Thr | Arg | Leu |
| | | 35 | | | | | 40 | | | | | 45 | | |

| | | | | | | | | | | | | | | |
|---|---|---|---|---|---|---|---|---|---|---|---|---|---|---|
| Pro | Gly | Ser | Ala | Ser | Glu | Leu | Ala | Phe | His | Leu | Ser | Ala | Phe | Gly | Gln |
| | 50 | | | | | 55 | | | | | 60 | | | | |

| | | | | | | | | | | | | | | |
|---|---|---|---|---|---|---|---|---|---|---|---|---|---|---|
| Gly | Phe | Val | Leu | Arg | Leu | Ala | Pro | Asp | Ala | Ser | Phe | Leu | Ala | Pro | Glu |
| 65 | | | | | 70 | | | | | 75 | | | | | 80 |

| | | | | | | | | | | | | | | |
|---|---|---|---|---|---|---|---|---|---|---|---|---|---|---|
| Phe | Lys | Ile | Glu | Arg | Leu | Gly | Gly | Ser | Ala | Ala | Gly | Gly | Glu |
| | | | | 85 | | | | | 90 | | | | | 95 |

| | | | | | | | | | | | | | | |
|---|---|---|---|---|---|---|---|---|---|---|---|---|---|---|
| Pro | Gly | Leu | Arg | Gly | Cys | Phe | Phe | Ser | Gly | Thr | Val | Asn | Gly | Glu | Arg |
| | | | 100 | | | | | 105 | | | | | 110 | | |

| | | | | | | | | | | | | | | |
|---|---|---|---|---|---|---|---|---|---|---|---|---|---|---|
| Glu | Ser | Leu | Ala | Ala | Met | Ser | Cys | Val | Ala | Gly | Trp | Ser | Gly | Ser | Phe |
| | | 115 | | | | | 120 | | | | | 125 | | | |

| | | | | | | | | | | | | | | |
|---|---|---|---|---|---|---|---|---|---|---|---|---|---|---|
| Leu | Leu | Ala | Gly | Glu | Glu | Phe | Thr | Ile | Gln | Pro | Gln | Gly | Ala | Gly | Asp |
| | 130 | | | | | 135 | | | | | 140 | | | | |

| | | | | | | | | | | | | | | |
|---|---|---|---|---|---|---|---|---|---|---|---|---|---|---|
| Ser | Leu | Asp | Gln | Pro | His | Arg | Leu | Gln | Arg | Trp | Gly | Pro | Gly | Gln | Arg |
| 145 | | | | | 150 | | | | | 155 | | | | | 160 |

| | | | | | | | | | | | | | | |
|---|---|---|---|---|---|---|---|---|---|---|---|---|---|---|
| Arg | Glu | Asp | Pro | Gly | Leu | Ala | Ala | Ala | Glu | Val | Phe | Pro | Leu | Pro | Gln |
| | | | | 165 | | | | | 170 | | | | | 175 | |

| | | | | | | | | | | | | | | |
|---|---|---|---|---|---|---|---|---|---|---|---|---|---|---|
| Gly | Leu | Glu | Trp | Glu | Val | Glu | Met | Gly | Asn | Gly | Gln | Gly | Gln | Glu | Arg |
| | | | 180 | | | | | 185 | | | | | 190 | | |

| | | | | | | | | | | | | | | |
|---|---|---|---|---|---|---|---|---|---|---|---|---|---|---|
| Ser | Asp | Asn | Glu | Glu | Asp | Lys | Lys | Gln | Asp | Lys | Glu | Gly | Leu | Leu | Lys |
| | | 195 | | | | | 200 | | | | | 205 | | | |

| | | | | | | | | | | | | | | |
|---|---|---|---|---|---|---|---|---|---|---|---|---|---|---|
| Glu | Thr | Glu | Asp | Ser | Arg | Lys | Val | Pro | Pro | Phe | Gly | Ser | Lys | Thr |
| | 210 | | | | | 215 | | | | | 220 | | | | |

| | | | | | | | | | | | | | | |
|---|---|---|---|---|---|---|---|---|---|---|---|---|---|---|
| Arg | Ser | Lys | Arg | Phe | Val | Ser | Glu | Ala | Arg | Phe | Val | Glu | Thr | Leu | Leu |
| 225 | | | | | 230 | | | | | 235 | | | | | 240 |

| | | | | | | | | | | | | | | |
|---|---|---|---|---|---|---|---|---|---|---|---|---|---|---|
| Val | Ala | Asp | Ala | Ser | Met | Ala | Ala | Phe | Tyr | Gly | Thr | Asp | Leu | Gln | Asn |
| | | | | 245 | | | | | 250 | | | | | 255 | |

| | | | | | | | | | | | | | | |
|---|---|---|---|---|---|---|---|---|---|---|---|---|---|---|
| His | Ile | Leu | Thr | Val | Met | Ser | Met | Ala | Ala | Arg | Ile | Tyr | Lys | His | Pro |
| | | | 260 | | | | | 265 | | | | | 270 | | |

| | | | | | | | | | | | | | | |
|---|---|---|---|---|---|---|---|---|---|---|---|---|---|---|
| Ser | Ile | Arg | Asn | Ser | Val | Asn | Leu | Val | Val | Lys | Val | Leu | Ile | Val |
| | | 275 | | | | | 280 | | | | | 285 | | | |

| | | | | | | | | | | | | | | |
|---|---|---|---|---|---|---|---|---|---|---|---|---|---|---|
| Glu | Lys | Glu | Arg | Trp | Gly | Pro | Glu | Val | Ser | Asp | Asn | Gly | Gly | Leu | Thr |
| | 290 | | | | | 295 | | | | | 300 | | | | |

| | | | | | | | | | | | | | | |
|---|---|---|---|---|---|---|---|---|---|---|---|---|---|---|
| Leu | Arg | Asn | Phe | Cys | Ser | Trp | Gln | Arg | Arg | Phe | Asn | Lys | Pro | Ser | Asp |
| 305 | | | | | 310 | | | | | 315 | | | | | 320 |

| | | | | | | | | | | | | | | |
|---|---|---|---|---|---|---|---|---|---|---|---|---|---|---|
| Arg | His | Pro | Glu | His | Tyr | Asp | Thr | Ala | Ile | Leu | Phe | Thr | Arg | Gln | Asn |
| | | | | 325 | | | | | 330 | | | | | 335 | |

| | | | | | | | | | | | | | | |
|---|---|---|---|---|---|---|---|---|---|---|---|---|---|---|
| Phe | Cys | Gly | Lys | Gly | Glu | Gln | Cys | Asp | Thr | Leu | Gly | Met | Ala | Asp | Val |
| | | | 340 | | | | | 345 | | | | | 350 | | |

| | | | | | | | | | | | | | | |
|---|---|---|---|---|---|---|---|---|---|---|---|---|---|---|
| Gly | Thr | Ile | Cys | Asp | Pro | Asp | Lys | Ser | Cys | Ser | Val | Ile | Lys | Asp | Glu |
| | | 355 | | | | | 360 | | | | | 365 | | | |

| | | | | | | | | | | | | | | |
|---|---|---|---|---|---|---|---|---|---|---|---|---|---|---|
| Gly | Leu | Gln | Ala | Ala | Tyr | Thr | Leu | Ala | His | Glu | Leu | Gly | His | Val | Leu |
| | 370 | | | | | 375 | | | | | 380 | | | | |

| | | | | | | | | | | | | | | |
|---|---|---|---|---|---|---|---|---|---|---|---|---|---|---|
| Ser | Met | Pro | His | Asp | Asp | Ser | Lys | Pro | Cys | Val | Arg | Leu | Phe | Gly | Pro |
| 385 | | | | | 390 | | | | | 395 | | | | | 400 |

```
Met Gly Lys Tyr His Met Met Ala Pro Phe Phe Ile His Val Asn Lys
                405                 410                 415

Thr Leu Pro Trp Ser Pro Cys Ser Ala Val Tyr Leu Thr Glu Leu Leu
            420                 425                 430

Asp Asp Gly His Gly Asp Cys Leu Leu Asp Ala Pro Thr Ser Val Leu
            435                 440                 445

Pro Leu Pro Thr Gly Leu Pro Gly His Ser Thr Leu Tyr Glu Leu Asp
            450                 455                 460

Gln Gln Cys Lys Gln Ile Phe Gly Pro Asp Phe Arg His Cys Pro Asn
465                 470                 475                 480

Thr Ser Val Glu Asp Ile Cys Val Gln Leu Cys Ala Arg His Arg Asp
                485                 490                 495

Ser Asp Glu Pro Ile Cys His Thr Lys Asn Gly Ser Leu Leu Trp Ala
                500                 505                 510

Asp Gly Thr Pro Cys Gly Pro Gly His Leu Cys Leu Asp Gly Ser Cys
            515                 520                 525

Val Leu Lys Glu Asp Val Glu Asn Pro Lys Ala Val Val Asp Gly Asp
            530                 535                 540

Trp Gly Pro Trp Arg Pro Trp Gly Gln Cys Ser Arg Thr Cys Gly Gly
545                 550                 555                 560

Gly Ile Gln Phe Ser Asn Arg Glu Cys Asp Asn Pro Met Pro Gln Asn
                565                 570                 575

Gly Gly Arg Phe Cys Leu Gly Glu Arg Val Lys Tyr Gln Ser Cys Asn
            580                 585                 590

Thr Glu Glu Cys Pro Pro Asn Gly Lys Ser Phe Arg Glu Gln Gln Cys
            595                 600                 605

Glu Lys Tyr Asn Ala Tyr Asn His Thr Asp Leu Asp Gly Asn Phe Leu
610                 615                 620

Gln Trp Val Pro Lys Tyr Ser Gly Val Ser Pro Arg Asp Arg Cys Lys
625                 630                 635                 640

Leu Phe Cys Arg Ala Arg Gly Arg Ser Glu Phe Lys Val Phe Glu Ala
                645                 650                 655

Lys Val Ile Asp Gly Thr Leu Cys Gly Pro Asp Thr Leu Ser Ile Cys
                660                 665                 670

Val Arg Gly Gln Cys Val Lys Ala Gly Cys Asp His Val Val Asn Ser
            675                 680                 685

Pro Lys Lys Leu Asp Lys Cys Gly Val Cys Gly Gly Lys Gly Thr Ala
            690                 695                 700

Cys Arg Lys Ile Ser Gly Ser Phe Thr Pro Phe Ser Tyr Gly Tyr Asn
705                 710                 715                 720

Asp Ile Val Thr Ile Pro Ala Gly Ala Thr Asn Ile Asp Val Lys Gln
                725                 730                 735

Arg Ser His Pro Gly Val Arg Asn Asp Gly Ser Tyr Leu Ala Leu Lys
                740                 745                 750

Thr Ala Asn Gly Gln Tyr Leu Leu Asn Gly Asn Leu Ala Ile Ser Ala
            755                 760                 765

Ile Glu Gln Asp Ile Leu Val Lys Gly Thr Ile Leu Lys Tyr Ser Gly
            770                 775                 780

Ser Met Ala Thr Leu Glu Arg Leu Gln Ser Phe Gln Ala Leu Pro Glu
785                 790                 795                 800

Pro Leu Thr Val Gln Leu Leu Thr Val Ser Gly Glu Val Phe Pro Pro
                805                 810                 815
```

```
Lys Val Arg Tyr Thr Phe Phe Val Pro Asn Asp Met Asp Phe Ser Val
            820                 825                 830

Gln Asn Ser Lys Glu Arg Ala Thr Thr Asn Ile Ile Gln Ser Leu Pro
            835                 840                 845

Ser Ala Glu Trp Val Leu Gly Asp Trp Ser Glu Cys Pro Ser Thr Cys
            850                 855                 860

Arg Gly Ser Trp Gln Arg Arg Thr Val Glu Cys Arg Asp Pro Ser Gly
865                 870                 875                 880

Gln Ala Ser Asp Thr Cys Asp Glu Ala Leu Lys Pro Glu Asp Ala Lys
            885                 890                 895

Pro Cys Gly Ser Gln Pro Cys Pro Leu
            900                 905

<210> SEQ ID NO 10
<211> LENGTH: 739
<212> TYPE: DNA
<213> ORGANISM: Homo sapiens ADAMTS-8
<220> FEATURE:
<221> NAME/KEY: CDS
<222> LOCATION: (3)..(737)

<400> SEQUENCE: 10 cg agg gca gaa ggc gct agc gag ccg cca ccg ccc ctg ggg gcc acg      47
   Arg Ala Glu Gly Ala Ser Glu Pro Pro Pro Pro Leu Gly Ala Thr
     1               5                  10                  15 agt agg acc aag cgg ttt gtg tct gag gcg cgc ttc gtg gag acg ctg     95
Ser Arg Thr Lys Arg Phe Val Ser Glu Ala Arg Phe Val Glu Thr Leu
             20                  25                  30 ctg gtg gcc gat gcg tcc atg gct gcc ttc tac ggg gcc gac ctg cag    143
Leu Val Ala Asp Ala Ser Met Ala Ala Phe Tyr Gly Ala Asp Leu Gln
         35                  40                  45 aac cac atc ctg acg tta atg tct gtg gca gcc cga atc tac aag cac    191
Asn His Ile Leu Thr Leu Met Ser Val Ala Ala Arg Ile Tyr Lys His
     50                  55                  60 ccc agc atc aag aat tcc atc aac ctg atg gtg gta aaa gtg ctg atc    239
Pro Ser Ile Lys Asn Ser Ile Asn Leu Met Val Val Lys Val Leu Ile
 65                  70                  75 gta gaa gat gaa aaa tgg ggc cca gag gtg tcc gac aat ggg ggg ctt    287
Val Glu Asp Glu Lys Trp Gly Pro Glu Val Ser Asp Asn Gly Gly Leu
 80                  85                  90                  95 aca ctg cgt aac ttc tgc aac tgg cag cgg cgt ttc aac cag ccc agc    335
Thr Leu Arg Asn Phe Cys Asn Trp Gln Arg Arg Phe Asn Gln Pro Ser
                100                 105                 110 gac cgc cac cca gag cac tac gac acg gcc atc ctg ctc acc aga cag    383
Asp Arg His Pro Glu His Tyr Asp Thr Ala Ile Leu Leu Thr Arg Gln
            115                 120                 125 aac ttc tgt ggg cag gag ggg ctg tgt gac acc ctg ggt gtg gca gac    431
Asn Phe Cys Gly Gln Glu Gly Leu Cys Asp Thr Leu Gly Val Ala Asp
        130                 135                 140 atc ggg acc att tgt gac ccc aac aaa agc tgc tcc gtg atc gag gat    479
Ile Gly Thr Ile Cys Asp Pro Asn Lys Ser Cys Ser Val Ile Glu Asp
    145                 150                 155 gag ggg ctc cag gcg gcc cac acc ctg gcc cat gaa cta ggg cac gtc    527
Glu Gly Leu Gln Ala Ala His Thr Leu Ala His Glu Leu Gly His Val
160                 165                 170                 175 ctc agc atg ccc cac gac gac tcc aag ccc tgc aca cgg ctc ttc ggg    575
Leu Ser Met Pro His Asp Asp Ser Lys Pro Cys Thr Arg Leu Phe Gly
                180                 185                 190 ccc atg ggc aag cac cac gtg atg gca ccg ctg ttc gtc cac ctg aac    623
Pro Met Gly Lys His His Val Met Ala Pro Leu Phe Val His Leu Asn
```

-continued

```
                195                 200                 205
cag acg ctg ccc tgg tcc ccc tgc agc gcc atg ttc tca ggc tgc cac     671
Gln Thr Leu Pro Trp Ser Pro Cys Ser Ala Met Phe Ser Gly Cys His
        210                 215                 220 ctg cag ggg tgg atc cat ttc aag tat tta tgc aaa tgt gtc tct gaa     719
Leu Gln Gly Trp Ile His Phe Lys Tyr Leu Cys Lys Cys Val Ser Glu
225                 230                 235 cta aag tgt gat ctt atg cc                                          739
Leu Lys Cys Asp Leu Met
240                 245

<210> SEQ ID NO 11
<211> LENGTH: 245
<212> TYPE: PRT
<213> ORGANISM: Homo sapiens ADAMTS-8

<400> SEQUENCE: 11

Arg Ala Glu Gly Ala Ser Glu Pro Pro Pro Leu Gly Ala Thr Ser
  1               5                  10                  15

Arg Thr Lys Arg Phe Val Ser Glu Ala Arg Phe Val Glu Thr Leu Leu
                 20                  25                  30

Val Ala Asp Ala Ser Met Ala Ala Phe Tyr Gly Ala Asp Leu Gln Asn
             35                  40                  45

His Ile Leu Thr Leu Met Ser Val Ala Ala Arg Ile Tyr Lys His Pro
         50                  55                  60

Ser Ile Lys Asn Ser Ile Asn Leu Met Val Val Lys Val Leu Ile Val
 65                  70                  75                  80

Glu Asp Glu Lys Trp Gly Pro Glu Val Ser Asp Asn Gly Gly Leu Thr
                 85                  90                  95

Leu Arg Asn Phe Cys Asn Trp Gln Arg Arg Phe Asn Gln Pro Ser Asp
            100                 105                 110

Arg His Pro Glu His Tyr Asp Thr Ala Ile Leu Leu Thr Arg Gln Asn
        115                 120                 125

Phe Cys Gly Gln Glu Gly Leu Cys Asp Thr Leu Gly Val Ala Asp Ile
    130                 135                 140

Gly Thr Ile Cys Asp Pro Asn Lys Ser Cys Ser Val Ile Glu Asp Glu
145                 150                 155                 160

Gly Leu Gln Ala Ala His Thr Leu Ala His Glu Leu Gly His Val Leu
                165                 170                 175

Ser Met Pro His Asp Asp Ser Lys Pro Cys Thr Arg Leu Phe Gly Pro
            180                 185                 190

Met Gly Lys His His Val Met Ala Pro Leu Phe Val His Leu Asn Gln
        195                 200                 205

Thr Leu Pro Trp Ser Pro Cys Ser Ala Met Phe Ser Gly Cys His Leu
    210                 215                 220

Gln Gly Trp Ile His Phe Lys Tyr Leu Cys Lys Cys Val Ser Glu Leu
225                 230                 235                 240

Lys Cys Asp Leu Met
                245

<210> SEQ ID NO 12
<211> LENGTH: 5804
<212> TYPE: DNA
<213> ORGANISM: Homo sapiens ADAMTS-9
<220> FEATURE:
<221> NAME/KEY: CDS
<222> LOCATION: (3)..(5648)
<221> NAME/KEY: misc_feature
```

```
<222> LOCATION: (1406)
<223> OTHER INFORMATION: n=T
<221> NAME/KEY: misc_feature
<222> LOCATION: (1563)
<223> OTHER INFORMATION: n=T

<400> SEQUENCE: 12 ga agc acc atg cag ttt gta tcc tgg gcc aca ctg cta acg ctc ctg        47
   Ser Thr Met Gln Phe Val Ser Trp Ala Thr Leu Leu Thr Leu Leu
    1               5                  10                  15 gtg cgg gac ctg gcc gag atg ggg agc cca gac gcc gcg gcg gcc gtg        95
Val Arg Asp Leu Ala Glu Met Gly Ser Pro Asp Ala Ala Ala Ala Val
                 20                  25                  30 cgc aag gac agg ctg cac ccg agg caa gtg aaa tta tta gag acc ctg       143
Arg Lys Asp Arg Leu His Pro Arg Gln Val Lys Leu Leu Glu Thr Leu
             35                  40                  45 agc gaa tac gaa atc gtg tct ccc atc cga gtg aac gct ctc gga gaa       191
Ser Glu Tyr Glu Ile Val Ser Pro Ile Arg Val Asn Ala Leu Gly Glu
         50                  55                  60 ccc ttt ccc acg aac gtc cac ttc aaa aga acg cga cgg agc att aac       239
Pro Phe Pro Thr Asn Val His Phe Lys Arg Thr Arg Arg Ser Ile Asn
 65                  70                  75 tct gcc act gac ccc tgg cct gcc ttc gcc tcc tcc tct tcc tcc tct       287
Ser Ala Thr Asp Pro Trp Pro Ala Phe Ala Ser Ser Ser Ser Ser Ser
 80                  85                  90                  95 acc tcc tcc cag gcg cat tac cgc ctc tct gcc ttc ggc cag cag ttt       335
Thr Ser Ser Gln Ala His Tyr Arg Leu Ser Ala Phe Gly Gln Gln Phe
                    100                 105                 110 cta ttt aat ctc acc gcc aat gcc gga ttt atc gct cca ctg ttc act       383
Leu Phe Asn Leu Thr Ala Asn Ala Gly Phe Ile Ala Pro Leu Phe Thr
                115                 120                 125 gtc acc ctc ctt ggg acg ccc ggg gtg aat cag acc aag ttt tat tcc       431
Val Thr Leu Leu Gly Thr Pro Gly Val Asn Gln Thr Lys Phe Tyr Ser
            130                 135                 140 gaa gag gaa gcg gaa cta aag cac tgt ttc tac aaa agg cta tgt caa       479
Glu Glu Glu Ala Glu Leu Lys His Cys Phe Tyr Lys Arg Leu Cys Gln
        145                 150                 155 tac caa ctc cga gca cac ggc cgt cat cag cct ctg ctc agg aat gaa       527
Tyr Gln Leu Arg Ala His Gly Arg His Gln Pro Leu Leu Arg Asn Glu
160                 165                 170                 175 cac aaa aat agg cac agt aaa gac aag aag aaa acc aga gca aga aaa       575
His Lys Asn Arg His Ser Lys Asp Lys Lys Lys Thr Arg Ala Arg Lys
                    180                 185                 190 tgg gga gaa agg att aac ctg gct ggt gac gta gca gca tta aac agc       623
Trp Gly Glu Arg Ile Asn Leu Ala Gly Asp Val Ala Ala Leu Asn Ser
                195                 200                 205 ggc tta gca aca gag gca ttt tct gct tat ggt aat aag acg gac aac       671
Gly Leu Ala Thr Glu Ala Phe Ser Ala Tyr Gly Asn Lys Thr Asp Asn
            210                 215                 220 aca aga gaa aag agg acc cac aga agg aca aaa cgt ttt tta tcc tat       719
Thr Arg Glu Lys Arg Thr His Arg Arg Thr Lys Arg Phe Leu Ser Tyr
        225                 230                 235 cca cgg ttt gta gaa gtc ttg gtg gtg gca gac aac aga atg gtt tca       767
Pro Arg Phe Val Glu Val Leu Val Val Ala Asp Asn Arg Met Val Ser
240                 245                 250                 255 tac cat gga gaa aac ctt caa cac tat att tta act tta atg tca att       815
Tyr His Gly Glu Asn Leu Gln His Tyr Ile Leu Thr Leu Met Ser Ile
                    260                 265                 270 gta gcc tct atc tat aaa gac cca agt att gga aat tta att aat att       863
Val Ala Ser Ile Tyr Lys Asp Pro Ser Ile Gly Asn Leu Ile Asn Ile
                275                 280                 285
```

```
gtt att gtg aac tta att gtg att cat aat gaa cag gat ggg cct tcc    911
Val Ile Val Asn Leu Ile Val Ile His Asn Glu Gln Asp Gly Pro Ser
        290                 295                 300 ata tct ttt aat gct cag aca aca tta aaa aac ttt tgc cag tgg cag    959
Ile Ser Phe Asn Ala Gln Thr Thr Leu Lys Asn Phe Cys Gln Trp Gln
        305                 310                 315 cat tcg aac agt cca ggt gga atc cat cat gat act gct gtt ctc tta   1007
His Ser Asn Ser Pro Gly Gly Ile His His Asp Thr Ala Val Leu Leu
320                 325                 330                 335 aca aga cag gat atc tgc aga gct cac gac aaa tgt gat acc tta ggc   1055
Thr Arg Gln Asp Ile Cys Arg Ala His Asp Lys Cys Asp Thr Leu Gly
                340                 345                 350 ctg gct gaa ctg gga acc att tgt gat ccc tat aga agc tgt tct att   1103
Leu Ala Glu Leu Gly Thr Ile Cys Asp Pro Tyr Arg Ser Cys Ser Ile
            355                 360                 365 agt gaa gat agt gga ttg agt aca gct ttt acg atc gcc cat gag ctg   1151
Ser Glu Asp Ser Gly Leu Ser Thr Ala Phe Thr Ile Ala His Glu Leu
        370                 375                 380 ggc cat gtg ttt aac atg cct cat gat gac aac aac aaa tgt aaa gaa   1199
Gly His Val Phe Asn Met Pro His Asp Asp Asn Asn Lys Cys Lys Glu
385                 390                 395 gaa gga gtt aag agt ccc cag cat gtc atg gct cca aca ctg aac ttc   1247
Glu Gly Val Lys Ser Pro Gln His Val Met Ala Pro Thr Leu Asn Phe
400                 405                 410                 415 tac acc aac ccc tgg atg tgg tca aag tgt agt cga aaa tat atc act   1295
Tyr Thr Asn Pro Trp Met Trp Ser Lys Cys Ser Arg Lys Tyr Ile Thr
                420                 425                 430 gag ttt tta gac act ggt tat ggc gag tgt ttg ctt aac gaa cct gaa   1343
Glu Phe Leu Asp Thr Gly Tyr Gly Glu Cys Leu Leu Asn Glu Pro Glu
            435                 440                 445 tcc aga ccc tac cct ttg cct gtc caa ctg cca ggc atc ctt tac aac   1391
Ser Arg Pro Tyr Pro Leu Pro Val Gln Leu Pro Gly Ile Leu Tyr Asn
        450                 455                 460 gtg aat aaa caa tgn gaa ttg att ttt gga cca ggt tct cag gtg tgc   1439
Val Asn Lys Gln Xaa Glu Leu Ile Phe Gly Pro Gly Ser Gln Val Cys
465                 470                 475 cca tat atg atg cag tgc aga cgg ctc tgg tgc aat aac gtc aat gga   1487
Pro Tyr Met Met Gln Cys Arg Arg Leu Trp Cys Asn Asn Val Asn Gly
480                 485                 490                 495 gta cac aaa ggc tgc cgg act cag cac aca ccc tgg gcc gat ggg acg   1535
Val His Lys Gly Cys Arg Thr Gln His Thr Pro Trp Ala Asp Gly Thr
                500                 505                 510 gag tgc gag cct gga aag cac tgc aag nat gga ttt tgt gtt ccc aaa   1583
Glu Cys Glu Pro Gly Lys His Cys Lys Xaa Gly Phe Cys Val Pro Lys
            515                 520                 525 gaa atg gat gtc ccc gtg aca gat gga tcc tgg gga agt tgg agt ccc   1631
Glu Met Asp Val Pro Val Thr Asp Gly Ser Trp Gly Ser Trp Ser Pro
        530                 535                 540 ttt gga acc tgc tcc aga aca tgt gga ggg ggc atc aaa aca gcc att   1679
Phe Gly Thr Cys Ser Arg Thr Cys Gly Gly Gly Ile Lys Thr Ala Ile
545                 550                 555 cga gag tgc aac aga cca gaa cca aaa aat ggt gga aaa tac tgt gta   1727
Arg Glu Cys Asn Arg Pro Glu Pro Lys Asn Gly Gly Lys Tyr Cys Val
560                 565                 570                 575 gga cgt aga atg aaa ttt aag tcc tgc aac acg gag cca tgt ctc aag   1775
Gly Arg Arg Met Lys Phe Lys Ser Cys Asn Thr Glu Pro Cys Leu Lys
                580                 585                 590 cag aag cga gac ttc cga gat gaa cag tgt gct cac ttt gac ggg aag   1823
Gln Lys Arg Asp Phe Arg Asp Glu Gln Cys Ala His Phe Asp Gly Lys
```

-continued

| | 595 | | | 600 | | | 605 | | | |
|---|---|---|---|---|---|---|---|---|---|---|
| cat | ttt | aac | atc | aac | ggt | ctg | ctt | ccc | aat | gtg | cgc | tgg | gtc | cct | aaa | 1871 |
| His | Phe | Asn | Ile | Asn | Gly | Leu | Leu | Pro | Asn | Val | Arg | Trp | Val | Pro | Lys | |
| | | | 610 | | | | 615 | | | | 620 | | | | | |

```
cat ttt aac atc aac ggt ctg ctt ccc aat gtg cgc tgg gtc cct aaa         1871
His Phe Asn Ile Asn Gly Leu Leu Pro Asn Val Arg Trp Val Pro Lys
            610                 615                 620 tac agt gga att ctg atg aag gac cgg tgc aag ttg ttc tgc aga gtg         1919
Tyr Ser Gly Ile Leu Met Lys Asp Arg Cys Lys Leu Phe Cys Arg Val
625                 630                 635 gca ggg aac aca gcc tac tat cag ctt cga gac aga gtg ata gat gga         1967
Ala Gly Asn Thr Ala Tyr Tyr Gln Leu Arg Asp Arg Val Ile Asp Gly
640                 645                 650                 655 act cct tgt ggc cag gac aca aat gat atc tgt gtc cag ggc ctt tgc         2015
Thr Pro Cys Gly Gln Asp Thr Asn Asp Ile Cys Val Gln Gly Leu Cys
                660                 665                 670 cgg caa gct gga tgc gat cat gtt tta aac tca aaa gcc cgg aga gat         2063
Arg Gln Ala Gly Cys Asp His Val Leu Asn Ser Lys Ala Arg Arg Asp
            675                 680                 685 aaa tgc ggg gtt tgt ggt ggc gat aat tct tca tgc aaa aca gtg gca         2111
Lys Cys Gly Val Cys Gly Gly Asp Asn Ser Ser Cys Lys Thr Val Ala
        690                 695                 700 gga aca ttt aat aca gta cat tat ggt tac aat act gtg gtc cga att         2159
Gly Thr Phe Asn Thr Val His Tyr Gly Tyr Asn Thr Val Val Arg Ile
    705                 710                 715 cca gct ggt gct acc aat att gat gtg cgg cag cac agt ttc tca ggg         2207
Pro Ala Gly Ala Thr Asn Ile Asp Val Arg Gln His Ser Phe Ser Gly
720                 725                 730                 735 gaa aca gac gat gac aac tac tta gct tta tca agc agt aaa ggt gaa         2255
Glu Thr Asp Asp Asp Asn Tyr Leu Ala Leu Ser Ser Ser Lys Gly Glu
                740                 745                 750 ttc ttg cta aat gga aac ttt gtt gtc aca atg gcc aaa agg gaa att         2303
Phe Leu Leu Asn Gly Asn Phe Val Val Thr Met Ala Lys Arg Glu Ile
            755                 760                 765 cgc att ggg aat gct gtg gta gag tac agt ggg tcc gag act gcc gta         2351
Arg Ile Gly Asn Ala Val Val Glu Tyr Ser Gly Ser Glu Thr Ala Val
        770                 775                 780 gaa aga att aac tca aca gat cgc att gag caa gaa ctt ttg ctt cag         2399
Glu Arg Ile Asn Ser Thr Asp Arg Ile Glu Gln Glu Leu Leu Leu Gln
    785                 790                 795 gtt ttg tcg gtg gga aag ttg tac aac ccc gat gta cgc tat tct ttc         2447
Val Leu Ser Val Gly Lys Leu Tyr Asn Pro Asp Val Arg Tyr Ser Phe
800                 805                 810                 815 aat att cca att gaa gat aaa cct cag cag ttt tac tgg aac agt cat         2495
Asn Ile Pro Ile Glu Asp Lys Pro Gln Gln Phe Tyr Trp Asn Ser His
                820                 825                 830 ggg cca tgg caa gca tgc agt aaa ccc tgc caa ggg gaa cgg aaa cga         2543
Gly Pro Trp Gln Ala Cys Ser Lys Pro Cys Gln Gly Glu Arg Lys Arg
            835                 840                 845 aaa ctt gtt tgc acc agg gaa tct gat cag ctt act gtt tct gat caa         2591
Lys Leu Val Cys Thr Arg Glu Ser Asp Gln Leu Thr Val Ser Asp Gln
        850                 855                 860 aga tgc gat cgg ctg ccc cag cct gga cac att act gaa ccc tgt ggt         2639
Arg Cys Asp Arg Leu Pro Gln Pro Gly His Ile Thr Glu Pro Cys Gly
    865                 870                 875 aca ggc tgt gac ctg agg tgg cat gtt gcc agc agg agt gaa tgt agt         2687
Thr Gly Cys Asp Leu Arg Trp His Val Ala Ser Arg Ser Glu Cys Ser
880                 885                 890                 895 gcc cag tgt ggc ttg ggt tac cgc aca ttg gac atc tac tgt gcc aaa         2735
Ala Gln Cys Gly Leu Gly Tyr Arg Thr Leu Asp Ile Tyr Cys Ala Lys
                900                 905                 910 tat agc agg ctg gat ggg aag act gag aag gtt gat gat ggt ttt tgc         2783
```

```
                                                               -continued

Tyr Ser Arg Leu Asp Gly Lys Thr Glu Lys Val Asp Asp Gly Phe Cys
            915                 920                 925 agc agc cat ccc aaa cca agc aac cgt gaa aaa tgc tca ggg gaa tgt        2831
Ser Ser His Pro Lys Pro Ser Asn Arg Glu Lys Cys Ser Gly Glu Cys
            930                 935                 940 aac acg ggt ggc tgg cgc tat tct gcc tgg act gaa tgt tca aaa agc        2879
Asn Thr Gly Gly Trp Arg Tyr Ser Ala Trp Thr Glu Cys Ser Lys Ser
    945                 950                 955 tgt gac ggt ggg acc cag agg aga agg gct att tgt gtc aat acc cga        2927
Cys Asp Gly Gly Thr Gln Arg Arg Arg Ala Ile Cys Val Asn Thr Arg
960                 965                 970                 975 aat gat gta ctg gat gac agc aaa tgc aca cat caa gag aaa gtt acc        2975
Asn Asp Val Leu Asp Asp Ser Lys Cys Thr His Gln Glu Lys Val Thr
                980                 985                 990 att cag agg tgc agt gag ttc cct tgt cca cag tgg aaa tct gga gac        3023
Ile Gln Arg Cys Ser Glu Phe Pro Cys Pro Gln Trp Lys Ser Gly Asp
            995                 1000                1005 tgg tca gag tgc ttg gtc acc tgt gga aaa ggg cat aag cac agc cag        3071
Trp Ser Glu Cys Leu Val Thr Cys Gly Lys Gly His Lys His Ser Gln
        1010                1015                1020 gtc tgg tgt cag ttt ggt gaa gat cga tta aat gat aga atg tgt gac        3119
Val Trp Cys Gln Phe Gly Glu Asp Arg Leu Asn Asp Arg Met Cys Asp
    1025                1030                1035 cct gag acc aag cca aca tct atg cag act tgt cag cag ccg gaa tgt        3167
Pro Glu Thr Lys Pro Thr Ser Met Gln Thr Cys Gln Gln Pro Glu Cys
1040                1045                1050                1055 gca tcc tgg cag gcg ggt ccc tgg gta cag tgc agt gtc act tgt gga        3215
Ala Ser Trp Gln Ala Gly Pro Trp Val Gln Cys Ser Val Thr Cys Gly
                1060                1065                1070 cag gga tac cag cta aga gca gtg aaa tgc atc att ggg act tat atg        3263
Gln Gly Tyr Gln Leu Arg Ala Val Lys Cys Ile Ile Gly Thr Tyr Met
            1075                1080                1085 tca gtg gta gat gac aat gac tgt aat gca gca act aga cca act gat        3311
Ser Val Val Asp Asp Asn Asp Cys Asn Ala Ala Thr Arg Pro Thr Asp
        1090                1095                1100 acc cag gac tgt gaa tta cca tca tgt cat cct ccc cca gct gcc ccg        3359
Thr Gln Asp Cys Glu Leu Pro Ser Cys His Pro Pro Pro Ala Ala Pro
    1105                1110                1115 gaa acg agg aga agc aca tac agt gca cca aga acc cag tgg cga ttt        3407
Glu Thr Arg Arg Ser Thr Tyr Ser Ala Pro Arg Thr Gln Trp Arg Phe
1120                1125                1130                1135 ggg tct tgg acc cca tgc tca gcc act tgt ggg aaa ggt acc cgg atg        3455
Gly Ser Trp Thr Pro Cys Ser Ala Thr Cys Gly Lys Gly Thr Arg Met
                1140                1145                1150 aga tac gtc agc tgc cga gat gag aat ggc tct gtg gct gac gag agt        3503
Arg Tyr Val Ser Cys Arg Asp Glu Asn Gly Ser Val Ala Asp Glu Ser
            1155                1160                1165 gcc tgt gct acc ctg cct aga cca gtg gca aag gaa gaa tgt tct gtg        3551
Ala Cys Ala Thr Leu Pro Arg Pro Val Ala Lys Glu Glu Cys Ser Val
        1170                1175                1180 aca ccc tgt ggg caa tgg aag gcc ttg gac tgg agc tct tgc tct gtg        3599
Thr Pro Cys Gly Gln Trp Lys Ala Leu Asp Trp Ser Ser Cys Ser Val
    1185                1190                1195 acc tgt ggg caa ggt agg gca acc cgg caa gtg atg tgt gtc aac tac        3647
Thr Cys Gly Gln Gly Arg Ala Thr Arg Gln Val Met Cys Val Asn Tyr
1200                1205                1210                1215 agt gac cac gtg atc gat cgg agt gag tgt gac cag gat tat atc cca        3695
Ser Asp His Val Ile Asp Arg Ser Glu Cys Asp Gln Asp Tyr Ile Pro
                1220                1225                1230
```

-continued

| | | |
|---|---|---|
| gaa act gac cag gac tgt tcc atg tca cca tgc cct caa agg acc cca<br>Glu Thr Asp Gln Asp Cys Ser Met Ser Pro Cys Pro Gln Arg Thr Pro<br>　　　　1235　　　　　　　　　1240　　　　　　　　　1245 | 3743 | |
| gac agt ggc tta gct cag cac ccc ttc caa aat gag gac tat cgt ccc<br>Asp Ser Gly Leu Ala Gln His Pro Phe Gln Asn Glu Asp Tyr Arg Pro<br>1250　　　　　　　　　1255　　　　　　　　　1260 | 3791 | |
| cgg agc gcc agc ccc agc cgc acc cat gtg ctc ggt gga aac cag tgg<br>Arg Ser Ala Ser Pro Ser Arg Thr His Val Leu Gly Gly Asn Gln Trp<br>　　1265　　　　　　　　　1270　　　　　　　　　1275 | 3839 | |
| aga act ggc ccc tgg gga gca tgt tcc agt acc tgt gct ggg gga tcc<br>Arg Thr Gly Pro Trp Gly Ala Cys Ser Ser Thr Cys Ala Gly Gly Ser<br>1280　　　　　　　　　1285　　　　　　　　　1290　　　　　　　　　1295 | 3887 | |
| cag cgg cgt gtt gtt gta tgt cag gat gaa aat gga tac acc gca aac<br>Gln Arg Arg Val Val Val Cys Gln Asp Glu Asn Gly Tyr Thr Ala Asn<br>　　　　　　　　　1300　　　　　　　　　1305　　　　　　　　　1310 | 3935 | |
| gac tgt gtg gag aga ata aaa cct gat gag caa aga gcc tgt gaa tcc<br>Asp Cys Val Glu Arg Ile Lys Pro Asp Glu Gln Arg Ala Cys Glu Ser<br>　　　　1315　　　　　　　　　1320　　　　　　　　　1325 | 3983 | |
| ggc cct tgt cct cag tgg gct tat ggc aac tgg gga gag tgc act aag<br>Gly Pro Cys Pro Gln Trp Ala Tyr Gly Asn Trp Gly Glu Cys Thr Lys<br>1330　　　　　　　　　1335　　　　　　　　　1340 | 4031 | |
| ctg tgt ggt gga ggc ata aga aca aga ctg gtg gtc tct cag cgg tcc<br>Leu Cys Gly Gly Gly Ile Arg Thr Arg Leu Val Val Ser Gln Arg Ser<br>　　1345　　　　　　　　　1350　　　　　　　　　1355 | 4079 | |
| aac ggt gaa cgg ttt cca gat ttg agc tgt gaa att ctt gat aaa cct<br>Asn Gly Glu Arg Phe Pro Asp Leu Ser Cys Glu Ile Leu Asp Lys Pro<br>1360　　　　　　　　　1365　　　　　　　　　1370　　　　　　　　　1375 | 4127 | |
| ccc gat cgt gag cag tgt aac aca cat gct tgt cca cac gac gct gca<br>Pro Asp Arg Glu Gln Cys Asn Thr His Ala Cys Pro His Asp Ala Ala<br>　　　　　　　　　1380　　　　　　　　　1385　　　　　　　　　1390 | 4175 | |
| tgg agt act ggc cct tgg agc tcg tgt tct gtc tct tgt ggt cga ggg<br>Trp Ser Thr Gly Pro Trp Ser Ser Cys Ser Val Ser Cys Gly Arg Gly<br>　　　　1395　　　　　　　　　1400　　　　　　　　　1405 | 4223 | |
| cat aaa caa cga aat gtt tac tgc atg gca aaa gat gga agc cat tta<br>His Lys Gln Arg Asn Val Tyr Cys Met Ala Lys Asp Gly Ser His Leu<br>1410　　　　　　　　　1415　　　　　　　　　1420 | 4271 | |
| gaa agt gat tac tgt aag cac ctg gct aag cca cat ggg cac aga aag<br>Glu Ser Asp Tyr Cys Lys His Leu Ala Lys Pro His Gly His Arg Lys<br>　　1425　　　　　　　　　1430　　　　　　　　　1435 | 4319 | |
| tgc cga gga gga aga tgc ccc aaa tgg aaa gct ggc gct tgg agt cag<br>Cys Arg Gly Gly Arg Cys Pro Lys Trp Lys Ala Gly Ala Trp Ser Gln<br>1440　　　　　　　　　1445　　　　　　　　　1450　　　　　　　　　1455 | 4367 | |
| tgc tct gtg tcc atg ggc cga ggc gta cag cag agg cat gtg ggc tgt<br>Cys Ser Val Ser Met Gly Arg Gly Val Gln Gln Arg His Val Gly Cys<br>　　　　　　　　　1460　　　　　　　　　1465　　　　　　　　　1470 | 4415 | |
| cag atc gga aca cac aaa ata gcc aga gag acc gag tgc aac cca tac<br>Gln Ile Gly Thr His Lys Ile Ala Arg Glu Thr Glu Cys Asn Pro Tyr<br>　　　　1475　　　　　　　　　1480　　　　　　　　　1485 | 4463 | |
| acc aga ccg gag tcg gaa tgc gaa tgc caa ggc cca cgg tgt ccc ctt<br>Thr Arg Pro Glu Ser Glu Cys Glu Cys Gln Gly Pro Arg Cys Pro Leu<br>1490　　　　　　　　　1495　　　　　　　　　1500 | 4511 | |
| tac act tgg agg gca gag gaa tgg caa gaa tgc acc aag acc tgc ggc<br>Tyr Thr Trp Arg Ala Glu Glu Trp Gln Glu Cys Thr Lys Thr Cys Gly<br>　　1505　　　　　　　　　1510　　　　　　　　　1515 | 4559 | |
| gaa ggc tcc agg tac cgc aag gtg gtg tgt gtg gat gac aac aaa aac<br>Glu Gly Ser Arg Tyr Arg Lys Val Val Cys Val Asp Asp Asn Lys Asn<br>1520　　　　　　　　　1525　　　　　　　　　1530　　　　　　　　　1535 | 4607 | |
| gag gtg cat ggg gca cgc tgt gac gtg agc aag cgg ccg gtg gac cgt<br>Glu Val His Gly Ala Arg Cys Asp Val Ser Lys Arg Pro Val Asp Arg<br>　　　　　　　　　1540　　　　　　　　　1545　　　　　　　　　1550 | 4655 | |

```
gaa agc tgt agt ttg caa ccc tgc gag tat gtc tgg act aca gga gaa      4703
Glu Ser Cys Ser Leu Gln Pro Cys Glu Tyr Val Trp Thr Thr Gly Glu
        1555                1560                1565 tgg tca gag tgc tca gtg acc tgt gga aaa ggc tac aaa caa agg ctt      4751
Trp Ser Glu Cys Ser Val Thr Cys Gly Lys Gly Tyr Lys Gln Arg Leu
    1570                1575                1580 gtc tcg tgc agc gag att tac acc ggg aaa gag aat tat gaa tac agc      4799
Val Ser Cys Ser Glu Ile Tyr Thr Gly Lys Glu Asn Tyr Glu Tyr Ser
1585                1590                1595 tac caa acc acc atc aac tgc cca ggc acg cag ccc ccc agt gtt cac      4847
Tyr Gln Thr Thr Ile Asn Cys Pro Gly Thr Gln Pro Pro Ser Val His
1600                1605                1610                1615 ccc tgt tac ctg agg gag tgc cct gtc tcg gcc acc tgg aga gtt ggc      4895
Pro Cys Tyr Leu Arg Glu Cys Pro Val Ser Ala Thr Trp Arg Val Gly
                1620                1625                1630 aac tgg ggg agc tgc tca gtg tct tgt ggt gtt gga gtg atg cag aga      4943
Asn Trp Gly Ser Cys Ser Val Ser Cys Gly Val Gly Val Met Gln Arg
            1635                1640                1645 tct gtg caa tgt tta acc aat gag gac caa ccc agc cac tta tgc cac      4991
Ser Val Gln Cys Leu Thr Asn Glu Asp Gln Pro Ser His Leu Cys His
        1650                1655                1660 act gat ctg aag cca gaa gaa cga aaa acc tgc cgt aat gtc tat aac      5039
Thr Asp Leu Lys Pro Glu Glu Arg Lys Thr Cys Arg Asn Val Tyr Asn
    1665                1670                1675 tgt gag tta ccc cag aat tgc aag gag gta aaa aga ctt aaa ggt gcc      5087
Cys Glu Leu Pro Gln Asn Cys Lys Glu Val Lys Arg Leu Lys Gly Ala
1680                1685                1690                1695 agt gaa gat ggt gaa tat ttc ctg atg att aga gga aag ctt ctg aag      5135
Ser Glu Asp Gly Glu Tyr Phe Leu Met Ile Arg Gly Lys Leu Leu Lys
                1700                1705                1710 ata ttc tgt gcg ggg atg cac tct gac cac ccc aaa gag tac gtg aca      5183
Ile Phe Cys Ala Gly Met His Ser Asp His Pro Lys Glu Tyr Val Thr
            1715                1720                1725 ctg gtg cat gga gac tct gag aat ttc tcc gag gtt tat ggg cac agg      5231
Leu Val His Gly Asp Ser Glu Asn Phe Ser Glu Val Tyr Gly His Arg
        1730                1735                1740 tta cac aac cca aca gaa tgt ccc tat aac ggg agc cgg cgc gat gac      5279
Leu His Asn Pro Thr Glu Cys Pro Tyr Asn Gly Ser Arg Arg Asp Asp
    1745                1750                1755 tgc caa tgt cgg aag gat tac acg gcc gct ggg ttt tcc agt ttt cag      5327
Cys Gln Cys Arg Lys Asp Tyr Thr Ala Ala Gly Phe Ser Ser Phe Gln
1760                1765                1770                1775 aaa atc aga ata gac ctg acc agc atg cag ata atc acc act gac tta      5375
Lys Ile Arg Ile Asp Leu Thr Ser Met Gln Ile Ile Thr Thr Asp Leu
                1780                1785                1790 cag ttt gca agg aca agc gaa gga cat ccc gtc cct ttt gcc aca gcc      5423
Gln Phe Ala Arg Thr Ser Glu Gly His Pro Val Pro Phe Ala Thr Ala
            1795                1800                1805 ggg gat tgc tac agc gct gcc aag tgc cca cag ggt cgt ttt agc atc      5471
Gly Asp Cys Tyr Ser Ala Ala Lys Cys Pro Gln Gly Arg Phe Ser Ile
        1810                1815                1820 aac ctt tat gga acc ggc ttg tct tta act gaa tct gcc aga tgg ata      5519
Asn Leu Tyr Gly Thr Gly Leu Ser Leu Thr Glu Ser Ala Arg Trp Ile
    1825                1830                1835 tca caa ggg aat tat gct gtc tct gac atc aag aag tcg ccg gat ggt      5567
Ser Gln Gly Asn Tyr Ala Val Ser Asp Ile Lys Lys Ser Pro Asp Gly
1840                1845                1850                1855 acc cga gtc gta ggg aaa tgc ggt ggt tac tgt gga aaa tgc act cca      5615
Thr Arg Val Val Gly Lys Cys Gly Gly Tyr Cys Gly Lys Cys Thr Pro
```

-continued

```
                   1860           1865           1870
tcc tct ggt act ggc ctg gag gtg cga gtt tta tagctaaggt gctttgaaga    5668
Ser Ser Gly Thr Gly Leu Glu Val Arg Val Leu
            1875            1880 ggaagccatt atggatggat gaaggatagt aatgcaatac ctccaccttta atttgggtgc   5728 atgtgtatgt gtgtgtgtgt ttgtgtgtga cttgtatgct tgtgtgtgta aatgtgtgta   5788
catatacata tataca                                                   5804
```

<210> SEQ ID NO 13
<211> LENGTH: 1882
<212> TYPE: PRT
<213> ORGANISM: Homo sapiens ADAMTS-9
<220> FEATURE:
<221> NAME/KEY: MOD_RES
<222> LOCATION: (468)
<223> OTHER INFORMATION: Xaa = C
<221> NAME/KEY: MOD_RES
<222> LOCATION: (521)
<223> OTHER INFORMATION: Xaa = Y

<400> SEQUENCE: 13

```
Ser Thr Met Gln Phe Val Ser Trp Ala Thr Leu Leu Thr Leu Leu Val
  1               5                  10                  15

Arg Asp Leu Ala Glu Met Gly Ser Pro Asp Ala Ala Ala Val Arg
             20                  25                  30

Lys Asp Arg Leu His Pro Arg Gln Val Lys Leu Leu Glu Thr Leu Ser
         35                  40                  45

Glu Tyr Glu Ile Val Ser Pro Ile Arg Val Asn Ala Leu Gly Glu Pro
     50                  55                  60

Phe Pro Thr Asn Val His Phe Lys Arg Thr Arg Arg Ser Ile Asn Ser
 65                  70                  75                  80

Ala Thr Asp Pro Trp Pro Ala Phe Ala Ser Ser Ser Ser Ser Thr
                 85                  90                  95

Ser Ser Gln Ala His Tyr Arg Leu Ser Ala Phe Gly Gln Gln Phe Leu
            100                 105                 110

Phe Asn Leu Thr Ala Asn Ala Gly Phe Ile Ala Pro Leu Phe Thr Val
        115                 120                 125

Thr Leu Leu Gly Thr Pro Gly Val Asn Gln Thr Lys Phe Tyr Ser Glu
    130                 135                 140

Glu Glu Ala Glu Leu Lys His Cys Phe Tyr Lys Arg Leu Cys Gln Tyr
145                 150                 155                 160

Gln Leu Arg Ala His Gly Arg His Gln Pro Leu Leu Arg Asn Glu His
                165                 170                 175

Lys Asn Arg His Ser Lys Asp Lys Lys Thr Arg Ala Arg Lys Trp
            180                 185                 190

Gly Glu Arg Ile Asn Leu Ala Gly Asp Val Ala Ala Leu Asn Ser Gly
        195                 200                 205

Leu Ala Thr Glu Ala Phe Ser Ala Tyr Gly Asn Lys Thr Asp Asn Thr
    210                 215                 220

Arg Glu Lys Arg Thr His Arg Arg Thr Lys Arg Phe Leu Ser Tyr Pro
225                 230                 235                 240

Arg Phe Val Glu Val Leu Val Val Ala Asp Asn Arg Met Val Ser Tyr
                245                 250                 255

His Gly Glu Asn Leu Gln His Tyr Ile Leu Thr Leu Met Ser Ile Val
            260                 265                 270

Ala Ser Ile Tyr Lys Asp Pro Ser Ile Gly Asn Leu Ile Asn Ile Val
```

-continued

```
               275                 280                 285
Ile Val Asn Leu Ile Val Ile His Asn Glu Gln Asp Gly Pro Ser Ile
            290                 295                 300
Ser Phe Asn Ala Gln Thr Thr Leu Lys Asn Phe Cys Gln Trp Gln His
305                 310                 315                 320
Ser Asn Ser Pro Gly Gly Ile His His Asp Thr Ala Val Leu Leu Thr
                325                 330                 335
Arg Gln Asp Ile Cys Arg Ala His Asp Lys Cys Asp Thr Leu Gly Leu
            340                 345                 350
Ala Glu Leu Gly Thr Ile Cys Asp Pro Tyr Arg Ser Cys Ser Ile Ser
            355                 360                 365
Glu Asp Ser Gly Leu Ser Thr Ala Phe Thr Ile Ala His Glu Leu Gly
370                 375                 380
His Val Phe Asn Met Pro His Asp Asp Asn Lys Cys Lys Glu Glu
385                 390                 395                 400
Gly Val Lys Ser Pro Gln His Val Met Ala Pro Thr Leu Asn Phe Tyr
                405                 410                 415
Thr Asn Pro Trp Met Trp Ser Lys Cys Ser Arg Lys Tyr Ile Thr Glu
            420                 425                 430
Phe Leu Asp Thr Gly Tyr Gly Glu Cys Leu Leu Asn Glu Pro Glu Ser
            435                 440                 445
Arg Pro Tyr Pro Leu Pro Val Gln Leu Pro Gly Ile Leu Tyr Asn Val
450                 455                 460
Asn Lys Gln Xaa Glu Leu Ile Phe Gly Pro Gly Ser Gln Val Cys Pro
465                 470                 475                 480
Tyr Met Met Gln Cys Arg Arg Leu Trp Cys Asn Asn Val Asn Gly Val
                485                 490                 495
His Lys Gly Cys Arg Thr Gln His Thr Pro Trp Ala Asp Gly Thr Glu
                500                 505                 510
Cys Glu Pro Gly Lys His Cys Lys Xaa Gly Phe Cys Val Pro Lys Glu
            515                 520                 525
Met Asp Val Pro Val Thr Asp Gly Ser Trp Gly Ser Trp Ser Pro Phe
530                 535                 540
Gly Thr Cys Ser Arg Thr Cys Gly Gly Gly Ile Lys Thr Ala Ile Arg
545                 550                 555                 560
Glu Cys Asn Arg Pro Glu Pro Lys Asn Gly Gly Lys Tyr Cys Val Gly
                565                 570                 575
Arg Arg Met Lys Phe Lys Ser Cys Asn Thr Glu Pro Cys Leu Lys Gln
            580                 585                 590
Lys Arg Asp Phe Arg Asp Glu Gln Cys Ala His Phe Asp Gly Lys His
            595                 600                 605
Phe Asn Ile Asn Gly Leu Leu Pro Asn Val Arg Trp Val Pro Lys Tyr
610                 615                 620
Ser Gly Ile Leu Met Lys Asp Arg Cys Lys Leu Phe Cys Arg Val Ala
625                 630                 635                 640
Gly Asn Thr Ala Tyr Tyr Gln Leu Arg Asp Arg Val Ile Asp Gly Thr
                645                 650                 655
Pro Cys Gly Gln Asp Thr Asn Asp Ile Cys Val Gln Gly Leu Cys Arg
            660                 665                 670
Gln Ala Gly Cys Asp His Val Leu Asn Ser Lys Ala Arg Arg Asp Lys
            675                 680                 685
Cys Gly Val Cys Gly Gly Asp Asn Ser Ser Cys Lys Thr Val Ala Gly
690                 695                 700
```

-continued

```
Thr Phe Asn Thr Val His Tyr Gly Tyr Asn Thr Val Arg Ile Pro
705                 710                 715                 720

Ala Gly Ala Thr Asn Ile Asp Val Arg Gln His Ser Phe Ser Gly Glu
            725                 730                 735

Thr Asp Asp Asn Tyr Leu Ala Leu Ser Ser Ser Lys Gly Glu Phe
        740                 745                 750

Leu Leu Asn Gly Asn Phe Val Val Thr Met Ala Lys Arg Glu Ile Arg
            755                 760                 765

Ile Gly Asn Ala Val Val Glu Tyr Ser Gly Ser Glu Thr Ala Val Glu
770                 775                 780

Arg Ile Asn Ser Thr Asp Arg Ile Glu Gln Glu Leu Leu Leu Gln Val
785                 790                 795                 800

Leu Ser Val Gly Lys Leu Tyr Asn Pro Asp Val Arg Tyr Ser Phe Asn
            805                 810                 815

Ile Pro Ile Glu Asp Lys Pro Gln Gln Phe Tyr Trp Asn Ser His Gly
            820                 825                 830

Pro Trp Gln Ala Cys Ser Lys Pro Cys Gln Gly Glu Arg Lys Arg Lys
            835                 840                 845

Leu Val Cys Thr Arg Glu Ser Asp Gln Leu Thr Val Ser Asp Gln Arg
850                 855                 860

Cys Asp Arg Leu Pro Gln Pro Gly His Ile Thr Glu Pro Cys Gly Thr
865                 870                 875                 880

Gly Cys Asp Leu Arg Trp His Val Ala Ser Arg Ser Glu Cys Ser Ala
            885                 890                 895

Gln Cys Gly Leu Gly Tyr Arg Thr Leu Asp Ile Tyr Cys Ala Lys Tyr
            900                 905                 910

Ser Arg Leu Asp Gly Lys Thr Glu Lys Val Asp Asp Gly Phe Cys Ser
            915                 920                 925

Ser His Pro Lys Pro Ser Asn Arg Glu Lys Cys Ser Gly Glu Cys Asn
    930                 935                 940

Thr Gly Gly Trp Arg Tyr Ser Ala Trp Thr Glu Cys Ser Lys Ser Cys
945                 950                 955                 960

Asp Gly Gly Thr Gln Arg Arg Arg Ala Ile Cys Val Asn Thr Arg Asn
            965                 970                 975

Asp Val Leu Asp Asp Ser Lys Cys Thr His Gln Glu Lys Val Thr Ile
            980                 985                 990

Gln Arg Cys Ser Glu Phe Pro Cys Pro Gln Trp Lys Ser Gly Asp Trp
    995                 1000                1005

Ser Glu Cys Leu Val Thr Cys Gly Lys Gly His Lys His Ser Gln Val
    1010                1015                1020

Trp Cys Gln Phe Gly Glu Asp Arg Leu Asn Asp Arg Met Cys Asp Pro
1025                1030                1035                1040

Glu Thr Lys Pro Thr Ser Met Gln Thr Cys Gln Pro Glu Cys Ala
            1045                1050                1055

Ser Trp Gln Ala Gly Pro Trp Val Gln Cys Ser Val Thr Cys Gly Gln
            1060                1065                1070

Gly Tyr Gln Leu Arg Ala Val Lys Cys Ile Ile Gly Thr Tyr Met Ser
        1075                1080                1085

Val Val Asp Asp Asn Asp Cys Asn Ala Ala Thr Arg Pro Thr Asp Thr
    1090                1095                1100

Gln Asp Cys Glu Leu Pro Ser Cys His Pro Pro Ala Ala Pro Glu
1105                1110                1115                1120
```

```
Thr Arg Arg Ser Thr Tyr Ser Ala Pro Arg Thr Gln Trp Arg Phe Gly
                1125                1130                1135

Ser Trp Thr Pro Cys Ser Ala Thr Cys Gly Lys Gly Thr Arg Met Arg
        1140                1145                1150

Tyr Val Ser Cys Arg Asp Glu Asn Gly Ser Val Ala Asp Glu Ser Ala
            1155                1160                1165

Cys Ala Thr Leu Pro Arg Pro Val Ala Lys Glu Glu Cys Ser Val Thr
    1170                1175                1180

Pro Cys Gly Gln Trp Lys Ala Leu Asp Trp Ser Ser Cys Ser Val Thr
1185                1190                1195                1200

Cys Gly Gln Gly Arg Ala Thr Arg Gln Val Met Cys Val Asn Tyr Ser
                1205                1210                1215

Asp His Val Ile Asp Arg Ser Glu Cys Asp Gln Asp Tyr Ile Pro Glu
                1220                1225                1230

Thr Asp Gln Asp Cys Ser Met Ser Pro Cys Pro Gln Arg Thr Pro Asp
            1235                1240                1245

Ser Gly Leu Ala Gln His Pro Phe Gln Asn Glu Asp Tyr Arg Pro Arg
        1250                1255                1260

Ser Ala Ser Pro Ser Arg Thr His Val Leu Gly Gly Asn Gln Trp Arg
1265                1270                1275                1280

Thr Gly Pro Trp Gly Ala Cys Ser Ser Thr Cys Ala Gly Gly Ser Gln
                1285                1290                1295

Arg Arg Val Val Val Cys Gln Asp Glu Asn Gly Tyr Thr Ala Asn Asp
                1300                1305                1310

Cys Val Glu Arg Ile Lys Pro Asp Glu Gln Arg Ala Cys Glu Ser Gly
            1315                1320                1325

Pro Cys Pro Gln Trp Ala Tyr Gly Asn Trp Gly Glu Cys Thr Lys Leu
    1330                1335                1340

Cys Gly Gly Gly Ile Arg Thr Arg Leu Val Val Ser Gln Arg Ser Asn
1345                1350                1355                1360

Gly Glu Arg Phe Pro Asp Leu Ser Cys Glu Ile Leu Asp Lys Pro Pro
                1365                1370                1375

Asp Arg Glu Gln Cys Asn Thr His Ala Cys Pro His Asp Ala Ala Trp
            1380                1385                1390

Ser Thr Gly Pro Trp Ser Ser Cys Ser Val Ser Cys Gly Arg Gly His
        1395                1400                1405

Lys Gln Arg Asn Val Tyr Cys Met Ala Lys Asp Gly Ser His Leu Glu
    1410                1415                1420

Ser Asp Tyr Cys Lys His Leu Ala Lys Pro His Gly His Arg Lys Cys
1425                1430                1435                1440

Arg Gly Gly Arg Cys Pro Lys Trp Lys Ala Gly Ala Trp Ser Gln Cys
                1445                1450                1455

Ser Val Ser Met Gly Arg Gly Val Gln Gln Arg His Val Gly Cys Gln
            1460                1465                1470

Ile Gly Thr His Lys Ile Ala Arg Glu Thr Glu Cys Asn Pro Tyr Thr
        1475                1480                1485

Arg Pro Glu Ser Glu Cys Glu Cys Gln Gly Pro Arg Cys Pro Leu Tyr
    1490                1495                1500

Thr Trp Arg Ala Glu Glu Trp Gln Glu Cys Thr Lys Thr Cys Gly Glu
1505                1510                1515                1520

Gly Ser Arg Tyr Arg Lys Val Val Cys Val Asp Asp Asn Lys Asn Glu
                1525                1530                1535

Val His Gly Ala Arg Cys Asp Val Ser Lys Arg Pro Val Asp Arg Glu
```

```
                  1540                1545                1550
Ser Cys Ser Leu Gln Pro Cys Glu Tyr Val Trp Thr Thr Gly Glu Trp
            1555                1560                1565

Ser Glu Cys Ser Val Thr Cys Gly Lys Gly Tyr Lys Gln Arg Leu Val
    1570                1575                1580

Ser Cys Ser Glu Ile Tyr Thr Gly Lys Glu Asn Tyr Glu Tyr Ser Tyr
1585                1590                1595                1600

Gln Thr Thr Ile Asn Cys Pro Gly Thr Gln Pro Ser Val His Pro
                1605                1610                1615

Cys Tyr Leu Arg Glu Cys Pro Val Ser Ala Thr Trp Arg Val Gly Asn
            1620                1625                1630

Trp Gly Ser Cys Ser Val Ser Cys Gly Val Gly Val Met Gln Arg Ser
            1635                1640                1645

Val Gln Cys Leu Thr Asn Glu Asp Gln Pro Ser His Leu Cys His Thr
    1650                1655                1660

Asp Leu Lys Pro Glu Glu Arg Lys Thr Cys Arg Asn Val Tyr Asn Cys
1665                1670                1675                1680

Glu Leu Pro Gln Asn Cys Lys Glu Val Lys Arg Leu Lys Gly Ala Ser
                1685                1690                1695

Glu Asp Gly Glu Tyr Phe Leu Met Ile Arg Gly Lys Leu Leu Lys Ile
            1700                1705                1710

Phe Cys Ala Gly Met His Ser Asp His Pro Lys Glu Tyr Val Thr Leu
            1715                1720                1725

Val His Gly Asp Ser Glu Asn Phe Ser Glu Val Tyr Gly His Arg Leu
    1730                1735                1740

His Asn Pro Thr Glu Cys Pro Tyr Asn Gly Ser Arg Arg Asp Asp Cys
1745                1750                1755                1760

Gln Cys Arg Lys Asp Tyr Thr Ala Ala Gly Phe Ser Ser Phe Gln Lys
                1765                1770                1775

Ile Arg Ile Asp Leu Thr Ser Met Gln Ile Ile Thr Thr Asp Leu Gln
            1780                1785                1790

Phe Ala Arg Thr Ser Glu Gly His Pro Val Pro Phe Thr Ala Gly
            1795                1800                1805

Asp Cys Tyr Ser Ala Ala Lys Cys Pro Gln Gly Arg Phe Ser Ile Asn
1810                1815                1820

Leu Tyr Gly Thr Gly Leu Ser Leu Thr Glu Ser Ala Arg Trp Ile Ser
1825                1830                1835                1840

Gln Gly Asn Tyr Ala Val Ser Asp Ile Lys Lys Ser Pro Asp Gly Thr
                1845                1850                1855

Arg Val Val Gly Lys Cys Gly Gly Tyr Cys Gly Lys Cys Thr Pro Ser
            1860                1865                1870

Ser Gly Thr Gly Leu Glu Val Arg Val Leu
        1875                1880

<210> SEQ ID NO 14
<211> LENGTH: 2625
<212> TYPE: DNA
<213> ORGANISM: Mus musculus ADAMTS-9
<220> FEATURE:
<221> NAME/KEY: CDS
<222> LOCATION: (2)..(2623)

<400> SEQUENCE: 14 g cac act gcg gtc atc agc ctg tgc tcc gga atg atg ggc acg ttc cgc    49
  His Thr Ala Val Ile Ser Leu Cys Ser Gly Met Met Gly Thr Phe Arg
    1               5                  10                  15
```

```
tct cac gat gga gat tat ttc att gaa cca ctg cag tct gtg gat gag      97
Ser His Asp Gly Asp Tyr Phe Ile Glu Pro Leu Gln Ser Val Asp Glu
            20                  25                  30 caa gag gat gaa gag gaa caa aac aaa ccc cac att att tat agg cac     145
Gln Glu Asp Glu Glu Gln Asn Lys Pro His Ile Ile Tyr Arg His
        35                  40                  45 agc acc cct cag agg gaa ccc tcc aca gga aag cat gcc tgt gcc acc     193
Ser Thr Pro Gln Arg Glu Pro Ser Thr Gly Lys His Ala Cys Ala Thr
 50                  55                  60 tca gaa ctc aaa aat agt cac agt aaa gac aag cgg aaa atc aga atg     241
Ser Glu Leu Lys Asn Ser His Ser Lys Asp Lys Arg Lys Ile Arg Met
 65                  70                  75                  80 cga aaa cgg aga aag agg aat agc ctg gct gac gac gtg gca ctg cta     289
Arg Lys Arg Arg Lys Arg Asn Ser Leu Ala Asp Asp Val Ala Leu Leu
                 85                  90                  95 aag agc ggt ttg gca aca aag gtg ctc tct ggc tat agc aac cag aca     337
Lys Ser Gly Leu Ala Thr Lys Val Leu Ser Gly Tyr Ser Asn Gln Thr
            100                 105                 110 aac aac aca agg gac aga tgg aac cac aaa aga acc aaa cgc ttt ctg     385
Asn Asn Thr Arg Asp Arg Trp Asn His Lys Arg Thr Lys Arg Phe Leu
        115                 120                 125 tcc tac cca cgg ttt gta gag gtg atg gtg gtg gct gac cac agg atg     433
Ser Tyr Pro Arg Phe Val Glu Val Met Val Val Ala Asp His Arg Met
 130                 135                 140 gtt tta tac cac gga gca aac ctt caa cat tat atc tta acc tta atg     481
Val Leu Tyr His Gly Ala Asn Leu Gln His Tyr Ile Leu Thr Leu Met
145                 150                 155                 160 tcc att gta gct tct atc tat aaa gac tca agt att gga aat tta att     529
Ser Ile Val Ala Ser Ile Tyr Lys Asp Ser Ser Ile Gly Asn Leu Ile
                165                 170                 175 aat att gtt att gtg aac tta gtt gtg att cat aat gaa cag gaa gga     577
Asn Ile Val Ile Val Asn Leu Val Val Ile His Asn Glu Gln Glu Gly
            180                 185                 190 cct tac ata aat ttc aat gcc cag aca aca tta aag aac ttt tgc cag     625
Pro Tyr Ile Asn Phe Asn Ala Gln Thr Thr Leu Lys Asn Phe Cys Gln
        195                 200                 205 tgg cag cac tca aag aac tac ttg ggt ggg att cag cac gac aca gcc     673
Trp Gln His Ser Lys Asn Tyr Leu Gly Gly Ile Gln His Asp Thr Ala
 210                 215                 220 gtt ctg gtc aca agg gaa gat atc tgc aga gct cag gac aaa tgt gac     721
Val Leu Val Thr Arg Glu Asp Ile Cys Arg Ala Gln Asp Lys Cys Asp
225                 230                 235                 240 acc tta ggt ctt gct gaa ctg gga acc att tgc gac ccc tac cga agc     769
Thr Leu Gly Leu Ala Glu Leu Gly Thr Ile Cys Asp Pro Tyr Arg Ser
                245                 250                 255 tgt tcc att agt gaa gac agt ggg ctg agc aca gct ttc aca ata gct     817
Cys Ser Ile Ser Glu Asp Ser Gly Leu Ser Thr Ala Phe Thr Ile Ala
            260                 265                 270 cac gag ctg ggc cat gtg ttt aat atg cct cac gat gac agc aat aaa     865
His Glu Leu Gly His Val Phe Asn Met Pro His Asp Asp Ser Asn Lys
        275                 280                 285 tgc aaa gaa gaa gga gtt aag agt ccc cag cat gtc atg gca cca aca     913
Cys Lys Glu Glu Gly Val Lys Ser Pro Gln His Val Met Ala Pro Thr
 290                 295                 300 ctg aac ttc tac acc aac ccc tgg atg tgg tca aag tgc agt cgg aaa     961
Leu Asn Phe Tyr Thr Asn Pro Trp Met Trp Ser Lys Cys Ser Arg Lys
305                 310                 315                 320 tac atc act gag ttc cta gac act ggg tac gga gag tgc ttg ctg aat    1009
Tyr Ile Thr Glu Phe Leu Asp Thr Gly Tyr Gly Glu Cys Leu Leu Asn
```

-continued

|  | 325 |  |  |  | 330 |  |  |  | 335 |  |  |  |  |
|---|---|---|---|---|---|---|---|---|---|---|---|---|---|
| gaa | cct | gca | tcc | agg | acc | tat | cct | ttg | cct | tcc | caa | ctg | ccc ggc ctt | 1057 |
| Glu | Pro | Ala | Ser | Arg | Thr | Tyr | Pro | Leu | Pro | Ser | Gln | Leu | Pro Gly Leu | |
|  |  | 340 |  |  |  | 345 |  |  |  | 350 | | | | |

| ctc | tac | aac | gtg | aat | aaa | caa | tgt | gaa | ctg | att | ttt | ggg | cca ggc tct | 1105 |
| Leu | Tyr | Asn | Val | Asn | Lys | Gln | Cys | Glu | Leu | Ile | Phe | Gly | Pro Gly Ser | |
|  | 355 |  |  |  | 360 |  |  |  | 365 | | | | | |

| caa | gtg | tgc | ccc | tat | atg | atg | cag | tgc | aga | cgg | ctc | tgg | tgc aat aat | 1153 |
| Gln | Val | Cys | Pro | Tyr | Met | Met | Gln | Cys | Arg | Arg | Leu | Trp | Cys Asn Asn | |
| 370 |  |  |  | 375 |  |  |  | 380 | | | | | | |

| gtg | gat | gga | gca | cac | aaa | ggc | tgc | aag | act | cag | cac | acg | ccc tgg gca | 1201 |
| Val | Asp | Gly | Ala | His | Lys | Gly | Cys | Lys | Thr | Gln | His | Thr | Pro Trp Ala | |
| 385 |  |  |  | 390 |  |  |  | 395 | | | | 400 | | |

| gat | gga | acc | gag | tgt | gag | cct | gga | aag | cac | tgc | aag | ttt | gga ttt tgt | 1249 |
| Asp | Gly | Thr | Glu | Cys | Glu | Pro | Gly | Lys | His | Cys | Lys | Phe | Gly Phe Cys | |
|  |  |  | 405 |  |  |  | 410 |  |  |  | 415 | | | |

| gtt | ccc | aaa | gaa | atg | gag | ggc | cct | gca | att | gat | gga | tcc | tgg gga ggt | 1297 |
| Val | Pro | Lys | Glu | Met | Glu | Gly | Pro | Ala | Ile | Asp | Gly | Ser | Trp Gly Gly | |
|  |  | 420 |  |  |  | 425 |  |  |  | 430 | | | | |

| tgg | agc | cac | ttt | ggg | acc | tgc | tca | aga | acg | tgt | gga | gga | ggc atc aaa | 1345 |
| Trp | Ser | His | Phe | Gly | Thr | Cys | Ser | Arg | Thr | Cys | Gly | Gly | Gly Ile Lys | |
|  | 435 |  |  |  | 440 |  |  |  | 445 | | | | | |

| aca | gcc | atc | aga | gag | tgc | aac | aga | cca | gag | cca | aaa | aat | ggt ggg aag | 1393 |
| Thr | Ala | Ile | Arg | Glu | Cys | Asn | Arg | Pro | Glu | Pro | Lys | Asn | Gly Gly Lys | |
|  | 450 |  |  |  | 455 |  |  |  | 460 | | | | | |

| tac | tgt | gta | gga | agg | aga | atg | aag | ttc | aaa | tcc | tgc | aac | acg gag ccc | 1441 |
| Tyr | Cys | Val | Gly | Arg | Arg | Met | Lys | Phe | Lys | Ser | Cys | Asn | Thr Glu Pro | |
| 465 |  |  |  | 470 |  |  |  | 475 |  |  |  | 480 | | |

| tgc | atg | aag | cag | aag | cga | gac | ttc | cga | gag | gag | cag | tgt | gct cac ttt | 1489 |
| Cys | Met | Lys | Gln | Lys | Arg | Asp | Phe | Arg | Glu | Glu | Gln | Cys | Ala His Phe | |
|  |  |  | 485 |  |  |  | 490 |  |  |  | 495 | | | |

| gat | ggc | aaa | cac | ttc | aac | atc | aat | ggt | ctg | ctg | ccc | agc | gta cgc tgg | 1537 |
| Asp | Gly | Lys | His | Phe | Asn | Ile | Asn | Gly | Leu | Leu | Pro | Ser | Val Arg Trp | |
|  |  |  | 500 |  |  |  | 505 |  |  |  | 510 | | | |

| ttt | cct | aag | tac | agc | gga | att | ttg | atg | aag | gac | cgg | tgc | aag ttg ttc | 1585 |
| Phe | Pro | Lys | Tyr | Ser | Gly | Ile | Leu | Met | Lys | Asp | Arg | Cys | Lys Leu Phe | |
|  |  | 515 |  |  |  | 520 |  |  |  | 525 | | | | |

| tgc | aga | gtg | gca | gga | aac | aca | gcc | tac | tac | cag | ctc | cga | gac aga gtg | 1633 |
| Cys | Arg | Val | Ala | Gly | Asn | Thr | Ala | Tyr | Tyr | Gln | Leu | Arg | Asp Arg Val | |
|  | 530 |  |  |  | 535 |  |  |  | 540 | | | | | |

| att | gac | gga | acc | cct | tgt | ggc | cag | gac | aca | aat | gac | atc | tgt gtc caa | 1681 |
| Ile | Asp | Gly | Thr | Pro | Cys | Gly | Gln | Asp | Thr | Asn | Asp | Ile | Cys Val Gln | |
| 545 |  |  |  | 550 |  |  |  | 555 |  |  |  | 560 | | |

| ggc | ctt | tgc | cgg | caa | gct | gga | tgt | gat | cat | att | tta | aac | tca aag gtc | 1729 |
| Gly | Leu | Cys | Arg | Gln | Ala | Gly | Cys | Asp | His | Ile | Leu | Asn | Ser Lys Val | |
|  |  |  | 565 |  |  |  | 570 |  |  |  | 575 | | | |

| cgg | aaa | gat | aaa | tgt | ggg | att | tgt | ggt | gga | gat | aat | tct | tca tgc aaa | 1777 |
| Arg | Lys | Asp | Lys | Cys | Gly | Ile | Cys | Gly | Gly | Asp | Asn | Ser | Ser Cys Lys | |
|  |  |  | 580 |  |  |  | 585 |  |  |  | 590 | | | |

| aca | gtg | gca | gga | aca | ttt | aac | act | gtc | cat | tat | ggt | tac | aat act gtt | 1825 |
| Thr | Val | Ala | Gly | Thr | Phe | Asn | Thr | Val | His | Tyr | Gly | Tyr | Asn Thr Val | |
|  | 595 |  |  |  | 600 |  |  |  | 605 | | | | | |

| gtc | cga | att | ccg | gct | ggt | gct | acc | agc | att | gac | gtg | cgt | cag cac agc | 1873 |
| Val | Arg | Ile | Pro | Ala | Gly | Ala | Thr | Ser | Ile | Asp | Val | Arg | Gln His Ser | |
|  | 610 |  |  |  | 615 |  |  |  | 620 | | | | | |

| ttc | tca | ggg | aag | tct | gag | gat | gac | aac | tac | cta | gct | tta | tca aac agt | 1921 |
| Phe | Ser | Gly | Lys | Ser | Glu | Asp | Asp | Asn | Tyr | Leu | Ala | Leu | Ser Asn Ser | |
| 625 |  |  |  | 630 |  |  |  | 635 |  |  |  | 640 | | |

| aaa | ggt | gaa | ttc | ctg | cta | aat | gga | gac | ttt | gtt | gtc | tcc | atg tcc aaa | 1969 |

```
                Lys Gly Glu Phe Leu Leu Asn Gly Asp Phe Val Ser Met Ser Lys
                                645                 650                 655 agg gag gtc cgc gtg ggg agc gcc gtc att gag tac agc gga tcg gac          2017
Arg Glu Val Arg Val Gly Ser Ala Val Ile Glu Tyr Ser Gly Ser Asp
            660                 665                 670 aat gtg tgt gaa aga ctg aac tgt acg gac cgt atc gag gaa gaa ctt          2065
Asn Val Cys Glu Arg Leu Asn Cys Thr Asp Arg Ile Glu Glu Glu Leu
        675                 680                 685 ctc ctt cag gtg ttg tcc gtg gga aag ctg tat aac cca gat gtg cgg          2113
Leu Leu Gln Val Leu Ser Val Gly Lys Leu Tyr Asn Pro Asp Val Arg
    690                 695                 700 tac tca ttc aat att ccc att gag gac aaa cct cag caa ttt tac tgg          2161
Tyr Ser Phe Asn Ile Pro Ile Glu Asp Lys Pro Gln Gln Phe Tyr Trp
705                 710                 715                 720 aac agt cac ggg ccg tgg caa gca tgc agc aag ccc tgc caa ggg gag          2209
Asn Ser His Gly Pro Trp Gln Ala Cys Ser Lys Pro Cys Gln Gly Glu
                725                 730                 735 cgg aga cca aaa ctt gtt tgc acc agg gag tct gat cag cta acc gtt          2257
Arg Arg Pro Lys Leu Val Cys Thr Arg Glu Ser Asp Gln Leu Thr Val
            740                 745                 750 tct gat caa aga tgt gac cgg ctg ccc cag cca gga cct gtc act gaa          2305
Ser Asp Gln Arg Cys Asp Arg Leu Pro Gln Pro Gly Pro Val Thr Glu
        755                 760                 765 gcg tgc ggc aca gac tgt gac ttg agg tgg cac gtt gcc agc aag agc          2353
Ala Cys Gly Thr Asp Cys Asp Leu Arg Trp His Val Ala Ser Lys Ser
    770                 775                 780 gaa tgc agt gcc cag tgt ggt ttg ggc tac cgt act tta gac atc cac          2401
Glu Cys Ser Ala Gln Cys Gly Leu Gly Tyr Arg Thr Leu Asp Ile His
785                 790                 795                 800 tgt gcc aaa tac agc agg atg gac ggg aag acg gag aag gtg gat gac          2449
Cys Ala Lys Tyr Ser Arg Met Asp Gly Lys Thr Glu Lys Val Asp Asp
                805                 810                 815 agt ttc tgt agc agt caa ccc aga ccg agt aac cag gag aaa tgc tca          2497
Ser Phe Cys Ser Ser Gln Pro Arg Pro Ser Asn Gln Glu Lys Cys Ser
            820                 825                 830 gga gag tgc agc aca ggt gga tgg cgc tat tca gcc tgg acc gaa tgt          2545
Gly Glu Cys Ser Thr Gly Gly Trp Arg Tyr Ser Ala Trp Thr Glu Cys
        835                 840                 845 tct aga agc tgt gat ggt ggt acc cac aga aga aga gca att tgt gtc          2593
Ser Arg Ser Cys Asp Gly Gly Thr His Arg Arg Arg Ala Ile Cys Val
    850                 855                 860 aac acc cgc aat gat gtc ctg gat gac agc aa                               2625
Asn Thr Arg Asn Asp Val Leu Asp Asp Ser
865                 870
```

<210> SEQ ID NO 15
<211> LENGTH: 874
<212> TYPE: PRT
<213> ORGANISM: Mus musculus ADAMTS-9

<400> SEQUENCE: 15

```
His Thr Ala Val Ile Ser Leu Cys Ser Gly Met Met Gly Thr Phe Arg
  1               5                  10                  15

Ser His Asp Gly Asp Tyr Phe Ile Glu Pro Leu Gln Ser Val Asp Glu
                20                  25                  30

Gln Glu Asp Glu Glu Glu Gln Asn Lys Pro His Ile Ile Tyr Arg His
            35                  40                  45

Ser Thr Pro Gln Arg Glu Pro Ser Thr Gly Lys His Ala Cys Ala Thr
        50                  55                  60
```

```
Ser Glu Leu Lys Asn Ser His Ser Lys Asp Lys Arg Lys Ile Arg Met
 65                  70                  75                  80

Arg Lys Arg Arg Lys Arg Asn Ser Leu Ala Asp Val Ala Leu Leu
             85                  90                  95

Lys Ser Gly Leu Ala Thr Lys Val Leu Ser Gly Tyr Ser Asn Gln Thr
            100                 105                 110

Asn Asn Thr Arg Asp Arg Trp Asn His Lys Arg Thr Lys Arg Phe Leu
            115                 120                 125

Ser Tyr Pro Arg Phe Val Glu Val Met Val Val Ala Asp His Arg Met
130                 135                 140

Val Leu Tyr His Gly Ala Asn Leu Gln His Tyr Ile Leu Thr Leu Met
145                 150                 155                 160

Ser Ile Val Ala Ser Ile Tyr Lys Asp Ser Ile Gly Asn Leu Ile
                165                 170                 175

Asn Ile Val Ile Val Asn Leu Val Val Ile His Asn Glu Gln Glu Gly
            180                 185                 190

Pro Tyr Ile Asn Phe Asn Ala Gln Thr Thr Leu Lys Asn Phe Cys Gln
            195                 200                 205

Trp Gln His Ser Lys Asn Tyr Leu Gly Gly Ile Gln His Asp Thr Ala
            210                 215                 220

Val Leu Val Thr Arg Glu Asp Ile Cys Arg Ala Gln Asp Lys Cys Asp
225                 230                 235                 240

Thr Leu Gly Leu Ala Glu Leu Gly Thr Ile Cys Asp Pro Tyr Arg Ser
                245                 250                 255

Cys Ser Ile Ser Glu Asp Ser Gly Leu Ser Thr Ala Phe Thr Ile Ala
            260                 265                 270

His Glu Leu Gly His Val Phe Asn Met Pro His Asp Asp Ser Asn Lys
            275                 280                 285

Cys Lys Glu Glu Gly Val Lys Ser Pro Gln His Val Met Ala Pro Thr
290                 295                 300

Leu Asn Phe Tyr Thr Asn Pro Trp Met Trp Ser Lys Cys Ser Arg Lys
305                 310                 315                 320

Tyr Ile Thr Glu Phe Leu Asp Thr Gly Tyr Gly Glu Cys Leu Leu Asn
                325                 330                 335

Glu Pro Ala Ser Arg Thr Tyr Pro Leu Pro Ser Gln Leu Pro Gly Leu
            340                 345                 350

Leu Tyr Asn Val Asn Lys Gln Cys Glu Leu Ile Phe Gly Pro Gly Ser
            355                 360                 365

Gln Val Cys Pro Tyr Met Met Gln Cys Arg Arg Leu Trp Cys Asn Asn
            370                 375                 380

Val Asp Gly Ala His Lys Gly Cys Lys Thr Gln His Thr Pro Trp Ala
385                 390                 395                 400

Asp Gly Thr Glu Cys Glu Pro Gly Lys His Cys Lys Phe Gly Phe Cys
                405                 410                 415

Val Pro Lys Glu Met Glu Gly Pro Ala Ile Asp Gly Ser Trp Gly Gly
            420                 425                 430

Trp Ser His Phe Gly Thr Cys Ser Arg Thr Cys Gly Gly Gly Ile Lys
            435                 440                 445

Thr Ala Ile Arg Glu Cys Asn Arg Pro Glu Pro Lys Asn Gly Gly Lys
            450                 455                 460

Tyr Cys Val Gly Arg Arg Met Lys Phe Lys Ser Cys Asn Thr Glu Pro
465                 470                 475                 480

Cys Met Lys Gln Lys Arg Asp Phe Arg Glu Glu Gln Cys Ala His Phe
```

```
                              485                 490                 495
Asp Gly Lys His Phe Asn Ile Asn Gly Leu Leu Pro Ser Val Arg Trp
                    500                 505                 510

Phe Pro Lys Tyr Ser Gly Ile Leu Met Lys Asp Arg Cys Lys Leu Phe
                515                 520                 525

Cys Arg Val Ala Gly Asn Thr Ala Tyr Tyr Gln Leu Arg Asp Arg Val
            530                 535                 540

Ile Asp Gly Thr Pro Cys Gly Gln Asp Thr Asn Asp Ile Cys Val Gln
545                 550                 555                 560

Gly Leu Cys Arg Gln Ala Gly Cys Asp His Ile Leu Asn Ser Lys Val
                565                 570                 575

Arg Lys Asp Lys Cys Gly Ile Cys Gly Gly Asp Asn Ser Ser Cys Lys
                580                 585                 590

Thr Val Ala Gly Thr Phe Asn Thr Val His Tyr Gly Tyr Asn Thr Val
                595                 600                 605

Val Arg Ile Pro Ala Gly Ala Thr Ser Ile Asp Val Arg Gln His Ser
            610                 615                 620

Phe Ser Gly Lys Ser Glu Asp Asn Tyr Leu Ala Leu Ser Asn Ser
625                 630                 635                 640

Lys Gly Glu Phe Leu Leu Asn Gly Asp Phe Val Val Ser Met Ser Lys
                645                 650                 655

Arg Glu Val Arg Val Gly Ser Ala Val Ile Glu Tyr Ser Gly Ser Asp
                660                 665                 670

Asn Val Cys Glu Arg Leu Asn Cys Thr Asp Arg Ile Glu Glu Leu
            675                 680                 685

Leu Leu Gln Val Leu Ser Val Gly Lys Leu Tyr Asn Pro Asp Val Arg
            690                 695                 700

Tyr Ser Phe Asn Ile Pro Ile Glu Asp Lys Pro Gln Gln Phe Tyr Trp
705                 710                 715                 720

Asn Ser His Gly Pro Trp Gln Ala Cys Ser Lys Pro Cys Gln Gly Glu
                725                 730                 735

Arg Arg Pro Lys Leu Val Cys Thr Arg Glu Ser Asp Gln Leu Thr Val
                740                 745                 750

Ser Asp Gln Arg Cys Asp Arg Leu Pro Gln Pro Gly Pro Val Thr Glu
                755                 760                 765

Ala Cys Gly Thr Asp Cys Asp Leu Arg Trp His Val Ala Ser Lys Ser
770                 775                 780

Glu Cys Ser Ala Gln Cys Gly Leu Gly Tyr Arg Thr Leu Asp Ile His
785                 790                 795                 800

Cys Ala Lys Tyr Ser Arg Met Asp Gly Lys Thr Glu Lys Val Asp Asp
                805                 810                 815

Ser Phe Cys Ser Ser Gln Pro Arg Pro Ser Asn Gln Glu Lys Cys Ser
                820                 825                 830

Gly Glu Cys Ser Thr Gly Gly Trp Arg Tyr Ser Ala Trp Thr Glu Cys
                835                 840                 845

Ser Arg Ser Cys Asp Gly Gly Thr His Arg Arg Arg Ala Ile Cys Val
                850                 855                 860

Asn Thr Arg Asn Asp Val Leu Asp Asp Ser
865                 870

<210> SEQ ID NO 16
<211> LENGTH: 3885
<212> TYPE: DNA
<213> ORGANISM: Homo sapiens ADAMTS-10
```

```
<220> FEATURE:
<221> NAME/KEY: CDS
<222> LOCATION: (1)..(3246)
<221> NAME/KEY: misc_feature
<222> LOCATION: (3877)
<223> OTHER INFORMATION: n=A
<221> NAME/KEY: misc_feature
<222> LOCATION: (3882)
<223> OTHER INFORMATION: n=C

<400> SEQUENCE: 16
```

| | | | | | | | | | | | | | | | | |
|---|---|---|---|---|---|---|---|---|---|---|---|---|---|---|---|---|
| tca | cgc | acg | cct | tcc | ggt | ctc | aag | atg | agt | tcc | tgt | cca | gtc | tgg | aga | 48 |
| Ser | Arg | Thr | Pro | Ser | Gly | Leu | Lys | Met | Ser | Ser | Cys | Pro | Val | Trp | Arg | |
| 1 | | | | 5 | | | | | 10 | | | | | 15 | | |
| gct | atg | aga | tcg | cct | tcc | cca | ccc | gcg | tgg | acc | aca | acg | ggc | cac | tgc | 96 |
| Ala | Met | Arg | Ser | Pro | Ser | Pro | Pro | Ala | Trp | Thr | Thr | Thr | Gly | His | Cys | |
| | | | 20 | | | | | 25 | | | | | 30 | | | |
| tgg | cct | tct | cgc | cac | ctc | ctc | ccc | gga | gca | gcg | ccg | cgg | cac | ggg | ggc | 144 |
| Trp | Pro | Ser | Arg | His | Leu | Leu | Pro | Gly | Ala | Ala | Pro | Arg | His | Gly | Gly | |
| | | 35 | | | | | 40 | | | | | 45 | | | | |
| cac | agc | cga | gtc | ccg | cct | ctt | cta | caa | agt | ggc | ctc | gcc | agc | acc | cac | 192 |
| His | Ser | Arg | Val | Pro | Pro | Leu | Leu | Gln | Ser | Gly | Leu | Ala | Ser | Thr | His | |
| | 50 | | | | | 55 | | | | | 60 | | | | | |
| ttc | ctg | ctg | aac | ctg | acc | cgc | agc | tcc | cgt | cta | ctg | gca | ggg | cgc | gtc | 240 |
| Phe | Leu | Leu | Asn | Leu | Thr | Arg | Ser | Ser | Arg | Leu | Leu | Ala | Gly | Arg | Val | |
| 65 | | | | 70 | | | | | 75 | | | | | 80 | | |
| tcc | gtg | gag | tac | tgg | aca | cgg | gag | ggc | ctg | gcc | tgg | cag | agg | gcg | gcc | 288 |
| Ser | Val | Glu | Tyr | Trp | Thr | Arg | Glu | Gly | Leu | Ala | Trp | Gln | Arg | Ala | Ala | |
| | | | 85 | | | | | 90 | | | | | 95 | | | |
| cgg | ccc | cac | tgc | ctc | tac | gct | ggt | cac | ctg | cag | ggc | cag | gcc | agc | agc | 336 |
| Arg | Pro | His | Cys | Leu | Tyr | Ala | Gly | His | Leu | Gln | Gly | Gln | Ala | Ser | Ser | |
| | | 100 | | | | | 105 | | | | | 110 | | | | |
| tcc | cat | gtg | gcc | atc | agc | acc | tgt | gga | ggc | ctg | cac | ggc | ctg | atc | gtg | 384 |
| Ser | His | Val | Ala | Ile | Ser | Thr | Cys | Gly | Gly | Leu | His | Gly | Leu | Ile | Val | |
| | 115 | | | | | 120 | | | | | 125 | | | | | |
| gca | gac | gag | gaa | gag | tac | ctg | att | gag | ccc | ctg | cac | ggt | ggg | ccc | aag | 432 |
| Ala | Asp | Glu | Glu | Glu | Tyr | Leu | Ile | Glu | Pro | Leu | His | Gly | Gly | Pro | Lys | |
| 130 | | | | | 135 | | | | | 140 | | | | | | |
| ggt | tct | cgg | agc | ccg | gag | gaa | agt | gga | cca | cat | tgt | gtg | tac | aag | cgt | 480 |
| Gly | Ser | Arg | Ser | Pro | Glu | Glu | Ser | Gly | Pro | His | Cys | Val | Tyr | Lys | Arg | |
| 145 | | | | | 150 | | | | | 155 | | | | | 160 | |
| tcc | tct | ctg | cgt | cac | ccc | cac | ctg | gac | aca | gcc | tgt | gga | gtg | aga | gat | 528 |
| Ser | Ser | Leu | Arg | His | Pro | His | Leu | Asp | Thr | Ala | Cys | Gly | Val | Arg | Asp | |
| | | | 165 | | | | | 170 | | | | | 175 | | | |
| gag | aaa | ccg | tgg | aaa | ggg | cgg | cca | tgg | tgg | ctg | cgg | acc | ttg | aag | cca | 576 |
| Glu | Lys | Pro | Trp | Lys | Gly | Arg | Pro | Trp | Trp | Leu | Arg | Thr | Leu | Lys | Pro | |
| | | 180 | | | | | 185 | | | | | 190 | | | | |
| ccg | cct | gcc | aga | ccc | ctg | ggg | aat | gaa | aca | gag | cgt | ggc | cag | cca | ggc | 624 |
| Pro | Pro | Ala | Arg | Pro | Leu | Gly | Asn | Glu | Thr | Glu | Arg | Gly | Gln | Pro | Gly | |
| | 195 | | | | | 200 | | | | | 205 | | | | | |
| ctg | aag | cga | tcg | gtc | agc | cga | gag | cgc | tac | gtg | gag | acc | atg | gat | gtg | 672 |
| Leu | Lys | Arg | Ser | Val | Ser | Arg | Glu | Arg | Tyr | Val | Glu | Thr | Met | Asp | Val | |
| 210 | | | | | 215 | | | | | 220 | | | | | | |
| gct | gac | aag | atg | atg | gtg | gcc | tat | cac | ggg | cgc | cgg | gat | gtg | gag | cag | 720 |
| Ala | Asp | Lys | Met | Met | Val | Ala | Tyr | His | Gly | Arg | Arg | Asp | Val | Glu | Gln | |
| 225 | | | | | 230 | | | | | 235 | | | | | 240 | |
| tat | gtc | ctg | gcc | atc | atg | aac | att | gtt | gcc | aaa | ctt | ttc | cag | gac | tcg | 768 |
| Tyr | Val | Leu | Ala | Ile | Met | Asn | Ile | Val | Ala | Lys | Leu | Phe | Gln | Asp | Ser | |
| | | | 245 | | | | | 250 | | | | | 255 | | | |
| agt | ctg | gga | agc | acc | gtt | aac | atc | ctc | gta | act | cgc | ctc | atc | ctg | ctc | 816 |
| Ser | Leu | Gly | Ser | Thr | Val | Asn | Ile | Leu | Val | Thr | Arg | Leu | Ile | Leu | Leu | |
| | | 260 | | | | | 265 | | | | | 270 | | | | |

```
acg gag gac cag ccc act ctg gag atc acc cac cat gcc ggg aag tcc    864
Thr Glu Asp Gln Pro Thr Leu Glu Ile Thr His His Ala Gly Lys Ser
        275                 280                 285 cta gac agc ttc tgt aag tgg cag aaa tcc atc gtg aac cac agc ggc    912
Leu Asp Ser Phe Cys Lys Trp Gln Lys Ser Ile Val Asn His Ser Gly
        290                 295                 300 cat ggc aat gcc att cca gag aac ggt gtg gct aac cat gac aca gca    960
His Gly Asn Ala Ile Pro Glu Asn Gly Val Ala Asn His Asp Thr Ala
305                 310                 315                 320 gtg ctc atc aca cgc tat gac atc tgc atc tac aag aac aaa ccc tgc   1008
Val Leu Ile Thr Arg Tyr Asp Ile Cys Ile Tyr Lys Asn Lys Pro Cys
                325                 330                 335 ggc aca cta ggc ctg gcc cgg tgg gcg gaa tgt gtg agc gcg aga gaa   1056
Gly Thr Leu Gly Leu Ala Arg Trp Ala Glu Cys Val Ser Ala Arg Glu
            340                 345                 350 gct gca gcg tca atg agg aca ttg gct gcc aca agc gtt cac cat tgc   1104
Ala Ala Ala Ser Met Arg Thr Leu Ala Ala Thr Ser Val His His Cys
        355                 360                 365 cac gag atc ggg cac aca ttc ggc atg aac cat gac ggc gtg gga aac   1152
His Glu Ile Gly His Thr Phe Gly Met Asn His Asp Gly Val Gly Asn
        370                 375                 380 agc tgt ggg gcc cgt ggt cag gac cca gcc aag ctc atg gct gcc cac   1200
Ser Cys Gly Ala Arg Gly Gln Asp Pro Ala Lys Leu Met Ala Ala His
385                 390                 395                 400 att acc atg aag acc aac cca ttc gtg tgg tca tcc tgc aac cgt gac   1248
Ile Thr Met Lys Thr Asn Pro Phe Val Trp Ser Ser Cys Asn Arg Asp
                405                 410                 415 tac atc acc agc ttt cta gac tcg ggc ctg ggg ctc tgc ctg aac aac   1296
Tyr Ile Thr Ser Phe Leu Asp Ser Gly Leu Gly Leu Cys Leu Asn Asn
            420                 425                 430 cgg ccc ccc aga cag gac ttt gtg tac ccg aca gtg gca ccg ggc caa   1344
Arg Pro Pro Arg Gln Asp Phe Val Tyr Pro Thr Val Ala Pro Gly Gln
        435                 440                 445 gcc tac gat gca gat gag caa tgc cgc ttt cag cat gga gtc aaa tcg   1392
Ala Tyr Asp Ala Asp Glu Gln Cys Arg Phe Gln His Gly Val Lys Ser
450                 455                 460 cgt cag tgt aaa tac ggg gag gtc tgc agc gag ctg tgg tgt ctg agc   1440
Arg Gln Cys Lys Tyr Gly Glu Val Cys Ser Glu Leu Trp Cys Leu Ser
465                 470                 475                 480 aag agc aac cgg tgc atc acc aac agc atc ccg gcc gcc gag ggc acg   1488
Lys Ser Asn Arg Cys Ile Thr Asn Ser Ile Pro Ala Ala Glu Gly Thr
                485                 490                 495 ctg tgc cag acg cac acc atc gac aag ggg tgg tgc tac aaa cgg gtc   1536
Leu Cys Gln Thr His Thr Ile Asp Lys Gly Trp Cys Tyr Lys Arg Val
            500                 505                 510 tgt gtc ccc ttt ggg tcg cgc cca gag ggt gtg gac gga gcc tgg ggg   1584
Cys Val Pro Phe Gly Ser Arg Pro Glu Gly Val Asp Gly Ala Trp Gly
        515                 520                 525 ccg tgg act cca tgg ggc gac tgc agc cgg acc tgt ggc ggc ggc gtg   1632
Pro Trp Thr Pro Trp Gly Asp Cys Ser Arg Thr Cys Gly Gly Gly Val
530                 535                 540 tcc tct tct agt cgt cac tgc gac agc ccc agg cca acc atc ggg ggc   1680
Ser Ser Ser Ser Arg His Cys Asp Ser Pro Arg Pro Thr Ile Gly Gly
545                 550                 555                 560 aag tac tgt ctg ggt gag aga agg cgg cac cgc tcc tgc aac acg gat   1728
Lys Tyr Cys Leu Gly Glu Arg Arg Arg His Arg Ser Cys Asn Thr Asp
                565                 570                 575 gac tgt ccc cct ggc tcc cag gac ttc aga gaa gtg cag tgt gct gaa   1776
Asp Cys Pro Pro Gly Ser Gln Asp Phe Arg Glu Val Gln Cys Ala Glu
```

-continued

| | | | | | | | | | | | | | | | | |
|---|---|---|---|---|---|---|---|---|---|---|---|---|---|---|---|---|
| | | 580 | | | | | 585 | | | | | 590 | | | | |
| ttt | gac | agc | atc | cct | ttc | cgt | ggg | aaa | ttc | tac | aag | tgg | aaa | acg | tac | 1824 |
| Phe | Asp | Ser | Ile | Pro | Phe | Arg | Gly | Lys | Phe | Tyr | Lys | Trp | Lys | Thr | Tyr | |
| | | 595 | | | | | 600 | | | | | 605 | | | | |
| cgg | gga | ggg | ggc | gtg | aag | gcc | tgc | tcg | ctc | acg | agc | cta | gcg | gaa | ggc | 1872 |
| Arg | Gly | Gly | Gly | Val | Lys | Ala | Cys | Ser | Leu | Thr | Ser | Leu | Ala | Glu | Gly | |
| | 610 | | | | | 615 | | | | | 620 | | | | | |
| ttc | aac | ttc | tac | acg | gag | agg | gcg | gca | gcc | gtg | gtg | gac | ggg | aca | ccc | 1920 |
| Phe | Asn | Phe | Tyr | Thr | Glu | Arg | Ala | Ala | Ala | Val | Val | Asp | Gly | Thr | Pro | |
| 625 | | | | | 630 | | | | | 635 | | | | | 640 | |
| tgc | cgt | cca | gac | acg | gtg | gac | att | tgc | gtc | agt | ggc | gaa | tgc | aag | cac | 1968 |
| Cys | Arg | Pro | Asp | Thr | Val | Asp | Ile | Cys | Val | Ser | Gly | Glu | Cys | Lys | His | |
| | | | 645 | | | | | 650 | | | | | 655 | | | |
| gtg | ggc | tgc | gac | cga | gtc | ctg | ggc | tcc | gac | ctg | cgg | gag | gac | aag | tgc | 2016 |
| Val | Gly | Cys | Asp | Arg | Val | Leu | Gly | Ser | Asp | Leu | Arg | Glu | Asp | Lys | Cys | |
| | | | 660 | | | | | 665 | | | | | 670 | | | |
| cga | gtg | tgt | ggc | ggt | gac | ggc | agt | gcc | tgc | gag | acc | atc | gag | ggc | gtc | 2064 |
| Arg | Val | Cys | Gly | Gly | Asp | Gly | Ser | Ala | Cys | Glu | Thr | Ile | Glu | Gly | Val | |
| | | 675 | | | | | 680 | | | | | 685 | | | | |
| ttc | agc | cca | gcc | tca | cct | ggg | gcc | ggg | tac | gag | gat | gtc | gtc | tgg | att | 2112 |
| Phe | Ser | Pro | Ala | Ser | Pro | Gly | Ala | Gly | Tyr | Glu | Asp | Val | Val | Trp | Ile | |
| | 690 | | | | | 695 | | | | | 700 | | | | | |
| ccc | aaa | ggc | tcc | gtc | cac | atc | ttc | atc | cag | gat | ctg | aac | ctc | tct | ctc | 2160 |
| Pro | Lys | Gly | Ser | Val | His | Ile | Phe | Ile | Gln | Asp | Leu | Asn | Leu | Ser | Leu | |
| 705 | | | | | 710 | | | | | 715 | | | | | 720 | |
| agt | cac | ttg | gcc | ctg | aag | gga | gac | cag | gag | tcc | ctg | ctg | ctg | gag | ggg | 2208 |
| Ser | His | Leu | Ala | Leu | Lys | Gly | Asp | Gln | Glu | Ser | Leu | Leu | Leu | Glu | Gly | |
| | | | | 725 | | | | | 730 | | | | | 735 | | |
| ctg | cct | ggg | acc | ccc | cag | ccc | cac | cgt | ctg | cct | cta | gct | ggg | acc | acc | 2256 |
| Leu | Pro | Gly | Thr | Pro | Gln | Pro | His | Arg | Leu | Pro | Leu | Ala | Gly | Thr | Thr | |
| | | | 740 | | | | | 745 | | | | | 750 | | | |
| ttt | caa | ctg | cga | cag | ggg | cca | gac | cag | gtc | cag | agc | ctc | gaa | gcc | ctg | 2304 |
| Phe | Gln | Leu | Arg | Gln | Gly | Pro | Asp | Gln | Val | Gln | Ser | Leu | Glu | Ala | Leu | |
| | | 755 | | | | | 760 | | | | | 765 | | | | |
| gga | ccg | att | aat | gca | tct | ctc | atc | gtc | atg | gtg | ctg | gcc | cgg | acc | gag | 2352 |
| Gly | Pro | Ile | Asn | Ala | Ser | Leu | Ile | Val | Met | Val | Leu | Ala | Arg | Thr | Glu | |
| | 770 | | | | | 775 | | | | | 780 | | | | | |
| ctg | cct | gcc | ctc | cgc | tac | cgc | ttc | aat | gcc | ccc | atc | gcc | cgt | gac | tcg | 2400 |
| Leu | Pro | Ala | Leu | Arg | Tyr | Arg | Phe | Asn | Ala | Pro | Ile | Ala | Arg | Asp | Ser | |
| 785 | | | | | 790 | | | | | 795 | | | | | 800 | |
| ctg | ccc | ccc | tac | tcc | tgg | cac | tat | gcg | ccc | tgg | acc | aag | tgc | tcg | gcc | 2448 |
| Leu | Pro | Pro | Tyr | Ser | Trp | His | Tyr | Ala | Pro | Trp | Thr | Lys | Cys | Ser | Ala | |
| | | | | 805 | | | | | 810 | | | | | 815 | | |
| cag | tgt | gca | ggc | ggt | agc | cag | gtg | cag | gcg | gtg | gag | tgc | cgc | aac | cag | 2496 |
| Gln | Cys | Ala | Gly | Gly | Ser | Gln | Val | Gln | Ala | Val | Glu | Cys | Arg | Asn | Gln | |
| | | | 820 | | | | | 825 | | | | | 830 | | | |
| ctg | gac | agc | tcc | gcg | gtc | gcc | ccc | cac | tac | tgc | agt | gcc | cac | agc | aag | 2544 |
| Leu | Asp | Ser | Ser | Ala | Val | Ala | Pro | His | Tyr | Cys | Ser | Ala | His | Ser | Lys | |
| | | 835 | | | | | 840 | | | | | 845 | | | | |
| ctg | ccc | aaa | agg | cag | cgc | gcc | tgc | aac | acg | gag | cct | tgc | cct | cca | gac | 2592 |
| Leu | Pro | Lys | Arg | Gln | Arg | Ala | Cys | Asn | Thr | Glu | Pro | Cys | Pro | Pro | Asp | |
| | 850 | | | | | 855 | | | | | 860 | | | | | |
| tgg | gtt | gta | ggg | aac | tgg | tcg | ctc | tgc | agc | cgc | agc | tgc | gat | gca | ggc | 2640 |
| Trp | Val | Val | Gly | Asn | Trp | Ser | Leu | Cys | Ser | Arg | Ser | Cys | Asp | Ala | Gly | |
| 865 | | | | | 870 | | | | | 875 | | | | | 880 | |
| gtg | cgc | agt | acg | tcg | gtc | gtg | tgc | cag | cgc | cgc | gtc | tct | gcc | gcg | gag | 2688 |
| Val | Arg | Ser | Thr | Ser | Val | Val | Cys | Gln | Arg | Arg | Val | Ser | Ala | Ala | Glu | |
| | | | | 885 | | | | | 890 | | | | | 895 | | |
| gag | aag | gcg | ctg | gac | gac | agc | gca | tgc | ccg | cag | ccg | cgc | cca | cct | gta | 2736 |

-continued

| | | | | | | | | | | | | | | | |
|---|---|---|---|---|---|---|---|---|---|---|---|---|---|---|---|
| Glu | Lys | Ala | Leu | Asp | Asp | Ser | Ala | Cys | Pro | Gln | Pro | Arg | Pro | Pro | Val |
| | | | 900 | | | | | 905 | | | | | 910 | | |

```
ctg gag gcc tgc cac ggc ccc act tgc cct ccg gag tgg gca acc ctc      2784
Leu Glu Ala Cys His Gly Pro Thr Cys Pro Pro Glu Trp Ala Thr Leu
        915                 920                 925 gac tgg tct gag tgt acc cca agc tgt ggg cct ggt ctc cgc cac cga      2832
Asp Trp Ser Glu Cys Thr Pro Ser Cys Gly Pro Gly Leu Arg His Arg
    930                 935                 940 gtg gtc ctt tgt aag agt gca gat caa cga tct act ctg ccc cct ggg      2880
Val Val Leu Cys Lys Ser Ala Asp Gln Arg Ser Thr Leu Pro Pro Gly
945                 950                 955                 960 cac tgc ctt cct gca gcc aag cca cca tct act atg cga tgt aac ttg      2928
His Cys Leu Pro Ala Ala Lys Pro Pro Ser Thr Met Arg Cys Asn Leu
                965                 970                 975 cgc cgc tgc cct cct gcc cgc tgg gtg acc agt gag tgg ggt gag tgt      2976
Arg Arg Cys Pro Pro Ala Arg Trp Val Thr Ser Glu Trp Gly Glu Cys
            980                 985                 990 tcc aca cag tgt ggc ctc ggc cag cag cag cgc aca gtg cgc tgc acc      3024
Ser Thr Gln Cys Gly Leu Gly Gln Gln Gln Arg Thr Val Arg Cys Thr
        995                 1000                1005 agc cac acc ggc cag cca tct cga gag tgc act gaa gcc ttg cgg cca      3072
Ser His Thr Gly Gln Pro Ser Arg Glu Cys Thr Glu Ala Leu Arg Pro
    1010                1015                1020 tcc acc atg cag cag tgt gag gcc aag tgt gac agt gtg gtg ccg cct      3120
Ser Thr Met Gln Gln Cys Glu Ala Lys Cys Asp Ser Val Val Pro Pro
1025                1030                1035                1040 gga gat ggc cca gaa gaa tgc aag gat gtg aac aag gtg gct tac tgc      3168
Gly Asp Gly Pro Glu Glu Cys Lys Asp Val Asn Lys Val Ala Tyr Cys
                1045                1050                1055 ccc ctg gtg ctc aaa ttt cag ttc tgt agc cga gcc tac ttc cgc cag      3216
Pro Leu Val Leu Lys Phe Gln Phe Cys Ser Arg Ala Tyr Phe Arg Gln
            1060                1065                1070 atg tgc tgc aaa acc tgc caa ggc cgc tag ggtacctgga accaacctgg        3266
Met Cys Cys Lys Thr Cys Gln Gly Arg
        1075                1080 agcacaggct gaggcagggg acatcccact ggagagggca tgagggaaag ggggcttga     3326 attgaagggt gagatgcagt tgaaagttat ttattgggta accctacagg gctcctgact    3386 aagggtgga  gaagagctgg ctacccaggg accctctgct gtatcttgcc cagttgatag    3446
tgaagagaga ggactccttg ttgcacacat atttaagtcc ctagcacccc tcccacccctt   3506 tgatcggaat atgtactgtg aagagtgggg gtggggaggg gtgtgctggt gccctgcccc    3566
ctgcactgtt ctatccctac actctgagct gggggattt  atatctgcta tgggggagt    3626 aggcttgata ccacctccct gtagccctcc cccagactga cgaaggggaa gatccacccc    3686
aacctctgcc ctgcctgccc caggggggag ttcaacatcc aggccgttcc ccatcatggt    3746
gctacaagcc ctgccctggg gcccacacac tcctcaccaa gaagccttac attaaaaaag    3806
ttgtgttatc ctacaaaaaa aaaaaaaaac tcgaggggg  gcccggtacc caattcgcgc    3866
tatagtaaat ngggtntta                                                 3885
```

<210> SEQ ID NO 17
<211> LENGTH: 1081
<212> TYPE: PRT
<213> ORGANISM: Homo sapiens ADAMTS-10

<400> SEQUENCE: 17

| | | | | | | | | | | | | | |
|---|---|---|---|---|---|---|---|---|---|---|---|---|---|
| Ser | Arg | Thr | Pro | Ser | Gly | Leu | Lys | Met | Ser | Ser | Cys | Pro | Val | Trp | Arg |
| 1 | | | | 5 | | | | | 10 | | | | | 15 | |

-continued

```
Ala Met Arg Ser Pro Ser Pro Ala Trp Thr Thr Thr Gly His Cys
            20                  25                  30

Trp Pro Ser Arg His Leu Leu Pro Gly Ala Ala Pro Arg His Gly Gly
        35                  40                  45

His Ser Arg Val Pro Pro Leu Leu Gln Ser Gly Leu Ala Ser Thr His
    50                  55                  60

Phe Leu Leu Asn Leu Thr Arg Ser Ser Arg Leu Leu Ala Gly Arg Val
65                  70                  75                  80

Ser Val Glu Tyr Trp Thr Arg Glu Gly Leu Ala Trp Gln Arg Ala Ala
                85                  90                  95

Arg Pro His Cys Leu Tyr Ala Gly His Leu Gln Gly Gln Ala Ser Ser
            100                 105                 110

Ser His Val Ala Ile Ser Thr Cys Gly Gly Leu His Gly Leu Ile Val
        115                 120                 125

Ala Asp Glu Glu Glu Tyr Leu Ile Glu Pro Leu His Gly Gly Pro Lys
    130                 135                 140

Gly Ser Arg Ser Pro Glu Glu Ser Gly Pro His Cys Val Tyr Lys Arg
145                 150                 155                 160

Ser Ser Leu Arg His Pro His Leu Asp Thr Ala Cys Gly Val Arg Asp
                165                 170                 175

Glu Lys Pro Trp Lys Gly Arg Pro Trp Trp Leu Arg Thr Leu Lys Pro
            180                 185                 190

Pro Pro Ala Arg Pro Leu Gly Asn Glu Thr Glu Arg Gly Gln Pro Gly
        195                 200                 205

Leu Lys Arg Ser Val Ser Arg Glu Arg Tyr Val Glu Thr Met Asp Val
    210                 215                 220

Ala Asp Lys Met Met Val Ala Tyr His Gly Arg Arg Asp Val Glu Gln
225                 230                 235                 240

Tyr Val Leu Ala Ile Met Asn Ile Val Ala Lys Leu Phe Gln Asp Ser
                245                 250                 255

Ser Leu Gly Ser Thr Val Asn Ile Leu Val Thr Arg Leu Ile Leu Leu
            260                 265                 270

Thr Glu Asp Gln Pro Thr Leu Glu Ile Thr His His Ala Gly Lys Ser
        275                 280                 285

Leu Asp Ser Phe Cys Lys Trp Gln Lys Ser Ile Val Asn His Ser Gly
    290                 295                 300

His Gly Asn Ala Ile Pro Glu Asn Gly Val Ala Asn His Asp Thr Ala
305                 310                 315                 320

Val Leu Ile Thr Arg Tyr Asp Ile Cys Ile Tyr Lys Asn Lys Pro Cys
                325                 330                 335

Gly Thr Leu Gly Leu Ala Arg Trp Ala Glu Cys Val Ser Ala Arg Glu
            340                 345                 350

Ala Ala Ala Ser Met Arg Thr Leu Ala Ala Thr Ser Val His His Cys
        355                 360                 365

His Glu Ile Gly His Thr Phe Gly Met Asn His Asp Gly Val Gly Asn
    370                 375                 380

Ser Cys Gly Ala Arg Gly Gln Asp Pro Ala Lys Leu Met Ala Ala His
385                 390                 395                 400

Ile Thr Met Lys Thr Asn Pro Phe Val Trp Ser Ser Cys Asn Arg Asp
                405                 410                 415

Tyr Ile Thr Ser Phe Leu Asp Ser Gly Leu Gly Leu Cys Leu Asn Asn
            420                 425                 430
```

-continued

```
Arg Pro Pro Arg Gln Asp Phe Val Tyr Pro Thr Val Ala Pro Gly Gln
            435                 440                 445

Ala Tyr Asp Ala Asp Glu Gln Cys Arg Phe Gln His Gly Val Lys Ser
        450                 455                 460

Arg Gln Cys Lys Tyr Gly Glu Val Cys Ser Glu Leu Trp Cys Leu Ser
465                 470                 475                 480

Lys Ser Asn Arg Cys Ile Thr Asn Ser Ile Pro Ala Ala Glu Gly Thr
                485                 490                 495

Leu Cys Gln Thr His Thr Ile Asp Lys Gly Trp Cys Tyr Lys Arg Val
            500                 505                 510

Cys Val Pro Phe Gly Ser Arg Pro Glu Gly Val Asp Gly Ala Trp Gly
            515                 520                 525

Pro Trp Thr Pro Trp Gly Asp Cys Ser Arg Thr Cys Gly Gly Gly Val
        530                 535                 540

Ser Ser Ser Ser Arg His Cys Asp Ser Pro Arg Pro Thr Ile Gly Gly
545                 550                 555                 560

Lys Tyr Cys Leu Gly Glu Arg Arg His Arg Ser Cys Asn Thr Asp
                565                 570                 575

Asp Cys Pro Pro Gly Ser Gln Asp Phe Arg Glu Val Gln Cys Ala Glu
            580                 585                 590

Phe Asp Ser Ile Pro Phe Arg Gly Lys Phe Tyr Lys Trp Lys Thr Tyr
            595                 600                 605

Arg Gly Gly Gly Val Lys Ala Cys Ser Leu Thr Ser Leu Ala Glu Gly
        610                 615                 620

Phe Asn Phe Tyr Thr Glu Arg Ala Ala Val Val Asp Gly Thr Pro
625                 630                 635                 640

Cys Arg Pro Asp Thr Val Asp Ile Cys Val Ser Gly Glu Cys Lys His
                645                 650                 655

Val Gly Cys Asp Arg Val Leu Gly Ser Asp Leu Arg Glu Asp Lys Cys
            660                 665                 670

Arg Val Cys Gly Gly Asp Gly Ser Ala Cys Glu Thr Ile Glu Gly Val
        675                 680                 685

Phe Ser Pro Ala Ser Pro Gly Ala Gly Tyr Glu Asp Val Val Trp Ile
690                 695                 700

Pro Lys Gly Ser Val His Ile Phe Ile Gln Asp Leu Asn Leu Ser Leu
705                 710                 715                 720

Ser His Leu Ala Leu Lys Gly Asp Gln Glu Ser Leu Leu Glu Gly
                725                 730                 735

Leu Pro Gly Thr Pro Gln Pro His Arg Leu Pro Leu Ala Gly Thr Thr
            740                 745                 750

Phe Gln Leu Arg Gln Gly Pro Asp Gln Val Gln Ser Leu Glu Ala Leu
        755                 760                 765

Gly Pro Ile Asn Ala Ser Leu Ile Val Met Val Leu Ala Arg Thr Glu
770                 775                 780

Leu Pro Ala Leu Arg Tyr Arg Phe Asn Ala Pro Ile Ala Arg Asp Ser
785                 790                 795                 800

Leu Pro Pro Tyr Ser Trp His Tyr Ala Pro Trp Thr Lys Cys Ser Ala
                805                 810                 815

Gln Cys Ala Gly Gly Ser Gln Val Gln Ala Val Glu Cys Arg Asn Gln
            820                 825                 830

Leu Asp Ser Ser Ala Val Ala Pro His Tyr Cys Ser Ala His Ser Lys
        835                 840                 845

Leu Pro Lys Arg Gln Arg Ala Cys Asn Thr Glu Pro Cys Pro Pro Asp
```

-continued

```
                                    850                 855                 860
Trp Val Val Gly Asn Trp Ser Leu Cys Ser Arg Ser Cys Asp Ala Gly
865                 870                 875                 880
Val Arg Ser Thr Ser Val Val Cys Gln Arg Val Ser Ala Ala Glu
                    885                 890                 895
Glu Lys Ala Leu Asp Asp Ser Ala Cys Pro Gln Pro Arg Pro Pro Val
                900                 905                 910
Leu Glu Ala Cys His Gly Pro Thr Cys Pro Pro Glu Trp Ala Thr Leu
            915                 920                 925
Asp Trp Ser Glu Cys Thr Pro Ser Cys Gly Pro Gly Leu Arg His Arg
        930                 935                 940
Val Val Leu Cys Lys Ser Ala Asp Gln Arg Ser Thr Leu Pro Pro Gly
945                 950                 955                 960
His Cys Leu Pro Ala Ala Lys Pro Pro Ser Thr Met Arg Cys Asn Leu
                965                 970                 975
Arg Arg Cys Pro Pro Ala Arg Trp Val Thr Ser Glu Trp Gly Glu Cys
                980                 985                 990
Ser Thr Gln Cys Gly Leu Gly Gln Gln Gln Arg Thr Val Arg Cys Thr
            995                 1000                1005
Ser His Thr Gly Gln Pro Ser Arg Glu Cys Thr Glu Ala Leu Arg Pro
        1010                1015                1020
Ser Thr Met Gln Gln Cys Glu Ala Lys Cys Asp Ser Val Val Pro Pro
1025                1030                1035                1040
Gly Asp Gly Pro Glu Glu Cys Lys Asp Val Asn Lys Val Ala Tyr Cys
                1045                1050                1055
Pro Leu Val Leu Lys Phe Gln Phe Cys Ser Arg Ala Tyr Phe Arg Gln
                1060                1065                1070
Met Cys Cys Lys Thr Cys Gln Gly Arg
            1075                1080
```

<210> SEQ ID NO 18
<211> LENGTH: 1642
<212> TYPE: DNA
<213> ORGANISM: Mus musculus ADAMTS-10
<220> FEATURE:
<221> NAME/KEY: CDS
<222> LOCATION: (2)..(1351)
<221> NAME/KEY: misc_feature
<222> LOCATION: (354)
<223> OTHER INFORMATION: n=C
<221> NAME/KEY: misc_feature
<222> LOCATION: (338)
<223> OTHER INFORMATION: n=C
<221> NAME/KEY: misc_feature
<222> LOCATION: (1511)
<223> OTHER INFORMATION: n=A, T, G, C, or I
<221> NAME/KEY: misc_feature
<222> LOCATION: (1553)
<223> OTHER INFORMATION: n=A, T, G, C, or I
<221> NAME/KEY: misc_feature
<222> LOCATION: (1584)
<223> OTHER INFORMATION: n=A, T, G, C, or I
<221> NAME/KEY: misc_feature
<222> LOCATION: (1616)
<223> OTHER INFORMATION: n=A, T, G, C, or I
<221> NAME/KEY: misc_feature
<222> LOCATION: (1642)
<223> OTHER INFORMATION: n=A, T, G, C, or I

<400> SEQUENCE: 18

```
a gca gca gct gtg gtg gat gga aca ccc tgc cgc cct gac acg gtg gac      49
  Ala Ala Ala Val Val Asp Gly Thr Pro Cys Arg Pro Asp Thr Val Asp
    1               5                  10                  15
```

```
att tgt gtc agc ggc gag tgc aag cat gta ggc tgt gac agg ctc ctg      97
Ile Cys Val Ser Gly Glu Cys Lys His Val Gly Cys Asp Arg Leu Leu
         20                  25                  30 ggt tct gat ctc cga gag gac aaa tgc cgt gtg tgt ggg ggt gat ggc     145
Gly Ser Asp Leu Arg Glu Asp Lys Cys Arg Val Cys Gly Gly Asp Gly
             35                  40                  45 agt gcc tgt gag acc att gaa ggt gtc ttt agc cca gct ttg cca gga     193
Ser Ala Cys Glu Thr Ile Glu Gly Val Phe Ser Pro Ala Leu Pro Gly
 50                  55                  60 act ggg tat gag gac gtc gtc tgg atc ccc aaa ggc tcg gtc cac att     241
Thr Gly Tyr Glu Asp Val Val Trp Ile Pro Lys Gly Ser Val His Ile
 65                  70                  75                  80 ttc atc caa gat ctg aac ctg tcc ctg agt cac ctg gcc cta aag ggg     289
Phe Ile Gln Asp Leu Asn Leu Ser Leu Ser His Leu Ala Leu Lys Gly
                 85                  90                  95 gac caa gag tct ctg cta ctg gag ggg cta cct ggg acc ccc caa cct     337
Asp Gln Glu Ser Leu Leu Leu Glu Gly Leu Pro Gly Thr Pro Gln Pro
            100                 105                 110 nac cgc ctt ccc ctg gnt ggg acc aca ttt cat cta cgg cag ggg ccg     385
Xaa Arg Leu Pro Leu Xaa Gly Thr Thr Phe His Leu Arg Gln Gly Pro
                115                 120                 125 gac cag gca cag agc ctg gaa gcc ctg gga ccc att aat gca tct ctc     433
Asp Gln Ala Gln Ser Leu Glu Ala Leu Gly Pro Ile Asn Ala Ser Leu
130                 135                 140 atc atc atg gtg ctg gcc cag gca gag ttg cct gct ctc cac tac cgc     481
Ile Ile Met Val Leu Ala Gln Ala Glu Leu Pro Ala Leu His Tyr Arg
145                 150                 155                 160 ttc aat gca ccc att gcc cgg gat gca ctg cct ccc tac tcc tgg cac     529
Phe Asn Ala Pro Ile Ala Arg Asp Ala Leu Pro Pro Tyr Ser Trp His
                165                 170                 175 tat gcc ccc tgg acc aaa tgc tca gcc cag tgt gca ggc ggc agc cag     577
Tyr Ala Pro Trp Thr Lys Cys Ser Ala Gln Cys Ala Gly Gly Ser Gln
                180                 185                 190 gtg caa gta gtg gag tgc cga aat cag ctg gac agc tca gca gtg gcc     625
Val Gln Val Val Glu Cys Arg Asn Gln Leu Asp Ser Ser Ala Val Ala
            195                 200                 205 cca cac tac tgt agt ggc cac agt aaa ttg ccc aag agg cag cgt gcc     673
Pro His Tyr Cys Ser Gly His Ser Lys Leu Pro Lys Arg Gln Arg Ala
210                 215                 220 tgc aac aca gaa cca tgt cca cca gat tgg gtt gta gga aac tgg tca     721
Cys Asn Thr Glu Pro Cys Pro Pro Asp Trp Val Val Gly Asn Trp Ser
225                 230                 235                 240 cgc tgc agc cgt agc tgt gac gct ggt gtg cgt agc cgc tca gtg gtg     769
Arg Cys Ser Arg Ser Cys Asp Ala Gly Val Arg Ser Arg Ser Val Val
                245                 250                 255 tgc caa cgc cgg gtg tct gct gca gag gaa aaa gcc tta gac gac agt     817
Cys Gln Arg Arg Val Ser Ala Ala Glu Glu Lys Ala Leu Asp Asp Ser
            260                 265                 270 gcc tgt cca cag cca cgc cca cct gtg ctg gag gcc tgc caa ggc cca     865
Ala Cys Pro Gln Pro Arg Pro Pro Val Leu Glu Ala Cys Gln Gly Pro
        275                 280                 285 atg tgc cct cct gag tgg gca acc ctc gac tgg tct gag tgt acc cca     913
Met Cys Pro Pro Glu Trp Ala Thr Leu Asp Trp Ser Glu Cys Thr Pro
    290                 295                 300 agc tgt ggg cct ggt ctc cgc cac cga gtg gtc ctt tgt aag agt gca     961
Ser Cys Gly Pro Gly Leu Arg His Arg Val Val Leu Cys Lys Ser Ala
305                 310                 315                 320 gat caa cga tct act ctg ccc cct ggg cac tgc ctt cct gca gcc aag    1009
Asp Gln Arg Ser Thr Leu Pro Pro Gly His Cys Leu Pro Ala Ala Lys
```

|  |  |  |  |  |  |  |  |  |  |  |  |  |  |  |  |
|---|---|---|---|---|---|---|---|---|---|---|---|---|---|---|---|
|  |  |  |  | 325 |  |  |  | 330 |  |  |  | 335 |  |  |  |
| cca | cca | tct | act | atg | cga | tgt | aac | ttg | cgc | cgc | tgc | cct | cct | gcc | cgc | 1057 |
| Pro | Pro | Ser | Thr | Met | Arg | Cys | Asn | Leu | Arg | Arg | Cys | Pro | Pro | Ala | Arg |
|  |  |  | 340 |  |  |  |  | 345 |  |  |  |  | 350 |  |  |
| tgg | gtg | acc | agt | gag | tgg | ggt | gag | tgt | tcc | aca | cag | tgt | ggc | ctc | ggc | 1105 |
| Trp | Val | Thr | Ser | Glu | Trp | Gly | Glu | Cys | Ser | Thr | Gln | Cys | Gly | Leu | Gly |
|  |  |  | 355 |  |  |  |  | 360 |  |  |  |  | 365 |  |  |
| cag | cag | cag | cgc | aca | gtg | cgc | tgc | acc | agc | cac | acc | ggc | cag | cca | tct | 1153 |
| Gln | Gln | Gln | Arg | Thr | Val | Arg | Cys | Thr | Ser | His | Thr | Gly | Gln | Pro | Ser |
|  | 370 |  |  |  |  | 375 |  |  |  |  | 380 |  |  |  |  |
| cga | gag | tgc | act | gaa | gcc | ttg | cgg | cca | tcc | acc | atg | cag | cag | tgt | gag | 1201 |
| Arg | Glu | Cys | Thr | Glu | Ala | Leu | Arg | Pro | Ser | Thr | Met | Gln | Gln | Cys | Glu |
| 385 |  |  |  |  | 390 |  |  |  |  | 395 |  |  |  |  | 400 |
| gcc | aag | tgt | gac | agt | gtg | gtg | ccg | cct | gga | gat | ggc | cca | gaa | gaa | tgc | 1249 |
| Ala | Lys | Cys | Asp | Ser | Val | Val | Pro | Pro | Gly | Asp | Gly | Pro | Glu | Glu | Cys |
|  |  |  |  | 405 |  |  |  |  | 410 |  |  |  |  | 415 |  |
| aag | gat | gtg | aac | aag | gtg | gct | tac | tgc | ccc | ctg | gtg | ctc | aaa | ttt | cag | 1297 |
| Lys | Asp | Val | Asn | Lys | Val | Ala | Tyr | Cys | Pro | Leu | Val | Leu | Lys | Phe | Gln |
|  |  |  | 420 |  |  |  |  | 425 |  |  |  |  | 430 |  |  |
| ttc | tgt | agc | cga | gcc | tac | ttc | cgc | cag | atg | agc | tgc | aaa | acc | tgc | caa | 1345 |
| Phe | Cys | Ser | Arg | Ala | Tyr | Phe | Arg | Gln | Met | Ser | Cys | Lys | Thr | Cys | Gln |
|  |  | 435 |  |  |  |  | 440 |  |  |  |  | 445 |  |  |  |
| ggc | cgc | tagggtacct | ggaaccaacc | tggagcacag | gctgaggcag | gggacatccc | 1401 |
| Gly | Arg |
|  | 450 | actggagagg gcatgaggga aagggggggct tgaattgaag ggtgagatgc aagttgaaag  1461 tatttatttg ggtaacccct acagggcttc tgacttaagg ggtggagaan agctggctac  1521 cccagggacc cttttgttgg atcttggccc anttgatagt gaagagagag gacttcttgg  1581 tgnacacatt tttaagtcct tagacccttc caccnttgat cggatatgtc tgggaagagg  1641 n  1642

<210> SEQ ID NO 19
<211> LENGTH: 450
<212> TYPE: PRT
<213> ORGANISM: Mus musculus ADAMTS-10
<220> FEATURE:
<221> NAME/KEY: MOD_RES
<222> LOCATION: (113)
<223> OTHER INFORMATION: Xaa = H
<221> NAME/KEY: MOD_RES
<222> LOCATION: (118)
<223> OTHER INFORMATION: Xaa = A

<400> SEQUENCE: 19

Ala Ala Ala Val Val Asp Gly Thr Pro Cys Arg Pro Asp Thr Val Asp
 1               5                  10                  15

Ile Cys Val Ser Gly Glu Cys Lys His Val Gly Cys Asp Arg Leu Leu
                20                  25                  30

Gly Ser Asp Leu Arg Glu Asp Lys Cys Arg Val Cys Gly Gly Asp Gly
            35                  40                  45

Ser Ala Cys Glu Thr Ile Glu Gly Val Phe Ser Pro Ala Leu Pro Gly
        50                  55                  60

Thr Gly Tyr Glu Asp Val Val Trp Ile Pro Lys Gly Ser Val His Ile
65                  70                  75                  80

Phe Ile Gln Asp Leu Asn Leu Ser Leu Ser His Leu Ala Leu Lys Gly
                85                  90                  95

Asp Gln Glu Ser Leu Leu Leu Glu Gly Leu Pro Gly Thr Pro Gln Pro
            100                 105                 110

Xaa Arg Leu Pro Leu Xaa Gly Thr Thr Phe His Leu Arg Gln Gly Pro
    115                 120                 125

Asp Gln Ala Gln Ser Leu Glu Ala Leu Gly Pro Ile Asn Ala Ser Leu
130                 135                 140

Ile Ile Met Val Leu Ala Gln Ala Glu Leu Pro Ala Leu His Tyr Arg
145                 150                 155                 160

Phe Asn Ala Pro Ile Ala Arg Asp Ala Leu Pro Pro Tyr Ser Trp His
                165                 170                 175

Tyr Ala Pro Trp Thr Lys Cys Ser Ala Gln Cys Ala Gly Gly Ser Gln
            180                 185                 190

Val Gln Val Val Glu Cys Arg Asn Gln Leu Asp Ser Ser Ala Val Ala
        195                 200                 205

Pro His Tyr Cys Ser Gly His Ser Lys Leu Pro Lys Arg Gln Arg Ala
    210                 215                 220

Cys Asn Thr Glu Pro Cys Pro Asp Trp Val Val Gly Asn Trp Ser
225                 230                 235                 240

Arg Cys Ser Arg Ser Cys Asp Ala Gly Val Arg Ser Arg Ser Val Val
                245                 250                 255

Cys Gln Arg Arg Val Ser Ala Ala Glu Glu Lys Ala Leu Asp Asp Ser
            260                 265                 270

Ala Cys Pro Gln Pro Arg Pro Val Leu Glu Ala Cys Gln Gly Pro
        275                 280                 285

Met Cys Pro Pro Glu Trp Ala Thr Leu Asp Trp Ser Glu Cys Thr Pro
    290                 295                 300

Ser Cys Gly Pro Gly Leu Arg His Arg Val Val Leu Cys Lys Ser Ala
305                 310                 315                 320

Asp Gln Arg Ser Thr Leu Pro Pro Gly His Cys Leu Pro Ala Ala Lys
                325                 330                 335

Pro Pro Ser Thr Met Arg Cys Asn Leu Arg Arg Cys Pro Pro Ala Arg
            340                 345                 350

Trp Val Thr Ser Glu Trp Gly Glu Cys Ser Thr Gln Cys Gly Leu Gly
        355                 360                 365

Gln Gln Gln Arg Thr Val Arg Cys Thr Ser His Thr Gly Gln Pro Ser
    370                 375                 380

Arg Glu Cys Thr Glu Ala Leu Arg Pro Ser Thr Met Gln Gln Cys Glu
385                 390                 395                 400

Ala Lys Cys Asp Ser Val Val Pro Pro Gly Asp Gly Pro Glu Glu Cys
                405                 410                 415

Lys Asp Val Asn Lys Val Ala Tyr Cys Pro Leu Val Leu Lys Phe Gln
            420                 425                 430

Phe Cys Ser Arg Ala Tyr Phe Arg Gln Met Ser Cys Lys Thr Cys Gln
        435                 440                 445

Gly Arg
    450

<210> SEQ ID NO 20
<211> LENGTH: 1803
<212> TYPE: DNA
<213> ORGANISM: Homo sapiens ADAMTS-R1
<220> FEATURE:
<221> NAME/KEY: CDS
<222> LOCATION: (51)..(1634)

<400> SEQUENCE: 20
gaattcggca cgaggcagtg tccgattctg attccggcaa ggatccaagc atg gaa      56

-continued

```
                                            Met Glu
                                             1
tgc tgc cgt cgg gca act cct ggc aca ctg ctc ctc ttt ctg gct ttc      104
Cys Cys Arg Arg Ala Thr Pro Gly Thr Leu Leu Leu Phe Leu Ala Phe
         5                  10                  15 ctg ctc ctg agt tcc agg acc gca cgc tcc gag gag gac cgg gac ggc      152
Leu Leu Leu Ser Ser Arg Thr Ala Arg Ser Glu Glu Asp Arg Asp Gly
     20                  25                  30 cta tgg gat gcc tgg ggc cca tgg agt gaa tgc tca cgc acc tgc ggg      200
Leu Trp Asp Ala Trp Gly Pro Trp Ser Glu Cys Ser Arg Thr Cys Gly
 35                  40                  45                  50 ggt ggg gcc gcc aac tct ctg agg cgc tgc ctg agc agc aag agc tgt      248
Gly Gly Ala Ala Asn Ser Leu Arg Arg Cys Leu Ser Ser Lys Ser Cys
                 55                  60                  65 gaa gga aga aat atc cga tac aga aca tgc agt aat gtg gac tgc cca      296
Glu Gly Arg Asn Ile Arg Tyr Arg Thr Cys Ser Asn Val Asp Cys Pro
             70                  75                  80 cca gaa gca ggt gat ttc cga gct cag caa tgc tca gct cat aat gat      344
Pro Glu Ala Gly Asp Phe Arg Ala Gln Gln Cys Ser Ala His Asn Asp
         85                  90                  95 gtc aag cac cat ggc cag ttt tat gaa tgg ctt cct gtg tct aat gac      392
Val Lys His His Gly Gln Phe Tyr Glu Trp Leu Pro Val Ser Asn Asp
    100                 105                 110 cct gac aac cca tgt tca ctc aag tgc caa gcc aaa gga aca acc ctg      440
Pro Asp Asn Pro Cys Ser Leu Lys Cys Gln Ala Lys Gly Thr Thr Leu
115                 120                 125                 130 gtt gtt gaa cta gca cct aag gtc tta gat ggt acg cgt tgc tat aca      488
Val Val Glu Leu Ala Pro Lys Val Leu Asp Gly Thr Arg Cys Tyr Thr
                135                 140                 145 gaa tct ttg gat atg tgc atc agt ggt tta tgc caa att gtt ggc tgc      536
Glu Ser Leu Asp Met Cys Ile Ser Gly Leu Cys Gln Ile Val Gly Cys
            150                 155                 160 gat cac cag ctg gga agc acc gtc aag gaa gat aac tgt ggg gtc tgc      584
Asp His Gln Leu Gly Ser Thr Val Lys Glu Asp Asn Cys Gly Val Cys
        165                 170                 175 aac gga gat ggg tcc acc tgc cgg ctg gtc cga ggg cag tat aaa tcc      632
Asn Gly Asp Gly Ser Thr Cys Arg Leu Val Arg Gly Gln Tyr Lys Ser
    180                 185                 190 cag ctc tcc gca acc aaa tcg gat gat act gtg gtt gca att ccc tat      680
Gln Leu Ser Ala Thr Lys Ser Asp Asp Thr Val Val Ala Ile Pro Tyr
195                 200                 205                 210 gga agt aga cat att cgc ctt gtc tta aaa ggt cct gat cac tta tat      728
Gly Ser Arg His Ile Arg Leu Val Leu Lys Gly Pro Asp His Leu Tyr
                215                 220                 225 ctg gaa acc aaa acc ctc cag ggg act aaa ggt gaa aac agt ctc agc      776
Leu Glu Thr Lys Thr Leu Gln Gly Thr Lys Gly Glu Asn Ser Leu Ser
            230                 235                 240 tcc aca gga act ttc ctt gtg gac aat tct agt gtg gac ttc cag aaa      824
Ser Thr Gly Thr Phe Leu Val Asp Asn Ser Ser Val Asp Phe Gln Lys
        245                 250                 255 ttt cca gac aaa gag ata ctg aga atg gct gga cca ctc aca gca gat      872
Phe Pro Asp Lys Glu Ile Leu Arg Met Ala Gly Pro Leu Thr Ala Asp
    260                 265                 270 ttc att gtc aag att cgt aac tcg ggc tcc gct gac agt aca gtc cag      920
Phe Ile Val Lys Ile Arg Asn Ser Gly Ser Ala Asp Ser Thr Val Gln
275                 280                 285                 290 ttc atc ttc tat caa ccc atc atc cac cga tgg agg gag acg gat ttc      968
Phe Ile Phe Tyr Gln Pro Ile Ile His Arg Trp Arg Glu Thr Asp Phe
                295                 300                 305
```

```
ttt cct tgc tca gca acc tgt gga gga ggt tat cag ctg aca tcg gct      1016
Phe Pro Cys Ser Ala Thr Cys Gly Gly Gly Tyr Gln Leu Thr Ser Ala
            310                 315                 320 gag tgc tac gat ctg agg agc aac cgt gtg gtt gct gac caa tac tgt      1064
Glu Cys Tyr Asp Leu Arg Ser Asn Arg Val Val Ala Asp Gln Tyr Cys
            325                 330                 335 cac tat tac cca gag aac atc aaa ccc aaa ccc aag ctt cag gag tgc      1112
His Tyr Tyr Pro Glu Asn Ile Lys Pro Lys Pro Lys Leu Gln Glu Cys
    340                 345                 350 aac ttg gat cct tgt cca gcc agt gac gga tac aag cag atc atg cct      1160
Asn Leu Asp Pro Cys Pro Ala Ser Asp Gly Tyr Lys Gln Ile Met Pro
355                 360                 365                 370 tat gac ctc tac cat ccc ctt cct cgg tgg gag gcc acc cca tgg acc      1208
Tyr Asp Leu Tyr His Pro Leu Pro Arg Trp Glu Ala Thr Pro Trp Thr
                375                 380                 385 gcg tgc tcc tcc tcg tgt ggg ggg ggc atc cag agc cgg gca gtt tcc      1256
Ala Cys Ser Ser Ser Cys Gly Gly Gly Ile Gln Ser Arg Ala Val Ser
            390                 395                 400 tgt gtg gag gag gac atc cag ggg cat gtc act tca gtg gaa gag tgg      1304
Cys Val Glu Glu Asp Ile Gln Gly His Val Thr Ser Val Glu Glu Trp
            405                 410                 415 aaa tgc atg tac acc cct aag atg ccc atc gcg cag ccc tgc aac att      1352
Lys Cys Met Tyr Thr Pro Lys Met Pro Ile Ala Gln Pro Cys Asn Ile
            420                 425                 430 ttt gac tgc cct aaa tgg ctg gca cag gag tgg tct ccg tgc aca gtg      1400
Phe Asp Cys Pro Lys Trp Leu Ala Gln Glu Trp Ser Pro Cys Thr Val
435                 440                 445                 450 acg tgt ggc cag ggc ctc aga tac cgt gtg gtc ctc tgc atc gac cat      1448
Thr Cys Gly Gln Gly Leu Arg Tyr Arg Val Val Leu Cys Ile Asp His
            455                 460                 465 cga gga atg cac aca gga ggc tgt agc cca aaa aca aag ccc cac ata      1496
Arg Gly Met His Thr Gly Gly Cys Ser Pro Lys Thr Lys Pro His Ile
            470                 475                 480 aaa gag gaa tgc atc gta ccc act ccc tgc tat aaa ccc aaa gag aaa      1544
Lys Glu Glu Cys Ile Val Pro Thr Pro Cys Tyr Lys Pro Lys Glu Lys
            485                 490                 495 ctt cca gtc gag gcc aag ttg cca tgg ttc aaa caa gct caa gag cta      1592
Leu Pro Val Glu Ala Lys Leu Pro Trp Phe Lys Gln Ala Gln Glu Leu
500                 505                 510 gaa gaa gga gct gct gtg tca gag gag ccc tcg taa gtt gta              1634
Glu Glu Gly Ala Ala Val Ser Glu Glu Pro Ser     Val Val
515                 520                 525 aaagcacaga ctgttctata tttgaaactt ttgtttaaag aaagcagtgt ctcactggtt    1694
gtagctttca tgggttctga actaagtgta atcatctcac caaagctttt tggctctcaa    1754
attaaagatt gattagtttc aaaaaaaaaa aaaaaaaaga tgcggccgc                1803

<210> SEQ ID NO 21
<211> LENGTH: 525
<212> TYPE: PRT
<213> ORGANISM: Homo sapiens ADAMTS-R1

<400> SEQUENCE: 21

Met Glu Cys Cys Arg Arg Ala Thr Pro Gly Thr Leu Leu Phe Leu
1               5                   10                  15

Ala Phe Leu Leu Leu Ser Ser Arg Thr Ala Arg Ser Glu Glu Asp Arg
                20                  25                  30

Asp Gly Leu Trp Asp Ala Trp Gly Pro Trp Ser Glu Cys Ser Arg Thr
            35                  40                  45
```

-continued

```
Cys Gly Gly Ala Ala Asn Ser Leu Arg Arg Cys Leu Ser Ser Lys
     50                  55                  60

Ser Cys Glu Gly Arg Asn Ile Arg Tyr Arg Thr Cys Ser Asn Val Asp
 65                  70                  75                  80

Cys Pro Pro Glu Ala Gly Asp Phe Arg Ala Gln Gln Cys Ser Ala His
                 85                  90                  95

Asn Asp Val Lys His His Gly Gln Phe Tyr Glu Trp Leu Pro Val Ser
             100                 105                 110

Asn Asp Pro Asp Asn Pro Cys Ser Leu Lys Cys Gln Ala Lys Gly Thr
         115                 120                 125

Thr Leu Val Val Glu Leu Ala Pro Lys Val Leu Asp Gly Thr Arg Cys
    130                 135                 140

Tyr Thr Glu Ser Leu Asp Met Cys Ile Ser Gly Leu Cys Gln Ile Val
145                 150                 155                 160

Gly Cys Asp His Gln Leu Gly Ser Thr Val Lys Glu Asp Asn Cys Gly
                165                 170                 175

Val Cys Asn Gly Asp Gly Ser Thr Cys Arg Leu Val Arg Gly Gln Tyr
            180                 185                 190

Lys Ser Gln Leu Ser Ala Thr Lys Ser Asp Asp Thr Val Val Ala Ile
        195                 200                 205

Pro Tyr Gly Ser Arg His Ile Arg Leu Val Leu Lys Gly Pro Asp His
    210                 215                 220

Leu Tyr Leu Glu Thr Lys Thr Leu Gln Gly Thr Lys Gly Glu Asn Ser
225                 230                 235                 240

Leu Ser Ser Thr Gly Thr Phe Leu Val Asp Asn Ser Ser Val Asp Phe
            245                 250                 255

Gln Lys Phe Pro Asp Lys Glu Ile Leu Arg Met Ala Gly Pro Leu Thr
        260                 265                 270

Ala Asp Phe Ile Val Lys Ile Arg Asn Ser Gly Ser Ala Asp Ser Thr
    275                 280                 285

Val Gln Phe Ile Phe Tyr Gln Pro Ile Ile His Arg Trp Arg Glu Thr
    290                 295                 300

Asp Phe Phe Pro Cys Ser Ala Thr Cys Gly Gly Gly Tyr Gln Leu Thr
305                 310                 315                 320

Ser Ala Glu Cys Tyr Asp Leu Arg Ser Asn Arg Val Val Ala Asp Gln
            325                 330                 335

Tyr Cys His Tyr Tyr Pro Glu Asn Ile Lys Pro Lys Pro Lys Leu Gln
        340                 345                 350

Glu Cys Asn Leu Asp Pro Cys Pro Ala Ser Asp Gly Tyr Lys Gln Ile
    355                 360                 365

Met Pro Tyr Asp Leu Tyr His Pro Leu Pro Arg Trp Glu Ala Thr Pro
    370                 375                 380

Trp Thr Ala Cys Ser Ser Cys Gly Gly Ile Gln Ser Arg Ala
385                 390                 395                 400

Val Ser Cys Val Glu Glu Asp Ile Gln Gly His Val Thr Ser Val Glu
            405                 410                 415

Glu Trp Lys Cys Met Tyr Thr Pro Lys Met Pro Ile Ala Gln Pro Cys
        420                 425                 430

Asn Ile Phe Asp Cys Pro Lys Trp Leu Ala Gln Glu Trp Ser Pro Cys
    435                 440                 445

Thr Val Thr Cys Gly Gln Gly Leu Arg Tyr Arg Val Val Leu Cys Ile
    450                 455                 460

Asp His Arg Gly Met His Thr Gly Gly Cys Ser Pro Lys Thr Lys Pro
```

```
                    465                 470                 475                 480
His Ile Lys Glu Glu Cys Ile Val Pro Thr Pro Cys Tyr Lys Pro Lys
                            485                 490                 495

Glu Lys Leu Pro Val Glu Ala Lys Leu Pro Trp Phe Lys Gln Ala Gln
            500                 505                 510

Glu Leu Glu Glu Gly Ala Ala Val Ser Glu Glu Pro Ser
            515                 520                 525

<210> SEQ ID NO 22
<211> LENGTH: 518
<212> TYPE: PRT
<213> ORGANISM: Homo sapiens ADAMTS-5
<220> FEATURE:
<221> NAME/KEY: MOD_RES
<222> LOCATION: (99)
<223> OTHER INFORMATION: Xaa = M

<400> SEQUENCE: 22

Gly His Leu Leu Gly Leu Ser His Asp Asp Ser Lys Phe Cys Glu Glu
  1               5                  10                  15

Thr Phe Gly Ser Thr Glu Asp Lys Arg Leu Met Ser Ser Ile Leu Thr
                 20                  25                  30

Ser Ile Asp Ala Ser Lys Pro Trp Ser Lys Cys Thr Ser Ala Thr Ile
             35                  40                  45

Thr Glu Phe Leu Asp Asp Gly His Gly Asn Cys Leu Leu Asp Leu Pro
         50                  55                  60

Arg Lys Gln Ile Leu Gly Pro Glu Glu Leu Pro Gly Gln Thr Tyr Asp
 65                  70                  75                  80

Ala Thr Gln Gln Cys Asn Leu Thr Phe Gly Pro Asp Tyr Ser Val Cys
                 85                  90                  95

Pro Gly Xaa Asp Val Cys Ala Arg Leu Trp Cys Ala Val Val Arg Gln
            100                 105                 110

Gly Gln Met Val Cys Leu Thr Lys Lys Leu Pro Ala Val Glu Gly Thr
            115                 120                 125

Pro Cys Gly Lys Gly Arg Ile Cys Leu Gln Gly Lys Cys Val Asp Lys
    130                 135                 140

Thr Lys Lys Tyr Tyr Ser Thr Ser Ser His Gly Asn Trp Gly Ser
145                 150                 155                 160

Trp Gly Ser Trp Gly Gln Cys Ser Arg Ser Cys Gly Gly Val Gln
                165                 170                 175

Phe Ala Tyr Arg His Cys Asn Asn Pro Ala Pro Arg Asn Asn Gly Arg
            180                 185                 190

Tyr Cys Thr Gly Lys Arg Ala Ile Tyr His Ser Cys Ser Leu Met Pro
        195                 200                 205

Cys Pro Pro Asn Gly Lys Ser Phe Arg His Glu Gln Cys Glu Ala Lys
    210                 215                 220

Asn Gly Tyr Gln Ser Asp Ala Lys Gly Val Lys Thr Phe Val Glu Trp
225                 230                 235                 240

Val Pro Lys Tyr Ala Gly Val Leu Pro Ala Asp Val Cys Lys Leu Thr
                245                 250                 255

Cys Arg Ala Lys Gly Thr Gly Tyr Tyr Val Val Phe Ser Pro Lys Val
            260                 265                 270

Thr Asp Gly Thr Glu Cys Arg Pro Tyr Ser Asn Ser Val Cys Val Arg
        275                 280                 285

Gly Lys Cys Val Arg Thr Gly Cys Asp Gly Ile Ile Gly Ser Lys Leu
    290                 295                 300
```

-continued

```
Gln Tyr Asp Lys Cys Gly Val Cys Gly Gly Asp Asn Ser Ser Cys Thr
305                 310                 315                 320

Lys Ile Val Gly Thr Phe Asn Lys Lys Ser Lys Gly Tyr Thr Asp Val
            325                 330                 335

Val Arg Ile Pro Glu Gly Ala Thr His Ile Lys Val Arg Gln Phe Lys
            340                 345                 350

Ala Lys Asp Gln Thr Arg Phe Thr Ala Tyr Leu Ala Leu Lys Lys Lys
            355                 360                 365

Asn Gly Glu Tyr Leu Ile Asn Gly Lys Tyr Met Ile Ser Thr Ser Glu
            370                 375                 380

Thr Ile Ile Asp Ile Asn Gly Thr Val Met Asn Tyr Ser Gly Trp Ser
385                 390                 395                 400

His Arg Asp Asp Phe Leu His Gly Met Gly Tyr Ser Ala Thr Lys Glu
                405                 410                 415

Ile Leu Ile Val Gln Ile Leu Ala Thr Asp Pro Thr Lys Pro Leu Asp
                420                 425                 430

Val Arg Tyr Ser Phe Phe Val Pro Lys Lys Ser Thr Lys Val Asn
            435                 440                 445

Ser Val Thr Ser His Gly Ser Asn Lys Val Gly Ser His Thr Ser Gln
450                 455                 460

Pro Gln Trp Val Thr Gly Pro Trp Leu Ala Cys Ser Arg Thr Cys Asp
465                 470                 475                 480

Thr Gly Trp His Thr Arg Thr Val Gln Cys Gln Asp Gly Asn Arg Lys
                485                 490                 495

Leu Ala Lys Gly Cys Pro Leu Ser Gln Arg Pro Ser Ala Phe Lys Gln
            500                 505                 510

Cys Leu Leu Lys Lys Cys
        515

<210> SEQ ID NO 23
<211> LENGTH: 16
<212> TYPE: PRT
<213> ORGANISM: synthetic construct

<400> SEQUENCE: 23

Ser Val Ser Ile Glu Arg Phe Val Glu Thr Leu Val Val Ala Asp Lys
1               5                   10                  15

<210> SEQ ID NO 24
<211> LENGTH: 19
<212> TYPE: PRT
<213> ORGANISM: synthetic construct

<400> SEQUENCE: 24

Glu Val Ala Glu Ala Ala Asn Phe Leu Ala Leu Arg Ser Glu Asp Pro
1               5                   10                  15

Asp Lys Tyr

<210> SEQ ID NO 25
<211> LENGTH: 18
<212> TYPE: PRT
<213> ORGANISM: synthetic construct

<400> SEQUENCE: 25

Val Lys Glu Asp Val Glu Asn Pro Lys Ala Val Val Asp Gly Asp Trp
1               5                   10                  15

Gly Pro
```

```
<210> SEQ ID NO 26
<211> LENGTH: 20
<212> TYPE: PRT
<213> ORGANISM: synthetic construct

<400> SEQUENCE: 26

Gln His Pro Phe Gln Asn Glu Asp Tyr Arg Pro Arg Ser Ala Ser Pro
 1               5                  10                  15

Ser Arg Thr His
            20

<210> SEQ ID NO 27
<211> LENGTH: 20
<212> TYPE: PRT
<213> ORGANISM: synthetic construct

<400> SEQUENCE: 27

Pro Gln Asn Cys Lys Glu Val Lys Arg Leu Lys Gly Ala Ser Glu Asp
 1               5                  10                  15

Gly Glu Tyr Phe
            20

<210> SEQ ID NO 28
<211> LENGTH: 14
<212> TYPE: PRT
<213> ORGANISM: synthetic construct

<400> SEQUENCE: 28

Gln Glu Leu Glu Glu Gly Ala Ala Val Ser Glu Glu Pro Ser
 1               5                  10

<210> SEQ ID NO 29
<211> LENGTH: 14
<212> TYPE: PRT
<213> ORGANISM: synthetic construct

<400> SEQUENCE: 29

Tyr Tyr Pro Glu Asn Ile Lys Pro Lys Pro Lys Leu Gln Glu
 1               5                  10

<210> SEQ ID NO 30
<211> LENGTH: 15
<212> TYPE: PRT
<213> ORGANISM: synthetic construct

<400> SEQUENCE: 30

His Ile Lys Val Arg Gln Phe Lys Ala Lys Asp Gln Thr Arg Phe
 1               5                  10                  15

<210> SEQ ID NO 31
<211> LENGTH: 26
<212> TYPE: PRT
<213> ORGANISM: synthetic construct

<400> SEQUENCE: 31

Cys Glu Ala Lys Asn Gly Tyr Gln Ser Asp Ala Lys Gly Val Lys Thr
 1               5                  10                  15

Phe Val Glu Trp Val Pro Lys Tyr Ala Gly
            20                  25
```